United States Patent
Ouyang et al.

(10) Patent No.: US 11,753,395 B2
(45) Date of Patent: Sep. 12, 2023

(54) INHIBITORS OF MET KINASE

(71) Applicant: Kinnate Biopharma Inc., San Diego, CA (US)

(72) Inventors: Xiaohu S. Ouyang, Rosemead, CA (US); Toufike Kanouni, Rancho Santa Fe, CA (US); John S. Tyhonas, San Diego, CA (US); Jason M. Cox, Rancho Santa Fe, CA (US); Robert S. Kania, San Diego, CA (US)

(73) Assignee: KINNATE BIOPHARMA INC., San Diego, CA (US)

( * ) Notice: Subject to any disclaimer, the term of this patent is extended or adjusted under 35 U.S.C. 154(b) by 0 days.

(21) Appl. No.: 18/066,056

(22) Filed: Dec. 14, 2022

(65) Prior Publication Data

US 2023/0219929 A1    Jul. 13, 2023

Related U.S. Application Data

(60) Provisional application No. 63/386,647, filed on Dec. 8, 2022, provisional application No. 63/380,049, filed on Oct. 18, 2022, provisional application No. 63/301,267, filed on Jan. 20, 2022, provisional application No. 63/290,291, filed on Dec. 16, 2021.

(51) Int. Cl.
| | |
|---|---|
| C07D 401/12 | (2006.01) |
| C07D 405/14 | (2006.01) |
| C07D 471/04 | (2006.01) |
| C07D 215/22 | (2006.01) |

(52) U.S. Cl.
CPC ......... *C07D 401/12* (2013.01); *C07D 215/22* (2013.01); *C07D 405/14* (2013.01); *C07D 471/04* (2013.01)

(58) Field of Classification Search
CPC .. C07D 401/12; C07D 215/22; C07D 405/14; C07D 405/04
See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 2005/0245530 | A1 | 11/2005 | Borzilleri et al. |
| 2006/0211695 | A1 | 9/2006 | Borzilleri et al. |
| 2009/0049035 | A1 | 2/2009 | He et al. |

FOREIGN PATENT DOCUMENTS

| | | |
|---|---|---|
| CN | 102827186 A | 12/2012 |
| CN | 105153026 A | 12/2015 |
| CN | 105732616 A | 7/2016 |
| CN | 109896997 A | 6/2019 |
| CN | 111196814 A | 5/2020 |
| JP | 2010126530 A | 6/2010 |
| KR | 101505783 B1 | 3/2015 |
| WO | WO-9717329 A1 | 5/1997 |
| WO | WO-2004105765 A1 | 12/2004 |
| WO | WO-2007076474 A1 | 7/2007 |
| WO | WO-2007146824 A2 | 12/2007 |
| WO | WO-2011017142 A1 | 2/2011 |
| WO | WO-2012028332 A1 | 3/2012 |
| WO | WO-2013078295 A2 | 5/2013 |
| WO | WO-2013180949 A1 | 12/2013 |
| WO | WO-2014000418 A1 | 1/2014 |
| WO | WO-2014194975 A1 | 12/2014 |
| WO | WO-2016166250 A1 | 10/2016 |
| WO | WO-2020047184 A1 | 3/2020 |
| WO | WO-2021062245 A1 | 4/2021 |

OTHER PUBLICATIONS

Berge et al. Pharmaceutical Salts. Journal of Pharmaceutical Sciences 66(1):1-19 (Jan. 1977).
CAS Report for KR101505783 retrieved Mar. 30, 2023.
Chemical Structure Search dated May 25, 2021.
Chemical Structure Search dated Sep. 27, 2021.
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).
PCT/US2022/081504 International Search Report and Written Opinion dated Mar. 15, 2023.
Qi et al. Discovery of N1-(4-((7-(3-(4-ethylpiperazin-1-yl)propoxy)-6-methoxyquinolin-4-yl)oxy)-3,5-difluorophenyl)-N3-(2-(2,6-difluorophenyl)-4-oxothiazolidin-3-yl)urea as a multi-tyrosine kinase inhibitor for drug-sensitive and drug-resistant cancers treatment. Eur J Med Chem 163:10-27 (2019).
Tang et al. Design, synthesis, and structure-activity relationships of novel 6,7-disubstituted-4-phenoxyquinoline derivatives as potential antitumor agents. Eur J Med Chem 69:77-89 (2013).
Chemical Structure Search Report in CAS Registry on Specifically Substituted Quinolines dated Apr. 3, 2023.

*Primary Examiner* — John M Mauro
(74) *Attorney, Agent, or Firm* — WILSON SONSINI GOODRICH & ROSATI

(57) ABSTRACT

Provided herein are inhibitors of MET receptor tyrosine kinase, pharmaceutical compositions comprising said inhibitory compounds, and methods for using said MET kinase inhibitory compounds for the treatment of disease.

30 Claims, No Drawings

INHIBITORS OF MET KINASE

CROSS-REFERENCE TO RELATED APPLICATION

This application claims the benefit of U.S. patent application No. 63/290,291, filed on Dec. 16, 2021; U.S. patent application No. 63/301,267, filed on Jan. 20, 2022; U.S. patent application No. 63/380,049, filed on Oct. 18, 2022; and U.S. patent application No. 63/386,647, filed on Dec. 8, 2022; each of which is hereby incorporated by reference in its entirety.

BACKGROUND

MET is a member of the class IV receptor tyrosine kinase family and is expressed on the surfaces of many different cell types, including epithelial cells of many organs, including the liver, pancreas, prostate, kidney, muscle, and bone marrow, during both embryogenesis and adulthood. Binding of the hepatocyte growth factor induces dimerization and activation of the receptor. MET modulates many essential cellular processes during development and wound healing, including cell proliferation, survival, motility, and morphogenesis. Aberrant MET activity is found in many different human cancers. Accordingly, therapies that target MET kinase activity are desired for use in the treatment of cancer and other disorders characterized by aberrant MET pathway signaling.

BRIEF SUMMARY OF THE INVENTION

Provided herein are inhibitors of MET kinase, pharmaceutical compositions comprising said inhibitory compounds, and methods for using said inhibitory compounds for the treatment of disease.

One embodiment provides a compound, or a pharmaceutically acceptable salt or solvate thereof, having the structure of Formula (I):

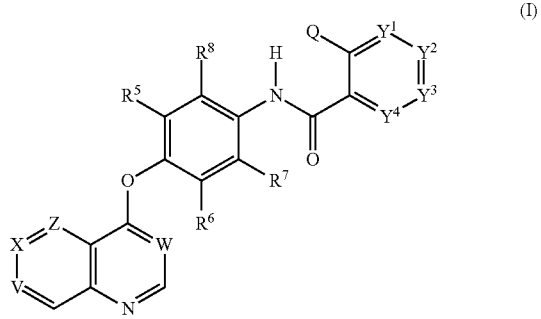

(I)

wherein,

V is independently N or C—L—R;
X is independently N, or C—$L^1$—$R^1$;
Z is N or C—$R^2$; provided that V, X, and Z are not all N;
W is C—H or N;
$Y^1$ is independently N or C—$R^3$;
$Y^2$ is independently N or C—$R^4$;
$Y^3$ is independently N or C—$R^3$;
$Y^4$ is independently N or C—$R^3$;
L is a bond, —O—, —NH—, —NHCO—, or —CONH—;
$L^1$ is a bond, —O—, —NH—, —NHCO—, or —CONH—;
R is selected from the group consisting of H, halogen, —CN, optionally substituted C1-C6 alkyl, optionally substituted C1-C6 alkenyl, optionally substituted C1-C6 alkynyl, optionally substituted C3-C6 cycloalkyl, optionally substituted cycloalkylalkyl, optionally substituted heterocyclyl, optionally substituted heterocyclylalkyl, optionally substituted heteroaryl, and optionally substituted heteroarylalkyl;
$R^1$ is selected from the group consisting of H, halogen, —CN, optionally substituted C1-C6 alkyl, optionally substituted C1-C6 alkenyl, optionally substituted C1-C6 alkynyl, optionally substituted C3-C6 cycloalkyl, optionally substituted cycloalkylalkyl, optionally substituted heterocyclyl, optionally substituted heterocyclylalkyl, optionally substituted heteroaryl, and optionally substituted heteroarylalkyl;
$R^2$ is H, halogen, —CN, optionally substituted C1-C6 alkyl, —NH(optionally substituted C1-C6 alkyl), or optionally substituted C1-C4 alkoxy;
each $R^3$ is selected from H, halogen, —CN, —$NH_2$, —NH(optionally substituted C1-C6 alkyl), —N(optionally substituted C1-C6 alkyl)$_2$, optionally substituted C1-C4 alkoxy, or optionally substituted C1-C4 alkyl;
$R^4$ is independently selected from H, halogen, —CN, optionally substituted C1-C6 alkyl, optionally substituted C1-C6 alkoxy, optionally substituted C3-C6 cycloalkyl, optionally substituted cycloalkylalkyl, optionally substituted heterocyclyl, optionally substituted heterocyclylalkyl, —$NH_2$, —NH(optionally substituted C1-C6 alkyl), or —N(optionally substituted C1-C6 alkyl)$_2$;
$R^5$ is fluoro;
$R^6$, $R^7$ and $R^8$ are each independently selected from H, halogen, optionally substituted C1-C4 alkyl, optionally substituted C1-C4 alkoxy, or —CN; provided that at least one of $R^6$, $R^7$ or $R^8$ is not H;
Q is F, or —$L^2$—$R^9$;
$L^2$ is —O—, or optionally substituted C1-C5 alkylene; and
$R^9$ is selected from the group consisting of halogen, optionally substituted C1-C6 alkyl, optionally substituted C1-C6 alkynyl, optionally substituted C1-C6 alkenyl, optionally substituted C3-C6 cycloalkyl, optionally substituted cycloalkylalkyl, optionally substituted heterocyclyl, and optionally substituted heterocyclylalkyl.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

DEFINITIONS

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n -pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π—electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above sub stituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —R$^b$—R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O -$R^c$-carbocyclyl where RC is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—(O)$_t$$OR^a$ (where t is 1 or 2) and —$R^b$—S(O)$_t$N($R^a$)$_2$ (where t is 1 or 2), where each $R^a$ independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O -$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π—electron system in accordance with the Eltickel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6, 6a, 7,8,9,10,10a-octahydrobenzo[h] quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from optionally substituted alkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O -$R^c$-heteroaryl, where RC is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

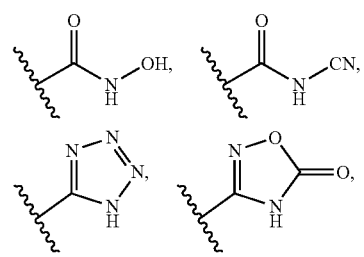

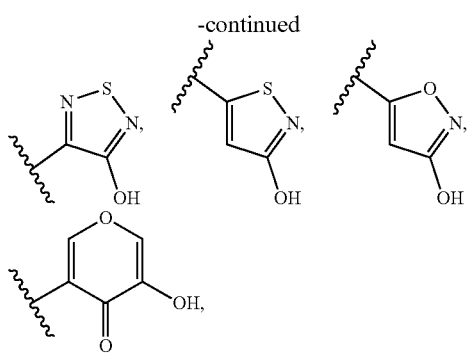

and the like.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

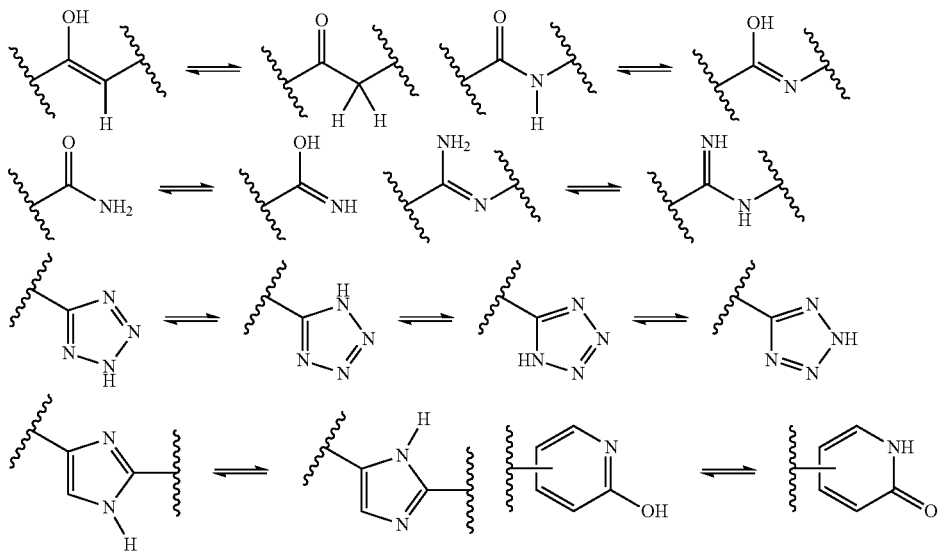

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in:

Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Raj ender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium -substituted carbon atom under nucleophilic substitution reaction conditions to the reaction substrate. The use of $CD_3I$ is illustrated, by way of example only, in the reaction schemes below.

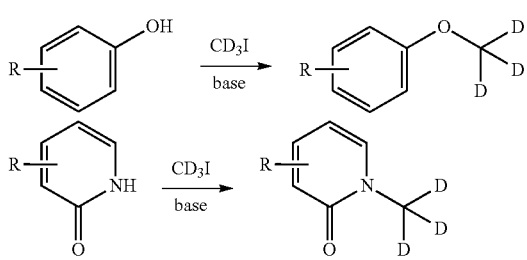

Deuterium-transfer reagents, such as lithium aluminum deuteride (LiAlD₄), are employed to transfer deuterium under reducing conditions to the reaction substrate. The use of LiAlD₄ is illustrated, by way of example only, in the reaction schemes below.

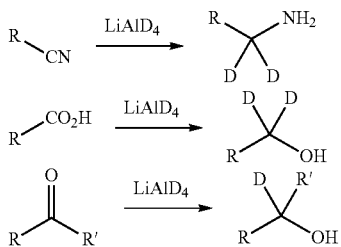

Deuterium gas and palladium catalyst are employed to reduce unsaturated carbon-carbon linkages and to perform a reductive substitution of aryl carbon-halogen bonds as illustrated, by way of example only, in the reaction schemes below.

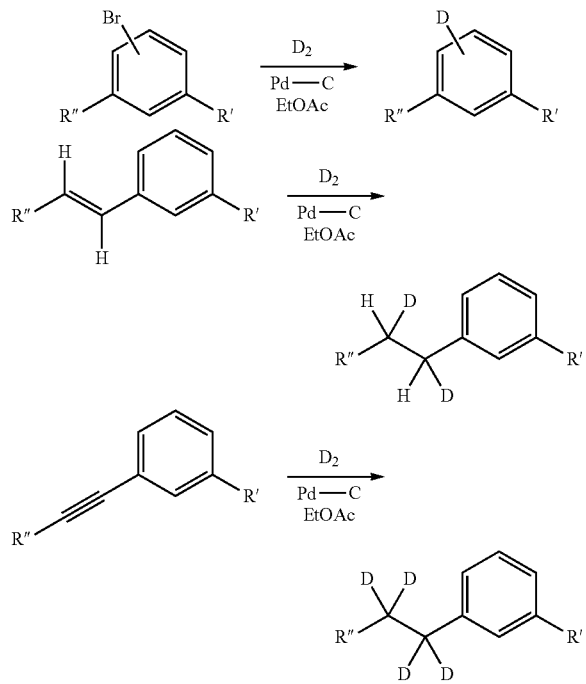

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the MET kinase inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

MET Tyrosine Kinase

The MET protein is a member of the class IV receptor tyrosine kinase family and is expressed on the surfaces of many different cell types, including epithelial cells of many organs, such as liver, pancreas, prostate, kidney, muscle, and bone marrow, during both embryogenesis and adulthood. MET modulates many essential cellular processes during development and wound healing, including cell proliferation, survival, motility, and morphogenesis. Aberrant MET activity is found in many different human cancers, such as non-small cell lung cancer, medulloblastoma, lymphoma, melanoma, glioma, breast cancer, pancreatic cancer, colorectal cancer, ovarian cancer and prostate cancer, as well as osteo- and some soft-tissue sarcomas.

The c-MET proto-oncogene is located on chromosome 7q21-31 and its transcription is regulated by Ets (E-twenty six), Pax3 (paired box 3), AP2 (activator protein-2) and Tcf-4 (transcription factor 4). It is expressed as multiple mRNA transcripts of 8, 7, 4.5, 3 and 1.5 kilobases. The protein product of this gene is the MET receptor tyrosine kinase.

Structurally, MET is a single pass transmembrane protein with an extracellular domain, a transmembrane hydrophobic sequence and an intracellular portion that comprises the tyrosine kinase domain. The extracellular domain of MET is composed of three domain types: a Semaphorin (Sema) domain, a PSI domain, and four immunoglobulin—plexin—transcription (IPT) domains. The N-terminal 500 residues fold to form the large Sema domain, which shares sequence homology with domains found in the semaphorin and plexin families. The PSI domain (found in plexins, semaphorins and integrins) follows the Sema domain, spans approximately 50 residues and connected the Sema domain to the IPT domains. The four IPT domains are related to immunoglobulin-like domains and are found in integrins, plexins and transcription factors. The IPT domain on the c-terminal side is, in turn, connected to the single transmembrane helix, which connects the extracellular domain to the intracellular domain. The intracellular domain of the MET receptor contains a juxtamembrane domain containing the Y1003 residue, which is involved in the receptor's down-regulation; a tyrosine kinase catalytic domain containing the Y1234 and Y1235 residues, which is involved in signal transduction; and a docking site for adaptor proteins containing Y1349 and Y1356 residues.

The extracellular portion of MET binds to its cognate ligands, hepatocyte growth factor (HGF) and its natural isoform, NK1, leading to the dimerization of two MET proteins. Dimerization leads to trans-autophosphorylation of two tyrosine residues (Y1234 and Y1235) located within the catalytic loop of the tyrosine kinase domain of the intracellular portion. Subsequently, tyrosine residues 1349 and 1356 in the carboxy-terminal tail are phosphorylated, thereby forming a unique tandem SH2 recognition motif and leading to recruitment of signal effector proteins (e.g., GAB1, GRB2, SHC, CRK, PI3K, PLCγ1, SHP2 and STAT3) responsible for downstream signaling.

HGF, the primary ligand of MET, is a secreted single chain 83 kDa precursor protein. Full length HGF contains an N-terminal (N) domain, four consecutive kringle (K1-K4) domains, and a serine protease homology (SPH) domain. Proteolytic cleavage between Arg494 and Val495 of HGF generates the 57 kDa α subunit and the 26 kDa β subunit, which are covalently linked by a disulfide bond between Cys487 of the α-subunit and Cys604 of the (β-subunit. While both of pro-HGF and cleaved HGF can bind to MET with high affinity, only cleaved mature HGF can activate MET signaling. NK1, a natural isoform of HGF can also bind to and activate MET.

In malignant solid tumors, HGF is primarily expressed and released by surrounding stromal cells, allowing the tumor and stromal cells communicate with each other through HGF, creating a microenvironment that contributes to cancer progression. For example, the HGF from the tumor stroma acts on tumor cells, stimulating not only to proliferation and metastasis, but also production of HGF-inducers. These HGF-inducers, including bFGF, IL-1β, TGF-α, PDGF and prostaglandin E2 (PGE2), act on stromal fibroblasts, inducing further HGF expression. This creates a feedback loop that drives increased 1MET activation in the tumor. In this way, the mutual interaction between tumor and stromal cells continually drives tumor growth, invasion, and metastasis. Furthermore, HGF can also be produced by the tumor itself, and this phenomenon has been detected in the renal cell carcinoma, colorectal cancer, breast cancer, glioma, multiple myeloma, and synovial sarcoma, osteosarcoma and fibrosarcoma.

Dysregulation of the MET pathway in cancer occurs through a variety of mechanisms, including gene mutation, amplification, rearrangement, and protein overexpression. Several MET fusions have been identified including a fusion between c-MET and TPR (translocated promoter region nuclear basket protein gene) found in a mutagenized osteosarcoma cell line, and a fusion between c-MET-KIF5B (kinesin family member 5B gene) detected in a patient with lung adenocarcinoma. Furthermore, Mutations in the splice site of MET that result in skipping of exon 14 are important molecular drivers in non-small cell lung cancer (NSCLC). Such exon-skipping mutations have recently been shown to occur in 3% to 4% of NSCLC adenocarcinomas, 2% of squamous cell carcinomas, and 1% to 8% of other subtypes of lung cancer. These exon-skipping mutations often result in perpetual 1MET activation, driving tumorigenesis through downstream signaling pathways.

MET Activation and Intracellular Signaling Pathways

Activation of MET initiates a series of intracellular signaling pathways, including PI3K/AKT, Ras/MAPK, JAK/STAT, SRC, Wnt/β-catenin, and other signaling pathways, thereby modulating proliferation, motility, migration, and invasion. Under normal physiological conditions, MET is important in the control of tissue homeostasis and wound healing, but in cancer, abnormal MET activation drives tumor proliferation, enhanced metastasis, and drug resistance through these pathways.

The Ras/MAPK/ERK signaling pathway communicates signals from cell surface receptors, including MET, to the DNA in the nucleus of the cell, where modulation of gene expression occurs. Although the signaling cascade comprises many different proteins that propagate the signal through protein phosphorylation, the pathway can generally be divided into 3 steps: (i) Ras activation, (ii) a kinase signal transduction cascade, and (iii) regulation of translation and transcription. Briefly, MET activation results in Ras activation, which phosphorylates and activates the protein kinase activity of RAF kinase. RAF kinase, in turn, phosphorylates and activates MEK (MEK1 and MEK2), which phosphorylates and activates a MAPK (also known as ERK) protein. MAPK activation regulates activities of several transcription factors and modulates protein expression. By altering the levels and activities of transcription factors, MAPK leads to altered transcription of genes that are important for the cell cycle. Depending upon the stimulus and cell type, this pathway can transmit signals that result in the prevention or induction of apoptosis or cell cycle progression. In cancer, aberrant Ras activation can lead to tumor growth, evasion of apoptosis, local tissue invasion, and metastasis.

The phosphatidylinositol 3-kinase (PI3K)/protein kinase B (PKB/AKT) signaling pathway is involved in the regulation of multiple cellular physiological processes, including metabolism, proliferation, cell survival, growth and angiogenesis. PI3K is a member of the lipid kinases family and is activated by phosphorylation of the 3-hydroxyl group of phosphatidylinositol lipids in the plasma membrane forming Phosphatidylinositol (3,4,5)-trisphosphate (PIP3). PIP3 binds to PKB/Akt at the plasma membrane, allowing pyruvate dehydrogenase kinase 1 (PDK1) to access and phosphorylate T308 in the "activation loop" of AKT leading to partial PKB/Akt activation. Subsequent phosphorylation of Akt at S473 in the carboxy-terminal hydrophobic motif, either by mTOR or by DNA-PK, stimulates full Akt activity. Activation of Akt leads to additional substrate-specific phosphorylation events in both the cytoplasm and nucleus, including activation of CREB, inhibition of p27, localization of FOXO in the cytoplasm, activation of PtdIns-3ps, and activation of mTOR. Through these downstream effectors, the PI3K/Akt pathway mediates numerous cellular functions that drive cancer progression including angiogenesis, metabolism, growth, proliferation, survival, protein synthesis, transcription, and apoptosis.

The JAK-STAT pathway is essential for a wide range of cytokines and growth factors, leading to critical cellular events, such as cell differentiation, hematopoiesis, and immune system development. The JAK/STAT signaling pathway also plays a major role in the proliferation and survival of different cancer types. Activation of Janus Kinases (JAKs) by MET leads to phosphorylation of Signal Transducers and Activators of Transcription (STAT) proteins, which subsequently dimerize and translocate into the nucleus, where they modulate gene expression and drive tumor proliferation. For example, STAT3 is a key driver of tumorigenesis, and modulates the expression of many oncogenes, including BCL-XL, c-MYC, Mcl1, Survivin, BEGF, HIF-1α, HGF, IL-12, and MMPs. In this way, the JAK/STAT pathway drives tumor progression by enhancing cell proliferation, angiogenesis, metastasis, and immune escape.

The Wnt/β-catenin signaling pathway, is a conserved signaling axis participating in diverse physiological processes such as proliferation, differentiation, apoptosis, migration, invasion, and tissue homeostasis. Activation of the Wnt/β-catenin signaling pathway leads to an elevation of cytosolic concentration of β-catenin, which migrates to the nucleus and interacts with T cell -specific factor (TCF)/lymphoid enhancer-binding factor (LEF) and its co-activators, such as Pygopus and Bcl-9. This, in turn, enhances expression of target genes, including c-Myc, cyclin D1 and CDKN1A, which drive cancer stem cell renewal, cell proliferation and differentiation, thus exerting crucial roles in tumorigenesis and therapy response. Thus, by modulating a variety of tumorigenic signaling pathways, MET is a major driver of tumor growth, survival, invasion, and metastasis.

MET Kinase Inhibitors

Several agents have been developed to target MET or HGF, including small molecule inhibitors and monoclonal antibodies. Monoclonal antibodies currently FDA-approved or undergoing clinical evaluation includes anti-MET antibodies (e.g., onartuzumab and emibetuzumab), anti -HGF antibodies (e.g., ficlatuzumab and rilotumumab), and anti-MET/EGFR bispecific (e.g., amivantamab). These therapies prevent HGF from binding to MET, thereby shutting down MET activation. In addition, many small molecule MET inhibitors have received FDA approval for the treatment of cancer, including capmatinib, tepotinib, crizotinib, cabozantinib, MGCD265, AMG208, altiratinib, and golvatinib. Of those, two selective MET inhibitors, capmatinib (Tabrecta®) and tepotinib (Tepmetko®), are FDA-approved for the treatment of patients with advanced NSCLC harboring MET exon 14 skipping mutations. Cabozantinib (Cabometyx®) is FDA-approved for the treatment of locally advanced or metastatic differentiated thyroid cancer.

Small-molecule MET-specific inhibitors are divided into two functionally distinct classes: type I inhibitors (e.g., crizotinib, capmatinib, tepotinib, and savolitinib), which preferentially bind to the active conformation of MET, and type II inhibitors (e.g., cabozantinib and glesatinib), which preferentially bind to the inactive conformations of MET. Additionally, selective MET inhibitors include the adenosine triphosphate—competitive agents and the adenosine triphosphate—noncompetitive agents (e.g., tivantinib). Type I MET inhibitors are further subclassified as type Ia (e.g., crizotinib), which interact with the solvent front G1163 residue, and type Ib (e.g., capmatinib, tepotinib, and savolitinib), which binds to the kinase domain.

Type I and type II inhibitors each have unique efficacy profiles with respect to secondary MET mutations that confer resistance to MET inhibitors. For example, mutation in residues D1228 and Y1230 of the kinase domain confers resistance to type I MET inhibitors in vitro by weakening the interaction between the drug and the MET kinase domain. Resistance to all type I MET inhibitors have been identified in the clinic, with patients having secondary mutations at these positions. In addition, the mutation at the solvent front G1163R confers resistance to crizotinib, a type Ia MET inhibitor, but not to type Ib MET inhibitors like tepotinib, savolitinib, or capmatinib in vitro. However, type II MET inhibitors retain varying degrees of efficacy against many cancers bearing these mutations that render type I inhibitors ineffective. In view of the considerable resistance that mutations confer against MET inhibitors, there is a serious unmet clinical need for MET inhibitors that maintain efficacy against tumors bearing these mutations and other mutations.

MET Kinase Inhibitory Compounds

In one aspect, provided herein is a MET kinase inhibitory compound.

One embodiment provides a compound, or a pharmaceutically acceptable salt or solvate thereof, having the structure of Formula (I):

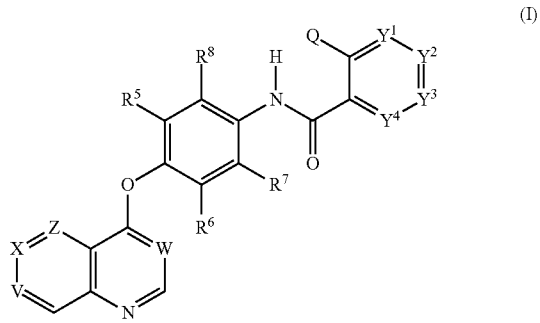

wherein,
V is independently N or C—L—R;
X is independently N, or C—L$^1$—R$^1$;
Z is N or C—R$^2$; provided that V, X, and Z are not all N;
W is C—H or N;
Y$^1$ is independently N or C—R$^3$;
Y$^2$ is independently N or C—R$^4$;
Y$^3$ is independently N or C—R$^3$;
Y$^4$ is independently N or C—R$^3$;
L is a bond, —O—, —NH—, —NHCO—, or —CONH—;

L$^1$ is a bond, —O—, —NH—, —NHCO—, or —CONH—;
R is selected from the group consisting of H, halogen, —CN, optionally substituted C1-C6 alkyl, optionally substituted C1-C6 alkenyl, optionally substituted C1-C6 alkynyl, optionally substituted C3-C6 cycloalkyl, optionally substituted cycloalkylalkyl, optionally substituted heterocyclyl, optionally substituted heterocyclylalkyl, optionally substituted heteroaryl, and optionally substituted heteroarylalkyl;
R$^1$ is selected from the group consisting of H, halogen, —CN, optionally substituted C1-C6 alkyl, optionally substituted C1-C6 alkenyl, optionally substituted C1-C6 alkynyl, optionally substituted C3-C6 cycloalkyl, optionally substituted cycloalkylalkyl, optionally substituted heterocyclyl, optionally substituted heterocyclylalkyl, optionally substituted heteroaryl, and optionally substituted heteroarylalkyl;
R$^2$ is H, halogen, —CN, optionally substituted C1-C6 alkyl, —NH(optionally substituted C1-C6 alkyl), or optionally substituted C1-C4 alkoxy;
each R$^3$ is selected from H, halogen, —CN, —NH$_2$, —NH(optionally substituted C1-C6 alkyl), —N(optionally substituted C1-C6 alkyl)$_2$, optionally substituted C1-C4 alkoxy, or optionally substituted C1-C4 alkyl;
R$^4$ is independently selected from H, halogen, —CN, optionally substituted C1-C6 alkyl, optionally substituted C1-C6 alkoxy, optionally substituted C3-C6 cycloalkyl, optionally substituted cycloalkylalkyl, optionally substituted heterocyclyl, optionally substituted heterocyclylalkyl, —NH$_2$, —NH(optionally substituted C1-C6 alkyl), or —N(optionally substituted C1-C6 alkyl)$_2$;
R$^5$ is fluoro;
R$^6$, R$^7$ and R$^8$ are each independently selected from H, halogen, optionally substituted C1-C4 alkyl, optionally substituted C1-C4 alkoxy, or —CN; provided that at least one of R$^6$, R$^7$ or R$^8$ is not H;
Q is F, or —L$^2$—R$^9$;
L$^2$ is —O—, or optionally substituted C1-C5 alkylene; and
R$^9$ is selected from the group consisting of halogen, optionally substituted C1-C6 alkyl, optionally substituted C1-C6 alkynyl, optionally substituted C1-C6 alkenyl, optionally substituted C3-C6 cycloalkyl, optionally substituted cycloalkylalkyl, optionally substituted heterocyclyl, and optionally substituted heterocyclylalkyl.

Another embodiment provides the compound of Formula (I), or a pharmaceutically acceptable salt or solvate thereof, wherein V is N.

Another embodiment provides the compound of Formula (I), or a pharmaceutically acceptable salt or solvate thereof, wherein V is C—L—R.

Another embodiment provides the compound of Formula (I), or a pharmaceutically acceptable salt or solvate thereof, wherein X is N.

Another embodiment provides the compound of Formula (I), or a pharmaceutically acceptable salt or solvate thereof, wherein X is C—L$^1$—R$^1$.

Another embodiment provides the compound of Formula (I), or a pharmaceutically acceptable salt or solvate thereof, wherein Z is N.

Another embodiment provides the compound of Formula (I), or a pharmaceutically acceptable salt or solvate thereof, wherein Z is C—R$^2$.

Another embodiment provides the compound of Formula (I), or a pharmaceutically acceptable salt or solvate thereof, wherein W is C—H.

Another embodiment provides the compound of Formula (I), or a pharmaceutically acceptable salt or solvate thereof, wherein W is N.

Another embodiment provides the compound of Formula (I), or a pharmaceutically acceptable salt or solvate thereof, wherein $Y^1$ is N.

Another embodiment provides the compound of Formula (I), or a pharmaceutically acceptable salt or solvate thereof, wherein $Y^1$ is C—$R^3$.

Another embodiment provides the compound of Formula (I), or a pharmaceutically acceptable salt or solvate thereof, wherein $Y^2$ is N.

Another embodiment provides the compound of Formula (I), or a pharmaceutically acceptable salt or solvate thereof, wherein $Y^2$ is C—$R^3$.

Another embodiment provides the compound of Formula (I), or a pharmaceutically acceptable salt or solvate thereof, wherein $Y^3$ is N.

Another embodiment provides the compound of Formula (I), or a pharmaceutically acceptable salt or solvate thereof, wherein $Y^3$ is C—$R^4$.

Another embodiment provides the compound of Formula (I), or a pharmaceutically acceptable salt or solvate thereof, wherein $Y^4$ is N.

Another embodiment provides the compound of Formula (I), or a pharmaceutically acceptable salt or solvate thereof, wherein $Y^4$ is C—$R^3$.

Another embodiment provides the compound of Formula (I), or a pharmaceutically acceptable salt or solvate thereof, wherein $R^6$ is fluoro. Another embodiment provides the compound of Formula (I), or a pharmaceutically acceptable salt or solvate thereof, wherein $L^2$ is —O—. Another embodiment provides the compound of Formula (I), or a pharmaceutically acceptable salt or solvate thereof, wherein $R^9$ is optionally substituted C1-C6 alkyl, or optionally substituted C3-C6 cycloalkyl.

Another embodiment provides the compound of Formula (I), or a pharmaceutically acceptable salt or solvate thereof, having the structure of Formula (II):

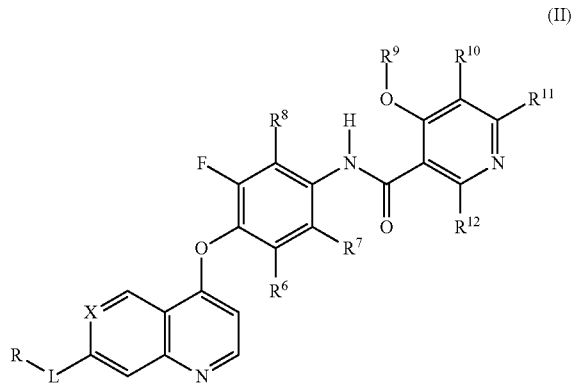

(II)

wherein, $R^6$, $R^7$ and $R^8$ are each independently selected from H or halogen; provided that at least one of $R^6$, $R^7$ or $R^8$ is not H;

$R^9$ is selected from the group consisting of optionally substituted C1-C6 alkyl, optionally substituted C3-C6 cycloalkyl, and optionally substituted cycloalkylalkyl;

$R^{10}$ is H;

$R^{11}$ is H, halogen, —$NH_2$, —CN, optionally substituted C1-C6 alkyl, optionally substituted C1-C6 alkoxy, —NH(optionally substituted C1-C6 alkyl), or —N(optionally substituted C1-C6 alkyl)$_2$;

$R^{12}$ is H, halogen, —$NH_2$, —CN, optionally substituted C1-C6 alkyl or optionally substituted C1-C6 alkoxy.

Another embodiment provides the compound of Formula (II), or a pharmaceutically acceptable salt or solvate thereof, wherein X is C—$L^1$—$R^1$.

Another embodiment provides the compound of Formula (II), or a pharmaceutically acceptable salt or solvate thereof, wherein $L^1$ is —O—.

Another embodiment provides the compound of Formula (II), or a pharmaceutically acceptable salt or solvate thereof, wherein $L^1$ is a bond.

Another embodiment provides the compound of Formula (II), or a pharmaceutically acceptable salt or solvate thereof, wherein $R^1$ is H.

Another embodiment provides the compound of Formula (I) or (II), or a pharmaceutically acceptable salt or solvate thereof, wherein $R^1$ is optionally substituted C1-C6 alkyl. Another embodiment provides the compound of Formula (I) or (II), or a pharmaceutically acceptable salt or solvate thereof, wherein $R^1$ is optionally substituted C1-C2 alkyl. Another embodiment provides the compound of Formula (I) or (II), or a pharmaceutically acceptable salt or solvate thereof, wherein $R^1$ is optionally substituted C1 alkyl.

Another embodiment provides the compound of Formula (I) or (II), or a pharmaceutically acceptable salt or solvate thereof, wherein $L^1$ is a bond and $R^1$ is hydrogen.

Another embodiment provides the compound of Formula (I) or (II), or a pharmaceutically acceptable salt or solvate thereof, wherein L is —O—.

Another embodiment provides the compound of Formula (I) or (II), or a pharmaceutically acceptable salt or solvate thereof, wherein R is optionally substituted C1-C6 alkyl. Another embodiment provides the compound of Formula (I) or (II), or a pharmaceutically acceptable salt or solvate thereof, wherein R is optionally substituted C1-C4 alkyl. Another embodiment provides the compound of Formula (I) or (II), or a pharmaceutically acceptable salt or solvate thereof, wherein R is optionally substituted C1-C2 alkyl.

Another embodiment provides the compound of Formula (I), or a pharmaceutically acceptable salt or solvate thereof, having the structure of Formula (III):

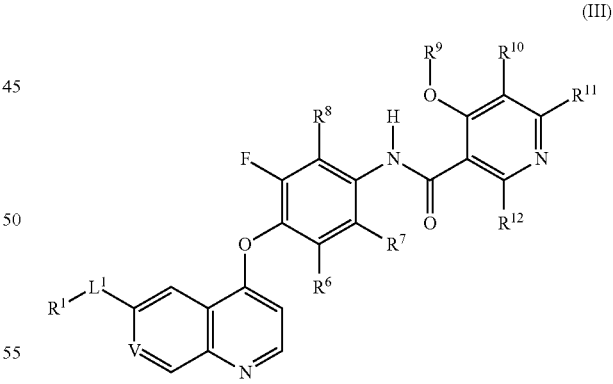

(III)

wherein, $R^6$, $R^7$ and $R^8$ are each independently selected from H or halogen; provided that at least one of $R^6$, $R^7$ or $R^8$ is not H;

$R^9$ is selected from the group consisting of optionally substituted C1-C6 alkyl, optionally substituted C3-C6 cycloalkyl, and optionally substituted cycloalkylalkyl;

$R^{10}$ is H;

$R^{11}$ is H, halogen, —$NH_2$, —CN, optionally substituted C1-C6 alkyl, optionally substituted C1-C6 alkoxy, —NH(optionally substituted C1-C6 alkyl), or —N(optionally substituted C1-C6 alkyl)$_2$;

$R^{12}$ is H, halogen, optionally substituted C1-C6 alkyl or optionally substituted C1-C6 alkoxy.

Another embodiment provides the compound of Formula (III), or a pharmaceutically acceptable salt or solvate thereof, wherein V is C—L—R. Another embodiment provides the compound of Formula (III), or a pharmaceutically acceptable salt or solvate thereof, wherein L is —O—. Another embodiment provides the compound of Formula (III), or a pharmaceutically acceptable salt or solvate thereof, wherein L is a bond. Another embodiment provides the compound of Formula (III), or a pharmaceutically acceptable salt or solvate thereof, wherein R is H.

Another embodiment provides the compound of Formula (I) or (III), or a pharmaceutically acceptable salt or solvate thereof, wherein R is optionally substituted C1-C6 alkyl. Another embodiment provides the compound of Formula (I) or (III), or a pharmaceutically acceptable salt or solvate thereof, wherein R is optionally substituted C1-C2 alkyl. Another embodiment provides the compound of Formula (I) or (III), or a pharmaceutically acceptable salt or solvate thereof, wherein R is optionally substituted C1 alkyl.

Another embodiment provides the compound of Formula (I) or (III), or a pharmaceutically acceptable salt or solvate thereof, wherein L is a bond and R is hydrogen. Another embodiment provides the compound of Formula (I) or (III), or a pharmaceutically acceptable salt or solvate thereof, wherein $L^1$ is —O—.

Another embodiment provides the compound of Formula (I) or (III), or a pharmaceutically acceptable salt or solvate thereof, wherein $R^1$ is optionally substituted C1-C6 alkyl. Another embodiment provides the compound of Formula (I) or (III), or a pharmaceutically acceptable salt or solvate thereof, wherein $R^1$ is optionally substituted C1-C4 alkyl. Another embodiment provides the compound of Formula (I) or (III), or a pharmaceutically acceptable salt or solvate thereof, wherein $R^1$ is optionally substituted C1-C2 alkyl.

Another embodiment provides the compound of Formula (I), or a pharmaceutically acceptable salt or solvate thereof, having the structure of Formula (IV):

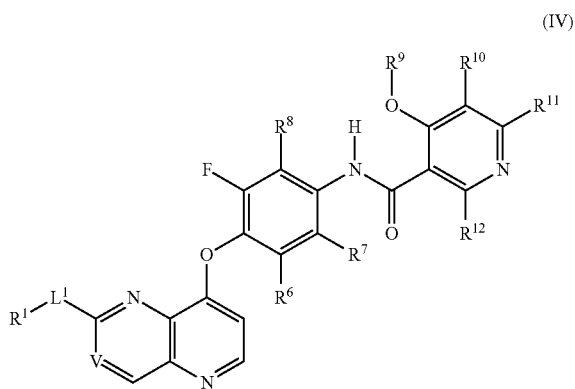

(IV)

wherein, $R^6$, $R^7$ and $R^8$ are each independently selected from H or halogen; provided that at least one of $R^6$, $R^7$ or le is not H;

$R^9$ is selected from the group consisting of optionally substituted C1-C6 alkyl, optionally substituted C3-C6 cycloalkyl, and optionally substituted cycloalkylalkyl;

$R^{10}$ is H;

$R^{11}$ is H, halogen, —$NH_2$, —CN, optionally substituted C1-C6 alkyl, optionally substituted C1-C6 alkoxy, —NH(optionally substituted C1-C6 alkyl), or —N(optionally substituted C1-C6 alkyl)$_2$;

$R^{12}$ is H, halogen, optionally substituted C1-C6 alkyl or optionally substituted C1-C6 alkoxy.

Another embodiment provides the compound of Formula (IV), or a pharmaceutically acceptable salt or solvate thereof, wherein V is C—L—R. Another embodiment provides the compound of Formula (IV), or a pharmaceutically acceptable salt or solvate thereof, wherein L is —O—. Another embodiment provides the compound of Formula (IV), or a pharmaceutically acceptable salt or solvate thereof, wherein L is a bond. Another embodiment provides the compound of Formula (IV), or a pharmaceutically acceptable salt or solvate thereof, wherein R is H.

Another embodiment provides the compound of Formula (I) or (IV), or a pharmaceutically acceptable salt or solvate thereof, wherein R is optionally substituted C1-C6 alkyl. Another embodiment provides the compound of Formula (I) or (IV), or a pharmaceutically acceptable salt or solvate thereof, wherein R is optionally substituted C1-C2 alkyl. Another embodiment provides the compound of Formula (I) or (IV), or a pharmaceutically acceptable salt or solvate thereof, wherein R is optionally substituted C1 alkyl.

Another embodiment provides the compound of Formula (I) or (IV), or a pharmaceutically acceptable salt or solvate thereof, wherein L is a bond and R is hydrogen. Another embodiment provides the compound of Formula (I) or (IV), or a pharmaceutically acceptable salt or solvate thereof, wherein $L^1$ is —O—.

Another embodiment provides the compound of Formula (I) or (IV), or a pharmaceutically acceptable salt or solvate thereof, wherein $R^1$ is optionally substituted C1-C6 alkyl. Another embodiment provides the compound of Formula (I) or (IV), or a pharmaceutically acceptable salt or solvate thereof, wherein $R^1$ is optionally substituted C1-C4 alkyl. Another embodiment provides the compound of Formula (I) or (IV), or a pharmaceutically acceptable salt or solvate thereof, wherein $R^1$ is optionally substituted C1-C2 alkyl.

Another embodiment provides the compound of Formula (I), (II), (III), or (IV), or a pharmaceutically acceptable salt or solvate thereof, wherein $R^9$ is optionally substituted C1-C6 alkyl. Another embodiment provides the compound of Formula (I), (II), (III), or (IV), or a pharmaceutically acceptable salt or solvate thereof, wherein $R^9$ is optionally substituted C1-C4 alkyl. Another embodiment provides the compound of Formula (I), (II), (III), or (IV), or a pharmaceutically acceptable salt or solvate thereof, wherein $R^9$ is optionally substituted C1-C2 alkyl. Another embodiment provides the compound of Formula (I), (II), (III), or (IV), or a pharmaceutically acceptable salt or solvate thereof, wherein $R^9$ is optionally substituted C1 alkyl. Another embodiment provides the compound of Formula (I), (II), (III), or (IV), or a pharmaceutically acceptable salt or solvate thereof, wherein $R^9$ is $CH_3$.

Another embodiment provides the compound of Formula (I), (II), (III), or (IV), or a pharmaceutically acceptable salt or solvate thereof, wherein $R^9$ is optionally substituted C3-C6 cycloalkyl. Another embodiment provides the compound of Formula (I), (II), (III), or (IV), or a pharmaceutically acceptable salt or solvate thereof, wherein $R^9$ is optionally substituted C3-C4 cycloalkyl. Another embodiment provides the compound of Formula (I), (II), (III), or (IV), or a pharmaceutically acceptable salt or solvate thereof, wherein $R^9$ is optionally substituted C5-C6 cycloalkyl. Another embodiment provides the compound of Formula (I), (II), (III), or (IV), or a pharmaceutically acceptable salt or solvate thereof, wherein $R^9$ is optionally substituted cyclopropyl. Another embodiment provides the compound of Formula (I), (II), (III), or (IV), or a pharmaceutically acceptable salt or solvate thereof, wherein $R^9$ is cyclopropyl.

Another embodiment provides the compound of Formula (I), (II), (III), or (IV), or a pharmaceutically acceptable salt or solvate thereof, wherein $R^{11}$ is hydrogen.

Another embodiment provides the compound of Formula (I), (II), (III), or (IV), or a pharmaceutically acceptable salt or solvate thereof, wherein $R^8$ is fluoro. Another embodiment provides the compound of Formula (I), (II), (III), or (IV), or a pharmaceutically acceptable salt or solvate thereof, wherein $R^8$ is hydrogen.

Another embodiment provides the compound of Formula (I), (II), (III), or (IV), or a pharmaceutically acceptable salt or solvate thereof, wherein $R^7$ is fluoro. Another embodiment provides the compound of Formula (I), (II), (III), or (IV), or a pharmaceutically acceptable salt or solvate thereof, wherein $R^7$ is hydrogen.

Another embodiment provides the compound of Formula (I), (II), (III), or (IV), or a pharmaceutically acceptable salt or solvate thereof, wherein $R^6$ is hydrogen. Another embodiment provides the compound of Formula (I), (II), (III), or (IV), or a pharmaceutically acceptable salt or solvate thereof, wherein $R^6$ is fluoro.

Another embodiment provides the compound of Formula (I), (II), (III), or (IV), or a pharmaceutically acceptable salt or solvate thereof, wherein Q is —$L^2$—$R^9$.

In some embodiments, the MET kinase inhibitory compound), or a pharmaceutically acceptable salt or solvate thereof, as described herein has a structure provided in Table 1.

TABLE 1

| Example No. | Compound Structure | Compound Name | Exact Mass [M + H]+ |
|---|---|---|---|
| 1 | 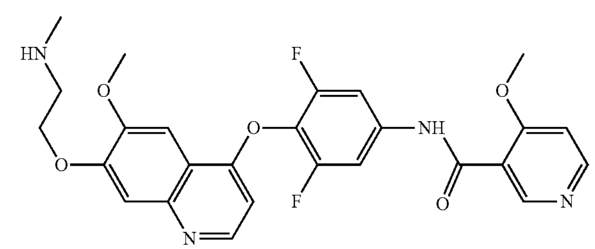 [SMILES: CNCCOc1cc2nccc(Oc3c(F)cc(NC(=O)c4cnccc4OC)cc3F)c2cc1OC] | N-[3,5-difluoro-4-({6-methoxy-7-[2-(methylamino)ethoxy]quinolin-4-yl}oxy)phenyl]-4-methoxypyridine-3-carboxamide | 511.17 |
| 2 | 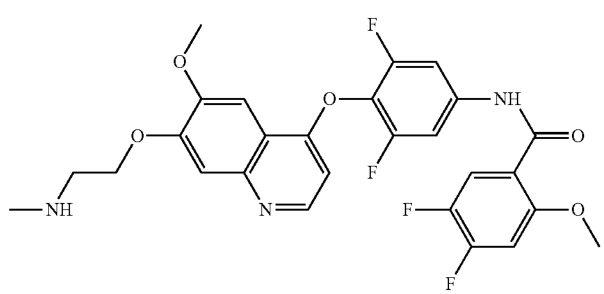 | N-(3,5-difluoro-4-((6-methoxy-7-(2-(methylamino)ethoxy)quinolin-4-yl)oxy)phenyl)-4,5-difluoro-2-methoxybenzamide | 546.16 |
| 3 | 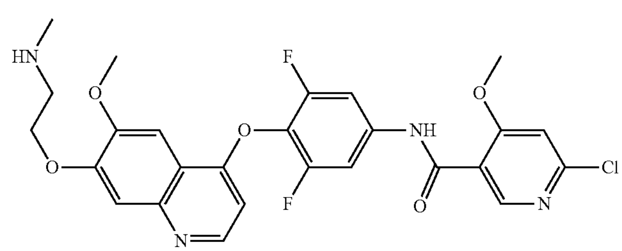 [SMILES: CNCCOc1cc2nccc(Oc3c(F)cc(NC(=O)c4cnc(Cl)cc4OC)cc3F)c2cc1OC] | 6-chloro-N-[3,5-difluoro-4-({6-methoxy-7-[2-(methylamino)ethoxy]quinolin-4-yl}oxy)phenyl]-4-methoxypyridine-3-carboxamide | 545.13 |
| 4 | 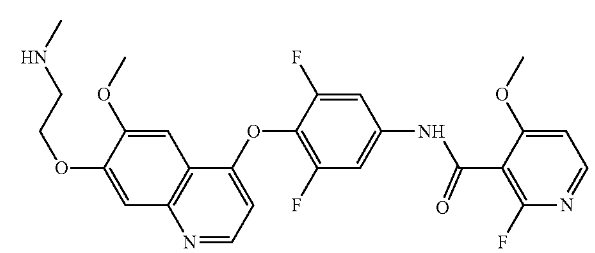 [SMILES: CNCCOc1cc2nccc(Oc3c(F)cc(NC(=O)c4c(OC)ccnc4F)cc3F)c2cc1OC] | N-(3,5-difluoro-4-((6-methoxy-7-(2-(methylamino)ethoxy)quinolin-4-yl)oxy)phenyl)-2-fluoro-4-methoxypyridine-3-carboxamide formate | 529.16 |

TABLE 1-continued

| Example No. | Compound Structure | Compound Name | Exact Mass [M + H]+ |
|---|---|---|---|
| 5 | 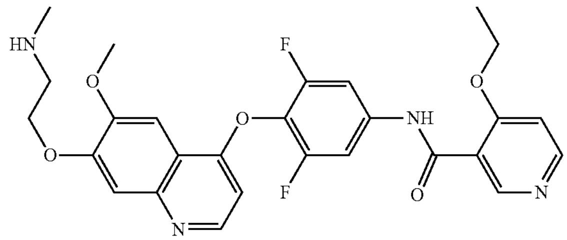 [SMILES: CCOc1ccncc1C(=O)Nc1cc(F)c(Oc2ccnc3cc(OCCNC)c(OC)cc23)c(F)c1] | N-[3,5-difluoro-4-({6-methoxy-7-[2-(methylamino)ethoxy]quinolin-4-yl}oxy)phenyl]-4-ethoxypyridine-3-carboxamide | 525.19 |
| 6 | 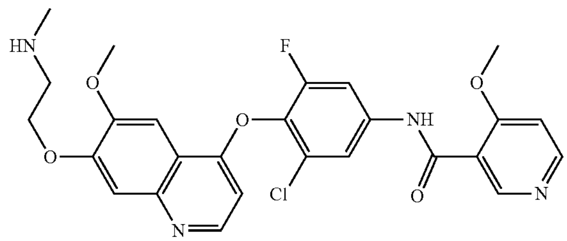 [SMILES: CNCCOc1cc2nccc(Oc3c(F)cc(NC(=O)c4cnccc4OC)cc3Cl)c2cc1OC] | N-(3-chloro-5-fluoro-4-((6-methoxy-7-(2-(methylamino)ethoxy)quinolin-4-yl)oxy)phenyl)-4-methoxypyridine-3-carboxamide | 527.14 |
| 7 | 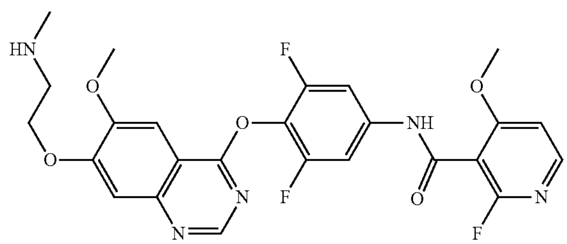 [SMILES: CNCCOc1cc2ncnc(Oc3c(F)cc(NC(=O)c4c(OC)ccnc4F)cc3F)c2cc1OC] | N-(3,5-difluoro-4-((6-methoxy-7-(2-(methylamino)ethoxy)quinazolin-4-yl)oxy)phenyl)-2-fluoro-4-methoxypyridine-3-carboxamide | 530.16 |
| 8 | 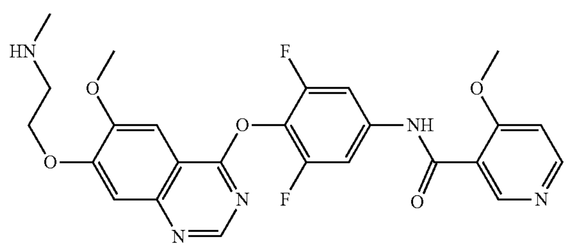 | N-(3,5-difluoro-4-((6-methoxy-7-(2-(methylamino)ethoxy)quinazolin-4-yl)oxy)phenyl)-4-methoxypyridine-3-carboxamide | 512.17 |
| 9 | 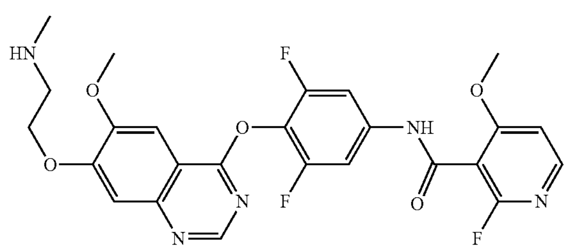 | N-(3,5-difluoro-4-((7-(2-(methylamino)ethoxy)quinolin-4-yl)oxy)phenyl)-2-fluoro-4-methoxypyridine-3-carboxamide | 499.15 |
| 10 | 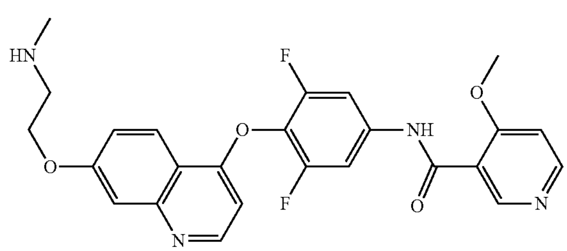 [SMILES: CNCCOc1ccc2c(Oc3c(F)cc(NC(=O)c4cnccc4OC)cc3F)ccnc2c1] | N-(3,5-difluoro-4-((7-(2-(methylamino)ethoxy)quinolin-4-yl)oxy)phenyl)-4-methoxypyridine-3-carboxamide | 481.16 |

TABLE 1-continued

| Example No. | Compound Name | Exact Mass [M + H]+ |
|---|---|---|
| 11 | N-(3,5-difluoro-4-((7-(2-(methylamino)ethoxy)quinolin-4-yl)oxy)phenyl)-4-ethoxypyridine-3-carboxamide | 495.18 |
| 12 | (S)-N-(4-((7-(2-aminopropoxy)quinolin-4-yl)oxy)-3,5-difluorophenyl)-2-fluoro-4-methoxypyridine-3-carboxamide | 499.15 |
| 13 | (R)-N-(4-((7-(2-aminopropoxy)quinolin-4-yl)oxy)-3,5-difluorophenyl)-2-fluoro-4-methoxypyridine-3-carboxamide | 499.15 |
| 14 | N-[2,3-difluoro-4-({6-methoxy-7-[2-(methylamino)ethoxy]quinolin-4-yl}oxy)phenyl]-4-methoxypyridine-3-carboxamide | 511.17 |
| 15 | N-[2,3-difluoro-4-({6-methoxy-7-[2-(methylamino)ethoxy]quinolin-4-yl}oxy)phenyl]-2-fluoro-4-methoxypyridine-3-carboxamide | 529.16 |
| 16 | N-[2,3-difluoro-4-({6-methoxy-7-[2-(methylamino)ethoxy]quinolin-4-yl}oxy)phenyl]-4-ethoxypyridine-3-carboxamide | 525.19 |

TABLE 1-continued

| Example No. | Compound Structure | Compound Name | Exact Mass [M + H]+ |
|---|---|---|---|
| 17 | 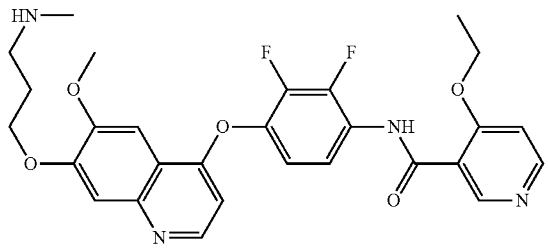 [SMILES: CCOc1ccncc1C(=O)Nc1ccc(Oc2ccnc3cc(OCCCNC)c(OC)cc23)c(F)c1F] | N-(2,3-difluoro-4-((6-methoxy-7-(3-(methylamino)propoxy)quinolin-4-yl)oxy)phenyl)-4-ethoxypyridine-3-carboxamide | 539.20 |
| 18 | 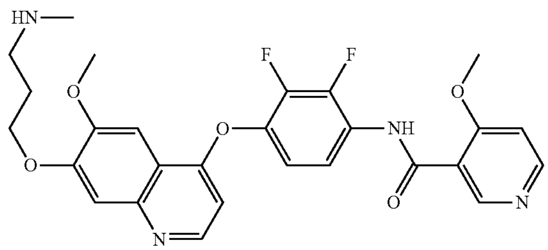 [SMILES: CNCCCOc1cc2nccc(Oc3ccc(NC(=O)c4cnccc4OC)c(F)c3F)c2cc1OC] | N-(2,3-difluoro-4-((6-methoxy-7-(3-(methylamino)propoxy)quinolin-4-yl)oxy)phenyl)-4-methoxypyridine-3-carboxamide | 525.19 |
| 19 | 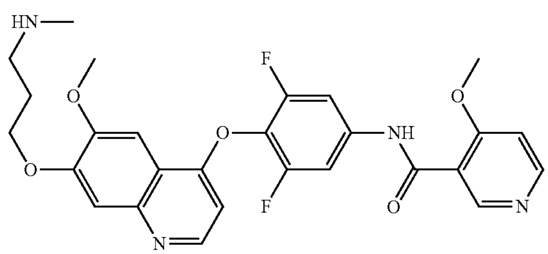 [SMILES: CNCCCOc1cc2nccc(Oc3c(F)cc(NC(=O)c4cnccc4OC)cc3F)c2cc1OC] | N-(3,5-difluoro-4-((6-methoxy-7-(3-(methylamino)propoxy)quinolin-4-yl)oxy)phenyl)-4-methoxypyridine-3-carboxamide | 525.19 |
| 20 | 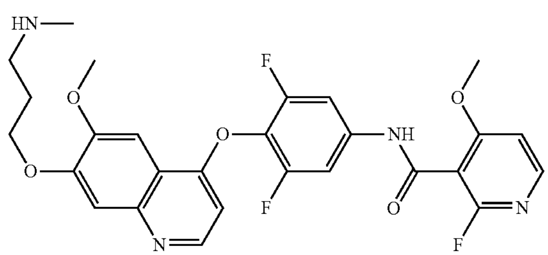 [SMILES: CNCCCOc1cc2nccc(Oc3c(F)cc(NC(=O)c4c(OC)ccnc4F)cc3F)c2cc1OC] | N-(3,5-difluoro-4-((6-methoxy-7-(3-(methylamino)propoxy)quinolin-4-yl)oxy)phenyl)-2-fluoro-4-methoxypyridine-3-carboxamide | 543.18 |
| 21 | 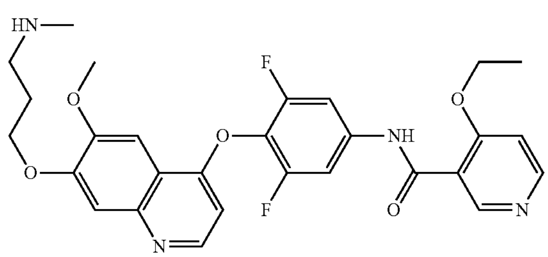 [SMILES: CCOc1ccncc1C(=O)Nc1cc(F)c(Oc2ccnc3cc(OCCCNC)c(OC)cc23)c(F)c1] | N-(3,5-difluoro-4-((6-methoxy-7-(3-(methylamino)propoxy)quinolin-4-yl)oxy)phenyl)-4-ethoxypyridine-3-carboxamide | 539.20 |
| 22 | 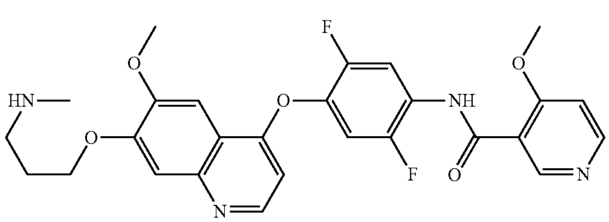 [SMILES: CNCCCOc1cc2nccc(Oc3cc(F)c(NC(=O)c4cnccc4OC)cc3F)c2cc1OC] | N-(2,5-difluoro-4-((6-methoxy-7-(3-(methylamino)propoxy)quinolin-4-yl)oxy)phenyl)-4-methoxypyridine-3-carboxamide | 525.19 |

TABLE 1-continued

| Example No. | Compound Structure | Compound Name | Exact Mass [M + H]+ |
|---|---|---|---|
| 23 | 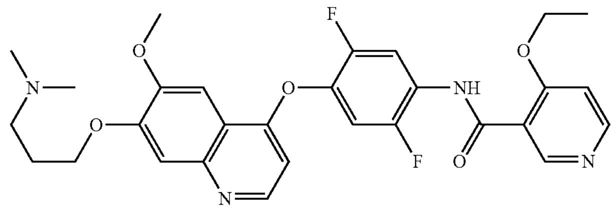 [SMILES: CCOc1ccncc1C(=O)Nc1cc(F)c(Oc2ccnc3cc(OCCCN(C)C)c(OC)cc23)cc1F] | N-(4-((7-(3-(dimethylamino)propoxy)-6-methoxyquinolin-4-yl)oxy)-2,5-difluorophenyl)-4-ethoxypyridine-3-carboxamide | 553.22 |
| 24 | 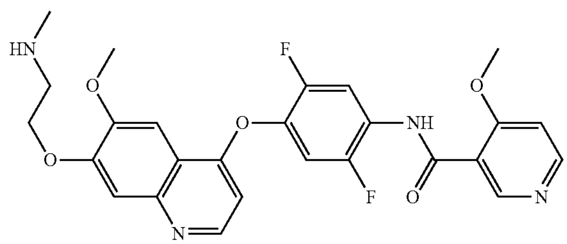 [SMILES: CNCCOc1cc2nccc(Oc3cc(F)c(NC(=O)c4cnccc4OC)cc3F)c2cc1OC] | N-[2,5-difluoro-4-({6-methoxy-7-[2-(methylamino)ethoxy]quinolin-4-yl}oxy)phenyl]-4-methoxypyridine-3-carboxamide | 511.17 |
| 25 | 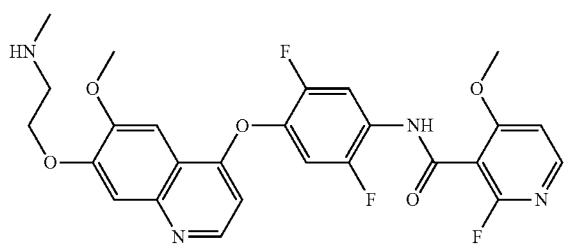 | N-(2,5-difluoro-4-((6-methoxy-7-(2-(methylamino)ethoxy)quinolin-4-yl)oxy)phenyl)-2-fluoro-4-methoxypyridine-3-carboxamide | 529.16 |
| 26 | 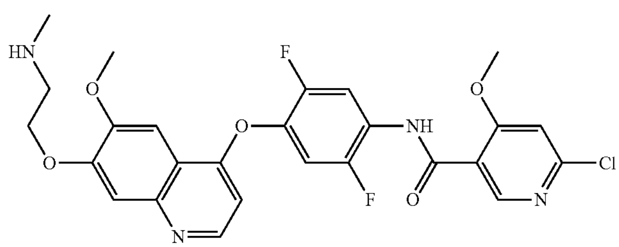 [SMILES: CNCCOc1cc2nccc(Oc3cc(F)c(NC(=O)c4cnc(Cl)cc4OC)cc3F)c2cc1OC] | 6-chloro-N-[2,5-difluoro-4-({6-methoxy-7-[2-(methylamino)ethoxy]quinolin-4-yl}oxy)phenyl]-4-methoxypyridine-3-carboxamide | 545.13 |
| 27 | 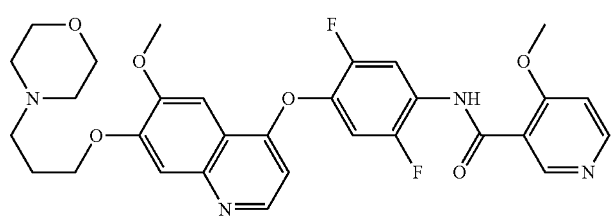 [SMILES: COc1cc2c(Oc3cc(F)c(NC(=O)c4cnccc4OC)cc3F)ccnc2cc1OCCCN1CCOCC1] | N-[2,5-difluoro-4-({6-methoxy-7-[3-(morpholin-4-yl)propoxy]quinolin-4-yl}oxy)phenyl]-4-methoxypyridine-3-carboxamide | 581.21 |
| 28 | 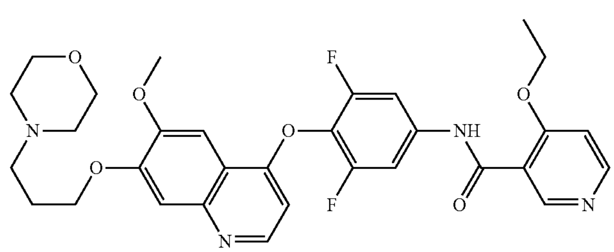 [SMILES: CCOc1ccncc1C(=O)Nc1cc(F)c(Oc2ccnc3cc(OCCCN4CCOCC4)c(OC)cc23)c(F)c1] | N-(3,5-difluoro-4-((6-methoxy-7-(3-morpholinopropoxy)quinolin-4-yl)oxy)phenyl)-4-ethoxypyridine-3-carboxamide | 595.23 |

TABLE 1-continued

| Example No. | Compound Structure | Compound Name | Exact Mass [M + H]+ |
|---|---|---|---|
| 29 | 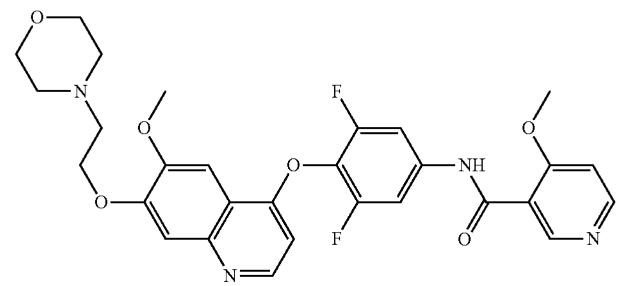 [SMILES: COc1cc2c(Oc3c(F)cc(NC(=O)c4cnccc4OC)cc3F)ccnc2cc1OCCN1CCOCC1] | N-[3,5-difluoro-4-({6-methoxy-7-[2-(morpholin-4-yl)ethoxy]quinolin-4-yl}oxy)phenyl]-4-methoxypyridine-3-carboxamide | 567.20 |
| 30 | 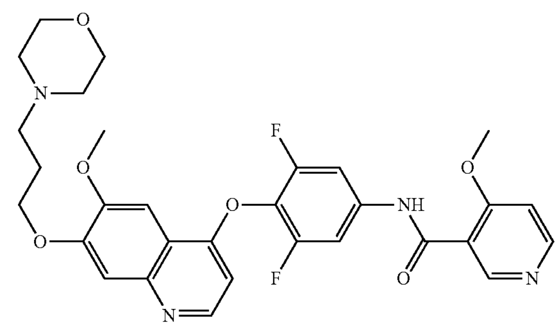 [SMILES: COc1cc2c(Oc3c(F)cc(NC(=O)c4cnccc4OC)cc3F)ccnc2cc1OCCCN1CCOCC1] | N-(3,5-difluoro-4-((6-methoxy-7-(3-morpholinopropoxy)quinolin-4-yl)oxy)phenyl)-4-methoxypyridine-3-carboxamide | 581.21 |
| 31 | 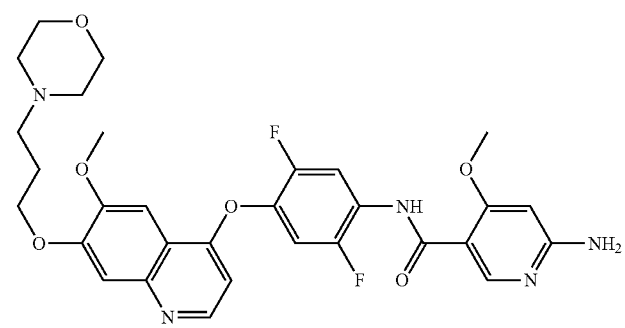 [SMILES: COc1cc2c(Oc3cc(F)c(NC(=O)c4cnc(N)cc4OC)cc3F)ccnc2cc1OCCCN1CCOCC1] | 6-amino-N-(2,5-difluoro-4-((6-methoxy-7-(3-morpholinopropoxy)quinolin-4-yl)oxy)phenyl)-4-methoxypyridine-3-carboxamide | 596.22 |
| 32 | 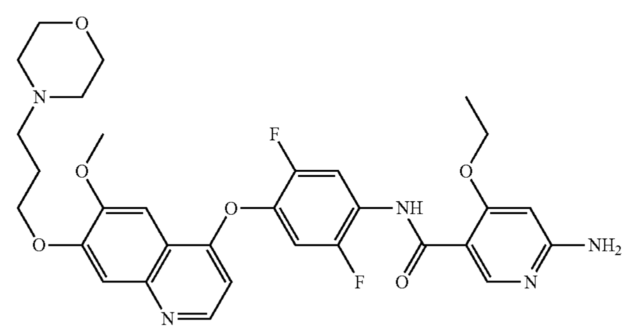 [SMILES: CCOc1cc(N)ncc1C(=O)Nc1cc(F)c(Oc2ccnc3cc(OCCCN4CCOCC4)c(OC)cc23)cc1F] | 6-amino-N-[2,5-difluoro-4-({6-methoxy-7-[3-(morpholin-4-yl)propoxy]quinolin-4-yl}oxy)phenyl]-4-ethoxypyridine-3-carboxamide | 610.24 |
| 33 | 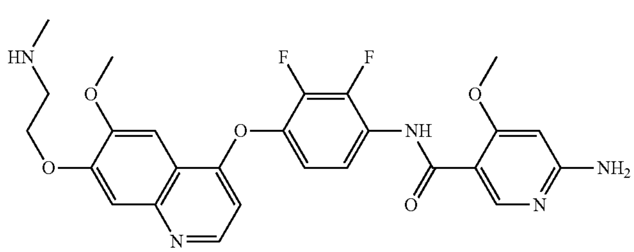 [SMILES: CNCCOc1cc2nccc(Oc3ccc(NC(=O)c4cnc(N)cc4OC)c(F)c3F)c2cc1OC] | 6-amino-N-[2,3-difluoro-4-({6-methoxy-7-[2-(methylamino)ethoxy]quinolin-4-yl}oxy)phenyl]-4-methoxypyridine-3-carboxamide | 526.18 |

TABLE 1-continued

| Example No. | Compound Structure | Compound Name | Exact Mass [M + H]+ |
|---|---|---|---|
| 34 | 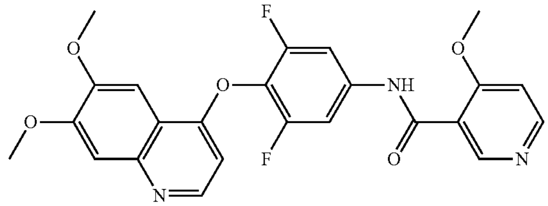 | N-(4-((6,7-dimethoxyquinolin-4-yl)oxy)-3,5-difluorophenyl)-4-methoxypyridine-3-carboxamide | 468.13 |
| 35 | 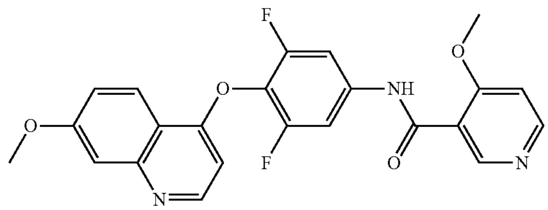 [SMILES: COc1ccc2c(Oc3c(F)cc(NC(=O)c4cnccc4OC)cc3F)ccnc2c1] | N-(3,5-difluoro-4-((7-methoxyquinolin-4-yl)oxy)phenyl)-4-methoxypyridine-3-carboxamide | 438.12 |
| 36 | 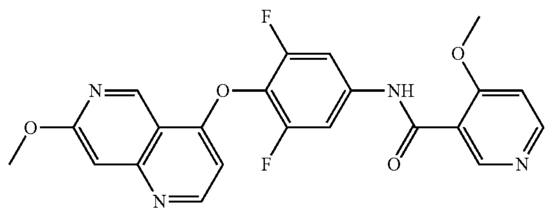 | N-(3,5-difluoro-4-((7-methoxy-1,6-naphthyridin-4-yl)oxy)phenyl)-4-methoxypyridine-3-carboxamide | 439.11 |
| 37 | 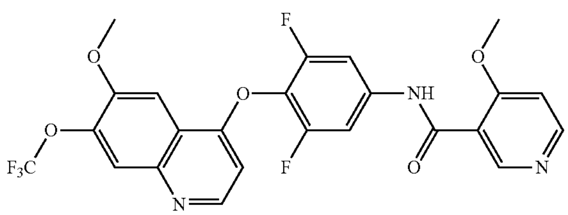 [SMILES: COc1cc2c(Oc3c(F)cc(NC(=O)c4cnccc4OC)cc3F)ccnc2cc1OC(F)(F)F] | N-(3,5-difluoro-4-((6-methoxy-7-(trifluoromethoxy)quinolin-4-yl)oxy)phenyl)-4-methoxypyridine-3-carboxamide | 522.10 |
| 38 | 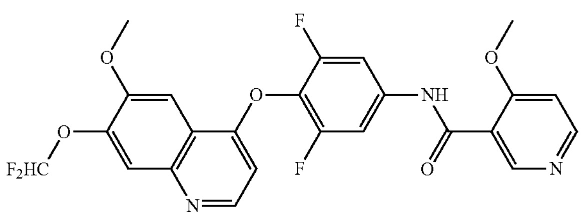 [SMILES: COc1cc2c(Oc3c(F)cc(NC(=O)c4cnccc4OC)cc3F)ccnc2cc1OC(F)F] | N-(4-((7-(difluoromethoxy)-6-methoxyquinolin-4-yl)oxy)-3,5-difluorophenyl)-4-methoxypyridine-3-carboxamide | 504.11 |
| 39 | 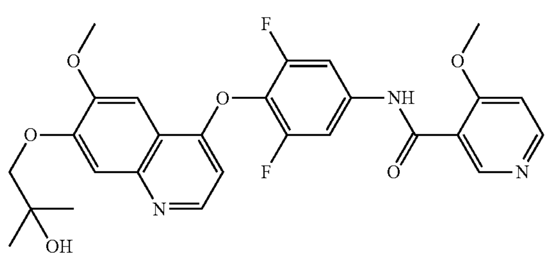 [SMILES: COc1cc2c(Oc3c(F)cc(NC(=O)c4cnccc4OC)cc3F)ccnc2cc1OCC(C)(C)O] | N-(3,5-difluoro-4-((7-(2-hydroxy-2-methylpropoxy)-6-methoxyquinolin-4-yl)oxy)phenyl)-4-methoxypyridine-3-carboxamide | 526.17 |
| 40 | 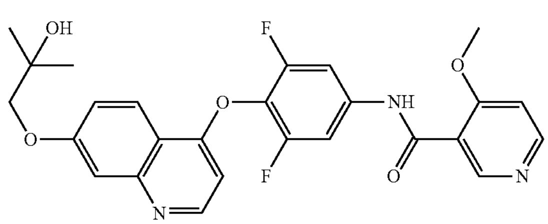 [SMILES: COc1ccncc1C(=O)Nc1cc(F)c(Oc2ccnc3cc(OCC(C)(C)O)ccc23)c(F)c1] | N-(3,5-difluoro-4-((7-(2-hydroxy-2-methylpropoxy)quinolin-4-yl)oxy)phenyl)-4-methoxypyridine-3-carboxamide | 496.16 |

TABLE 1-continued

| Example No. | Compound Structure | Compound Name | Exact Mass [M + H]+ |
|---|---|---|---|
| 41 | 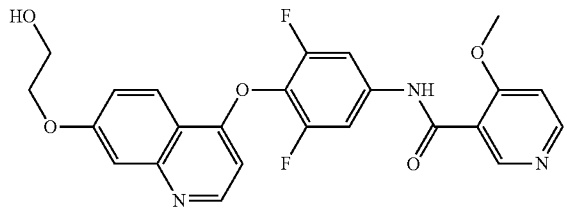 [SMILES: COc1ccncc1C(=O)Nc1cc(F)c(Oc2ccnc3cc(OCCO)ccc23)c(F)c1] | N-(3,5-difluoro-4-((7-(2-hydroxyethoxy)quinolin-4-yl)oxy)phenyl)-4-methoxypyridine-3-carboxamide | 468.13 |
| 42 | 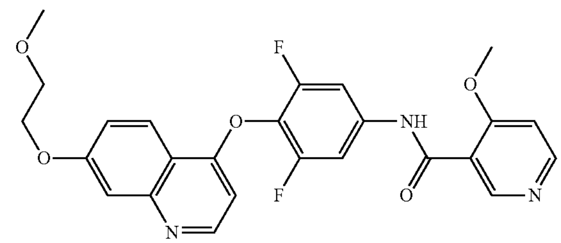 [SMILES: COCCOc1ccc2c(Oc3c(F)cc(NC(=O)c4cnccc4OC)cc3F)ccnc2c1] | N-(3,5-difluoro-4-((7-(2-methoxyethoxy)quinolin-4-yl)oxy)phenyl)-4-methoxypyridine-3-carboxamide | 482.14 |
| 43 | 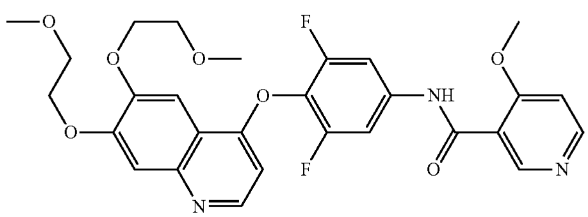 [SMILES: COCCOc1cc2nccc(Oc3c(F)cc(NC(=O)c4cnccc4OC)cc3F)c2cc1OCCOC] | N-(4-((6,7-bis(2-methoxyethoxy)quinolin-4-yl)oxy)-3,5-difluorophenyl)-4-methoxypyridine-3-carboxamide | 556.18 |
| 44 | 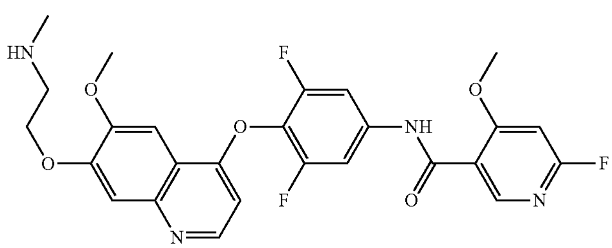 [SMILES: CNCCOc1cc2nccc(Oc3c(F)cc(NC(=O)c4cnc(F)cc4OC)cc3F)c2cc1OC] | N-(3,5-difluoro-4-((6-methoxy-7-(2-(methylamino)ethoxy)quinolin-4-yl)oxy)phenyl)-6-fluoro-4-methoxypyridine-3-carboxamide | 529.16 |
| 45 | 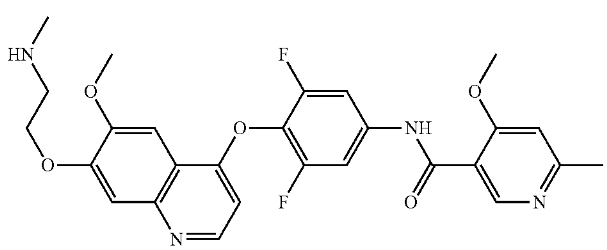 [SMILES: CNCCOc1cc2nccc(Oc3c(F)cc(NC(=O)c4cnc(C)cc4OC)cc3F)c2cc1OC] | N-(3,5-difluoro-4-((6-methoxy-7-(2-(methylamino)ethoxy)quinolin-4-yl)oxy)phenyl)-4-methoxy-6-methylpyridine-3-carboxamide | 525.19 |
| 46 | 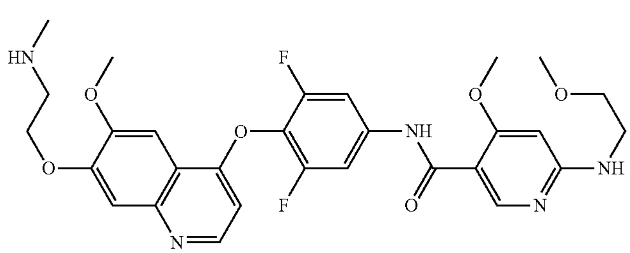 [SMILES: CNCCOc1cc2nccc(Oc3c(F)cc(NC(=O)c4cnc(NCCOC)cc4OC)cc3F)c2cc1OC] | N-(3,5-difluoro-4-((6-methoxy-7-(2-(methylamino)ethoxy)quinolin-4-yl)oxy)phenyl)-4-methoxy-6-((2-methoxyethyl)amino)pyridine-3-carboxamide | 584.22 |

TABLE 1-continued

| Example No. | Compound Structure | Compound Name | Exact Mass [M + H]+ |
|---|---|---|---|
| 47 | 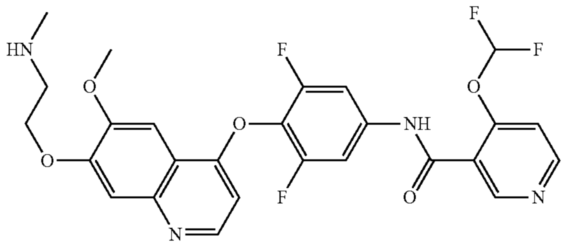 [SMILES: CNCCOc1cc2nccc(Oc3c(F)cc(NC(=O)c4cnccc4OC(F)F)cc3F)c2cc1OC] | N-[3,5-difluoro-4-({6-methoxy-7-[2-(methylamino)ethoxy]quinolin-4-yl}oxy)phenyl]-4-(difluoromethoxy)pyridine-3-carboxamide | 547.15 |
| 48 | 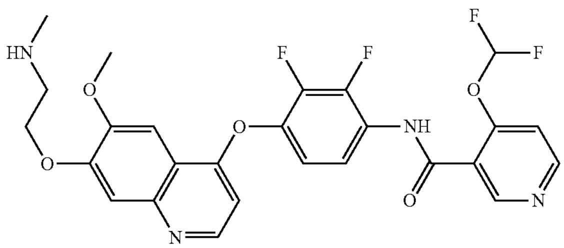 [SMILES: CNCCOc1cc2nccc(Oc3ccc(NC(=O)c4cnccc4OC(F)F)c(F)c3F)c2cc1OC] | N-(2,3-difluoro-4-((6-methoxy-7-(2-(methylamino)ethoxy)quinolin-4-yl)oxy)phenyl)-4-(difluoromethoxy)pyridine-3-carboxamide | 547.15 |
| 49 | 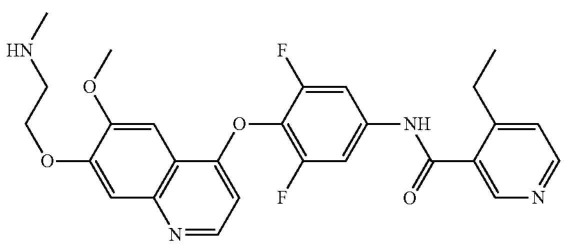 [SMILES: CCc1ccncc1C(=O)Nc1cc(F)c(Oc2ccnc3cc(OCCNC)c(OC)cc23)c(F)c1] | N-(3,5-difluoro-4-((6-methoxy-7-(2-(methylamino)ethoxy)quinolin-4-yl)oxy)phenyl)-4-ethylpyridine-3-carboxamide | 509.19 |
| 50 | 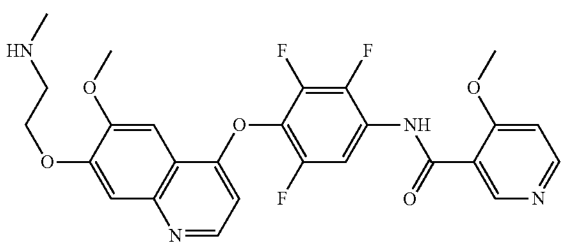 | 4-methoxy-N-[2,3,5-trifluoro-4-({6-methoxy-7-[2-(methylamino)ethoxy]quinolin-4-yl}oxy)phenyl]pyridine-3-carboxamide | 529.16 |
| 51 | 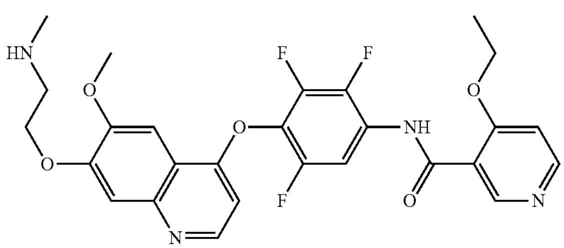 | 4-ethoxy-N-(2,3,5-trifluoro-4-((6-methoxy-7-(2-(methylamino)ethoxy)quinolin-4-yl)oxy)phenyl)pyridine-3-carboxamide | 543.18 |
| 52 | 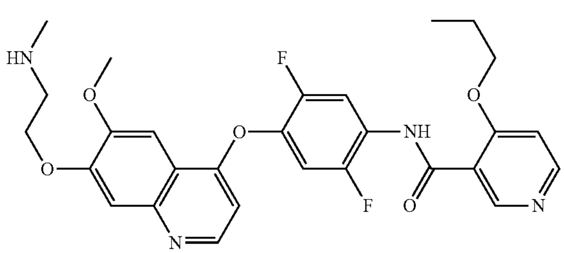 [SMILES: CCCOc1ccncc1C(=O)Nc1cc(F)c(Oc2ccnc3cc(OCCNC)c(OC)cc23)cc1F] | N-[2,5-difluoro-4-({6-methoxy-7-[2-(methylamino)ethoxy]quinolin-4-yl}oxy)phenyl]-4-propoxypyridine-3-carboxamide | 539.20 |

TABLE 1-continued

| Example No. | Compound Structure | Compound Name | Exact Mass [M + H]+ |
|---|---|---|---|
| 53 | 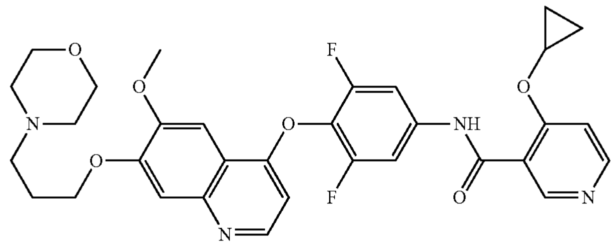 | 4-cyclopropoxy-N-(3,5-difluoro-4-((6-methoxy-7-(3-morpholinopropoxy)quinolin-4-yl)oxy)phenyl)pyridine-3-carboxamide | 607.23 |
| 54 | 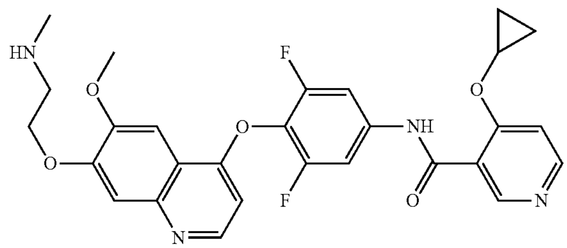 [SMILES: CNCCOc1cc2nccc(Oc3c(F)cc(NC(=O)c4cnccc4OC4CC4)cc3F)c2cc1OC] | 4-cyclopropoxy-N-[3,5-difluoro-4-({6-methoxy-7-[2-(methylamino)ethoxy]quinolin-4-yl}oxy)phenyl]pyridine-3-carboxamide | 537.19 |
| 55 | 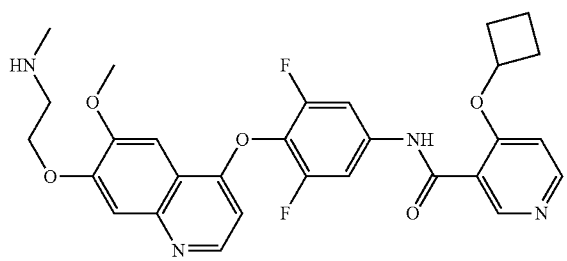 [SMILES: CNCCOc1cc2nccc(Oc3c(F)cc(NC(=O)c4cnccc4OC4CCC4)cc3F)c2cc1OC] | 4-cyclobutoxy-N-(3,5-difluoro-4-((6-methoxy-7-(2-(methylamino)ethoxy)quinolin-4-yl)oxy)phenyl)pyridine-3-carboxamide | 551.20 |
| 56 | 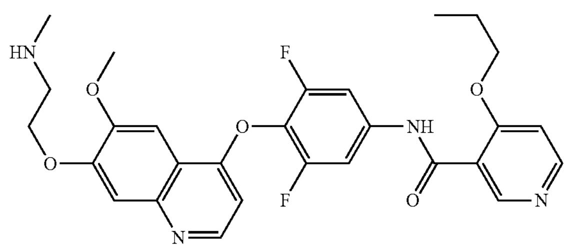 [SMILES: CCCOc1ccncc1C(=O)Nc1cc(F)c(Oc2ccnc3cc(OCCNC)c(OC)cc23)c(F)c1] | N-[3,5-difluoro-4-({6-methoxy-7-[2-(methylamino)ethoxy]quinolin-4-yl}oxy)phenyl]-4-propoxypyridine-3-carboxamide | 539.20 |
| 57 | 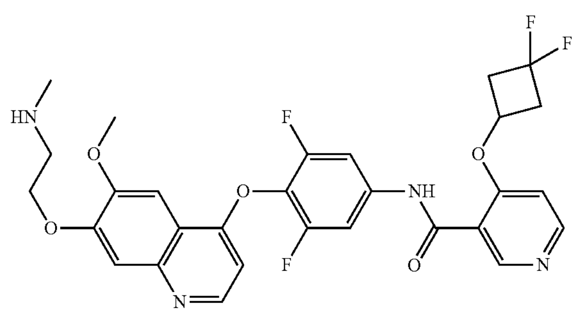 [SMILES: CNCCOc1cc2nccc(Oc3c(F)cc(NC(=O)c4cnccc4OC4CC(F)(F)C4)cc3F)c2cc1OC] | N-(3,5-difluoro-4-((6-methoxy-7-(2-(methylamino)ethoxy)quinolin-4-yl)oxy)phenyl)-4-(3,3-difluorocyclobutoxy)pyridine-3-carboxamide | 587.18 |
| 58 | 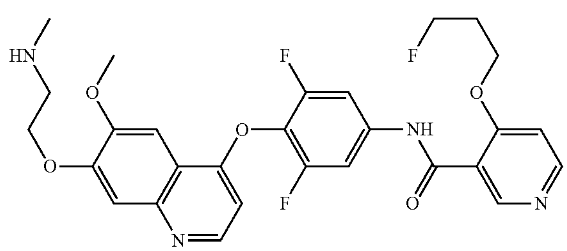 | N-(3,5-difluoro-4-((6-methoxy-7-(2-(methylamino)ethoxy)quinolin-4-yl)oxy)phenyl)-4-(3-fluoropropoxy)pyridine-3-carboxamide | 557.19 |

TABLE 1-continued

| Example No. | Compound Structure | Compound Name | Exact Mass [M + H]+ |
|---|---|---|---|
| 59 | 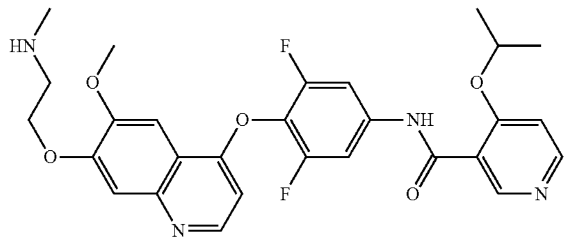 [SMILES: CNCCOc1cc2nccc(Oc3c(F)cc(NC(=O)c4cnccc4OC(C)C)cc3F)c2cc1OC] | N-(3,5-difluoro-4-((6-methoxy-7-(2-(methylamino)ethoxy)quinolin-4-yl)oxy)phenyl)-4-isopropoxypyridine-3-carboxamide | 539.20 |
| 60 | 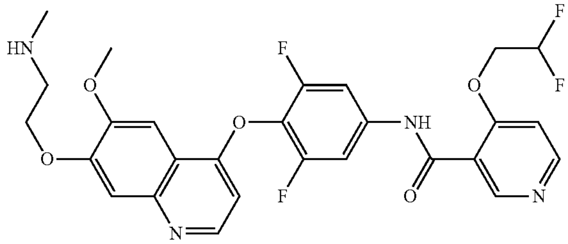 | N-(3,5-difluoro-4-((6-methoxy-7-(2-(methylamino)ethoxy)quinolin-4-yl)oxy)phenyl)-4-(2,2-difluoroethoxy)pyridine-3-carboxamide | 561.17 |
| 61 | 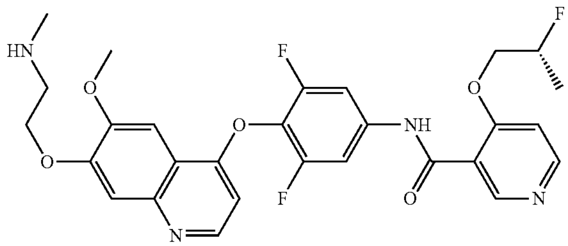 [SMILES: CNCCOc1cc2nccc(Oc3c(F)cc(NC(=O)c4cnccc4OCC(F)F)cc3F)c2cc1OC] | (R)-N-(3,5-difluoro-4-((6-methoxy-7-(2-(methylamino)ethoxy)quinolin-4-yl)oxy)phenyl)-4-(2-fluoropropoxy)pyridine-3-carboxamide | 557.19 |
| 62 | 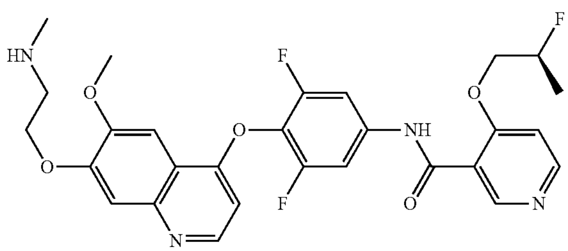 [SMILES: CNCCOc1cc2nccc(Oc3c(F)cc(NC(=O)c4cnccc4OC[C@H](C)F)cc3F)c2cc1OC] | (S)-N-(3,5-difluoro-4-((6-methoxy-7-(2-(methylamino)ethoxy)quinolin-4-yl)oxy)phenyl)-4-(2-fluoropropoxy)pyridine-3-carboxamide | 557.19 |
| 63 | 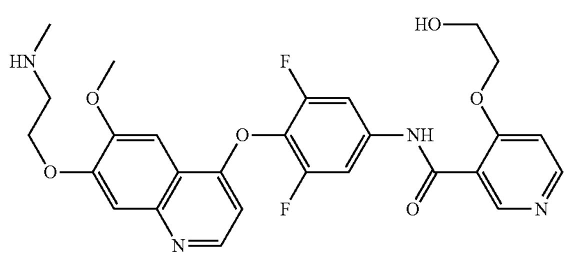 [SMILES: CNCCOc1cc2nccc(Oc3c(F)cc(NC(=O)c4cnccc4OCCO)cc3F)c2cc1OC] | N-(3,5-difluoro-4-((6-methoxy-7-(2-(methylamino)ethoxy)quinolin-4-yl)oxy)phenyl)-4-(2-hydroxyethoxy)pyridine-3-carboxamide | 541.18 |
| 64 | 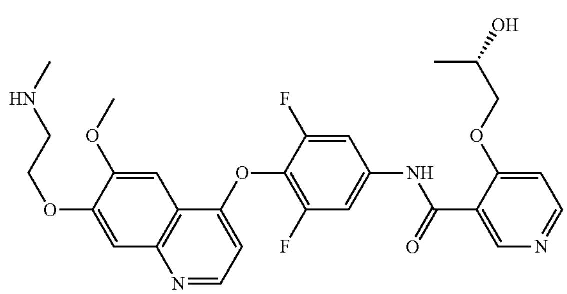 [SMILES: CNCCOc1cc2nccc(Oc3c(F)cc(NC(=O)c4cnccc4OC[C@H](C)O)cc3F)c2cc1OC] | (S)-N-(3,5-difluoro-4-((6-methoxy-7-(2-(methylamino)ethoxy)quinolin-4-yl)oxy)phenyl)-4-(2-hydroxypropoxy)pyridine-3-carboxamide | 555.20 |

TABLE 1-continued

| Example No. | Compound Name | Exact Mass [M + H]+ |
|---|---|---|
| 65 | (R)-N-(3,5-difluoro-4-((6-methoxy-7-(2-(methylamino)ethoxy)quinolin-4-yl)oxy)phenyl)-4-(2-hydroxypropoxy)pyridine-3-carboxamide | 555.20 |
| 66 | N-(3,5-difluoro-4-((6-methoxy-7-(2-(methylamino)ethoxy)quinolin-4-yl)oxy)phenyl)-4-(2-hydroxy-2-methylpropoxy)pyridine-3-carboxamide | 569.21 |
| 67 | N-(3,5-difluoro-4-((6-methoxy-7-(2-(methylamino)ethoxy)quinolin-4-yl)oxy)phenyl)-4-(2-methoxyethoxy)pyridine-3-carboxamide | 555.20 |
| 68 | N-(3,5-difluoro-4-((6-methoxy-7-(2-(methylamino)ethoxy)quinolin-4-yl)oxy)phenyl)-4-(oxetan-3-yloxy)pyridine-3-carboxamide | 553.18 |
| 69 | 4-butoxy-N-(3,5-difluoro-4-((6-methoxy-7-(2-(methylamino)ethoxy)quinolin-4-yl)oxy)phenyl)pyridine-3-carboxamide | 553.22 |

TABLE 1-continued

| Example No. | Compound Structure | Compound Name | Exact Mass [M + H]+ |
|---|---|---|---|
| 70 | 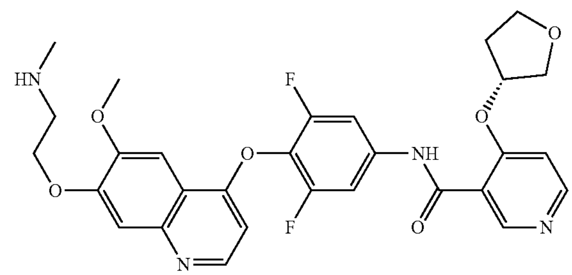 [SMILES: CNCCOc1cc2nccc(Oc3c(F)cc(NC(=O)c4cnccc4O[C@@H]4CCOC4)cc3F)c2cc1OC] | (R)-N-(3,5-difluoro-4-((6-methoxy-7-(2-(methylamino)ethoxy)quinolin-4-yl)oxy)phenyl)-4-((tetrahydrofuran-3-yl)oxy)pyridine-3-carboxamide | 567.20 |
| 71 | 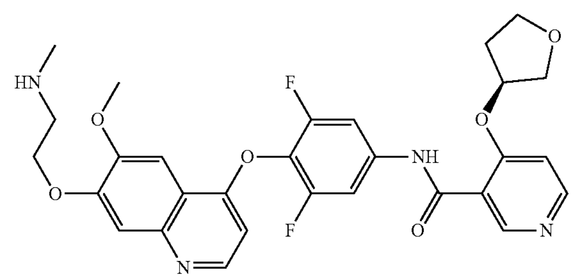 [SMILES: CNCCOc1cc2nccc(Oc3c(F)cc(NC(=O)c4cnccc4O[C@H]4CCOC4)cc3F)c2cc1OC] | (S)-N-(3,5-difluoro-4-((6-methoxy-7-(2-(methylamino)ethoxy)quinolin-4-yl)oxy)phenyl)-4-((tetrahydrofuran-3-yl)oxy)pyridine-3-carboxamide | 567.20 |
| 72 | 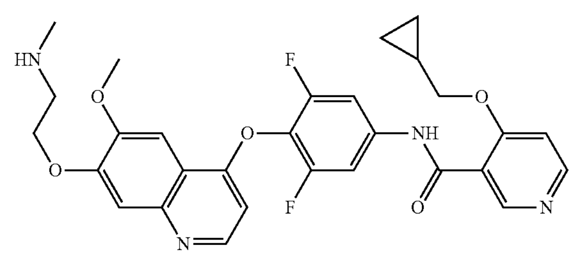 [SMILES: CNCCOc1cc2nccc(Oc3c(F)cc(NC(=O)c4cnccc4OCC4CC4)cc3F)c2cc1OC] | 4-(cyclopropylmethoxy)-N-(3,5-difluoro-4-((6-methoxy-7-(2-(methylamino)ethoxy)quinolin-4-yl)oxy)phenyl)pyridine-3-carboxamide | 551.20 |
| 73 | 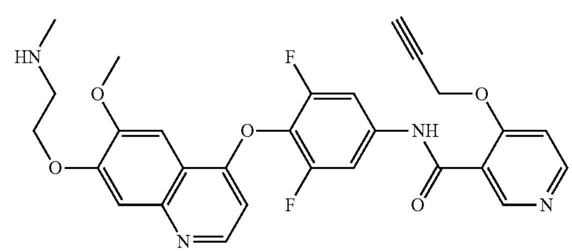 [SMILES: C#CCOc1ccncc1C(=O)Nc1cc(F)c(Oc2ccnc3cc(OCCNC)c(OC)cc23)c(F)c1] | N-(3,5-difluoro-4-((6-methoxy-7-(2-(methylamino)ethoxy)quinolin-4-yl)oxy)phenyl)-4-(prop-2-yn-1-yloxy)pyridine-3-carboxamide | 535.17 |
| 74 | 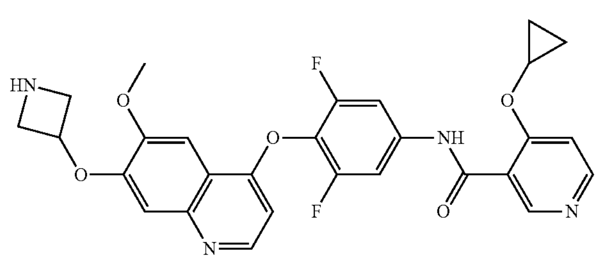 [SMILES: COc1cc2c(Oc3c(F)cc(NC(=O)c4cnccc4OC4CC4)cc3F)ccnc2cc1OC1CNC1] | N-(4-((7-(azetidin-3-yloxy)-6-methoxyquinolin-4-yl)oxy)-3,5-difluorophenyl)-4-cyclopropoxypyridine-3-carboxamide | 535.17 |

TABLE 1-continued

| Example No. | Compound Structure | Compound Name | Exact Mass [M + H]+ |
|---|---|---|---|
| 75 | 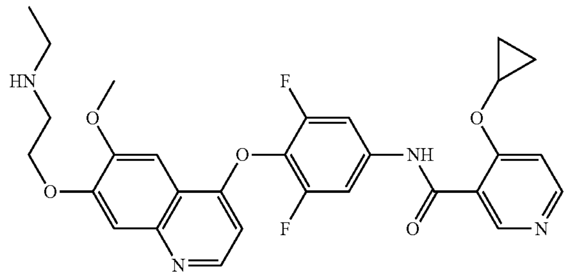 [SMILES: CCNCCOc1cc2nccc(Oc3c(F)cc(NC(=O)c4cnccc4OC4CC4)cc3F)c2cc1OC] | 4-cyclopropoxy-N-(4-((7-(2-(ethylamino)ethoxy)-6-methoxyquinolin-4-yl)oxy)-3,5-difluorophenyl)pyridine-3-carboxamide | 551.20 |
| 76 | 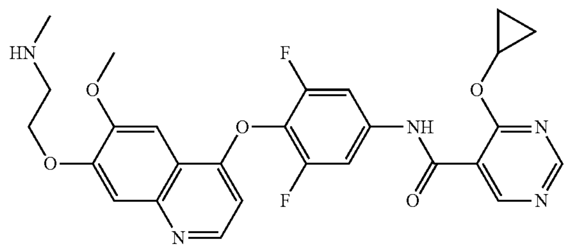 | 4-cyclopropoxy-N-(3,5-difluoro-4-((6-methoxy-7-(2-(methylamino)ethoxy)quinolin-4-yl)oxy)phenyl)pyrimidine-5-carboxamide | 538.18 |
| 77 | 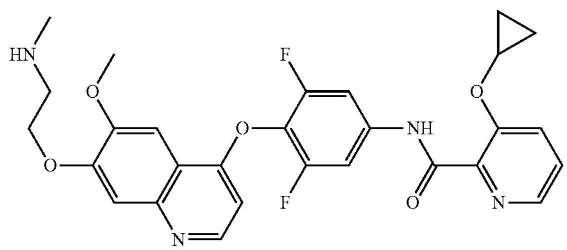 [SMILES: CNCCOc1cc2nccc(Oc3c(F)cc(NC(=O)c4ncccc4OC4CC4)cc3F)c2cc1OC] | 3-cyclopropoxy-N-(3,5-difluoro-4-((6-methoxy-7-(2-(methylamino)ethoxy)quinolin-4-yl)oxy)phenyl)picolinamide | 537.19 |
| 78 | 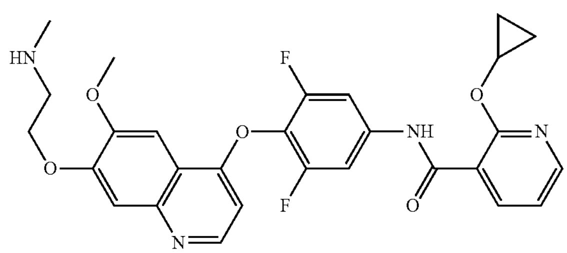 [SMILES: CNCCOc1cc2nccc(Oc3c(F)cc(NC(=O)c4cccnc4OC4CC4)cc3F)c2cc1OC] | 2-cyclopropoxy-N-(3,5-difluoro-4-((6-methoxy-7-(2-(methylamino)ethoxy)quinolin-4-yl)oxy)phenyl)pyridine-3-carboxamide | 537.19 |
| 79 | 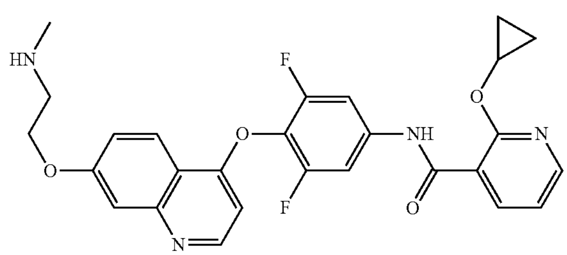 | 2-cyclopropoxy-N-(3,5-difluoro-4-((7-(2-(methylamino)ethoxy)quinolin-4-yl)oxy)phenyl)pyridine-3-carboxamide | 507.18 |
| 80 | 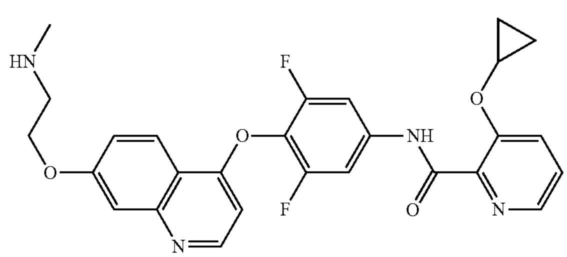 [SMILES: CNCCOc1ccc2c(Oc3c(F)cc(NC(=O)c4ncccc4OC4CC4)cc3F)ccnc2c1] | 3-cyclopropoxy-N-(3,5-difluoro-4-((7-(2-(methylamino)ethoxy)quinolin-4-yl)oxy)phenyl)picolinamide | 507.18 |

TABLE 1-continued

| Example No. | Compound Structure | Compound Name | Exact Mass [M + H]+ |
|---|---|---|---|
| 81 | 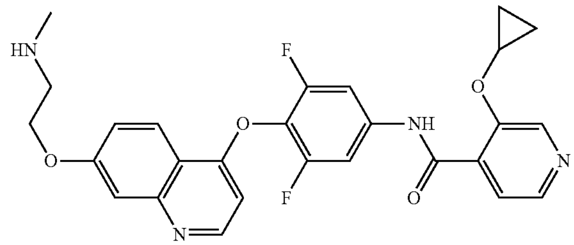 [SMILES: CNCCOc1ccc2c(Oc3c(F)cc(NC(=O)c4ccncc4OC4CC4)cc3F)ccnc2c1] | 3-cyclopropoxy-N-(3,5-difluoro-4-((7-(2-(methylamino)ethoxy)quinolin-4-yl)oxy)phenyl)isonicotinamide | 507.18 |
| 82 | 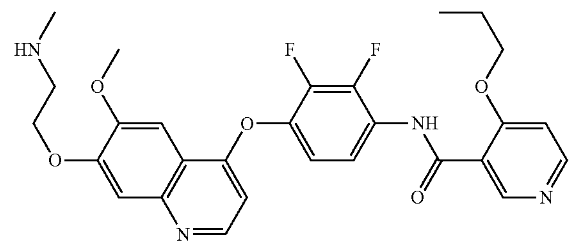 [SMILES: CCCOc1ccncc1C(=O)Nc1ccc(Oc2ccnc3cc(OCCNC)c(OC)cc23)c(F)c1F] | N-[2,3-difluoro-4-({6-methoxy-7-[2-(methylamino)ethoxy]quinolin-4-yl}oxy)phenyl]-4-propoxypyridine-3-carboxamide | 539.20 |
| 83 | 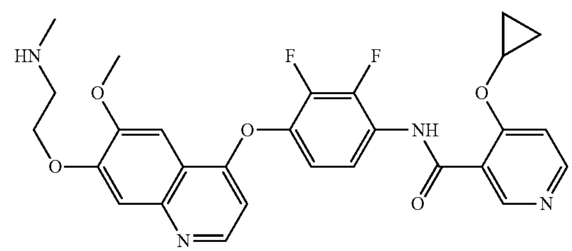 [SMILES: CNCCOc1cc2nccc(Oc3ccc(NC(=O)c4cnccc4OC4CC4)c(F)c3F)c2cc1OC] | 4-cyclopropoxy-N-(2,3-difluoro-4-((6-methoxy-7-(2-(methylamino)ethoxy)quinolin-4-yl)oxy)phenyl)pyridine-3-carboxamide | 537.19 |
| 84 | 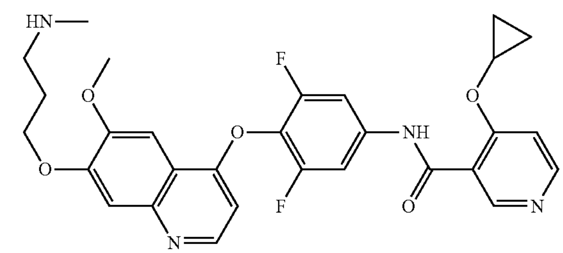 [SMILES: CNCCCOc1cc2nccc(Oc3c(F)cc(NC(=O)c4cnccc4OC4CC4)cc3F)c2cc1OC] | 4-cyclopropoxy-N-(3,5-difluoro-4-((6-methoxy-7-(3-(methylamino)propoxy)quinolin-4-yl)oxy)phenyl)pyridine-3-carboxamide | 551.20 |
| 85 | 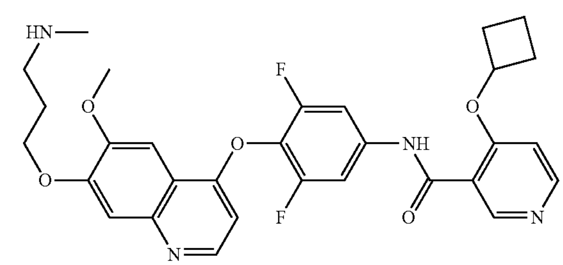 [SMILES: CNCCCOc1cc2nccc(Oc3c(F)cc(NC(=O)c4cnccc4OC4CCC4)cc3F)c2cc1OC] | 4-cyclobutoxy-N-(3,5-difluoro-4-((6-methoxy-7-(3-(methylamino)propoxy)quinolin-4-yl)oxy)phenyl)pyridine-3-carboxamide | 565.22 |
| 86 | 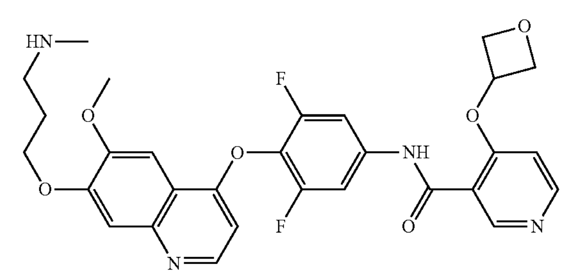 [SMILES: CNCCCOc1cc2nccc(Oc3c(F)cc(NC(=O)c4cnccc4OC4COC4)cc3F)c2cc1OC] | N-(3,5-difluoro-4-((6-methoxy-7-(3-(methylamino)propoxy)quinolin-4-yl)oxy)phenyl)-4-(oxetan-3-yloxy)pyridine-3-carboxamide | 567.20 |

TABLE 1-continued

| Example No. | Compound Structure | Compound Name | Exact Mass [M + H]+ |
|---|---|---|---|
| 87 | 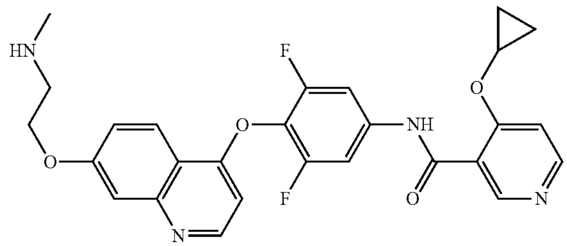 [SMILES: CNCCOc1ccc2c(Oc3c(F)cc(NC(=O)c4cnccc4OC4CC4)cc3F)ccnc2c1] | 4-cyclopropoxy-N-(3,5-difluoro-4-((7-(2-(methylamino)ethoxy)quinolin-4-yl)oxy)phenyl)pyridine-3-carboxamide | 507.18 |
| 88 | 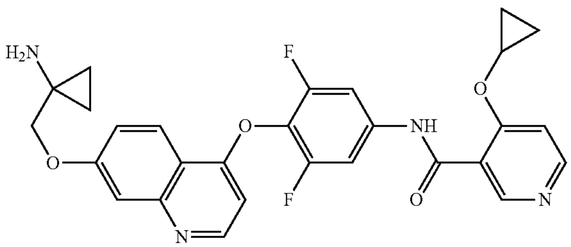 [SMILES: NC1(COc2ccc3c(Oc4c(F)cc(NC(=O)c5cnccc5OC5CC5)cc4F)ccnc3c2)CC1] | N-(4-((7-((1-aminocyclopropyl)methoxy)quinolin-4-yl)oxy)-3,5-difluorophenyl)-4-cyclopropoxypyridine-3-carboxamide | 519.18 |
| 89 | 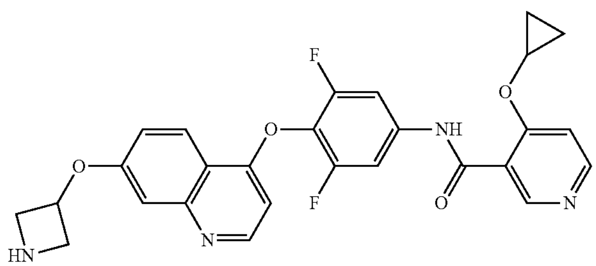 [SMILES: O=C(Nc1cc(F)c(Oc2ccnc3cc(OC4CNC4)ccc23)c(F)c1)c1cnccc1OC1CC1] | N-(4-((7-(azetidin-3-yloxy)quinolin-4-yl)oxy)-3,5-difluorophenyl)-4-cyclopropoxypyridine-3-carboxamide | 505.16 |
| 90 | 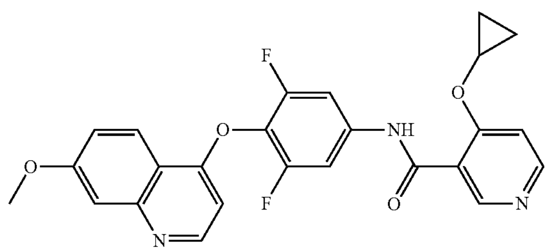 | 4-cyclopropoxy-N-(3,5-difluoro-4-((7-methoxyquinolin-4-yl)oxy)phenyl)pyridine-3-carboxamide | 464.13 |
| 91 | 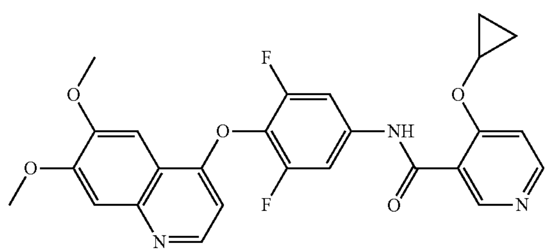 | 4-cyclopropoxy-N-(4-((6,7-dimethoxyquinolin-4-yl)oxy)-3,5-difluorophenyl)pyridine-3-carboxamide | 494.14 |
| 92 | 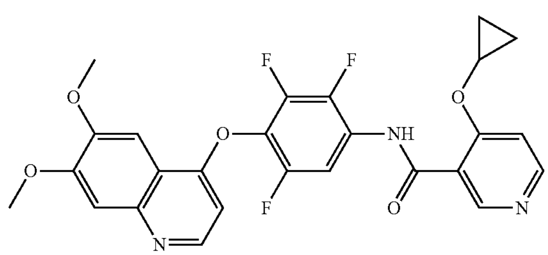 [SMILES: COc1cc2nccc(Oc3c(F)cc(NC(=O)c4cnccc4OC4CC4)c(F)c3F)c2cc1OC] | 4-cyclopropoxy-N-(4-((6,7-dimethoxyquinolin-4-yl)oxy)-2,3,5-trifluorophenyl)pyridine-3-carboxamide | 512.14 |

TABLE 1-continued

| Example No. | Compound Name | Exact Mass [M + H]+ |
|---|---|---|
| 93 | 4-cyclopropoxy-N-(2,3,5-trifluoro-4-((6-methoxy-7-(2-(methylamino)ethoxy)quinolin-4-yl)oxy)phenyl)pyridine-3-carboxamide | 555.18 |
| 94 | 4-cyclopropoxy-N-(2,3,5-trifluoro-4-((7-(2-(methylamino)ethoxy)quinolin-4-yl)oxy)phenyl)pyridine-3-carboxamide | 525.17 |
| 95 | N-(4-((6,7-dimethoxyquinolin-4-yl)oxy)-3,5-difluorophenyl)-4-(2-hydroxyethoxy)pyridine-3-carboxamide | 498.14 |
| 96 | 4-cyclopropoxy-N-(3,5-difluoro-4-((7-methoxy-1,6-naphthyridin-4-yl)oxy)phenyl)pyridine-3-carboxamide | 465.13 |
| 97 | 4-cyclopropoxy-N-(3,5-difluoro-4-((7-(2-hydroxyethoxy)-6-methoxyquinolin-4-yl)oxy)phenyl)pyridine-3-carboxamide | 524.16 |
| 98 | (S)-4-cyclopropoxy-N-(3,5-difluoro-4-((7-(2-hydroxypropoxy)-6-methoxyquinolin-4-yl)oxy)phenyl)pyridine-3-carboxamide | 538.17 |

TABLE 1-continued

| Example No. | Compound Structure | Compound Name | Exact Mass [M + H]+ |
|---|---|---|---|
| 99 | 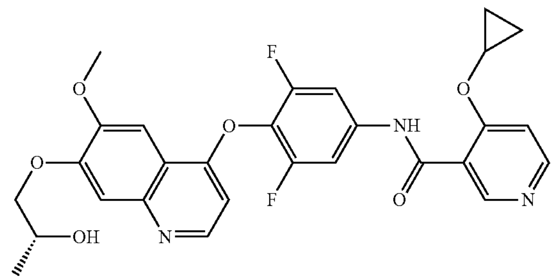 [SMILES: COc1cc2c(Oc3c(F)cc(NC(=O)c4cnccc4OC4CC4)cc3F)ccnc2cc1OC[C@@H](C)O] | (R)-4-cyclopropoxy-N-(3,5-difluoro-4-((7-(2-hydroxypropoxy)-6-methoxyquinolin-4-yl)oxy)phenyl)pyridine-3-carboxamide | 538.17 |
| 100 | 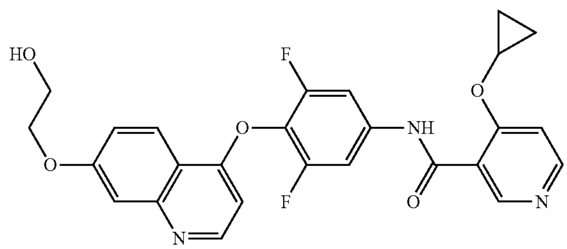 [SMILES: O=C(Nc1cc(F)c(Oc2ccnc3cc(OCCO)ccc23)c(F)c1)c1cnccc1OC1CC1] | 4-cyclopropoxy-N-(3,5-difluoro-4-((7-(2-hydroxyethoxy)quinolin-4-yl)oxy)phenyl)pyridine-3-carboxamide | 494.14 |
| 101 | 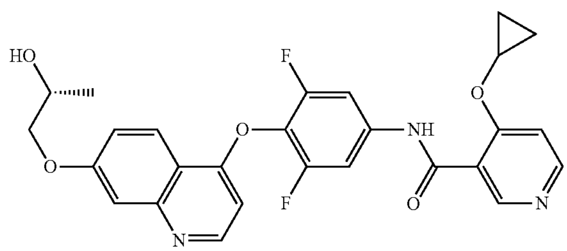 [SMILES: C[C@@H](O)COc1ccc2c(Oc3c(F)cc(NC(=O)c4cnccc4OC4CC4)cc3F)ccnc2c1] | (R)-4-cyclopropoxy-N-(3,5-difluoro-4-((7-(2-hydroxypropoxy)quinolin-4-yl)oxy)phenyl)pyridine-3-carboxamide | 508.16 |
| 102 | 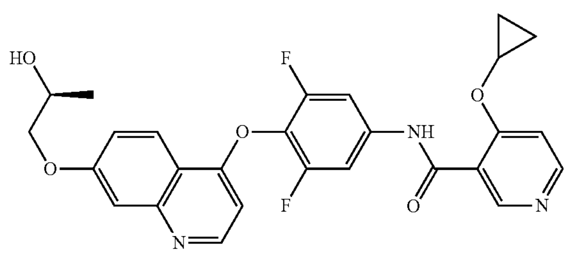 [SMILES: C[C@H](O)COc1ccc2c(Oc3c(F)cc(NC(=O)c4cnccc4OC4CC4)cc3F)ccnc2c1] | (S)-4-cyclopropoxy-N-(3,5-difluoro-4-((7-(2-hydroxypropoxy)quinolin-4-yl)oxy)phenyl)pyridine-3-carboxamide | 508.16 |
| 103 | 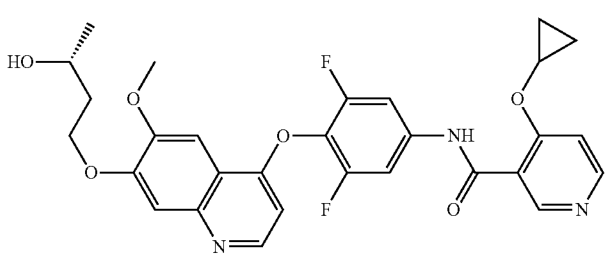 [SMILES: COc1cc2c(Oc3c(F)cc(NC(=O)c4cnccc4OC4CC4)cc3F)ccnc2cc1OCC[C@@H](C)O] | (R)-4-cyclopropoxy-N-(3,5-difluoro-4-((7-(3-hydroxybutoxy)-6-methoxyquinolin-4-yl)oxy)phenyl)pyridine-3-carboxamide | 552.19 |
| 104 | 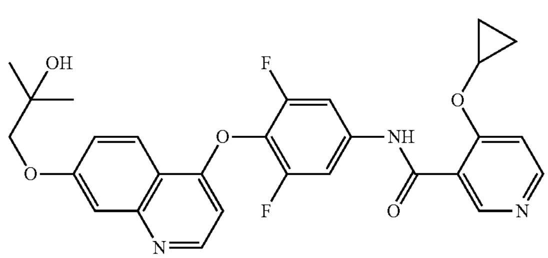 [SMILES: CC(C)(O)COc1ccc2c(Oc3c(F)cc(NC(=O)c4cnccc4OC4CC4)cc3F)ccnc2c1] | 4-cyclopropoxy-N-(3,5-difluoro-4-((7-(2-hydroxy-2-methylpropoxy)quinolin-4-yl)oxy)phenyl)pyridine-3-carboxamide | 522.18 |

TABLE 1-continued

| Example No. | Compound Structure | Compound Name | Exact Mass [M + H]+ |
|---|---|---|---|
| 105 | 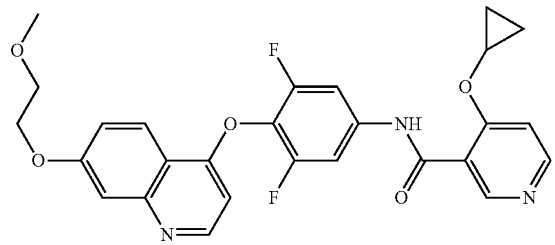 [SMILES: COCCOc1ccc2c(Oc3c(F)cc(NC(=O)c4cnccc4OC4CC4)cc3F)ccnc2c1] | 4-cyclopropoxy-N-(3,5-difluoro-4-((7-(2-methoxyethoxy)quinolin-4-yl)oxy)phenyl)pyridine-3-carboxamide | 508.16 |
| 106 | 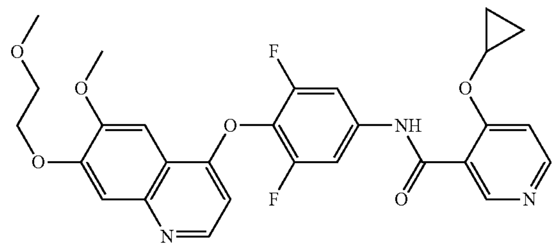 [SMILES: COCCOc1cc2nccc(Oc3c(F)cc(NC(=O)c4cnccc4OC4CC4)cc3F)c2cc1OC] | 4-cyclopropoxy-N-(3,5-difluoro-4-((6-methoxy-7-(2-methoxyethoxy)quinolin-4-yl)oxy)phenyl)pyridine-3-carboxamide | 538.17 |
| 107 | 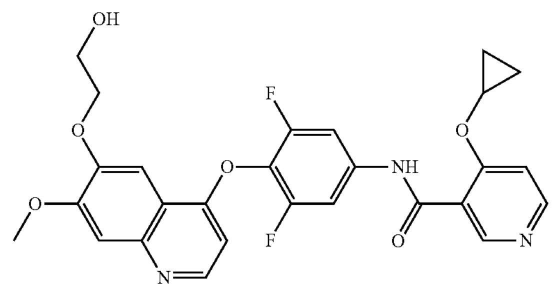 | 4-cyclopropoxy-N-(3,5-difluoro-4-((6-(2-hydroxyethoxy)-7-methoxyquinolin-4-yl)oxy)phenyl)pyridine-3-carboxamide | 524.16 |
| 108 | 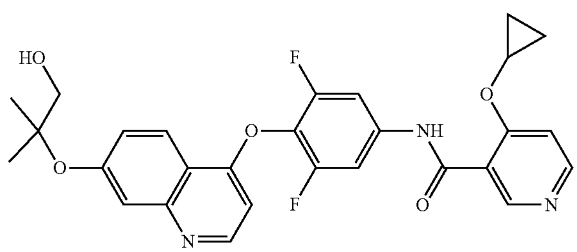 [SMILES: CC(C)(CO)Oc1ccc2c(Oc3c(F)cc(NC(=O)c4cnccc4OC4CC4)cc3F)ccnc2c1] | 4-cyclopropoxy-N-(3,5-difluoro-4-((7-((1-hydroxy-2-methylpropan-2-yl)oxy)quinolin-4-yl)oxy)phenyl)pyridine-3-carboxamide | 522.18 |
| 109 | 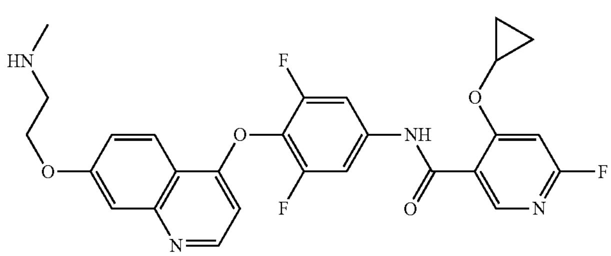 [SMILES: CNCCOc1ccc2c(Oc3c(F)cc(NC(=O)c4cnc(F)cc4OC4CC4)cc3F)ccnc2c1] | 4-cyclopropoxy-N-(3,5-difluoro-4-((7-(2-(methylamino)ethoxy)quinolin-4-yl)oxy)phenyl)-6-fluoropyridine-3-carboxamide | 525.17 |
| 110 | 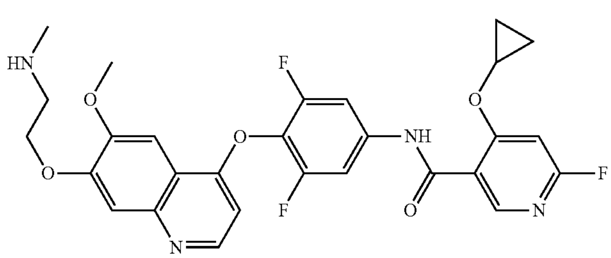 [SMILES: CNCCOc1cc2nccc(Oc3c(F)cc(NC(=O)c4cnc(F)cc4OC4CC4)cc3F)c2cc1OC] | 4-cyclopropoxy-N-(3,5-difluoro-4-((6-methoxy-7-(2-(methylamino)ethoxy)quinolin-4-yl)oxy)phenyl)-6-fluoropyridine-3-carboxamide | 555.18 |

TABLE 1-continued

| Example No. | Compound Structure | Compound Name | Exact Mass [M + H]+ |
|---|---|---|---|
| 111 | 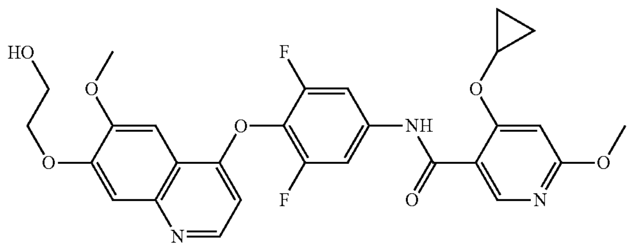 [SMILES: COc1cc(OC2CC2)c(C(=O)Nc2cc(F)c(Oc3ccnc4cc(OCCO)c(OC)cc34)c(F)c2)cn1] | 4-cyclopropoxy-N-(3,5-difluoro-4-((7-(2-hydroxyethoxy)-6-methoxyquinolin-4-yl)oxy)phenyl)-6-methoxypyridine-3-carboxamide | 554.17 |
| 112 | 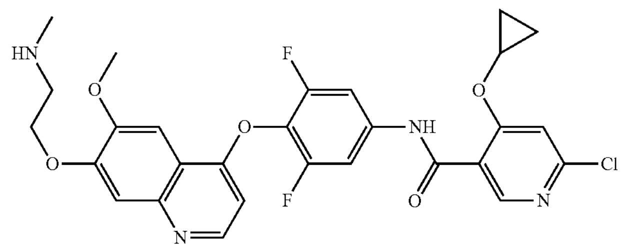 [SMILES: CNCCOc1cc2nccc(Oc3c(F)cc(NC(=O)c4cnc(Cl)cc4OC4CC4)cc3F)c2cc1OC] | 6-chloro-4-cyclopropoxy-N-(3,5-difluoro-4-((6-methoxy-7-(2-(methylamino)ethoxy)quinolin-4-yl)oxy)phenyl)pyridine-3-carboxamide | 571.15 |
| 113 | 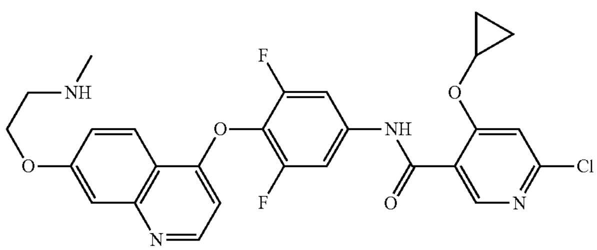 [SMILES: CNCCOc1ccc2c(Oc3c(F)cc(NC(=O)c4cnc(Cl)cc4OC4CC4)cc3F)ccnc2c1] | 6-chloro-4-cyclopropoxy-N-(3,5-difluoro-4-((7-(2-(methylamino)ethoxy)quinolin-4-yl)oxy)phenyl)pyridine-3-carboxamide | 541.14 |
| 114 | 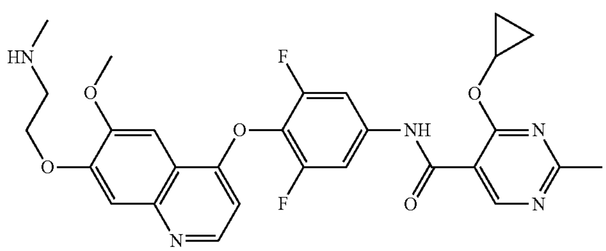 [SMILES: CNCCOc1cc2nccc(Oc3c(F)cc(NC(=O)c4cnc(C)nc4OC4CC4)cc3F)c2cc1OC] | 4-cyclopropoxy-N-(3,5-difluoro-4-((6-methoxy-7-(2-(methylamino)ethoxy)quinolin-4-yl)oxy)phenyl)-2-methylpyrimidine-5-carboxamide | 552.20 |
| 115 | 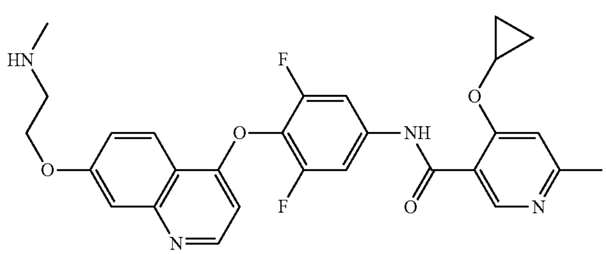 [SMILES: CNCCOc1ccc2c(Oc3c(F)cc(NC(=O)c4cnc(C)cc4OC4CC4)cc3F)ccnc2c1] | 4-cyclopropoxy-N-(3,5-difluoro-4-((7-(2-(methylamino)ethoxy)quinolin-4-yl)oxy)phenyl)-6-methylpyridine-3-carboxamide | 521.19 |
| 116 | 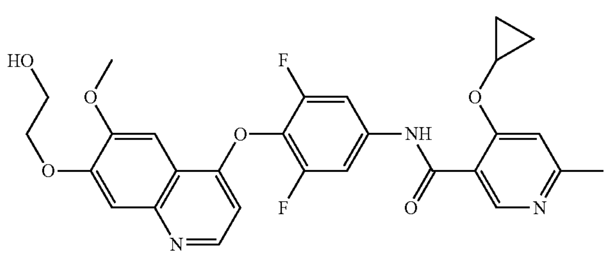 [SMILES: COc1cc2c(Oc3c(F)cc(NC(=O)c4cnc(C)cc4OC4CC4)cc3F)ccnc2cc1OCCO] | 4-cyclopropoxy-N-(3,5-difluoro-4-((7-(2-hydroxyethoxy)-6-methoxyquinolin-4-yl)oxy)phenyl)-6-methylpyridine-3-carboxamide | 538.17 |

TABLE 1-continued

| Example No. | Compound Structure | Compound Name | Exact Mass [M + H]+ |
|---|---|---|---|
| 117 | 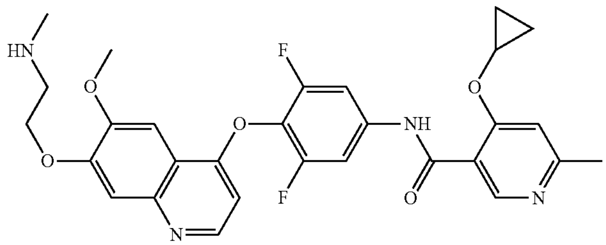 [SMILES: CNCCOc1cc2nccc(Oc3c(F)cc(NC(=O)c4cnc(C)cc4OC4CC4)cc3F)c2cc1OC] | 4-cyclopropoxy-N-(3,5-difluoro-4-((6-methoxy-7-(2-(methylamino)ethoxy)quinolin-4-yl)oxy)phenyl)-6-methylpyridine-3-carboxamide | 551.20 |
| 118 | 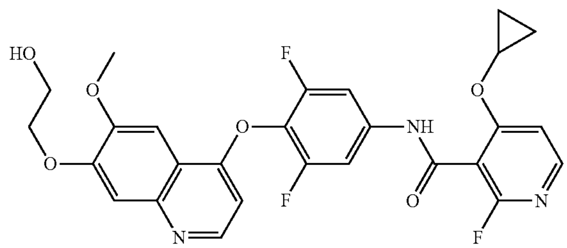 [SMILES: COc1cc2c(Oc3c(F)cc(NC(=O)c4c(OC5CC5)ccnc4F)cc3F)ccnc2cc1OCCO] | 4-cyclopropoxy-N-(3,5-difluoro-4-((7-(2-hydroxyethoxy)-6-methoxyquinolin-4-yl)oxy)phenyl)-2-fluoropyridine-3-carboxamide | 542.15 |
| 119 | 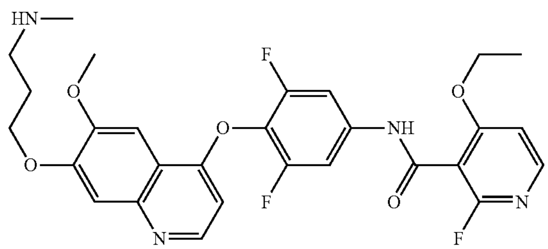 [SMILES: CCOc1ccnc(F)c1C(=O)Nc1cc(F)c(Oc2ccnc3cc(OCCCNC)c(OC)cc23)c(F)c1] | N-(3,5-difluoro-4-((6-methoxy-7-(3-(methylamino)propoxy)quinolin-4-yl)oxy)phenyl)-4-ethoxy-2-fluoropyridine-3-carboxamide | 557.19 |
| 120 | 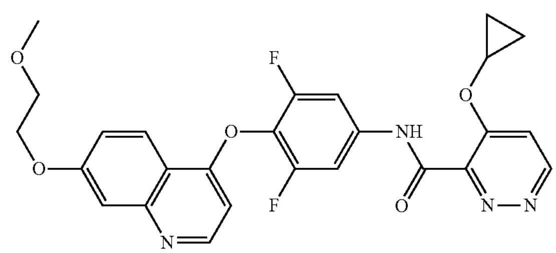 [SMILES: COCCOc1ccc2c(Oc3c(F)cc(NC(=O)c4nnccc4OC4CC4)cc3F)ccnc2c1] | 4-cyclopropoxy-N-(3,5-difluoro-4-((7-(2-methoxyethoxy)quinolin-4-yl)oxy)phenyl)pyridazine-3-carboxamide | 509.16 |
| 121 | 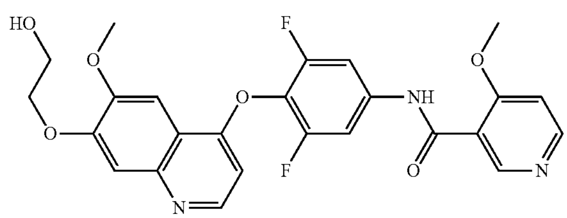 | N-(3,5-difluoro-4-((7-(2-hydroxyethoxy)-6-methoxyquinolin-4-yl)oxy)phenyl)-4-methoxypyridine-3-carboxamide | 498.14 |
| 122 | 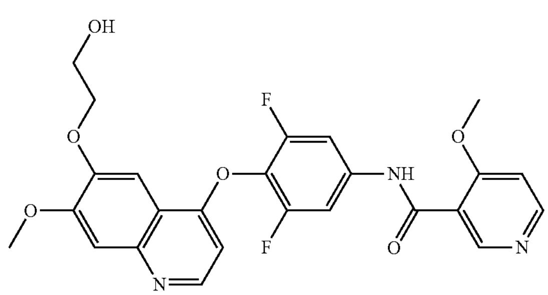 | N-(3,5-difluoro-4-{[6-(2-hydroxyethoxy)-7-methoxyquinolin-4-yl]oxy}phenyl)-4-methoxypyridine-3-carboxamide | 498.14 |

TABLE 1-continued

| Example No. | Compound Structure | Compound Name | Exact Mass [M + H]+ |
|---|---|---|---|
| 123 | 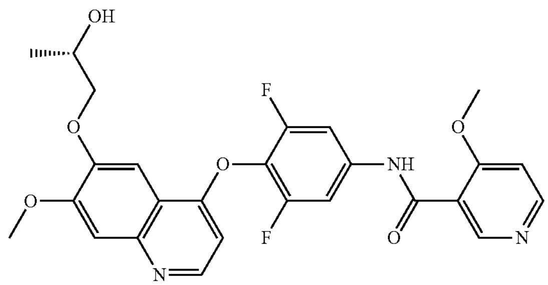 [SMILES: COc1cc2nccc(Oc3c(F)cc(NC(=O)c4cnccc4OC)cc3F)c2cc1OC[C@H](C)O] | (S)-N-(3,5-difluoro-4-([6-(2-hydroxypropoxy)-7-methoxyquinolin-4-yl]oxy}phenyl)-4-methoxypyridine-3-carboxamide | 512.16 |
| 124 | 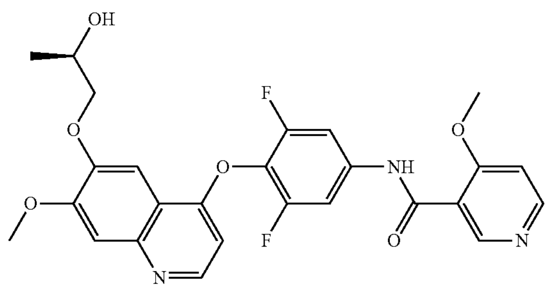 [SMILES: COc1cc2nccc(Oc3c(F)cc(NC(=O)c4cnccc4OC)cc3F)c2cc1OC[C@@H](C)O] | (R)-N-(3,5-difluoro-4-{[6-(2-hydroxypropoxy)-7-methoxyquinolin-4-yl]oxy}phenyl)-4-methoxypyridine-3-carboxamide | 512.16 |
| 125 | 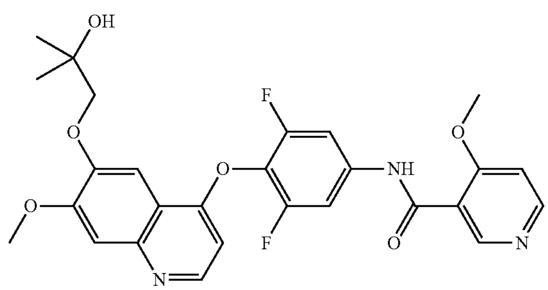 [SMILES: COc1cc2nccc(Oc3c(F)cc(NC(=O)c4cnccc4OC)cc3F)c2cc1OCC(C)(C)O] | N-(3,5-difluoro-4-{[6-(2-hydroxy-2-methylpropoxy)-7-methoxyquinolin-4-yl]oxy}phenyl)-4-methoxypyridine-3-carboxamide | 526.17 |
| 126 | 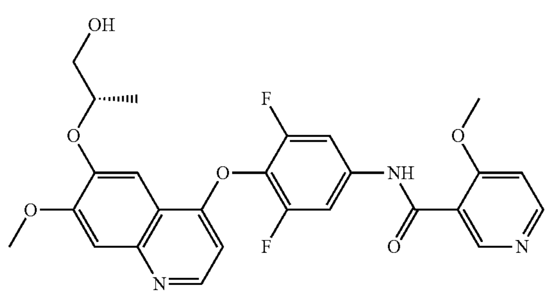 | (S)-N-(3,5-difluoro-4-{[6-((1-hydroxypropan-2-yl)oxy)-7-methoxyquinolin-4-yl]oxy}phenyl)-4-methoxypyridine-3-carboxamide | 512.16 |
| 127 | 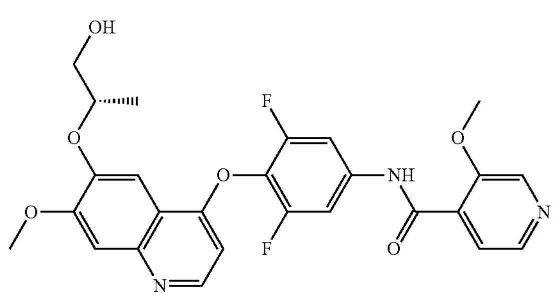 [SMILES: COc1cc2nccc(Oc3c(F)cc(NC(=O)c4ccncc4OC)cc3F)c2cc1O[C@@H](C)CO] | (S)-N-(3,5-difluoro-4-((6-((1-hydroxypropan-2-yl)oxy)-7-methoxyquinolin-4-yl)oxy)phenyl)-3-methoxyisonicotinamide | 512.16 |

TABLE 1-continued

| Example No. | Compound Name | Exact Mass [M + H]+ |
|---|---|---|
| 128 | (S)-N-(3,5-difluoro-4-((7-methoxy-6-((1-methoxypropan-2-yl)oxy)quinolin-4-yl)oxy)phenyl)-4-methoxynicotinamide | 526.17 |
| 129 | (S)-4-cyclopropoxy-N-(3,5-difluoro-4-((6-((1-hydroxypropan-2-yl)oxy)-7-methoxyquinolin-4-yl)oxy)phenyl)nicotinamide | 538.17 |
| 130 | (S)-N-(3,5-difluoro-4-((6-((1-hydroxypropan-2-yl)oxy)quinolin-4-yl)oxy)phenyl)-4-methoxynicotinamide | 482.14 |
| 131 | (R)-N-(3,5-difluoro-4-([6-((1-hydroxypropan-2-yl)oxy)-7-methoxyquinolin-4-yl]oxy}phenyl)-4-methoxypyridine-3-carboxamide | 512.16 |
| 132 | N-(3,5-difluoro-4-((6-(1-(hydroxymethyl)cyclopropoxy)-7-methoxyquinolin-4-yl)oxy)phenyl)-4-methoxynicotinamide | 524.16 |

TABLE 1-continued

| Example No. | Compound Name | Exact Mass [M + H]+ |
|---|---|---|
| 133 | (S)-4-methoxy-N-(2,3,5-trifluoro-4-((6-((1-hydroxypropan-2-yl)oxy)-7-methoxyquinolin-4-yl)oxy)phenyl)nicotinamide | 530.15 |
| 134 | N-(3,5-difluoro-4-((7-(2-hydroxyethoxy)-6-methoxyquinolin-4-yl)oxy)phenyl)-2-fluorobenzamide | 485.12 |
| 135 | N-(3,5-difluoro-4-((7-(2-hydroxyethoxy)-6-methoxyquinolin-4-yl)oxy)phenyl)-4-(2,2-difluoroethoxy)pyridine-3-carboxamide | 548.14 |
| 136 | 4-cyclopropoxy-N-(3,5-difluoro-4-((6-methoxy-7-(2-methoxyethoxy)-1,5-naphthyridin-4-yl)oxy)phenyl)pyridine-3-carboxamide | 539.17 |
| 137 | N-(3,5-difluoro-4-((6-methoxy-7-(2-methoxyethoxy)-1,5-naphthyridin-4-yl)oxy)phenyl)-4-methoxypyridine-3-carboxamide | 513.15 |
| 138 | N-(3,5-difluoro-4-((7-(2-hydroxyethoxy)-6-methoxy-1,5-naphthyridin-4-yl)oxy)phenyl)-4-methoxypyridine-3-carboxamide | 499.14 |

TABLE 1-continued

| Example No. | Compound Name | Exact Mass [M + H]+ |
|---|---|---|
| 139 | N-(3,5-difluoro-4-((7-(2-methoxyethoxy)-1,5-naphthyridin-4-yl)oxy)phenyl)-4-methoxypyridine-3-carboxamide | 483.14 |
| 140 | N-(3,5-difluoro-4-((7-(2-methoxyethoxy)-1,5-naphthyridin-4-yl)oxy)phenyl)-2-fluorobenzamide | 470.12 |
| 141 | N-(3,5-difluoro-4-((7-(2-hydroxyethoxy)-6-methoxyquinolin-4-yl)oxy)phenyl)-4-(2,2-difluoroethoxy)-2-fluoropyridine-3-carboxamide | 566.13 |
| 142 | N-(3,5-difluoro-4-((6-(2-hydroxyethoxy)-7-methoxyquinolin-4-yl)oxy)phenyl)-4-(2,2-difluoroethoxy)-2-fluoropyridine-3-carboxamide | 566.13 |
| 143 | N-(3,5-difluoro-4-((6-(2-hydroxyethoxy)-7-methoxyquinolin-4-yl)oxy)phenyl)-4-(2,2-difluoroethoxy)pyridine-3-carboxamide | 548.14 |

TABLE 1-continued

| Example No. | Compound Structure | Compound Name | Exact Mass [M + H]+ |
|---|---|---|---|
| 144 | 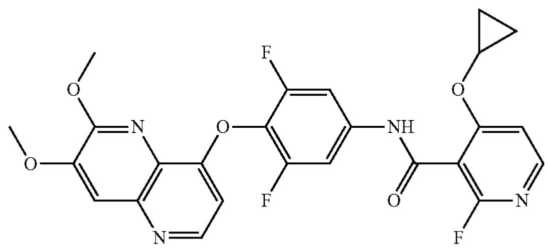 [SMILES: COc1cc2nccc(Oc3c(F)cc(NC(=O)c4c(OC5CC5)ccnc4F)cc3F)c2nc1OC] | 4-cyclopropoxy-N-(4-((6,7-dimethoxy-1,5-naphthyridin-4-yl)oxy)-3,5-difluorophenyl)-2-fluoropyridine-3-carboxamide | 513.13 |
| 145 | 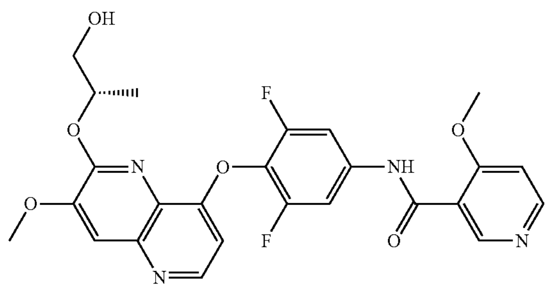 [SMILES: COc1ccncc1C(=O)Nc1cc(F)c(Oc2ccnc3cc(OC)c(O[C@@H](C)CO)nc23)c(F)c1] | (S)-N-(3,5-difluoro-4-((6-((1-hydroxypropan-2-yl)oxy)-7-methoxy-1,5-naphthyridin-4-yl)oxy)phenyl)-4-methoxynicotinamide | 513.15 |
| 146 | 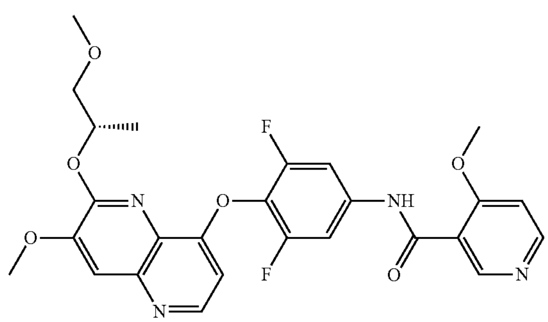 [SMILES: COC[C@H](C)Oc1nc2c(Oc3c(F)cc(NC(=O)c4cnccc4OC)cc3F)ccnc2cc1OC] | (S)-N-(3,5-difluoro-4-((7-methoxy-6-((1-methoxypropan-2-yl)oxy)-1,5-naphthyridin-4-yl)oxy)phenyl)-4-methoxynicotinamide | 527.17 |
| 147 | 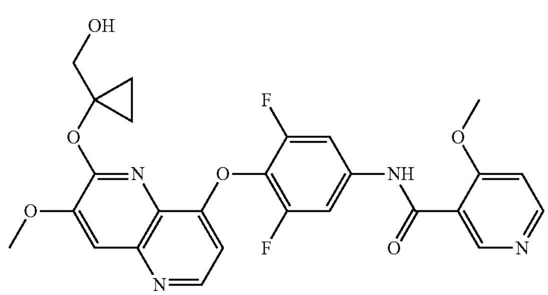 [SMILES: COc1ccncc1C(=O)Nc1cc(F)c(Oc2ccnc3cc(OC)c(OC4(CO)CC4)nc23)c(F)c1] | N-(3,5-difluoro-4-((6-(1-(hydroxymethyl)cyclopropoxy)-7-methoxy-1,5-naphthyridin-4-yl)oxy)phenyl)-4-methoxynicotinamide | 525.15 |
| 148 | 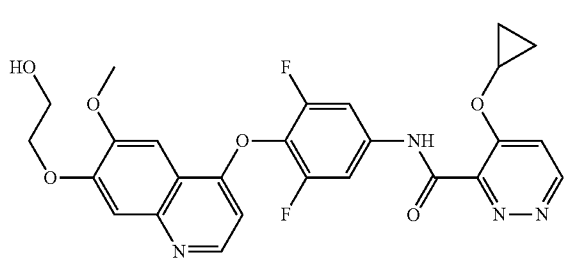 [SMILES: COc1cc2c(Oc3c(F)cc(NC(=O)c4nnccc4OC4CC4)cc3F)ccnc2cc1OCCO] | 4-cyclopropoxy-N-(3,5-difluoro-4-((7-(2-hydroxyethoxy)-6-methoxyquinolin-4-yl)oxy)phenyl)pyridazine-3-carboxamide | 525.15 |

TABLE 1-continued

| Example No. | Compound Structure | Compound Name | Exact Mass [M + H]+ |
|---|---|---|---|
| 149 | 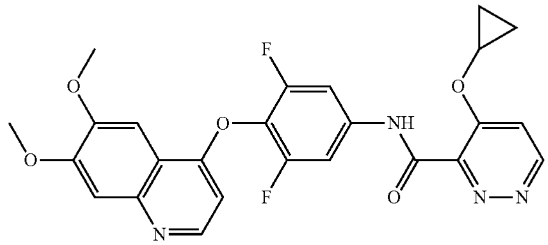 [SMILES: COc1cc2nccc(Oc3c(F)cc(NC(=O)c4nnccc4OC4CC4)cc3F)c2cc1OC] | 4-cyclopropoxy-N-(4-((6,7-dimethoxyquinolin-4-yl)oxy)-3,5-difluorophenyl)pyridazine-3-carboxamide | 495.14 |

Preparation of Compounds

The compounds used in the synthetic chemistry reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, CN), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

General Synthetic Method 1 (below) was used to prepare examples 1-51, 121-134, 137-140, 145-147. Halo-heterocycles (a) were reacted with nitrophenols (b) in the presence of a base such as DIEA (N,N-diisopropylethylamine) to give nitro compounds (c). Compounds (c) were reduced with a reducing agent, such as hydrogen gas in the presence of Pd/C, to yield amine compounds (d). Subsequently, amines (d) were coupled with acids (e) using a coupling agent, such as HATU, to provide compounds of formula (A). Alternatively, amines (d) were reacted with acid chlorides (f) in the presence of a base such as DIEA to provide compounds with formula (A).

General Synthetic Method 1

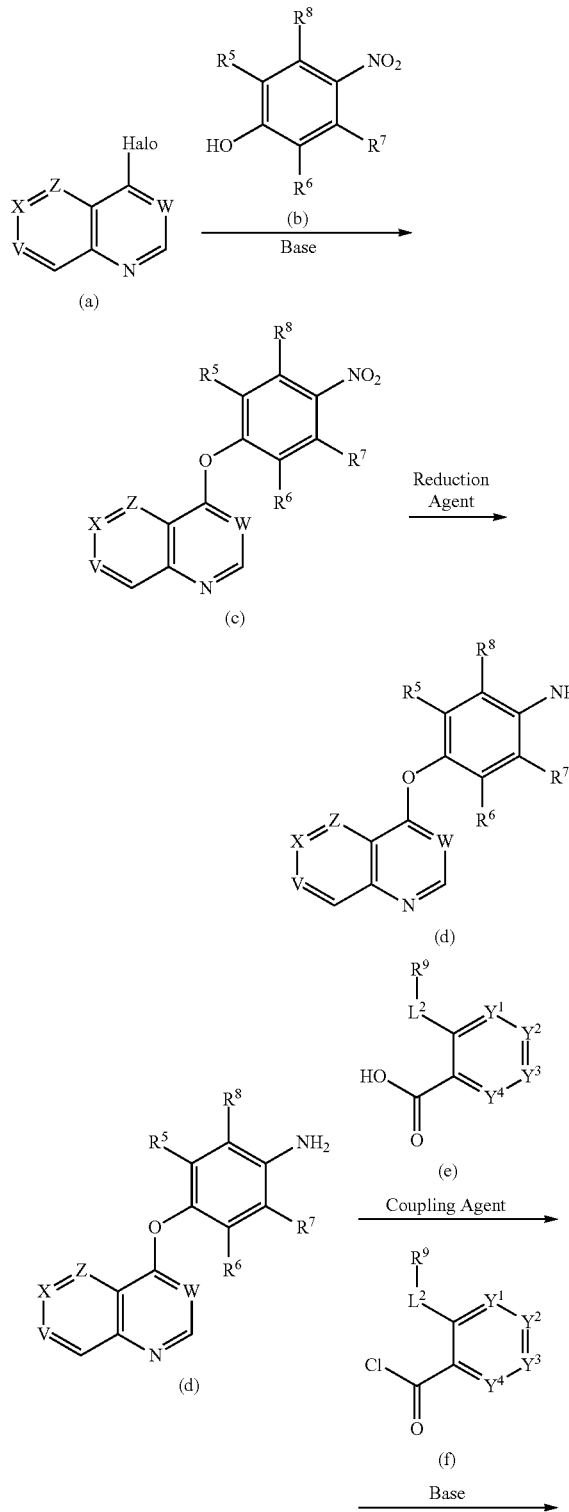

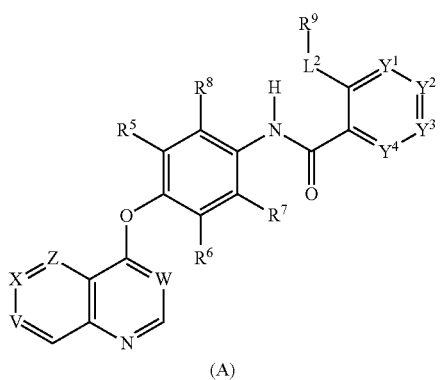

Halo-heterocycles (g) were reacted with 2-fluoro-4-nitrophenols (h) to give ethers (i), which were reduced to amines (j) using the same method described in General Synthetic Method 1.

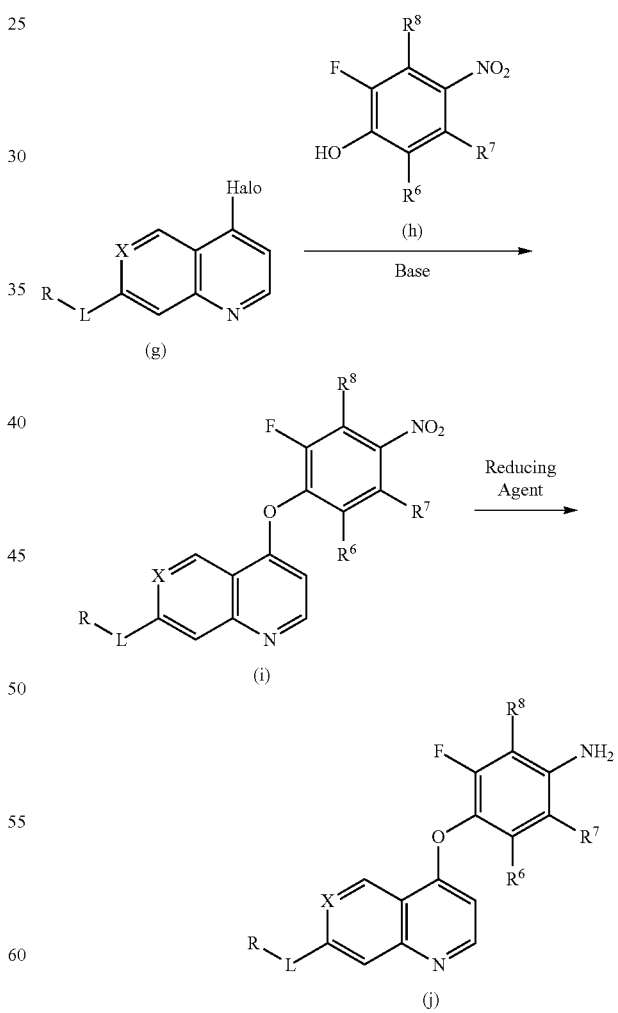

General Synthetic Method 2 (below) was used to prepare examples 52-108, 135-136, and 143. Amines (j) were coupled with acids (k) using a coupling agent, such as HATU, to give (1). Compounds (1) were then reacted with alcohols (m) using a base, such as DBU, to yield compounds with formula (B).

General Synthetic Method 2

General Synthetic Method 3

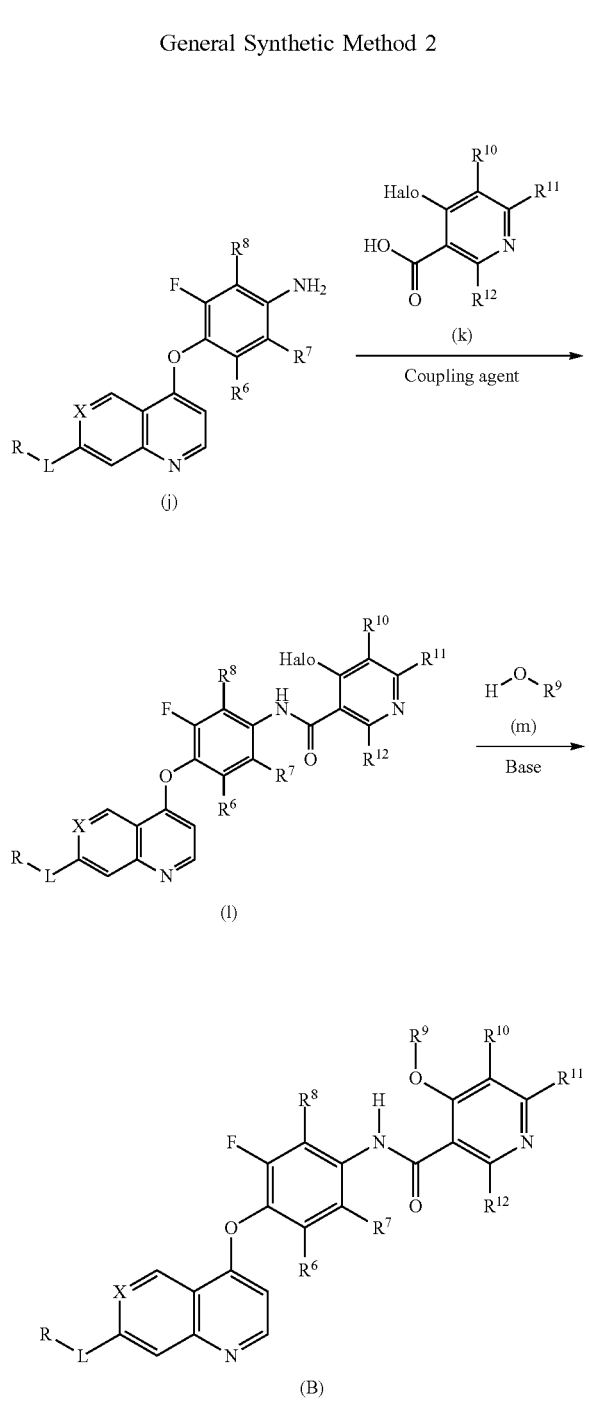

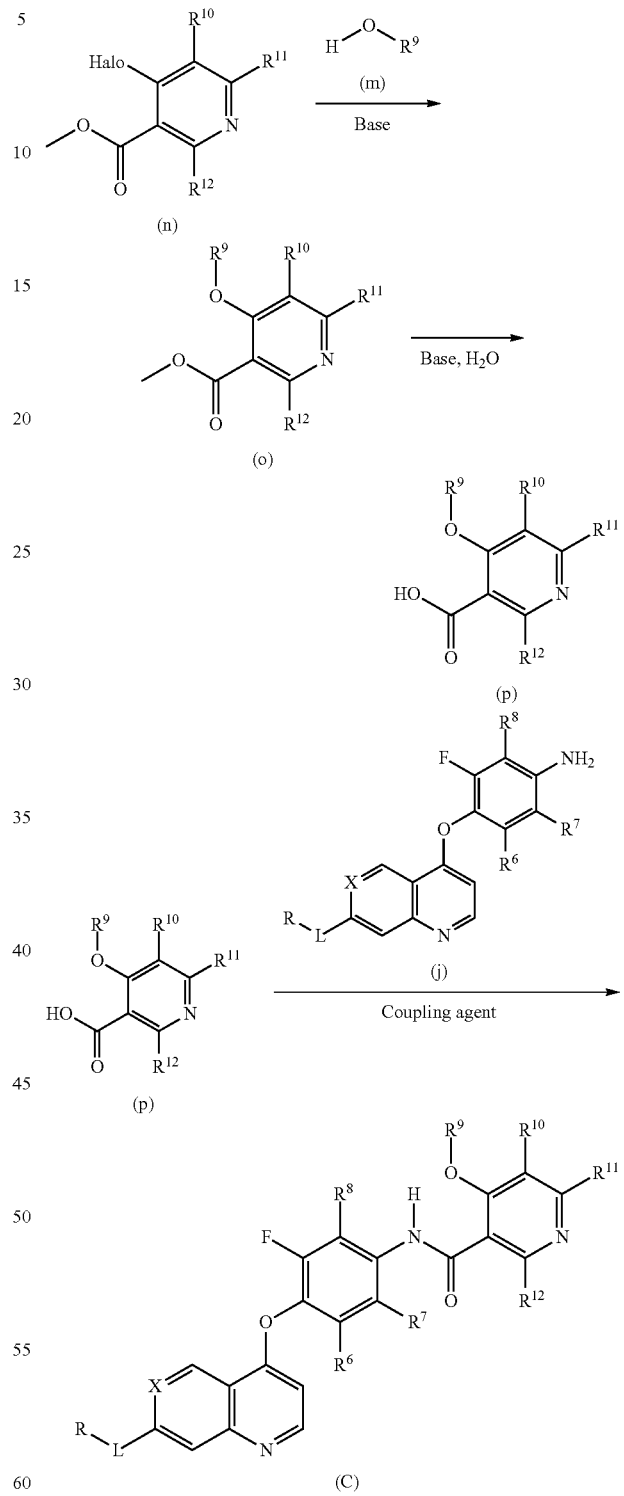

General Synthetic Method 3 (below) was used to prepare examples 109-120, 141-142, 144, 148-149. Esters (n) were reacted with alcohols (m) using a base, such as DBU, to give intermediates (o), which were then saponified to acids (p) with a base, such as lithium hydroxide, in water. Subsequently, acids (p) were coupled with amines (j) using a coupling agent, such as HATU, to yield compounds with formula (C).

Using appropriate starting materials, the MET kinase inhibitory compound described herein by Table 1, or Formulas (I), (II), (III), or (IV), were synthesized using the General Synthetic Methods 1, 2, or 3 described above for the synthesis of compounds with formula (A), (B), or (C).

Pharmaceutical Compositions

In certain embodiments, the MET kinase inhibitory compound described herein is administered as a pure chemical. In other embodiments, the MET kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one MET kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), or a pharmaceutically acceptable salt or solvate thereof.

One embodiment provides a method of preparing a pharmaceutical composition comprising mixing a compound of Formula (I), or a pharmaceutically acceptable salt or solvate thereof, and a pharmaceutically acceptable carrier.

In certain embodiments, the MET kinase inhibitory compound as described by Formula (I), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Formula (II), or a pharmaceutically acceptable salt or solvate thereof.

One embodiment provides a method of preparing a pharmaceutical composition comprising mixing a compound of Formula (II), or a pharmaceutically acceptable salt or solvate thereof, and a pharmaceutically acceptable carrier.

In certain embodiments, the MET kinase inhibitory compound as described by Formula (II), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Formula (III), or a pharmaceutically acceptable salt or solvate thereof.

One embodiment provides a method of preparing a pharmaceutical composition comprising mixing a compound of Formula (III), or a pharmaceutically acceptable salt or solvate thereof, and a pharmaceutically acceptable carrier.

In certain embodiments, the MET kinase inhibitory compound as described by Formula (III), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Formula (IV), or a pharmaceutically acceptable salt or solvate thereof.

One embodiment provides a method of preparing a pharmaceutical composition comprising mixing a compound of Formula (IV), or a pharmaceutically acceptable salt or solvate thereof, and a pharmaceutically acceptable carrier.

In certain embodiments, the MET kinase inhibitory compound as described by Formula (IV), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Table 1, or a pharmaceutically acceptable salt or solvate thereof.

One embodiment provides a method of preparing a pharmaceutical composition comprising mixing a compound of Table 1, or a pharmaceutically acceptable salt or solvate thereof, and a pharmaceutically acceptable carrier.

In certain embodiments, the MET kinase inhibitory compound as described by Table 1, or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the MET kinase inhibitory compound as described by Formula (I), (II), (III), or (IV), or Table 1, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one MET kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented).

An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), or a pharmaceutically acceptable salt or solvate thereof, for use in a method of treatment of the human or animal body.

One embodiment provides a compound of Formula (I), or a pharmaceutically acceptable salt or solvate thereof, for use in a method of treatment of cancer or neoplastic disease.

One embodiment provides a pharmaceutical composition comprising a compound of Formula (I), or a pharmaceutically acceptable salt or solvate thereof, and a pharmaceutically acceptable excipient for use in a method of treatment of cancer or neoplastic disease.

One embodiment provides a use of a compound of Formula (I), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (I), or a pharmaceutically acceptable salt or solvate thereof. In some embodiments is provided a method of treating cancer, in a patient in need thereof, comprising administering to the patient a pharmaceutical composition comprising a compound of Formula (I), or a pharmaceutically acceptable salt or solvate thereof, and a pharmaceutically acceptable excipient.

One embodiment provides a compound of Formula (II), or a pharmaceutically acceptable salt or solvate thereof, for use in a method of treatment of the human or animal body.

One embodiment provides a compound of Formula (II), or a pharmaceutically acceptable salt or solvate thereof, for use in a method of treatment of cancer or neoplastic disease.

One embodiment provides a pharmaceutical composition comprising a compound of Formula (II), or a pharmaceutically acceptable salt or solvate thereof, and a pharmaceutically acceptable excipient for use in a method of treatment of cancer or neoplastic disease.

One embodiment provides a use of a compound of Formula (II), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (II), or a pharmaceutically acceptable salt or solvate thereof. In some embodiments is provided a method of treating cancer, in a patient in need thereof, comprising administering to the patient a pharmaceutical composition comprising a compound of Formula (II), or a pharmaceutically acceptable salt or solvate thereof, and a pharmaceutically acceptable excipient.

One embodiment provides a compound of Formula (III), or a pharmaceutically acceptable salt or solvate thereof, for use in a method of treatment of the human or animal body.

One embodiment provides a compound of Formula (III), or a pharmaceutically acceptable salt or solvate thereof, for use in a method of treatment of cancer or neoplastic disease.

One embodiment provides a pharmaceutical composition comprising a compound of Formula (III), or a pharmaceutically acceptable salt or solvate thereof, and a pharmaceutically acceptable excipient for use in a method of treatment of cancer or neoplastic disease.

One embodiment provides a use of a compound of Formula (III), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (III), or a pharmaceutically acceptable salt or solvate thereof. In some embodiments is provided a method of treating cancer, in a patient in need thereof, comprising administering to the patient a pharmaceutical composition comprising a compound of Formula (III), or a pharmaceutically acceptable salt or solvate thereof, and a pharmaceutically acceptable excipient.

One embodiment provides a compound of Formula (IV), or a pharmaceutically acceptable salt or solvate thereof, for use in a method of treatment of the human or animal body.

One embodiment provides a compound of Formula (IV), or a pharmaceutically acceptable salt or solvate thereof, for use in a method of treatment of cancer or neoplastic disease.

One embodiment provides a pharmaceutical composition comprising a compound of Formula (IV), or a pharmaceutically acceptable salt or solvate thereof, and a pharmaceutically acceptable excipient for use in a method of treatment of cancer or neoplastic disease.

One embodiment provides a use of a compound of Formula (IV), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (IV), or a pharmaceutically acceptable salt or solvate thereof. In some embodiments is provided a method of treating cancer, in a patient in need thereof, comprising administering to the patient a pharmaceutical composition comprising a compound of Formula (IV), or a pharmaceutically acceptable salt or solvate thereof, and a pharmaceutically acceptable excipient.

One embodiment provides a compound of Table 1, or a pharmaceutically acceptable salt or solvate thereof, for use in a method of treatment of the human or animal body.

One embodiment provides a compound of Table 1, or a pharmaceutically acceptable salt or solvate thereof, for use in a method of treatment of cancer or neoplastic disease.

One embodiment provides a pharmaceutical composition comprising a compound of Table 1, or a pharmaceutically acceptable salt or solvate thereof, and a pharmaceutically acceptable excipient for use in a method of treatment of cancer or neoplastic disease.

One embodiment provides a use of a compound of Table 1, or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Table 1, or a pharmaceutically acceptable salt or solvate thereof. In some embodiments is provided a method of treating cancer, in a patient in need thereof, comprising administering to the patient a pharmaceutical composition comprising a compound of Table 1, or a pharmaceutically acceptable salt or solvate thereof, and a pharmaceutically acceptable excipient.

Provided herein is the method wherein the pharmaceutical composition is administered orally.

Provided herein is the method wherein the pharmaceutical composition is administered by injection.

One embodiment provides a method of inhibiting a MET kinase comprising contacting the MET kinase with a compound of Formula (I), (II), (III), or (IV), or Table 1. Another embodiment provides the method of inhibiting a MET kinase, wherein the MET kinase is contacted in an in vivo setting. Another embodiment provides the method of inhibiting a MET kinase, wherein the MET kinase is contacted in an in vitro setting.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the MET kinase inhibitory compounds disclosed herein are synthesized according to the following examples. As used below, and throughout the description of the invention, the following abbreviations, unless otherwise indicated, shall be understood to have the following meanings:

° C. degrees Celsius
$\delta_H$ chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran Example 1: N-(3,5-difluoro-4-((6-methoxy-7-(2-(methylamino)ethoxy)quinolin-4-yl)oxy)phenyl)-4-methoxypyridine-3-carboxamide

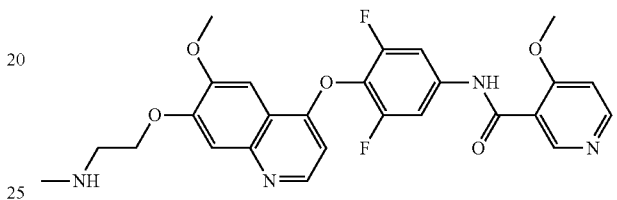

Step 1: tert-butyl N-{2-[(4-chloro-6-methoxyquinolin-7-yl)oxy]ethyl}-N-methylcarbamate To a stirred solution of tert-butyl N-(2-hydroxyethyl)-N-methylcarbamate (627 mg, 3.578 mmol) and 4-chloro-6-methoxyquinolin-7-ol (500 mg, 2.385 mmol) in tetrahydrofuran (10 mL) was added triphenylphosphine (1.25 g, 4.770 mmol) and diisopropyl azodicarboxylate (965 mg, 4.772 mmol) at 0° C. The resulting mixture was stirred at room temperature under nitrogen atmosphere for 16 h. The reaction was quenched with water (100 mL) at room temperature. The resulting mixture was extracted with ethyl acetate (3×100 mL). The combined organic layers were washed with brine (3×50 mL), dried over anhydrous sodium sulfate. After filtration, the filtrate was concentrated under reduced pressure. The residue was purified by silica gel column chromatography, eluted with petroleum ether/ethyl acetate (1/1) and the fractions containing desired product were collected, concentrated under reduced pressure to afford tert-butyl N-{2-[(4-chloro-6-methoxyquinolin-7-yl)oxy]ethyl}-N-methylcarbamate (850 mg, 97%) as a brown yellow oil. MS ESI calculated for $C_{18}H_{23}ClN_2O_4$ $[M+H]^+$, 367.13, 369.13 found 367.10, 369.10. $^1H$ NMR (400 MHz, $CDCl_3$) δ 8.59 (d, J=4.8 Hz, 1H), 7.43 (d, J=3.6 Hz, 2H), 7.38 (d, J=4.8 Hz, 1H), 4.31 (s, 2H), 4.05 (s, 3H), 3.75 (q, J=5.2 Hz, 2H), 3.07 (s, 3H), 1.48 (d, J=3.2 Hz, 9H).

Step 2: tert-butyl N-(2-{[4-(2,6-difluoro-4-nitrophenoxy)-6-methoxyquinolin-7-yl]oxy}ethyl)-N-methylcarbamate To a stirred mixture of tert-butyl N-{2-[(4-chloro-6-methoxyquinolin-7-yl)oxy]ethyl}-N-methylcarbamate (500 mg, 1.363 mmol) and 2,6-difluoro-4-nitrophenol (286 mg, 1.636 mmol) in 1-methyl-2-pyrrolidinone (5 mL) was added N,N-diisopropylethylamine (528 mg, 4.089 mmol) at room temperature. The resulting mixture was stirred at 140° C. under a nitrogen atmosphere for 16 h. The mixture was allowed to cool down to room temperature. The reaction was quenched by the addition of water (100 mL) at room temperature. The resulting mixture was extracted with ethyl acetate (3×100 mL). The combined organic layers were washed with brine (3×60 mL), dried over anhydrous sodium sulfate. After filtration, the filtrate was concentrated under reduced pressure. The residue was purified by silica gel column chromatography, eluted with petroleum ether/ethyl acetate (3/7). The fractions containing desired product were collected, concentrated under reduced pressure to afford tert-butyl N-(2-{[4-(2,6-difluoro-4-nitrophenoxy)-6-methoxyquinolin-7-yl]oxy}ethyl)-N-methyl-carbamate (370 mg, 54%) as a light yellow solid. MS ESI calculated for $C_{24}H_{25}F_2N_3O_7$ [M+H]$^+$, 506.17 found 506.20; $^1$H NMR (400 MHz, CDCl$_3$) δ 8.55 (d, J=5.2 Hz, 1H), 8.11-8.04 (m, 2H), 7.56 (s, 1H), 7.48 (s, 1H), 6.42 (d, J=5.2 Hz, 1H), 4.42-4.29 (m, 2H), 4.06 (s, 3H), 3.82-3.71 (m, 2H), 3.08 (s, 3H), 1.48 (s, 9H). $^{19}$F NMR (376 MHz, CDCl$_3$) δ −119.85 (2F).

Step 3: tert-butyl N-(2-{[4-(4-amino-2,6-difluorophenoxy)-6-methoxyquinolin-7-yl]oxy}ethyl) -N-methylcarbamate To a stirred mixture of tert-butyl N-(2-{[4-(2,6-difluoro-4-nitrophenoxy)-6-methoxyquinolin-7-yl]oxy}ethyl)-N-methylcarbamate (380 mg, 0.752 mmol) in tetrahydrofuran (5 mL) and water (2.5 mL) was added iron powder (210 mg, 3.760 mmol) and ammonium chloride (80 mg, 1.504 mmol) at room temperature. The resulting mixture was stirred at 70° C. for 3 h. The mixture was allowed to cool down to room temperature. The reaction was quenched by the addition of water (50 mL) at room temperature. The resulting mixture was extracted with ethyl acetate (3×50 mL). The combined organic layers were washed with brine (3×50 mL), dried over anhydrous sodium sulfate. After filtration, the filtrate was concentrated under reduced pressure. The residue was purified by silica gel column chromatography, eluted with petroleum ether/ethyl acetate/ethyl alcohol (2/3/1). The fractions containing desired product were collected, concentrated under reduced pressure to afford tert-butyl N-(2-{[4-(4-amino-2,6-difluorophenoxy)-6-methoxyquinolin-7-yl]oxy}ethyl)-N-methyl-carbamate (280 mg, 73%) as a yellow solid. MS ESI calculated for $C_{24}H_{27}F_2N_3O_5$ [M+H]$^+$, 476.19 found 476.15; $^1$H NMR (400 MHz, CDCl$_3$) δ 8.51 (d, J=5.2 Hz, 1H), 7.62 (s, 1H), 7.45 (s, 1H), 6.48 (d, J=5.2 Hz, 1H), 6.41-6.32 (m, 2H), 4.39-4.27 (m, 2H), 4.05 (s, 3H), 3.81-3.71 (m, 2H), 3.07 (s, 3H), 1.48 (s, 9H). $^{19}$F NMR (377 MHz, CDCl$_3$) δ −126.68 (2F).

Step 4: tert-butyl N-[2-({4-[2,6-difluoro-4-(4-methoxypyridine-3-amido)phenoxy]-6-methoxyquinolin-7-yl}oxy)ethyl]-N-methylcarbamate To a stirred mixture of 4-methoxypyridine-3-carboxylic acid (39 mg, 0.252 mmol) and O-(7-azabenzotriazol-1-yl)-N,N,N',N'-tetramethyluronium hexafluorophosphate (120 mg, 0.315 mmol) in N,N-dimethylformamide (1 mL) was added tert-butyl N-(2-{[4-(4-amino-2,6-difluorophenoxy)-6-methoxyquinolin-7-yl]oxy}ethyl)-N-methylcarbamate (100 mg, 0.210 mmol) and N,N-diisopropylethylamine (81 mg, 0.630 mmol) at room temperature. The resulting mixture was stirred at 70° C. for 24 h. The mixture was allowed to cool down to room temperature. The reaction was quenched with water (50 mL) at room temperature. The resulting mixture was extracted with ethyl acetate (3×50 mL). The combined organic layers were washed with brine (3×50 mL), dried over anhydrous sodium sulfate. After filtration, the filtrate was concentrated under reduced pressure. The residue was purified by silica gel column chromatography, eluted with petroleum ether/ethyl acetate/ethyl alcohol (1/6/2). The fractions containing desired product were collected, concentrated under reduced pressure to afford tert-butyl N-[2-({4-[2,6-difluoro-4-(4-methoxypyridine-3-amido)phenoxy]-6-methoxyquinolin-7-yl}oxy) ethyl]-N-methylcarbamate (100 mg, 78%) as a white solid. MS ESI calculated for $C_{31}H_{32}F_2N_4O_7$ [M+H]$^+$, 611.22 found 611.20; $^1$H NMR (400 MHz, DMSO-d$_6$) δ 10.69 (s, 1H), 8.64 (s, 1H), 8.62 (d, J=5.6 Hz, 1H), 8.51 (d, J=5.2 Hz, 1H), 7.80-7.71 (m, 2H), 7.57 (s, 1H), 7.48 (s, 1H), 7.28 (d, J=5.6 Hz, 1H), 6.62 (d, J=5.2 Hz, 1H), 4.35-4.24 (m, 2H), 4.01-3.92 (m, 6H), 3.68-3.60 (m, 2H), 2.92 (s, 3H), 1.44-1.30 (m, 9H). $^{19}$F NMR (377 MHz, DMSO-d$_6$) δ −126.60 (2F).

Step 5: N-[3,5-difluoro-4-({6-methoxy-7-[2-(methylamino)ethoxy]quinolin-4-yl}oxy)phenyl]-4-methoxypyridine-3-carboxamide To a stirred mixture of tert-butyl N-[2-({4-[2,6-difluoro-4-(4-methoxypyridine-3-amido)phenoxy]-6-methoxyquinolin-7-yl}oxy)ethyl]-N-methylcarbamate (100 mg, 0.164 mmol) in dichloromethane (2 mL) was added trifluoroacetic acid (0.4 mL) at room temperature. The resulting mixture was stirred at room temperature for 4 h. The resulting mixture was concentrated under reduced pressure. The crude product (100 mg) was purified by Prep-HPLC with the following conditions (Column: XBridge Prep OBD C18 Column, 30×150 mm, 5 µm; Mobile Phase A: water (plus 10 mmol/L ammonium bicarbonate), Mobile Phase B: acetonitrile; Flow rate: 60 mL/min; Gradient: 22% to 32% B in 8 min; Detector: UV 254/220 nm). The fractions containing desired product were collected, concentrated and lyophilized to afford N-[3,5-difluoro -4-({6-methoxy-7-[2-(methylamino)ethoxy]quinolin-4-yl}oxy)phenyl]-4-methoxypyridine-3-carboxamide (32.6 mg, 39%) as a white solid. MS ESI calculated for $C_{26}H_{24}F_2N_4O_5$ [M+H]$^+$, 511.17 found 511.20; $^1$H NMR (400 MHz, DMSO-d$_6$) δ 10.70 (s, 1H), 8.67-8.57 (m, 2H), 8.50 (d, J=5.2 Hz, 1H), 7.80-7.70 (m, 2H), 7.56 (s, 1H), 7.45 (s, 1H), 7.28 (d, J=5.6 Hz, 1H), 6.61 (d, J=5.2 Hz, 1H), 4.22 (t, J=5.6 Hz, 2H), 4.02-3.94 (m, 6H), 2.94 (t, J=5.6 Hz, 2H), 2.39 (s, 3H). $^{19}$F NMR (377 MHz, DMSO-d$_6$) δ −126.58 (2F).

Example 2: N-(3,5-difluoro-4-((6-methoxy-7-(2-(methylamino)ethoxy)quinolin-4-yl)oxy)phenyl)-4,5-difluoro-2-methoxybenzamide

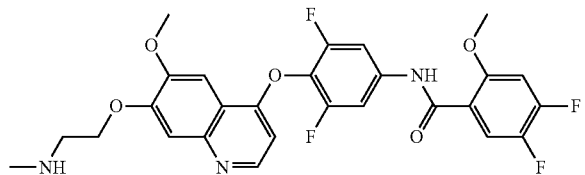 [SMILES: CNCCOc1cc2nccc(Oc3c(F)cc(NC(=O)c4cc(F)c(F)cc4OC)cc3F)c2cc1OC]

Synthesized using the similar method as in example 1. Followed similar procedure described before. Off-white solid. MS ESI calculated for $C_{27}H_{23}F_4N_3O_5$ [M+H]$^+$, $^1$H NMR (400 MHz, DMSO-d$_6$) δ 10.60 (s, 1H), 8.50 (d, J=5.2 Hz, 1H), 7.80-7.70 (m, 3H), 7.56 (s, 1H), 7.50-7.38 (m, 2H), 6.60 (d, J=5.2 Hz, 1H), 4.22 (t, J=5.6 Hz, 2H), 3.98 (s, 3H), 3.93 (s, 3H), 2.95 (d, J=5.6 Hz, 2H), 2.39 (s, 3H). $^{19}$F NMR (376 MHz, DMSO-d$_6$) δ −126.63 (2F), −131.31 (1F), −148.45 (1F).

Example 3: 6-chloro-N-(3,5-difluoro-4-((6-methoxy-7-(2-(methylamino)ethoxy)quinolin-4-yl)oxy)phenyl)-4-methoxypyridine-3-carboxamide

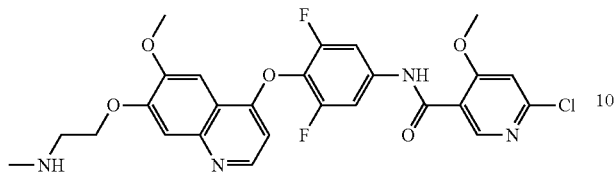

Synthesized using the similar method as in example 1. Obtained a white solid. MS ESI calculated for $C_{26}H_{23}ClF_2N_4O_5$ [M+H]$^+$, 545.13, 547.13 found 545.20, 547.20. $^1$H NMR (400 MHz, DMSO-d$_6$) δ 10.75 (s, 1H), 8.3-8.65 (m, 2H), 7.7-7.76 (m, 2H), 7.55 (s, 1H), 7.46-7.42 (m, 2H), 6.61 (d, J=5.2 Hz, 1H), 4.22 (t, J=5.6 Hz, 2H), 4.01 (s, 3H), 3.98 (s, 3H), 2.94 (m, t, J=5.6 Hz, 2H), 2.38 (s, 3H). $^{19}$F NMR (376 MHz, DMSO-d$_6$) δ -126.44 (2F).

Example 4: N-(3,5-difluoro-4-((6-methoxy-7-(2-(methylamino)ethoxy)quinolin-4-yl)oxy)phenyl)-2-fluoro-4-methoxypyridine-3-carboxamide

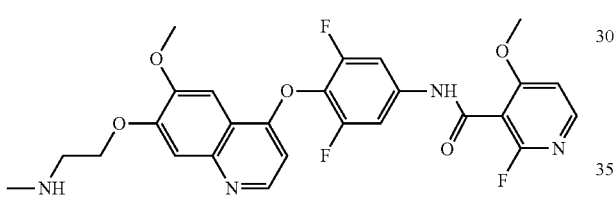

Synthesized using the similar method as in example 1. White solid. MS ESI calculated for $C_{26}H_{23}F_3N_4O_5$ [M+H]$^+$, 529.16 found 529.15; $^1$H NMR (400 MHz, DMSO-d$_6$) δ 11.20-11.12 (m, 1H), 8.55-8.45 (m, 1H), 8.33-8.21 (m, 2H), 7.71-7.63 (m, 2H), 7.57 (s, 1H), 7.46 (s, 1H), 7.28 (d, J=6.0 Hz, 1H), 6.66 (d, J=5.2 Hz, 1H), 4.33-4.23 (m, 2H), 4.00-3.94 (m, 6H), 3.11-3.00 (m, 2H), 2.47-2.41 (m, 2H). $^{19}$F NMR (377 MHz, DMSO-d$_6$) δ -72.53 (1F), -126.11 (2F).

Example 5: N-(3,5-difluoro-4-((6-methoxy-7-(2-(methylamino)ethoxy)quinolin-4-yl)oxy)phenyl)-4-ethoxypyridine-3-carboxamide

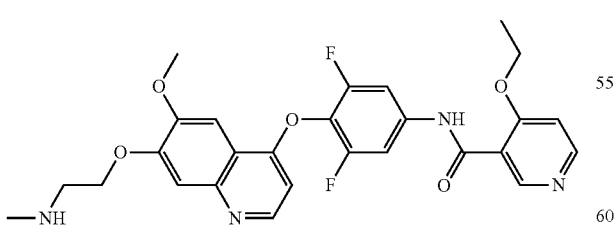

Synthesized using the similar method as in example 1. White solid. MS ESI calculated for $C_{27}H_{26}F_2N_4O_5$ [M+H]$^+$, 525.19 found 525.20. $^1$H NMR (400 MHz, DMSO-d$_6$) δ 10.64 (s, 1H), 8.64 (s, 1H), 8.59 (d, J=5.6 Hz, 1H), 8.51 (d, J=5.2 Hz, 1H), 7.69-7.79 (m, 2H), 7.45 (s, 1H), 7.56 (s, 1H), 7.25 (d, J=5.6 Hz, 1H), 6.62 (d, J=5.2 Hz, 1H), 4.18-4.32 (m, 4H), 3.98 (s, 3H), 2.94 (t, J=5.6 Hz, 2H), 2.39 (s, 3H), 1.41 (t, J=6.8 Hz, 3H). $^{19}$F NMR (376 MHz, DMSO-d$_6$) δ -126.51 (2F).

Example 6: N-(3-chloro-5-fluoro-4-((6-methoxy-7-(2-(methylamino)ethoxy)quinolin-4-yl)oxy)phenyl)-4-methoxypyridine-3-carboxamide

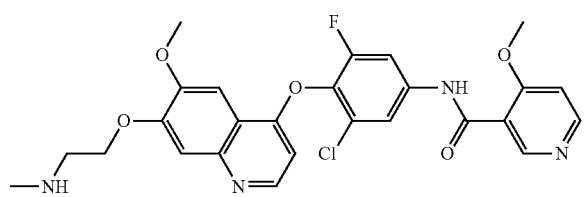

Synthesized using the similar method as in example 1. Off-white solid. MS ESI calculated for $C_{26}H_{24}ClFN_4O_5$ [M+H]$^+$, 527.00, 529.00 found 527.20, 529.20. $^1$H NMR (400 MHz, DMSO-d$_6$) δ 10.66 (s, 1H), 8.65 (s, 1H), 8.62 (d, J=6.0 Hz, 1H), 8.49 (d, J=5.2 Hz, 1H), 7.99-7.92 (m, 2H), 7.57 (s, 1H), 7.45 (s, 1H), 7.28 (d, J=6.0 Hz, 1H), 6.50 (d, J=5.2 Hz, 1H), 4.22 (t, J=5.6 Hz, 2H), 3.98 (s, 6H), 2.94 (t, J=5.6 Hz, 2H), 2.39 (s, 3H). $^{19}$F NMR (377 MHz, DMSO-d$_6$) δ -125.17 (1F).

Example 7: N-(3,5-difluoro-4-((6-methoxy-7-(2-(methylamino)ethoxy)quinazolin-4-yl)oxy)phenyl)-2-fluoro-4-methoxypyridine-3-carboxamide

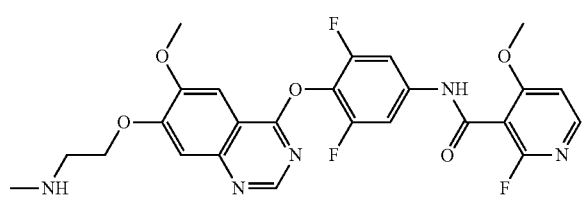

Synthesized using the similar method as in example 1. White solid. MS ESI calculated for $C_{25}H_{22}F_3N_5O_5$ [M+H]$^+$, 530.16, found 530.30; $^1$H NMR (400 MHz, DMSO-d$_6$) δ 11.09 (s, 1H), 8.59 (s, 1H), 8.29 (d, J=6.0 Hz, 1H), 7.64 (s, 1H), 7.62-7.59 (m, 2H), 7.47 (s, 1H), 7.28 (d, J=6.0 Hz, 1H), 4.28 (t, J=5.2 Hz, 2H), 4.01 (s, 3H), 3.99 (s, 3H), 2.96 (t, J=5.2 Hz, 2H), 2.39 (s, 3H); $^{19}$F NMR (376 MHz, DMSO-d$_6$) δ -72.56 (1F), -125.40 (1F), -125.83 (1F).

Example 8: N-(3,5-difluoro-4-((6-methoxy-7-(2-(methylamino)ethoxy)quinazolin-4-yl)oxy)phenyl)-4-methoxypyridine-3-carboxamide

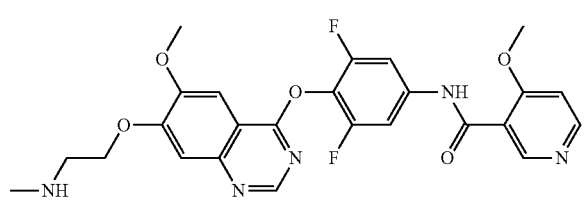

Synthesized using the similar method as in example 1. White solid. MS ESI calculated for $C_{25}H_{23}F_2N_5O_5$ [M+H]$^+$, 512.17, found 512.30; $^1$H NMR (400 MHz, DMSO-d$_6$) δ

10.65 (s, 1H), 8.64-8.59 (m, 3H), 7.71-7.69 (m, 2H), 7.60-7.46 (m, 2H), 7.60 (s, 1H), 7.47 (s, 1H), 7.30-7.26 (m, 1H), 4.27 (t, J=5.6 Hz, 2H), 4.01 (s, 3H), 3.97 (s, 3H), 2.94 (t, J=5.6 Hz, 2H), 2.37 (s, 3H); $^{19}$F NMR (376 MHz, DMSO-$d_6$) δ −125.90 (2F).

Example 9: N-(3,5-difluoro-4-((7-(2-(methylamino)ethoxy)quinolin-4-yl)oxy)phenyl)-2-fluoro-4-methoxypyridine-3-carboxamide

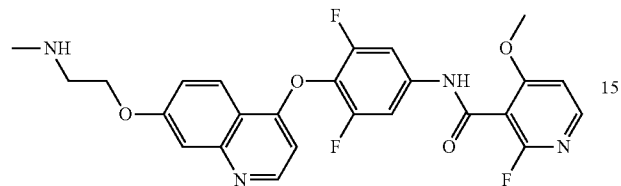

Synthesized using the similar method as in example 1. White solid. MS ESI calculated for $C_{25}H_{21}F_3N_4O_4$ [M+H]$^+$, 499.15 found 499.10. $^1$H NMR (400 MHz, DMSO-$d_6$) δ 11.16 (s, 1H), 8.63 (d, J=5.2 Hz, 1H), 8.30 (d, J=6.0 Hz, 1H), 8.26 (d, J=9.2 Hz, 1H), 7.71-7.64 (m, 2H), 7.45 (d, J=2.4 Hz, 1H), 7.35 (dd, J=9.2, 2.4 Hz, 1H), 7.28 (d, J=6.0 Hz, 1H), 6.67 (d, J=5.2 Hz, 1H), 4.22 (t, J=5.6 Hz, 2H), 3.98 (s, 3H), 2.93 (d, J=5.6 Hz, 2H), 2.38 (s, 3H). $^{19}$F NMR (376 MHz, DMSO-$d_6$) δ −72.56(1F), −126.28 (2F).

Example 10: N-(3,5-difluoro-4-((7-(2-(methylamino)ethoxy)quinolin-4-yl)oxy)phenyl)-4-methoxypyridine-3-carboxamide

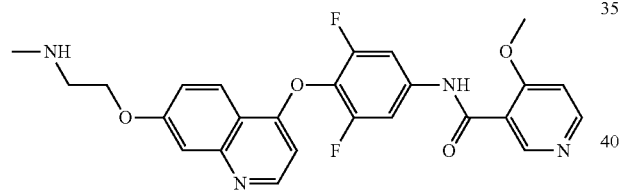

Synthesized using the similar method as in example 1. White solid. MS ESI calculated for $C_{25}H_{22}F_2N_4O_4$ [M+H]$^+$, 481.16, found 481.15. $^1$H NMR (400 MHz, DMSO-$d_6$) δ 10.72 (s, 1H), 8.67-8.59 (m, 3H), 8.27 (d, J=9.2 Hz, 1H), 7.79-7.71 (m, 2H), 7.45 (s, 1H), 7.35 (d, J=9.2 Hz, 1H), 7.28 (d, J=6.0 Hz, 1H), 6.64 (d, J=5.2 Hz, 1H), 4.22 (t, J=5.6 Hz, 2H), 3.97 (s, 3H), 3.27-3.21 (m, 1H) 2.94 (t, J=5.6 Hz, 2H), 2.38 (s, 3H). $^{19}$F NMR (376 MHz, DMSO-$d_6$) δ −126.76 (2F).

Example 11: N-(3,5-difluoro-4-((7-(2-(methylamino)ethoxy)quinolin-4-yl)oxy)phenyl)-4-ethoxypyridine-3-carboxamide

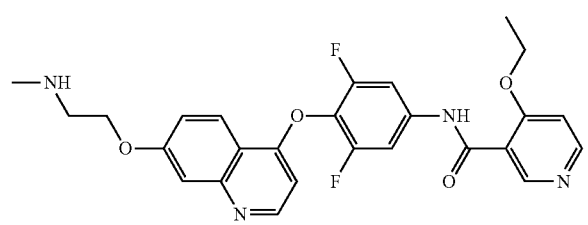 [SMILES: CCOc1ccncc1C(=O)Nc1cc(F)c(Oc2ccnc3cc(OCCNC)ccc23)c(F)c1]

Synthesized using the similar method as in example 1. White solid. MS ESI calculated for $C_{26}H_{24}F_2N_4O_4$ [M+H]$^+$, 495.18, found 495.30. $^1$H NMR (400 MHz, DMSO-$d_6$) δ 10.66 (s, 1H), 8.66-8.62 (m, 2H), 8.59 (d, J=6.0 Hz, 1H), 8.26 (d, J=9.2 Hz, 1H), 7.80-7.70 (m, 2H), 7.45 (d, J=2.4 Hz, 1H), 7.35 (dd, J=9.2, 2.4 Hz, 1H), 7.26 (d, J=6.0 Hz, 1H), 6.64 (d, J=5.2 Hz, 1H), 4.27 (q, J=6.8 Hz, 2H), 4.22 (t, J=5.6 Hz, 2H), 2.92 (t, J=5.6 Hz, 2H), 2.38 (s, 3H), 1.40 (t, J=6.8 Hz, 3H). $^{19}$F NMR (376 MHz, DMSO) δ −126.68(2F).

Example 12: (S)-N-(4-((7-(2-aminopropoxy)quinolin-4-yl)oxy)-3,5-difluorophenyl)-4-cyclopropoxy-pyridine-3-carboxamide

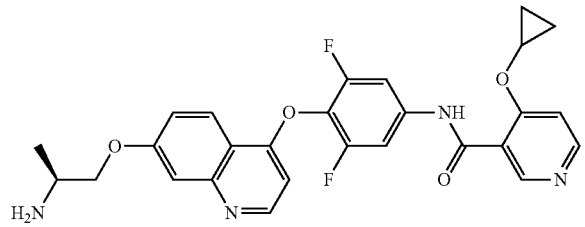 [SMILES: C[C@H](N)COc1ccc2c(Oc3c(F)cc(NC(=O)c4cnccc4OC4CC4)cc3F)ccnc2c1]

Synthesized using the similar method as in example 1. White solid. MS ESI calculated for $C_{27}H_{24}F_2N_4O_4$ [M+H]$^+$, 507.18 found 507.15. $^1$H NMR (400 MHz, DMSO-$d_6$) δ 10.65 (s, 1H), 8.66-8.60 (m, 3H), 8.27 (d, J=9.2 Hz, 1H), 7.74-7.68 (m, 2H), 7.51 (d, J=6.0 Hz, 1H), 7.44 (d, J=2.4 Hz, 1H), 7.37 (dd, J=9.2, 2.4 Hz, 1H), 6.64 (d, J=5.2 Hz, 1H), 4.13-3.90 (m, 3H), 3.30-3.22 (m, 1H), 1.14 (dd, J=6.4, 1.6 Hz, 3H), 0.92-0.78 (m, 4H). $^{19}$F NMR (376 MHz, DMSO-$d_6$) δ −126.67 (2F).

Example 13: (R)-N-(4-((7-(2-aminopropoxy)quinolin-4-yl)oxy)-3,5-difluorophenyl)-4-cyclopropoxy-pyridine-3-carboxamide

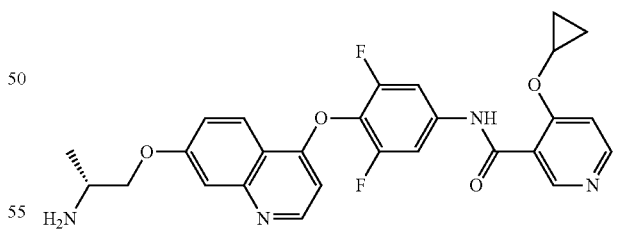

Synthesized using the similar method as in example 1. Off-white solid. MS ESI calculated for $C_{27}H_{24}F_2N_4O_4$ [M+H]$^+$, 507.18, found 507.10. $^1$H NMR (400 MHz, DMSO-$d_6$) δ 10.64 (s, 1H), 8.67-8.59 (m, 3H), 8.27 (d, J=9.2 Hz, 1H), 7.76-7.67 (m, 2H), 7.51 (d, J=6.0 Hz, 1H), 7.43 (d, J=2.4 Hz, 1H), 7.36 (dd, J=9.2, 2.4 Hz, 1H), 6.64 (d, J=5.2 Hz, 1H), 4.12-4.09 (m, 1H), 4.00-3.88 (m, 2H), 3.29-3.19 (m, 1H), 1.26-1.22 (m, 2H), 1.12 (d, J=6.8 Hz, 3H), 0.98-0.76 (m, 4H).

Example 14: N-(2,3-difluoro-4-((6-methoxy-7-(2-(methylamino)ethoxy)quinolin-4-yl)oxy)phenyl)-4-methoxypyridine-3-carboxamide

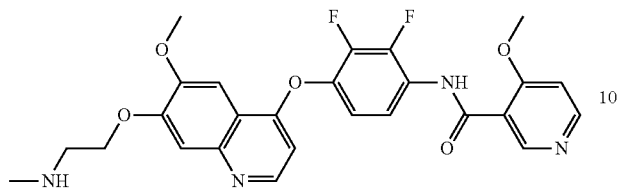

Synthesized using the similar method as in example 1. White solid. MS ESI calculated for $C_{26}H_{24}F_2N_4O_5$ [M+H]$^+$, 511.17 found 511.20. $^1$H NMR (400 MHz, DMSO-d$_6$) δ 10.26 (s, 1H), 8.79 (s, 1H), 8.63 (d, J=5.6 Hz, 1H), 8.52 (d, J=5.2 Hz, 1H), 7.99-7.92 (m, 1H), 7.55 (s, 1H), 7.45 (s, 1H), 7.40-7.27 (m, 2H), 6.62 (d, J=5.2 Hz, 1H), 4.22 (t, J=5.6 Hz, 2H), 4.03 (s, 3H), 3.97 (s, 3H), 2.94 (t, J=5.6 Hz, 2H), 2.39 (s, 3H). $^{19}$F NMR (376 MHz, DMSO-d$_6$) δ −144.18 (1F), −152.75 (1F).

Example 15: N-(2,3-difluoro-4-((6-methoxy-7-(2-(methylamino)ethoxy)quinolin-4-yl)oxy)phenyl)-2-fluoro-4-methoxypyridine-3-carboxamide

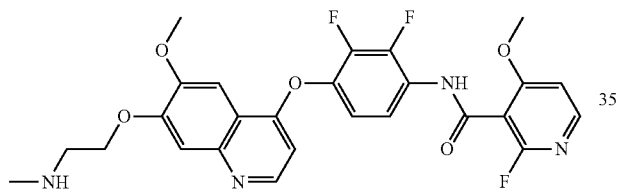

Synthesized using the similar method as in example 1. White solid. MS ESI calculated for $C_{26}H_{23}F_3N_4O_5$ [M+H]$^+$, 529.16 found 529.20. $^1$H NMR (400 MHz, DMSO-d$_6$) δ 10.78 (s, 1H), 8.51 (d, J=5.2 Hz, 1H), 8.26 (d, J=6.0 Hz, 1H), 7.90-7.88 (m, 1H), 7.54 (s, 1H), 7.44 (s, 1H), 7.37-7.35 (m, 1H), 7.24 (d, J=6.0 Hz, 1H), 6.66 (d, J=5.2 Hz, 1H), 4.22 (t, J=5.6 Hz, 2H), 4.01-3.92 (m, 6H), 2.94 (t, J=5.6 Hz, 2H), 2.39 (s, 3H). $^{19}$F NMR (376 MHz, DMSO-d$_6$) δ −72.71 (1F), −143.54 (1F), −152.46 (1F).

Example 16: N-(2,3-difluoro-4-((6-methoxy-7-(2-(methylamino)ethoxy)quinolin-4-yl)oxy)phenyl)-4-ethoxypyridine-3-carboxamide

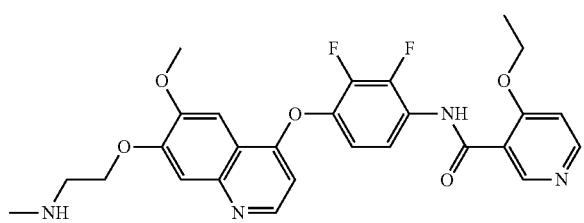 [SMILES: CCOc1ccncc1C(=O)Nc1ccc(Oc2ccnc3cc(OCCNC)c(OC)cc23)c(F)c1F]

Synthesized using the similar method as in example 1. White solid. MS ESI calculated for $C_{27}H_{26}F_2N_4O_5$ [M+H]$^+$, 523.19 found 523.20. $^1$H NMR (400 MHz, DMSO-d$_6$) δ 10.25 (s, 1H), 8.87 (s, 1H), 8.61 (d, J=5.6 Hz, 1H), 8.51 (d, J=5.2 Hz, 1H), 8.20-8.07 (m, 1H), 7.54 (s, 1H), 7.44 (s, 1H), 7.39-7.37 (m, 1H), 7.29 (d, J=5.6 Hz, 1H), 6.62 (d, J=5.2 Hz, 1H), 4.42-4.16 (m, 4H), 3.96 (s, 3H), 2.93 (t, J=5.6 Hz, 2H), 2.38 (s, 3H), 1.48 (t, J=7.2 Hz, 3H). $^{19}$F NMR (376 MHz, DMSO-d$_6$) δ −146.26 (1F), −152.68 (1F).

Example 17: N-[2,3-difluoro-4-({6-methoxy-7-[3-(methylamino)propoxy]quinolin-4-yl}oxy)phenyl]-4-ethoxypyridine-3-carboxamide

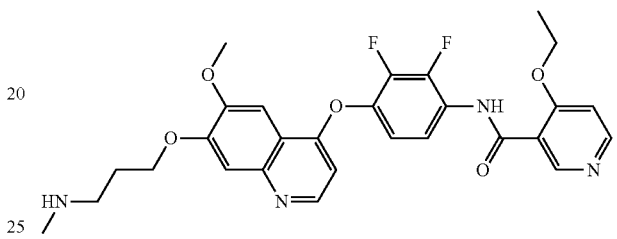

Synthesized using the similar method as in example 1. White solid. MS ESI calculated for $C_{28}H_{28}F_2N_4O_5$ [M+H]$^+$, 539.20 found 539.35. $^1$H NMR (400 MHz, CD$_3$OD) δ 9.07 (s, 1H), 8.60 (d, J=6.0 Hz, 1H), 8.48 (d, J=5.4 Hz, 1H), 8.38-8.33 (m, 1H), 7.67 (s, 1H), 7.40 (s, 1H), 7.32 (d, J=6.0 Hz, 1H), 7.31-7.28 (m, 1H), 6.67-6.61 (m, 1H), 4.47-4.43 (m, 2H), 4.31 (t, J=6.0 Hz, 2H), 4.05 (s, 3H), 2.91 (t, J=6.8 Hz, 2H), 2.50 (s, 3H), 2.17-2.13 (m, 2H), 1.65 (t, J=7.0 Hz, 3H). $^{19}$F NMR (376 MHz, CD$_3$OD) δ −150.01 (1F), −154.42 (1F).

Example 18: N-[2,3-difluoro-4-({6-methoxy-7-[3-(methylamino)propoxy]quinolin-4-yl}oxy)phenyl]-4-methoxypyridine-3-carboxamide

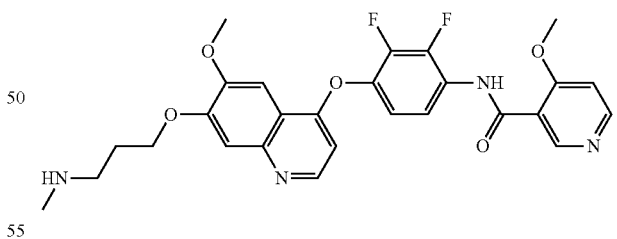

Synthesized using the similar method as in example 1. White solid. MS ESI calculated for $C_{27}H_{26}F_2N_4O_5$ [M+H]$^+$, 525.20 found 525.15. $^1$H NMR (400 MHz, CD$_3$OD) δ 9.01 (s, 1H), 8.66-8.60 (m, 1H), 8.51-8.49 (m, 1H), 8.17-8.15 (m, 1H), 7.67 (dd, J=4.4, 2.0 Hz, 1H), 7.43-7.38 (m, 1H), 7.38-7.33 (m, 1H), 7.28 (t, J=8.8 Hz, 1H), 6.64 (s, 1H), 4.31 (s, 2H), 4.19 (d, J=1.2 Hz, 3H), 4.05 (dd, J=3.4, 1.6 Hz, 3H), 2.93 (d, J=7.6 Hz, 2H), 2.52 (dd, J=8.4, 3.4 Hz, 3H), 2.21-2.14 (m, 2H). $^{19}$F NMR (376 MHz, CD$_3$OD) δ −148.81 (1F), −154.31(1F).

Example 19: N-(3,5-difluoro-4-((6-methoxy-7-(3-(methylamino)propoxy)quinolin-4-yl)amino)phenyl)-4-methoxypyridine-3-carboxamide

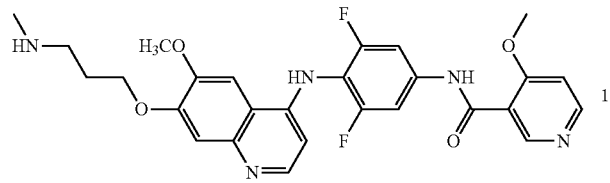

Synthesized using the similar method as in example 1. Light brown solid as a TFA salt. $^1$H NMR (400 MHz, DMSO-d$_6$): δ 14.27 (brs, 1H), 10.85 (s, 1H), 10.26 (s, 1H), 8.68 (d, J=8.8 Hz, 2H), 8.46 (brs, 3H), 8.04 (s, 1H), 7.78 (d, J=10 Hz, 2H), 7.41 (s, 1H), 7.36 (d, J=6.0 Hz, 1H), 6.57 (d, J=7.2 Hz, 1H), 4.29 (t, J=5.6 Hz, 2H), 4.01 (s, 3H), 3.99 (s, 3H), 3.12 (brs, 2H), 2.65 (t, J=5.6 Hz, 3H), 2.18 (brs, 2H) ppm; $^{19}$F NMR (400 MHz, DMSO-d$_6$): δ −117.104. LCMS m/z: 524.59 [M+H]$^+$ Example 20: N-(3,5-difluoro-4-((6-methoxy-7-(3-(methylamino)propoxy)quinolin-4-yl)oxy)phenyl)-2-fluoro-4-methoxypyridine-3-carboxamide

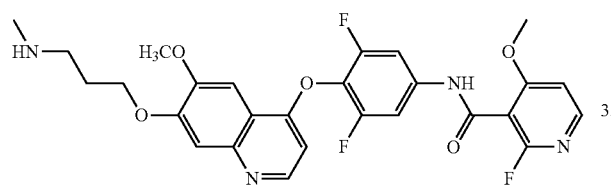

Synthesized using the similar method as in example 1. Light brown solid. $^1$H NMR (400 MHz, DMSO-d$_6$) δ 11.21 (s, 1H), 8.69 (brs, 1H), 8.59 (brs, 2H), 8.29 (d, J=6.0 Hz, 1H), 7.72 (s, 1H), 7.69 (S, 1H), 7.56 (s, 1H), 7.28 (d, J=6.0 Hz, 1H), 6.99 (brs, 1H), 4.32 (t, J=6.0 Hz, 2H), 4.03 (s, 3H), 3.98 (s, 3H), 3.15-3.08 (m, 2H), 2.63 (t, J=5.2 Hz, 3H), 2.21-2.16 (m, 2H), 1.24 (brs, 1H) ppm; LCMS m/z: 543 [M+H]$^+$.

Example 21: N-(3,5-difluoro-4-((6-methoxy-7-(3-(methylamino)propoxy)quinolin-4-yl)oxy)phenyl)-4-ethoxypyridine-3-carboxamide

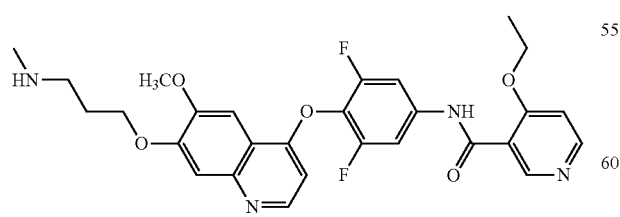

Synthesized using the similar method as in example 1. Off white solid. $^1$H NMR (400 MHz, DMSO-d$_6$) δ 11.06 (s, 1H), 8.82 (s, 1H), 8.79-8.70 (m, 4H), 7.79 (d, J=10.0 Hz, 1H), 7.52 (d, J=5.6 Hz, 1H), 7.07 (brs, 1H), 4.40-4.31 (m, 4H), 4.04 (s, 3H), 3.55-3.38 (m, 2H), 3.11 (t, J=6.8Hz 2H), 2.61 (t, J=5.2 Hz 3H), 2.22 (t, J=6.0 Hz 2H), 1.41 (t, J=5.6 Hz 3H), 1.23 (brs, 1H) ppm; LCMS m/z: 539 [M+H]$^+$.

Example 22: N-[2,5-difluoro-4-({6-methoxy-7-[3-(methylamino)propoxy]quinolin-4-yl}oxy)phenyl]-4-methoxypyridine-3-carboxamide

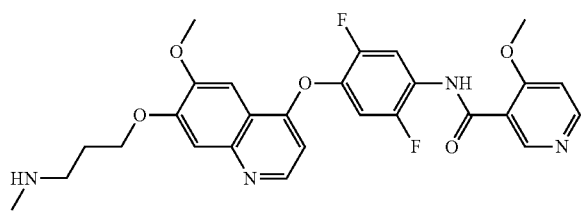 [SMILES: CNCCCOc1cc2nccc(Oc3cc(F)c(NC(=O)c4cnccc4OC)cc3F)c2cc1OC]

Synthesized using the similar method as in example 1. Off-white solid. MS ESI calculated for $C_{27}H_{26}F_2N_4O_5$ [M+H]$^+$, 525.19 found 525.35. $^1$H NMR (400 MHz, DMSO-d$_6$) δ 10.29 (s, 1H), 8.82 (s, 1H), 8.65 (d, J=5.8 Hz, 1H), 8.52 (d, J=5.2 Hz, 1H), 8.30 (dd, J=12.4, 6.8 Hz, 1H), 7.73 (dd, J=10.8, 7.4 Hz, 1H), 7.53 (s, 1H), 7.43 (s, 1H), 7.32 (d, J=5.8 Hz, 1H), 6.59 (d, J=5.2 Hz, 1H), 4.23 (t, J=6.4 Hz, 2H), 4.05 (s, 3H), 3.97 (s, 3H), 2.67 (t, J=6.6 Hz, 2H), 2.32 (s, 3H), 2.00-1.96 (m, 2H), 1.24 (s, 1H). $^{19}$F NMR (376 MHz, DMSO-d$_6$) δ −126.89 (1F), −132.81 (1F).

Example 23: N-(4-((7-(3-(dimethylamino)propoxy)-6-methoxyquinolin-4-yl)oxy)-2,5-difluorophenyl)-4-ethoxypyridine-3-carboxamide

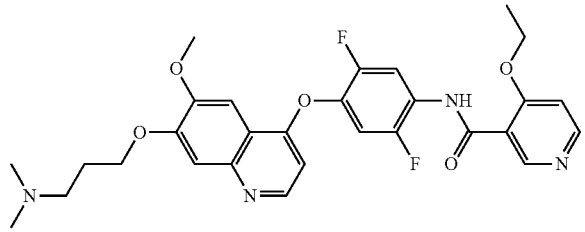 [SMILES: CCOc1ccncc1C(=O)Nc1cc(F)c(Oc2ccnc3cc(OCCCN(C)C)c(OC)cc23)cc1F]

Synthesized using the similar method as in example 1. Light brown solid. $^1$H NMR (400 MHz, DMSO-d$_6$) δ 10.26 (brs, 1H), 8.86 (s, 1H), 8.59 (d, J=6.0 Hz, 1H), 8.50-8.43 (m, 2H), 7.67 (brs, 1H), 7.52 (s, 1H), 7.40 (s, 1H), 7.26 (d, J=5.2 Hz, 1H), 6.57 (d, J=4.8 Hz, 1H), 4.33 (q, J=7.2 Hz, 2H), 4.19 (t, J=6.4 Hz, 2H), 3.96 (s, 3H), 2.40 (t, J=7.2 Hz, 2H), 2.17 (s, 6H), 1.99-1.91 (m, 2H), 1.47 (t, J=7.2 Hz, 3H) ppm; LCMS m/z: [M+H]$^+$553.

Example 24: N-[2,5-difluoro-4-({6-methoxy-7-[2-(methylamino)ethoxy]quinolin-4-yl}oxy)phenyl]-4-methoxypyridine-3-carboxamide

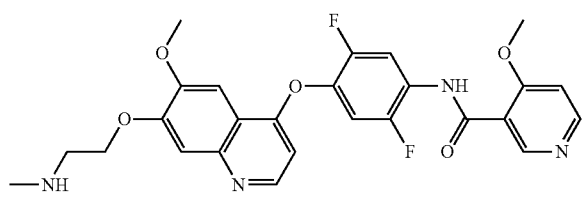 [SMILES: CNCCOc1cc2nccc(Oc3cc(F)c(NC(=O)c4cnccc4OC)cc3F)c2cc1OC]

Synthesized using the similar method as in example 1. White solid. MS ESI calculated for $C_{28}H_{24}F_2N_4O_5$ [M+H]$^+$, 511.17 found 511.15. $^1$H NMR (400 MHz, DMSO-d$_6$) δ 10.26 (s, 1H), 8.82 (s, 1H), 8.64 (d, J=5.6 Hz, 1H), 8.51 (d, J=5.2 Hz, 1H), 8.29 (dd, J=12.0, 7.2 Hz, 1H), 7.71 (dd, J=10.8, 7.2 Hz, 1H), 7.53 (s, 1H), 7.44 (s, 1H), 7.31 (d, J=5.6 Hz, 1H), 6.59 (d, J=5.2 Hz, 1H), 4.21 (t, J=5.6 Hz, 2H), 4.04 (s, 3H), 3.97 (s, 3H), 2.94 (t, J=5.6 Hz, 2H), 2.38 (s, 3H). $^{19}$F NMR (376 MHz, DMSO-d$_6$) δ −127.00 (1F), −132.86 (1F).

Example 25: N-[2,5-difluoro-4-({6-methoxy-7-[2-(methylamino)ethoxy]quinolin-4-yl}oxy)phenyl]-2-fluoro-4-methoxypyridine-3-carboxamide

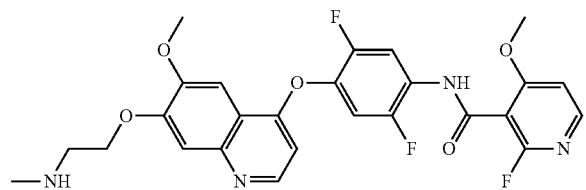

Synthesized using the similar method as in example 1. White solid. MS ESI calculated for $C_{26}H_{23}F_3N_4O_5$ [M+H]$^+$, 529.16 found 529.20. $^1$H NMR (400 MHz, DMSO-d$_6$) δ 10.84-10.79 (m, 1H), 8.50 (d, J=5.2 Hz, 1H), 8.25 (dd, J=10.2, 6.4 Hz, 2H), 7.68 (dd, J=10.6, 7.4 Hz, 1H), 7.53 (s, 1H), 7.44 (s, 1H), 7.24 (d, J=6.0 Hz, 1H), 6.62 (dd, J=5.2, 1.2 Hz, 1H), 4.21 (t, J=5.6 Hz, 2H), 3.97 (s, 6H), 2.99-2.90 (m, 2H), 2.38 (s, 3H). $^{19}$F NMR (376 MHz, DMSO-d$_6$) δ −72.69 (1F), −125.42 (1F), −132.70 (1F).

Example 26: 6-chloro-N-[2,5-difluoro-4-({6-methoxy-7-[2-(methylamino)ethoxy]quinolin-4-yl}oxy)phenyl]-4-methoxypyridine-3-carboxamide

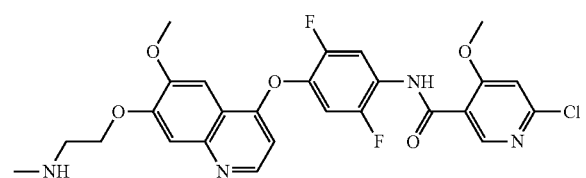 [SMILES: CNCCOc1cc2nccc(Oc3cc(F)c(NC(=O)c4cnc(Cl)cc4OC)cc3F)c2cc1OC]

Synthesized using the similar method as in example 1. White solid. MS ESI calculated for $C_{26}H_{23}ClF_2N_4O_5$ [M+H]$^+$, 545.13, 547.13 found 545.15, 547.15. $^1$H NMR (400 MHz, DMSO -d$_6$) δ 10.26 (s, 1H), 8.60 (s, 1H), 8.51 (d, J=5.2 Hz, 1H), 8.24 (dd, J=12.0, 6.8 Hz, 1H), 7.70 (dd, J=10.8, 7.2 Hz, 1H), 7.53 (s, 1H), 7.47-7.41 (m, 2H), 6.59 (d, J=5.2 Hz, 1H), 4.22 (t, J=5.6 Hz, 2H), 4.06 (s, 3H), 3.97 (s, 3H), 2.97 (t, J=5.6 Hz, 2H), 2.40 (s, 3H). $^{19}$F NMR (377 MHz, DMSO-d$_6$) δ −126.40 (1F), −132.83 (1F).

Example 27: N-[2,5-difluoro-4-({6-methoxy-7-[3-(morpholin-4-yl)propoxy]quinolin-4-yl}oxy)phenyl]-4-methoxypyridine-3-carboxamide

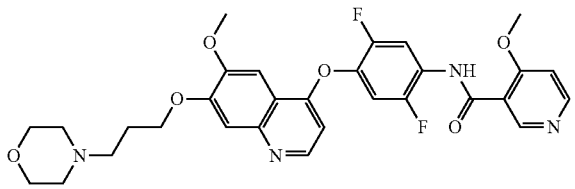 [SMILES: COc1cc2c(Oc3cc(F)c(NC(=O)c4cnccc4OC)cc3F)ccnc2cc1OCCCN1CCOCC1]

A solution of 4-methoxypyridine-3-carboxylic acid (68 mg, 0.448 mmol) in ethyl acetate was treated with propanephosphonic acid cyclic anhydride (2 mL) and N,N-diisopropylethylamine (0.2 mL). The resulted mixture was stirred at room temperature for 10 minutes, followed by adding 2,5-difluoro-4-({6-methoxy-7-[3-(morpholin-4-yl)propoxy]quinolin-4-yl}oxy)aniline (100 mg, 0.224 mmol) in ethyl acetate (2 mL) dropwise. The resulting mixture was stirred at 70° C. for 12 h. The mixture was allowed to cool down to room temperature. The resulting mixture was concentrated under reduced pressure. The residue was purified by silica gel column chromatography, eluted with dichloromethane/methyl alcohol (10/1). The fractions containing desired product were collected and concentrated under reduced pressure to afford crude product. The crude product was purified by Prep-HPLC with the following conditions (Column: XBridge Shield RP18 OBD Column, 19×250 mm, 10 μm; Mobile Phase A: water (plus 10 mmol/L ammonium bicarbonate), Mobile Phase B: acetonitrile; Flow rate: 25 mL/min; Gradient: 44% to 49% B in 8 min; Detector: UV 254/220 nm). The fractions containing desired product were collected, concentrated and lyophilized to afford N-[2,5-difluoro-4-({6-methoxy-7-[3-(morpholin -4-yl)propoxy] quinolin-4-yl}oxy)phenyl]-4-methoxypyridine-3-carboxamide (34.4 mg, 26%) as a light yellow solid. MS ESI calculated for $C_{30}H_{30}F_2N_4O_6$ [M+H]$^+$, 581.21 found 581.25. $^1$H NMR (400 MHz, DMSO-d$_6$) δ 10.30-10.25 (m, 1H), 8.82 (s, 1H), 8.64 (d, J=6.0 Hz, 1H), 8.51 (d, J=5.2 Hz, 1H), 8.29 (dd, J=12.0, 7.2 Hz, 1H), 7.71 (dd, J=10.8, 7.2 Hz, 1H), 7.53 (s, 1H), 7.43 (s, 1H), 7.31 (d, J=6.0 Hz, 1H), 6.59 (d, J=5.2 Hz, 1H), 4.21 (t, J=6.4 Hz, 2H), 4.04 (s, 3H), 3.96 (s, 3H), 3.60 (t, J=6.4 Hz, 4H), 2.49-2.45 (m, 2H), 2.40 (s, 4H), 2.03-1.95 (m, 2H). $^{19}$F NMR (376 MHz, DMSO-d$_6$) δ −129.93 (1F), 132.86 (1F).

Example 28: N-[3,5-difluoro-4-({6-methoxy-7-[3-(morpholin-4-yl)propoxy]quinolin yl}oxy)phenyl]-4-ethoxypyridine-3-carboxamide

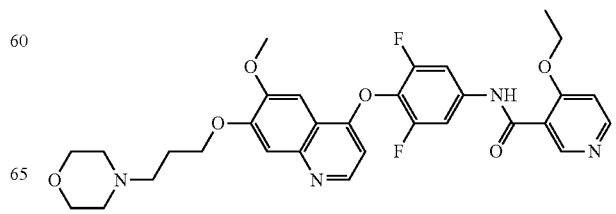

Synthesized using the similar method as in example 27. White solid. MS ESI calculated for $C_{31}H_{32}F_2N_4O_6$ [M+H]$^+$, 595.23 found 595.25; $^1$H NMR (400 MHz, DMSO-d$_6$) δ 10.67 (s, 1H), 8.64 (s, 1H), 8.59 (d, J=5.6 Hz, 1H), 8.50 (d, J=5.2 Hz, 1H), 7.74 (d, J=10.2 Hz, 2H), 7.55 (s, 1H), 7.43 (s, 1H), 7.26 (d, J=5.6 Hz, 1H), 6.62 (d, J=5.2 Hz, 1H), 4.37-4.15 (m, 4H), 3.97 (s, 3H), 3.68-3.60 (m, 4H), 2.51-2.46 (m, 6H), 1.99 (t, J=6.8 Hz, 2H), 1.40 (d, J=6.8 Hz, 3H). $^{19}$F NMR (376 MHz, DMSO) δ -126.49 (2F).

Example 29: N-[3,5-difluoro-4-({6-methoxy-7-[2-(morpholin-4-yl)ethoxy]quinolin-4-yl}oxy)phenyl]-4-methoxypyridine-3-carboxamide

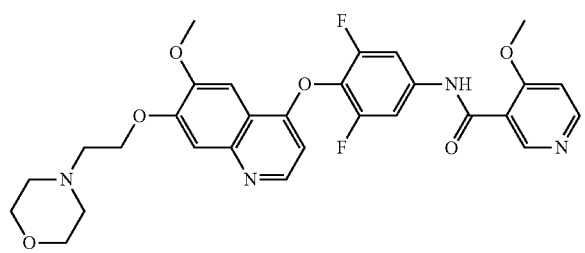 [SMILES: COc1cc2c(Oc3c(F)cc(NC(=O)c4cnccc4OC)cc3F)ccnc2cc1OCCN1CCOCC1]

Synthesized using the similar method as in example 27. White solid. MS ESI calculated for $C_{29}H_{28}F_2N_4O_6$ [M+H]$^+$, 567.20 found 567.25; $^1$H NMR (400 MHz, DMSO-d$_6$) δ 10.69 (s, 1H), 8.67-8.58 (m, 2H), 8.51 (d, J=5.2 Hz, 1H), 7.80-7.71 (m, 2H), 7.56 (s, 1H), 7.47 (s, 1H), 7.28 (d, J=6.0 Hz, 1H), 6.61 (d, J=5.2 Hz, 1H), 4.30 (t, J=6.0 Hz, 2H), 3.97 (s, 6H), 3.63-3.56 (m, 4H), 2.81 (t, J=5.6 Hz, 2H), 2.57-2.52 (m, 4H). $^{19}$F NMR (377 MHz, DMSO-d$_6$) δ -126.58 (2F).

Example 30: N-(3,5-difluoro-4-((6-methoxy-7-(3-morpholinopropoxy)quinolin-4-yl)oxy)phenyl)-4-methoxypyridine-3-carboxamide

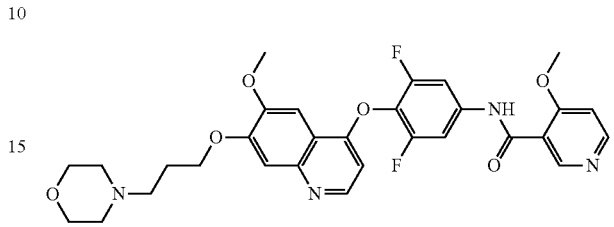

Synthesized using the similar method as in example 27. Off-white solid. $^1$H NMR (400 MHz, CDCl$_3$) δ 8.62 (t, J=10.0, 2H), 8.51 (t, J=11.6, 1H), 7.76 (d, J=10.0 Hz, 2H), 7.54 (s, 1H), 7.42 (s, 1H), 7.28 (d, J=6.0, 1H), 6.61 (d, J=5.2, 1H), 4.23 (t, J=12.8 Hz, 2H), 3.96 (s, 6H), 3.60 (t, J=9.2 Hz, 4H), 2.47 (d, J=7.2 Hz, 2H), 2.39 (s, 4H), 2.0 (t, J=13.6 2H) ppm; LCMS m/z: 581.48 [M+H]$^+$.

Example 31: 6-amino-N-(2,5-difluoro-4-((6-methoxy-7-(3-morpholinopropoxy)quinolin-4-yl)oxy)phenyl)-4-methoxypyridine-3-carboxamide

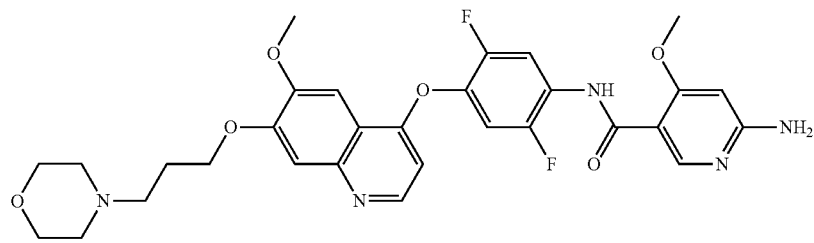 [SMILES: COc1cc2c(Oc3cc(F)c(NC(=O)c4cnc(N)cc4OC)cc3F)ccnc2cc1OCCCN1CCOCC1]

Step 1: 4-chloro-6-methoxy-7-[3-(morpholin-4-yl)propoxy]quinoline

A solution of 3-(morpholin-4-yl)propan-1-ol (1.52 g, 10.49 mmol) and 4-chloro-6-methoxyquinolin-7-ol (2.00 g, 9.541 mmol) in tetrahydrofuran (10 mL) was stirred at 0° C. under nitrogen atmosphere for 20 min. To the above mixture was added diisopropyl azodicarboxylate (3.86 g, 19.08 mmol) dropwise at 0° C. The resulting mixture was stirred at room temperature under nitrogen atmosphere for 16 h. The reaction was quenched with water (100 mL) at room temperature. The resulting mixture was extracted with ethyl acetate (3×100 mL). The combined organic layers were washed with brine (2×100 mL), dried over anhydrous sodium sulfate. After filtration, the filtrate was concentrated under reduced pressure. The residue was purified by silica gel column chromatography, eluted with dichloromethane/methyl alcohol (10/1) concentrated under reduced pressure to afford 4-chloro-6-methoxy-7-[3-(morpholin-4-yl)propoxy]quinoline (2.66 g, 82%) as a light yellow solid. MS ESI calculated for $C_{17}H_{21}ClN_2O_3$ [M+H]$^+$, 337.12, 339.12 found 337.10, 339.10. $^1$H NMR (400 MHz, CDCl$_3$) δ 8.59 (d, J=4.8 Hz, 1H), 7.46 (s, 1H), 7.42 (s, 1H), 7.36 (d, J=4.8 Hz, 1H), 4.28 (t, J=6.8 Hz, 2H), 4.06 (s, 3H), 3.78-3.75 (m, 4H), 2.60 (t, J=7.2 Hz, 2H), 2.51 (t, J=4.8 Hz, 4H), 2.15 (d, J=6.8 Hz, 2H).

Step 2: 4-(2,5-difluoro-4-nitrophenoxy)-6-methoxy-7-[3-(morpholin-4-yl)propoxy]quinoline To a stirred solution of 4-chloro-6-methoxy-7-[3-(morpholin-4-yl)propoxy]quinoline (1.8 g, 5.34 mmol) and 2,5-difluoro-4-nitrophenol (1.87 g, 10.21 mmol) in 1-methyl-2-pyrrolidinone (20 mL) was added N,N-diisopropylethylamine (1.38 g, 10.68 mmol) dropwise at room temperature under nitrogen atmosphere. The resulted mixture was stirred under nitrogen atmosphere at 140° C. for 16 h. The mixture was allowed to cool down to room temperature. The reaction was quenched with water (100 mL) at room temperature. The resulting mixture was extracted with ethyl acetate (3×100 mL). The combined organic layers were washed with brine (1×150 mL), dried over anhydrous sodium sulfate. After filtration, the filtrate was concentrated under reduced pressure. The residue was purified by silica gel column chromatography, eluted with DCM/methanol (10/1) and concentrated under reduced pressure to afford 4-(2,5-difluoro-4-nitrophenoxy)-6-methoxy-7-[3-(morpholin-4-yl)propoxy]quinoline (1.28 g, 50%) as a brown crude oil. MS ESI calculated for $C_{23}H_{23}F_2N_3O_6$ [M+H]$^+$, 476.16 found 476.15. $^1$H NMR (400 MHz, CD$_3$OD) δ 8.54 (d, J=3.2 Hz, 1H), 8.28 (d, J=6.8 Hz, 1H), 7.56-7.48 (m, 2H), 7.42 (d, J=6.8 Hz, 1H), 6.84 (d, J=5.2 Hz, 1H), 4.28 (d, J=6.4 Hz, 2H), 4.02 (d, J=11.6 Hz, 3H), 3.74 (d, J=6.4 Hz, 5H), 3.32 (d, J=1.6 Hz, 5H), 2.67-2.65 (m, 2H).

Step 3: 2,5-difluoro-4-({6-methoxy-7-[3-(morpholin-4-yl)propoxy]quinolin-4-yl}oxy)aniline To a stirred solution of 4-(2,5-difluoro-4-nitrophenoxy)-6-methoxy-7-[3-(morpholin-4yl)propoxy]quinoline (1.28 g, 2.69 mmol), iron powder (375 mg, 6.730 mmol) and ammonium chloride (288 mg, 5.384 mmol) in tetrahydrofuran (8 mL) was added water (4 mL) at room temperature. The resulting mixture was stirred at 70° C. for 16 h. The mixture was allowed to cool down to room temperature. The reaction was quenched with water (100 mL) at room temperature. The resulting mixture was extracted with ethyl acetate (3×100 mL). The combined organic layers were washed with brine (3×100 mL), dried over anhydrous sodium sulfate. After filtration, the filtrate was concentrated under reduced pressure. The residue was purified by silica gel column chromatography, eluted with dichloromethane/ methyl alcohol (10/1) and concentrated under reduced pressure to afford 2,5-difluoro-4-({6-methoxy-7-[3-(morpholin-4-yl)propoxy]quinolin-4-yl}oxy)aniline (820 mg, 68%) as a brown solid. MS ESI calculated for $C_{23}H_{25}F_2N_3O_4$ [M+H]$^+$, 446.18 found 446.20. $^1$H NMR (400 MHz, CDCl$_3$) δ 8.51 (d, J=5.2 Hz, 1H), 7.57 (s, 1H), 7.47 (s, 1H), 7.02-6.98 (m, 1H), 6.70 (d, J=8.4 Hz, 1H), 6.45 (d, J=1.2 Hz, 1H), 4.30 (d, J=6.8 Hz, 2H), 4.06 (s, 3H), 3.89 (s, 2H), 3.77 (d, J=4.8 Hz, 4H), 2.65 (d, J=7.2 Hz, 2H), 2.56 (s, 4H), 2.18 (d, J=6.8 Hz, 2H).

Step 4: 6-chloro-N-[2,5-difluoro-4-({6-methoxy-7-[3-(morpholin-4-yl)propoxy]quinolin-4-yl}oxy)phenyl]-4-methoxypyridine-3-carboxamide A solution of 6-chloro-4-methoxypyridine-3-carboxylic acid (101 mg, 0.539 mmol) in sulfinyl chloride (260 mg, 0.673 mmol) was stirred at 75° C. for 3 h, to the above mixture was added N,N -diisopropylethylamine (0.3 mL) and 2,5-difluoro-4-({6-methoxy-7-[3-(morpholin-4-yl)propoxy]quinolin-4-yl}oxy)aniline (200 mg, 0.449 mmol) in dichloromethane (3 mL) dropwise at room temperature. The resulting mixture was stirred at room temperature for 4 h. The reaction was quenched with water (50 mL) at room temperature. The resulting mixture was extracted with ethyl acetate (3×50 mL). The combined organic layers were washed with brine (3×50 mL), dried over anhydrous sodium sulfate. After filtration, the filtrate was concentrated under reduced pressure. The residue was purified by Prep-TLC (dichloromethane/methyl alcohol=10/1) and concentrated under reduced pressure to afford 6-chloro-N-[2,5-difluoro-4-({6-methoxy-7-[3 -(morpholin-4-yl)propoxy]-quinolin-4-yl}oxy)phenyl]-4-methoxypyridine-3-carboxamide (200 mg, 72%) as a brown solid. MS ESI calculated for $C_{30}H_{29}ClF_2N_4O_6$ [M+H]$^+$, 615.17, 617.17 found 615.20, 617.20. $^1$H NMR (400 MHz, CDCl$_3$) δ 9.84 (d, J=3.6 Hz, 1H), 9.18 (s, 1H), 8.64 (d, J=7.2 Hz, 1H), 8.52 (d, J=5.2 Hz, 1H), 7.56 (d, J=6.4 Hz, 1H), 7.48 (s, 1H), 7.14 (d, J=6.8 Hz, 1H), 7.08-6.92 (m, 1H), 6.48 (d, J=5.2 Hz, 1H), 4.30 (d, J=2.8 Hz, 2H), 4.20 (s, 2H), 4.06 (d, J=1.6 Hz, 3H), 3.92-3.74 (m, 5H), 2.66 (d, J=7.2 Hz, 2H), 2.58 (s, 4H), 2.28-2.14 (m, 2H).

Step 5: N-[2,5-difluoro-4-({6-methoxy-7-[3-(morpholin-4-yl)propoxy]quinolin-4-yl}oxy)phenyl]-4-methoxy-6-{[(4-methoxyphenyl)methyl]amino}pyridine-3-carboxamide A solution of 6-chloro-N-[2,5-difluoro-4-({6-methoxy-7-[3-(morpholin-4-yl)propoxy]quinolin-4-yl}oxy)-phenyl]-4-methoxypyridine-3-carboxamide (100 mg, 0.163 mmol); (4-methoxyphenyl)methanamine (110 mg, 0.815 mmol); BrettPhos (CAS:1070663-78-3) (17 mg, 0.033 mmol); BrettPhos Pd G3 (CAS:1470372-59-8) (15 mg, 0.016 mmol) and sodium tert -butoxide (32 mg, 0.326 mmol) in 1,4-dioxane (5 ml) was stirred at 90° C. under nitrogen atmosphere for 16 h. The mixture was allowed to cool down to room temperature. The reaction was quenched with water (100 mL) at room temperature. The resulting mixture was extracted with ethyl acetate (3×50 mL). The combined organic layers were washed with brine (3×50 mL), dried over anhydrous sodium sulfate. After filtration, the filtrate was concentrated under reduced pressure. The residue was purified by Prep-TLC (dichloromethane/methyl alcohol=10/1) and concentrated under reduced pressure to afford compound N-[2,5-difluoro-4-({6-methoxy-7-[3-(morpholin-4-yl)propoxy]quinolin-4-yl}oxy)-phenyl]-4-methoxy-6-{[(4-methoxyphenyl)methyl]amino}-pyridine-3-carboxamide (60 mg, 51%) as a brown solid. MS ESI calculated for $C_{38}H_{39}F_2N_5O_7$ [M+H]$^+$, 716.28 found 716.25.

Step 6: 6-amino-N-[2,5-difluoro-4-({6-methoxy-7-[3-(morpholin-4-yl)propoxy]quinolin-4-yl}oxy)phenyl]-4-methoxypyridine-3-carboxamide A solution of N-[2,5-difluoro-4-({6-methoxy-7-[3-(morpholin-4-yl)propoxy]quinolin-4-yl}oxy)phenyl]-4-methoxy-6-{[(4-methoxyphenyl)methyl]amino}pyridine-3-carboxamide (60 mg, 0.084 mmol) and trifluoromethanesulfonic acid (0.5 mL) in dichloromethane (6 mL) was stirred at room temperature under nitrogen atmosphere for 12 h. The reaction was quenched with water (50 mL) at room temperature. The resulting mixture was extracted with ethyl acetate (3×50 mL). The combined organic layers were washed with brine (2×50 mL), dried over anhydrous sodium sulfate. After filtration, the filtrate was concentrated under reduced pressure. The residue was purified by Prep-TLC (dichloromethane/methyl alcohol=10/

1) to afford crude product. The crude product was purified by Prep-HPLC with the following conditions (Column: XBridge Prep OBD C18 Column, 30×15 mm, 5 μm; Mobile Phase A: Water (plus 10 mmol/L ammonium bicarbonate), Mobile Phase B: acetonitrile; Flow rate: 60 mL/min; Gradient: 28% to 38% B in 8 min, 38% B; Wave Length: 254/220 nm) and the fractions containing desired product were collected, concentrated and lyophilized to afford compound 6-amino-N-[2,5-difluoro-4-({6-methoxy-7-[3-(morpholin-4-yl)propoxy]-quinolin-4-yl}oxy)phenyl]-4-methoxypyridine-3-carboxamide (4.2 mg, 8%) as a white solid. MS ESI calculated for $C_{30}H_{31}F_2N_5O_6$ [M+H]$^+$, 596.22 found 596.25. $^1$H NMR (400 MHz, DMSO-d$_6$) δ 9.86 (d, J=2.8 Hz, 1H), 8.52-8.40 (m, 3H), 7.74-7.68 (m, 1H), 7.52 (s, 1H), 7.42 (s, 1H), 6.76 (s, 2H), 6.57 (dd, J=5.2, 1.2 Hz, 1H), 6.13 (s, 1H), 4.22 (d, J=6.4 Hz, 2H), 3.98 (d, J=13.2 Hz, 6H), 3.60 (d, J=4.8 Hz, 4H), 2.47 (d, J=7.2 Hz, 2H), 2.40 (d, J=4.8 Hz, 4H), 1.99 (d, J=6.8 Hz, 2H). $^{19}$F NMR (377 MHz, DMSO -d$_6$) δ −130.61 (1F), −132.70 (1F).

Example 32: 6-amino-N-[2,5-difluoro-4-({6-methoxy-7-[3-(morpholin-4-yl)propoxy]quinolin-4-yl}oxy)phenyl]-4-ethoxypyridine-3-carboxamide

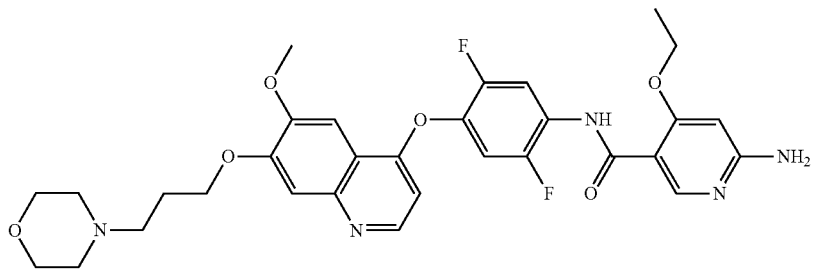 [SMILES: CCOc1cc(N)ncc1C(=O)Nc1cc(F)c(Oc2ccnc3cc(OCCCN4CCOCC4)c(OC)cc23)cc1F]

Synthesized using the similar method as in example 31. White solid. MS ESI calculated for $C_{31}H_{33}F_2N_5O_6$ [M+H]$^+$, 610.24 found 610.25. $^1$H NMR (400 MHz, DMSO-d$_6$) δ 9.98 (s, 1H), 8.62-8.53 (m, 1H), 8.57 (s, 1H), 8.50 (d, J=5.2 Hz, 1H), 7.71 (dd, J=11.2, 7.2 Hz, 1H), 7.52 (s, 1H), 7.42 (s, 1H), 6.77 (s, 2H), 6.57 (d, J=5.2 Hz, 1H), 6.11 (s, 1H), 4.26-4.22 (m, 4H), 3.96 (s, 3H), 3.63-3.57 (m, 4H), 2.50-2.45 (m, 2H), 2.43-2.37 (m, 4H), 2.02-1.95 (m, 2H), 1.55-1.47 (m, 3H). $^{19}$F NMR (376 MHz, DMSO) δ −131.21 (1F), −132.43 (1F).

Example 33: 6-amino-N-[2,3-difluoro-4-({6-methoxy-7-[2-(methylamino)ethoxy]quinolin-4-yl}oxy)phenyl]-4-methoxypyridine-3-carboxamide

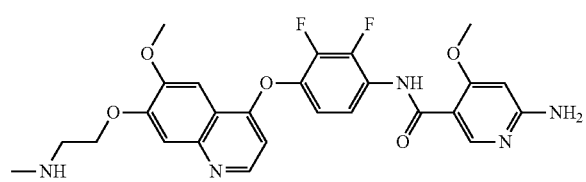 [SMILES: CNCCOc1cc2nccc(Oc3ccc(NC(=O)c4cnc(N)cc4OC)c(F)c3F)c2cc1OC]

Synthesized using the similar method as in example 31. White solid. MS ESI calculated for $C_{26}H_{25}F_2N_5O_5$ [M+H]$^+$, 526.18 found 526.20. $^1$H NMR (400 MHz, DMSO-d$_6$) δ 9.80 (s, 1H), 8.54-8.48 (m, 2H), 8.19-8.04 (m, 1H), 7.54 (s, 1H), 7.44 (s, 1H), 7.38-7.29 (m, 1H), 6.75 (s, 2H), 6.61-6.57 (m, 1H), 6.13 (s, 1H), 4.21 (t, J=5.6 Hz, 2H), 4.01-3.94 (m, 6H), 2.93 (t, J=5.6 Hz, 2H), 2.38 (s, 3H). $^{19}$F NMR (376 MHz, DMSO-d$_6$) δ −147.81 (1F), −153.14 (1F).

Example 34: N-(4-((6,7-dimethoxyquinolin-4-yl)oxy)-3,5-difluorophenyl)-4-methoxypyridine-3-carboxamide

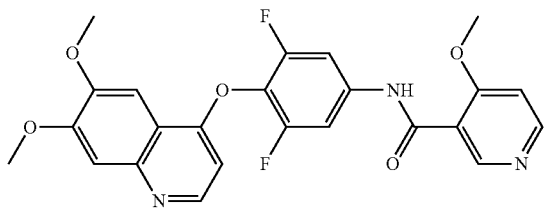

Step 1: 4-(2,6-difluoro-4-nitrophenoxy)-6,7-dimethoxyquinoline

To a stirred mixture of 4-chloro-6,7-dimethoxyquinoline (200 mg, 0.894 mmol) and 2,6-difluoro-4-nitrophenol (187 mg, 1.073 mmol) in 1-methyl-2-pyrrolidinone (5 mL) was added N,N-diisopropylethylamine (346 mg, 2.682 mmol) at room temperature. The resulting mixture was stirred at 140° C. under nitrogen atmosphere for 16 h. The mixture was allowed to cool down to room temperature. The reaction was quenched with water (30 mL) at room temperature. The resulting mixture was extracted with ethyl acetate (3×50 mL). The combined organic layers were washed with brine (1×100 mL), dried over anhydrous sodium sulfate. After filtration, the filtrate was concentrated under reduced pressure. The crude product 4-(2,6-difluoro-4-nitrophenoxy)-6,7-dimethoxyquinoline (330 mg, 90%) was obtained as a brown solid and used in the next step without further purification. MS ESI calculated for $C_{17}H_{12}BrF_2N_2O_5$ [M+H]$^+$, 363.07 found 363.05.

Step 2: 4-[(6,7-dimethoxyquinolin-4-yl)oxy]-3,5-difluoroaniline

To a stirred solution of 4-(2,6-difluoro-4-nitrophenoxy)-6,7-dimethoxyquinoline (330 mg, 0.806 mmol) in tetrahydrofuran (7 mL) and water (7 mL) were added iron powder (225 mg, 4.030 mmol) and ammonium chloride (86 mg, 1.612 mmol) at room temperature. The resulting mixture was stirred at 70° C. for 16 h. The mixture was allowed to cool down to room temperature. The reaction was diluted with water (100 mL) and extracted with ethyl acetate (3×100 mL). The combined organic layers were washed with brine (1×150 mL), dried over anhydrous sodium sulfate. After filtration, the filtrate was concentrated under reduced pressure. The residue was purified by silica gel column chromatography, eluted with petroleum ether/ethyl acetate (1/10). The fractions containing desired product were collected and dried under reduced pressure to afford 4-[(6,7-dimethoxyquinolin-4-yl)oxy]-3,5-difluoroaniline (180 mg, 67%) as a yellow solid. MS ESI calculated for $C_{17}H_{14}F_2N_2O_3$ [M+H]$^+$, 333.10 found 333.10; $^1$H NMR (400 MHz, DMSO-d$_6$) δ 8.49 (d, J=5.2 Hz, 1H), 7.51 (s, 1H), 7.41 (s, 1H), 6.51 (d, J=5.2 Hz, 1H), 6.43 (s, 1H), 6.39 (s, 1H), 5.82 (s, 2H), 3.95 (s, 6H). $^{19}$F NMR (37 MHz, DMSO-d$_6$) δ −129.14 (2F).

Step 3: N-{4-[(6,7-dimethoxyquinolin-4-yl)oxy]-3,5-difluorophenyl}-4-methoxypyridine-3-carboxamide To a stirred mixture of 4-methoxypyridine-3-carboxylic acid (92 mg, 0.600 mmol) and O-(7-azabenzotriazol-1-yl)-N,N,N',N'-tetramethyluronium hexafluorophosphate (171 mg, 0.450 mmol) in N,N-dimethylformamide (1 mL) was added N,N-diisopropylethylamine (78 mg, 0.600 mmol) and 4-[(6,7-dimethoxyquinolin-4-yl)oxy]-3,5-difluoroaniline (50 mg, 0.150 mmol) at room temperature. The mixture was stirred at room temperature for 16 h. The reaction was quenched with water (100 mL) at room temperature. The resulting mixture was extracted with ethyl acetate (3×50 mL). The combined organic layers were washed with brine (1×80 mL), dried over anhydrous sodium sulfate. After filtration, the filtrate was concentrated under reduced pressure. The residue was purified by reverse flash chromatography with the following conditions: Column: C18 Column 120 g; Mobile Phase A: water (plus 10 mmol/L ammonium bicarbonate), Mobile Phase B: acetonitrile; Flow rate: 80 mL/min; Gradient: 40% to 80% B in 30 min; Detector: UV 220/254 nm. The fractions containing desired product were collected, concentrated and lyophilized to afford N-{4-[(6,7-dimethoxyquinolin-4-yl)oxy]-3,5-difluorophenyl}-4-methoxypyridine-3-carboxamide (22 mg, 31%) as a white solid. MS ESI calculated for $C_{24}H_{19}F_2N_3O_5$ [M+H]$^+$, 468.13 found 468.15. $^1$H NMR (400 MHz, DMSO-d$_6$) δ 10.71 (s, 1H), 8.68-8.55 (m, 2H), 8.51 (d, J=5.2 Hz, 1H), 7.81-7.71 (m, 2H), 7.56 (s, 1H), 7.44 (s, 1H), 7.28 (d, J=6.0 Hz, 1H), 6.62 (d, J=5.2 Hz, 1H), 3.99-3.96 (m, 9H). $^{19}$F NMR (376 MHz, DMSO-d$_6$) δ −126.56 (2F).

Example 35: N-{3,5-difluoro-4-[(7-methoxyquinolin-4-yl)oxy]phenyl}-4-methoxypyridine-3-carboxamide

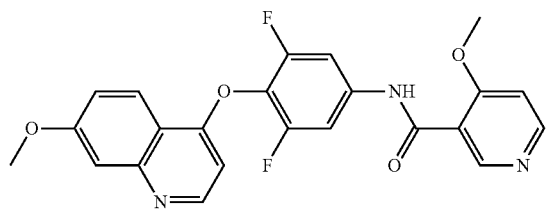

Synthesized using the similar method as in example 34. White solid. MS ESI calculated for $C_{23}H_{17}F_2N_3O_4$ [M+H]$^+$, 437.12 found 438.20. $^1$H NMR (400 MHz, DMSO-d$_6$) δ 10.71 (s, 1H), 8.68-8.59 (m, 3H), 8.27 (d, J=9.2 Hz, 1H), 7.81-7.71 (m, 2H), 7.46 (d, J=2.4 Hz, 1H), 7.35-7.18 (m, 2H), 6.67-6.61 (m, 1H), 3.97 (d, J=5.2 Hz, 6H). $^{19}$F NMR (376 MHz, DMSO-d$_6$) δ −127.17 (2F).

Example 36: N-{3,5-difluoro-4-[(7-methoxy-1,6-naphthyridin-4-yl)oxy]phenyl}-4-methoxypyridine-3-carboxamide

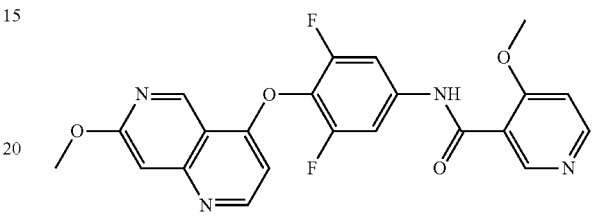

Synthesized using the similar method as in example 34. Off-white solid. MS ESI calculated for $C_{22}H_{16}F_2N_4O_4$ [M+H]$^+$, 439.11 found 439.10. $^1$H NMR (400 MHz, DMSO-d$_6$) δ 10.72 (s, 1H), 9.51 (s, 1H), 8.82 (d, J=5.2 Hz, 1H), 8.64 (s, 1H), 8.62 (d, J=6.0 Hz), 7.83-7.73 (m, 2H), 7.32-7.28 (m, 2H), 6.73 (d, J=5.2 Hz, 1H), 4.04 (s, 3H), 3.98 (s, 3H). $^{19}$F NMR (377 MHz, DMSO-d$_6$) δ −126.63 (2F).

Example 37: N-(3,5-difluoro-4-((6-methoxy-7-(trifluoromethoxy)quinolin-4-yl)oxy)phenyl)-4-methoxypyridine-3-carboxamide

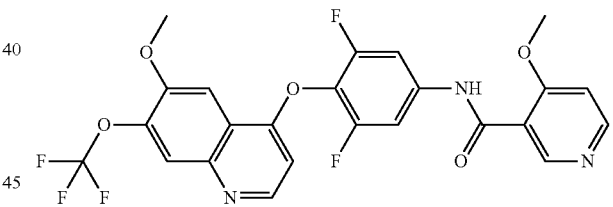

Step 1: 7-(bromodifluoromethoxy)-4-chloro-6-methoxyquinoline

To a stirred mixture of 4-chloro-6-methoxyquinolin-7-ol (1.20 g, 5.72 mmol) and potassium carbonate (2.37 g, 17.17 mmol) in N,N-dimethylformamide (120 mL) was added dibromodifluoromethane (2.40 g, 11.44 mmol) at −60° C. The resulting mixture was stirred at 100° C. for 2 h. The mixture was allowed to cool down to room temperature. The resulting mixture was diluted with water (300 mL). The resulting mixture was extracted with ethyl acetate (3×300 mL), dried over anhydrous sodium sulfate. After filtration, the filtrate was concentrated under reduced pressure. The residue was purified by silica gel column chromatography, eluted with petroleum ether/ethyl acetate (1/1) concentrated under reduced pressure to afford 7-(bromodifluoromethoxy)-4-chloro-6-methoxyquinoline (238.2 mg, 12%) as a white solid. MS ESI calculated for $C_{11}H_7BrClF_2NO_2$ [M+H]$^+$, 337.90, 339.90 found 338.10, 340.10. $^1$H NMR (400 MHz, CDCl$_3$) δ 8.72 (d, J=4.8 Hz, 1H), 8.11 (d, J=1.8 Hz, 1H), 7.59 (s, 1H), 7.55 (s, 1H), 4.09 (s, 3H).

Step 2:
4-chloro-6-methoxy-7-(trifluoromethoxy)quinoline

A mixture of 7-(bromodifluoromethoxy)-4-chloro-6-methoxyquinoline (238 mg, 0.704 mmol) and silver tetrafluoroborate (274 mg, 1.408 mmol) in dichloromethane (1 mL) was stirred at room temperature for 2 h. The resulting mixture was concentrated under reduced pressure. The residue was purified by reverse phase Flash chromatography with the following conditions: Column: WelFlash™ C18-I, 20-40 µm, 120 g; Eluent A: Water (plus 10 mmol/L ammonium bicarbonate); Eluent B: acetonitrile; Gradient: 65% to 85% B in 25 min; Flow rate: 60 mL/min; Detector: 220/254 nm; desired fractions were collected and concentrated under reduced pressure to afford 4-chloro-6-methoxy-7-(trifluoromethoxy)quinoline (130 mg, 66%) as a white solid. MS ESI calculated for C$_{11}$H$_7$ClF$_3$NO$_2$ [M+H]$^+$, 278.01, 280.01 found 278.20, 280.20. $^1$H NMR (400 MHz, CDCl$_3$) δ 8.71 (d, J=4.8 Hz, 1H), 8.04 (d, J=1.6 Hz, 1H), 7.56 (s, 1H), 7.54 (s, 1H), 4.09 (s, 3H).

Step 3: 4-(2,6-difluoro-4-nitrophenoxy)-6-methoxy-7-(trifluoromethoxy)quinoline

To a stirred mixture of 4-chloro-6-methoxy-7-(trifluoromethoxy)quinoline (100 mg, 0.360 mmol) and 2,6-difluoro-4-nitrophenol (75 mg, 0.432 mmol) in 1-methyl-2-pyrrolidinone (2 mL) was added N,N-diisopropylethylamine (93 mg, 0.720 mmol) at room temperature. The resulting mixture was stirred at 140° C. for 16 h. The mixture was allowed to cool down to room temperature. The residue was purified by reverse phase Flash chromatography with the following conditions: Column: WelFlash™ C18-I, 20-40 µm, 120 g; Eluent A: Water (plus 10 mmol/L ammonium bicarbonate); Eluent B: acetonitrile; Gradient: 25% to 45% B in 25 min; Flow rate: 60 mL/min; Detector: 220/254 nm; desired fractions were collected and concentrated under reduced pressure to afford 4-(2,6-difluoro-4-nitrophenoxy)-6-methoxy-7-(trifluoromethoxy)quinoline (111 mg, 74%) as a yellow solid. MS ESI calculated for C$_{17}$H$_9$F$_5$N$_2$O$_5$ [M+H]$^+$, 417.04 found 417.25. $^1$H NMR (400 MHz, CDCl$_3$) δ 8.68 (d, J=5.2 Hz, 1H), 8.14-8.10 (m, 3H), 7.72 (s, 1H), 7.28 (s, 1H), 4.11 (s, 3H).

Step 4: 3,5-difluoro-4-{[6-methoxy-7-(trifluoromethoxy)quinolin-4-yl]oxy}aniline To a stirred mixture of 4-(2,6-difluoro-4-nitrophenoxy)-6-methoxy-7-(trifluoromethoxy)quinoline (111 mg, 0.267 mmol) and Fe (74 mg, 1.335 mmol) in tetrahydrofuran (2 mL) and water (1 mL) was added ammonium chloride (28 mg, 0.534 mmol) at room temperature. The resulting mixture was stirred at 70° C. for 16 h. The mixture was allowed to cool down to room temperature. The resulting mixture was concentrated under reduced pressure. The residue was purified by reverse phase Flash chromatography with the following conditions: Column: WelFlash™ C18-I, 20-40 µm, 120 g; Eluent A: Water (plus 10 mmol/L ammonium bicarbonate); Eluent B: acetonitrile; Gradient: 65% to 85% B in 25 min; Flow rate: 60 mL/min; Detector: 220/254 nm; desired fractions were collected and concentrated under reduced pressure to afford 3,5-difluoro-4-{[6-methoxy-7-(trifluoromethoxy)quinolin-4-yl]oxy}aniline (93 mg, 90%) as a yellow solid. MS ESI calculated for C$_{17}$H$_{11}$F$_5$N$_2$O$_3$ [M+H]$^+$, 387.27 found 387.30.

Step 5: N-(3,5-difluoro-4-{[6-methoxy-7-(trifluoromethoxy)quinolin-4-yl]oxy}phenyl)-4-methoxypyridine-3-carboxamide To a stirred mixture of 3,5-difluoro-4-{[6-methoxy-7-(trifluoromethoxy)quinolin-4-yl]oxy}aniline (90 mg, 0.233 mmol) and 4-methoxypyridine-3-carboxylic acid (71 mg, 0.466 mmol) in N,N-dimethylformamide (2 mL) was added O-(7-azabenzotriazol-1-yl)-N,N,N',N'-tetramethyluronium hexafluorophosphate (132 mg, 0.350 mmol) and N,N-diisopropylethylamine (90 mg, 0.699 mmol) at room temperature. The resulting mixture was stirred at room temperature for 16 h. The crude product was purified by Prep-HPLC with the following conditions (Column: XBridge Prep OBD C18 Column, 30*150 mm, 5 µm; Mobile Phase A: Water (plus 10 mmol/L ammonium bicarbonate), Mobile Phase B: acetonitrile; Flow rate: 60 mL/min; Gradient: 45% to 55% B in 8 min, 55% B; Wavelength: 254/220 nm; RTI(min): 7; Number of Runs: 0). The fractions containing desired product were collected, concentrated and lyophilized to afford N-(3,5-difluoro-4-{[6-methoxy-7-(trifluoromethoxy)quinolin-4-yl]oxy}phenyl)-4-methoxypyridine -3-carboxamide (13.5 mg, 11%) as a white solid. MS ESI calculated for C$_{24}$H$_{16}$F$_5$N$_3$O$_5$ [M+H]$^+$, 522.10 found 522.25. $^1$H NMR (400 MHz, DMSO-d$_6$) δ 10.71 (s, 1H), 8.73-8.53 (m, 3H), 8.08-8.03 (m, 1H), 7.85 (s, 1H), 7.78 (d, J=10.4 Hz, 2H), 7.28 (d, J=5.8 Hz, 1H), 6.87 (d, J=5.2 Hz, 1H), 4.08 (s, 3H), 3.98 (s, 3H). $^{19}$F NMR (376 MHz, DMSO-d$_6$) δ −57.01 (2F), −128.45 (3F).

Example 38: N-(4-((7-(difluoromethoxy)-6-methoxyquinolin-4-yl)oxy)-3,5-difluorophenyl)-4-methoxypyridine-3-carboxamide

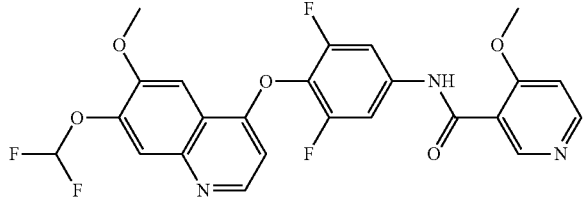 [SMILES: COc1cc2c(Oc3c(F)cc(NC(=O)c4cnccc4OC)cc3F)ccnc2cc1OC(F)F]

Step 1:
4-chloro-7-(difluoromethoxy)-6-methoxyquinoline

To a stirred solution of 4-chloro-6-methoxyquinolin-7-ol (500 mg, 2.385 mmol) and sodium 2-chloro-2,2-difluoroacetate (727 mg, 4.770 mmol) in N,N-dimethylformamide (5 mL) and water (0.5 mL) was added potassium carbonate (495 mg, 3.577 mmol) in portions at room temperature. The resulting mixture was stirred at 120° C. for 45 min. The mixture was allowed to cool down to room temperature. The residue was purified by reverse phase Flash chromatography with the following conditions: Column: WelFlash™ C18-I, 20-40 µm, 80 g; Eluent A: water (plus 10 mmol/L ammonium bicarbonate); Eluent B: acetonitrile; Gradient: 25% to 45% B in 25 min; Flow rate: 60 mL/min; Detector: UV 220/254 nm; desired fractions were collected at 42% B and concentrated under reduced pressure to afford 4-chloro-7-(difluoromethoxy)-6-methoxyquinoline (69 mg, 11%) as a brown solid. MS ESI calculated for C₁₁H₈ClF₂NO₂ [M+H]⁺, 260.60 found 260.20.

Step 2: 4-(2,6-difluoro-4-nitrophenoxy)-7-(difluoromethoxy)-6-methoxyquinoline

To a stirred solution of 4-chloro-7-(difluoromethoxy)-6-methoxyquinoline (90 mg, 0.347 mmol) and 2,6-difluoro-4-nitrophenol (61 mg, 0.347 mmol) in 1-methyl-2-pyrrolidinone (0.5 mL) was added N,N-diisopropylethylamine (134 mg, 1.041 mmol) dropwise at room temperature. The resulting mixture was stirred at 140° C. for 16 h. The mixture was allowed to cool down to room temperature. The residue was purified by reverse phase Flash chromatography with the following conditions: Column: WelFlash™ C18-I, 20-40 μm, 40 g; Eluent A: water (plus 10 mmol/L ammonium bicarbonate); Eluent B: acetonitrile; Gradient: 30% to 60% B in 25 min; Flow rate: 60 mL/min; Detector: UV 220/254 nm; desired fractions were collected and concentrated under reduced pressure to afford 4-(2,6-difluoro-4-nitrophenoxy)-7-(difluoromethoxy)-6-methoxyquinoline (47 mg, 34%) as a brown solid. MS ESI calculated for C₁₇H₁₀F₄N₂O₅ [M+H]⁺, 399.30 found 399.25. ¹H NMR (400 MHz, CDCl₃) δ 8.64 (d, J=5.2 Hz, 1H), 8.14-8.04 (m, 2H), 7.88 (s, 1H), 7.69 (s, 1H), 6.97-6.57 (m, 1H), 6.51 (d, J=5.2 Hz, 1H), 4.10 (s, 3H).

Step 3: 4-{[7-(difluoromethoxy)-6-methoxyquinolin-4-yl]oxy}-3,5-difluoroaniline

To a stirred solution of 4-(2,6-difluoro-4-nitrophenoxy)-7-(difluoromethoxy)-6-methoxyquinoline (47 mg, 0.118 mmol) and iron powder (27 mg, 0.472 mmol) in tetrahydrofuran (0.5 mL) and water (0.1 mL) was added ammonium chloride (32 mg, 0.590 mmol) in portions at room temperature. The resulting mixture was stirred at 70° C. for 16 h. The mixture was allowed to cool down to room temperature. The resulting mixture was filtered. The resulting mixture was filtered, the filter cake was washed with dichloromethane (3×100 mL). The filtrate was concentrated under reduced pressure to afford 4-{[7-(difluoromethoxy)-6-methoxyquinolin-4-yl]oxy}-3,5-difluoroaniline (15 mg, 35%) as a light yellow solid. MS ESI calculated for C₁₇H₁₂F₄N₂O₃ [M+H]⁺, 369.30 found 369.25. ¹H NMR (400 MHz, CDCl₃) δ 8.62 (d, J=5.2 Hz, 1H), 7.99 (s, 1H), 7.76 (s, 1H), 6.98-6.42 (m, 2H), 6.42-6.37 (m, 2H), 4.10 (s, 3H).

Step 4: N-(4-{[7-(difluoromethoxy)-6-methoxyquinolin-4-yl]oxy}-3,5-difluorophenyl)-4-methoxypyridine-3-carboxamide To a stirred solution of 4-{[7-(difluoromethoxy)-6-methoxyquinolin-4-yl]oxy}-3,5-difluoroaniline (15 mg, 0.041 mmol), 4-methoxypyridine-3-carboxylic acid (8 mg, 0.049 mmol) and O-(7-Azabenzotriazol-1-yl)-N,N,N,N-tetramethyluronium hexafluorophosphate (24 mg, 0.061 mmol) in N,N-dimethylformamide (0.5 mL) was added N,N-diisopropylethylamine (16 mg, 0.123 mmol) at room temperature. The resulting mixture was stirred at room temperature for 16 h. The crude product was purified by Prep-HPLC with the following conditions (Column: Xselect CSH C18 OBD Column 30×150mm 5 μm; Mobile Phase A: water (plus 10 mmol/L ammonium bicarbonate), Mobile Phase B: acetonitrile; Flow rate: plus 60 mL/min; Gradient: 25% to 30% B in 12 min; Detector: UV 220/254 nm;). The fractions containing desired product were collected, concentrated, and lyophilized to afford N-(4-{[7-(difluoromethoxy)methoxyquinolin-4-yl]oxy}-3,5-difluorophenyl)-4-methoxypyridine-3-carboxamide (2 mg, 8%) as an off-white solid. MS ESI calculated for C₂₄H₁₇F₄N₃O₅ [M+H]⁺, 504.40 found 504.10. ¹H NMR (400 MHz, DMSO-d₆) δ 10.75 (s, 1H), 8.66-8.59 (m, 3H), 7.83-7.73 (m, 4H), 7.66-7.26 (m, 2H), 6.79 (d, J=5.2 Hz, 1H), 4.04 (s, 3H), 3.97 (s, 3H). ¹⁹F NMR (376 MHz, DMSO-d₆) δ −82.82 (2F), −126.56 (2F).

Example 39: N-(3,5-difluoro-4-((7-(2-hydroxy-2-methylpropoxy)-6-methoxyquinolin-4-yl)oxy)phenyl)-4-methoxypyridine-3-carboxamide

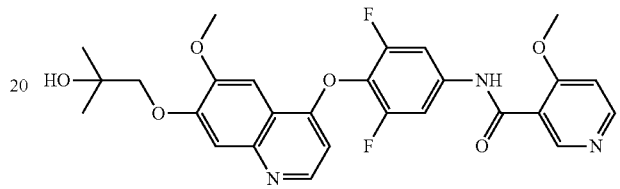

Step 1: 1-[(4-chloro-6-methoxyquinolin-7-yl)oxy]-2-methylpropan-2-ol

To a stirred mixture of 4-chloro-6-methoxyquinolin-7-ol (500 mg, 2.385 mmol) and potassium carbonate (659 mg, 4.770 mmol) in N,N-dimethylformamide was added 2,2-dimethyloxirane (206 mg, 2.862 mmol) in portions at room temperature. The resulting mixture was stirred at 120 ° C. for 2 h. The mixture was allowed to cool down to room temperature. The residue was purified by reverse phase Flash chromatography with the following conditions: Column: WelFlash™ C18-I, 20-40 μm, 80 g; Eluent A: water (plus 10 mmol/L ammonium bicarbonate); Eluent B: acetonitrile; Gradient: 25% to 45% B in 25 min; Flow rate: 50 mL/min; Detector: UV 220/254 nm; desired fractions were collected and concentrated under reduced pressure to afford 1-[(4-chloro-6-methoxyquinolin-7-yl)oxy]-2-methylpropan-2-ol (354 mg, 52%) as a yellow oil. MS ESI calculated for C₁₄H₁₆ClNO₃ [M+H]⁺, 282.08, 284.08 found 282.05, 284.05. ¹H NMR (400 MHz, CDCl₃) δ 8.59 (d, J=4.8 Hz, 1H), 7.42 (s, 1H), 7.41 (s, 1H), 7.37 (d, J=4.8 Hz, 1H), 4.04 (s, 3H), 4.00 (s, 2H), 1.43 (s, 6H).

Step 2: 1-{[4-(2,6-difluoro-4-nitrophenoxy)-6-methoxyquinolin-7-yl]oxy}-2-methylpropan-2-ol To a stirred mixture of 1-[(4-chloro-6-methoxyquinolin-7-yl)oxy]-2-methylpropan-2-ol (350 mg, 1.242 mmol) and 2,6-difluoro-4-nitrophenol (217 mg, 1.242 mmol) in 1-methyl-2-pyrrolidinone was added N,N-diisopropylethylamine (321 mg, 2.484 mmol) at room temperature. The resulting mixture was stirred at 140° C. for 16 h. The mixture was allowed to cool down to room temperature. The residue was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 35% to 75% B in 25 min; Flow rate: 60 mL/min; Detector: UV 220/254 nm; desired fractions were collected and concentrated under reduced pressure to afford 1-{[4-(2,6-difluoro-4-nitrophenoxy)-6-methoxyquinolin-7-yl]oxy}-2-methylpropan-2-ol (250 mg, 47%) as a brown oil. MS ESI calculated for $C_{20}H_{18}F_2N_2O_6$ [M+H]$^+$, 421.37 found 421.30. $^1$H NMR (400 MHz, CDCl$_3$) δ 8.55 (d, J=5.2 Hz, 1H), 8.02-8.12 (m, 2H), 7.56 (s, 1H), 7.47 (s, 1H), 6.42 (d, J=5.2 Hz, 1H), 4.06 (s, 3H), 4.02 (s, 2H), 1.44 (s, 6H).

Step 3: 1-{[4-(4-amino-2,6-difluorophenoxy)-6-methoxyquinolin-7-yl]oxy}-2-methylpropan-2-ol To a stirred mixture of 1-{[4-(2,6-difluoro-4-nitrophenoxy)-6-methoxyquinolin-7-yl]oxy}-2-methylpropan-2-ol (250 mg, 0.595 mmol) and iron powder (166 mg, 2.975 mmol) was added ammonium bicarbonate (63 mg, 1.190 mmol) and water (2 mL) at room temperature. The resulting mixture was stirred at 70° C. for 16 h. The mixture was allowed to cool down to room temperature. The resulting mixture was concentrated under reduced pressure. The resulting mixture was filtered, the filter cake was washed with methanol (3×10 mL). The filtrate was concentrated under reduced pressure. The residue was purified by reverse phase Flash chromatography with the following conditions: Column: WelFlash™ C18-I, 20-40 μm, 80 g; Eluent A: water (plus 10 mmol/L ammonium bicarbonate); Eluent B: acetonitrile; Gradient: 45% to 65% B in 25 min; Flow rate: 50 mL/min; Detector: UV 220/254 nm; desired fractions were collected and concentrated under reduced pressure to afford 1-{[4-(4-amino-2,6-difluorophenoxy)-6-methoxyquinolin-7-yl]oxy}-2-methylpropan-2-ol (136 mg, 58%) as a brown solid. MS ESI calculated for $C_{20}H_{20}F_2N_2O_4$ [M+H]$^+$, 391.14 found 391.35. $^1$H NMR (400 MHz, CDCl$_3$) δ 8.52 (d, J=5.2 Hz, 1H), 7.62 (s, 1H), 7.46 (s, 1H), 6.49 (d, J=5.2 Hz, 1H), 6.33-6.43 (m, 2H), 4.05 (s, 3H), 4.02 (s, 2H), 1.43 (s, 6H).

Step 4: N-(3,5-difluoro-4-{[7-(2-hydroxy-2-methylpropoxy)-6-methoxyquinolin-4-yl]oxy}phenyl)-4-methoxypyridine-3-carboxamide To a stirred mixture of 1-{[4-(4-amino-2,6-difluorophenoxy)-6-methoxyquinolin-7-yl]oxy}-2-methylpropan-2-ol (136 mg, 0.348 mmol) and 4-methoxypyridine-3-carboxylic acid (64 mg, 0.418 mmol) in N,N-dimethylformamide was added O-(7-Azabenzotriazol-1-yl)-N,N,N',N'-tetramethyluronium hexafluoro-phosphate (198 mg, 0.522 mmol) and N,N-diisopropylethylamine (180 mg, 1.392 mmol) at room temperature. The resulting mixture was stirred at room temperature for 16 h. The mixture was purified by Prep-HPLC with the following conditions (Column: XBridge Shield RP18 OBD Column, 19×250 mm, 10 μm; Mobile Phase A: water (plus 10 mmol/L ammonium bicarbonate), Mobile Phase B: methanol; Flow rate: 25 mL/min; Gradient: 44% to 64% B in 8 min; Detector: UV 220/254 nm;) and concentrated under reduced pressure to afford compound N-(3,5-difluoro-4-{[7-(2-hydroxy-2-methylpropoxy)-6-methoxy -quinolin-4-yl]oxy}-phenyl)-4-methoxypyridine-3-carboxamide (23 mg, 12%) as a white solid. MS ESI calculated for $C_{27}H_{25}F_2N_3O_6$ [M+H]$^+$, 526.51 found 526.25. $^1$H NMR (400 MHz, DMSO-d$_6$) δ 10.69 (s, 1H) 8.64 (s, 1H), 8.62 (d, J=6.0 Hz), 8.50 (d, J=5.2 Hz, 1H), 7.80-7.72 (m, 2H), 7.57 (s, 1H), 7.42 (s, 1H), 7.28 (d, J=6.0 Hz, 1H), 6.61 (d, J=5.2 Hz, 1H), 4.68 (s, 1H), 3.99 (s, 3H), 3.98 (s, 3H), 3.92 (s, 2H), 1.28 (s, 6H). $^{19}$F NMR (377 MHz, DMSO-d$_6$) δ –126.58 (2F).

Example 40: N-(3,5-difluoro-4-{[7-(2-hydroxy-2-methylpropoxy)quinolin-4-yl]oxy}phenyl)-4-methoxypyridine-3-carboxamide

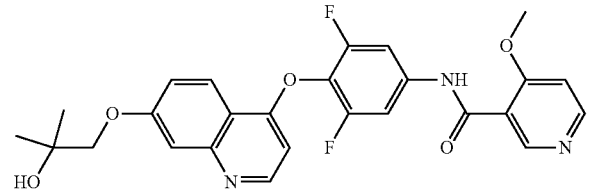 [SMILES: COc1ccncc1C(=O)Nc1cc(F)c(Oc2ccnc3cc(OCC(C)(C)O)ccc23)c(F)c1]

Synthesized using the similar method as in example 39. white solid. MS ESI calculated for $C_{26}H_{23}F_2N_3O_5$ [M+H]$^+$, 496.16 found 496.20. $^1$H NMR (400 MHz, DMSO-d$_6$) δ 10.71 (s, 1H), 8.64 (d, J=5.2 Hz, 1H), 8.64 (s, 1H), 8.62 (d, J=6.0 Hz, 1H), 8.27 (d, J=9.2 Hz, 1H), 7.81-7.71 (m, 2H), 7.42 (d, J=2.4 Hz, 1H), 7.37 (dd, J=9.2, 2.4 Hz, 1H), 7.28 (d, J=6.0 Hz, 1H), 6.63 (d, J=5.2 Hz, 1H), 4.74 (s, 1H), 3.97 (s, 3H), 3.93 (s, 2H), 1.27 (s, 6H). $^{19}$F NMR (376 MHz, DMSO-d$_6$) δ –126.51 (2F).

Example 41: N-(3,5-difluoro-4-((7-(2-hydroxyethoxy)quinolin-4-yl)oxy)phenyl)-4-methoxypyridine-3-carboxamide

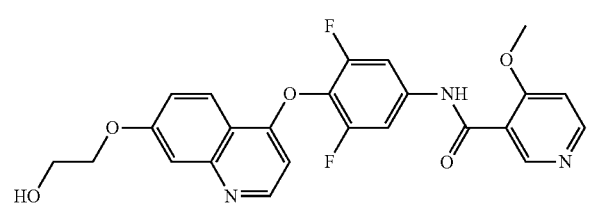 [SMILES: COc1ccncc1C(=O)Nc1cc(F)c(Oc2ccnc3cc(OCCO)ccc23)c(F)c1]

Step 1: 2-[(4-chloroquinolin-7-yl)oxy]ethanol

To a stirred mixture of 4-chloroquinolin-7-ol (300 mg, 1.670 mmol) and triphenylphosphine (657 mg, 2.505 mmol) in tetrahydrofuran (5 mL) was added diisopropyl azodicarboxylate (675 mg, 3.340 mmol) and ethylene glycol (124 mg, 2.004 mmol) at 0° C. The resulting mixture was stirred at room temperature for 16 h. The resulting mixture was concentrated under reduced pressure. The residue was purified by silica gel column chromatography, eluted with petroleum ether/ethyl acetate (1/2) concentrated under reduced pressure to afford 2-[(4-chloroquinolin-7-yl)oxy]ethanol (200 mg, 53%) as a light yellow oil. MS ESI calculated for $C_{11}H_{10}ClNO_2$ [M+H]$^+$. 224.04, 226.04 found 224.10, 226.10. $^1$H NMR (400 MHz, CDCl$_3$) δ 8.68 (d, J=4.8 Hz, 1H), 8.14 (d, J=9.2 Hz, 1H), 7.67 (d, J=1.4 Hz, 1H), 7.52-7.51 (m, 1H), 7.38 (d, J=4.8 Hz, 1H), 4.27 (dd, J=5.2, 4.2 Hz, 2H), 4.10-4.06 (m, 2H).

Step 2: 2-{[4-(2,6-difluoro-4-nitrophenoxy)quinolin-7-yl]oxy}ethanol

To a stirred mixture of 2-[(4-chloroquinolin-7-yl)oxy] ethanol (200 mg, 0.894 mmol) and 2,6-difluoro-4-nitrophenol (188 mg, 1.073 mmol,) in 1-methyl-2-pyrrolidinone (4 mL) was added N, N-diisopropylethylamine (173 mg, 1.341 mmol) at room temperature. The resulting mixture was stirred at 100° C. for 16 h. The mixture was allowed to cool down to room temperature. The residue was purified by reverse phase Flash chromatography with the following conditions: Column: WelFlash™ C18-I, 20-40 μm, 120 g; Eluent A: Water (plus 10 mmol/L ammonium bicarbonate); Eluent B: acetonitrile; Gradient: 30% to 45% B in 15 min; Detector: UV 254/220 nm. The fractions containing desired product were collected, concentrated, and lyophilized to afford 2-{[4-(2,6-difluoro-4-nitrophenoxy)quinolin-7-yl]oxy}ethanol (200 mg, 62%) as a yellow solid. MS ESI calculated for $C_{17}H_{12}F_2N_2O_5$ [M+H]$^+$, 363.07 found 363.05. $^1$H NMR (400 MHz, CDCl$_3$) δ 8.70 (d, J=5.4 Hz, 1H), 8.30 (s, 1H), 8.10 (d, J=3.4 Hz, 1H), 7.72 (d, J=1.8 Hz, 1H), 7.55 (d, J=1.6 Hz, 1H), 7.51 (d, J=2.8 Hz, 1H), 7.38 (dd, J=9.2, 2.4 Hz, 1H), 4.34-4.30 (m, 2H), 4.13-4.08 (m, 2H). $^{19}$F NMR (377 MHz, CDCl$_3$) δ −119.75 (2F).

Step 3: 2-{[4-(4-amino-2,6-difluorophenoxy)quinolin-7-yl]oxy}ethanol

To a stirred mixture of 2-{[4-(2,6-difluoro-4-nitrophenoxy)quinolin-7-yl]oxy}ethanol (200 mg, 0.552 mmol) in water (1 mL) and tetrahydrofuran (2 mL) were added Fe (154 mg, 2.760 mmol) and ammonium chloride (59 mg, 1.104 mmol) at room temperature. The resulting mixture was stirred at 70° C. for 16 h. The residue was purified by reverse phase Flash chromatography with the following conditions: Column: WelFlash™ C18-I, 20-40 μm, 120 g; Eluent A: Water (plus 10 mmol/L ammonium bicarbonate); Eluent B: acetonitrile; Gradient: 30% to 50% B in 25 min; Detector: UV 254/220 nm. The fractions containing desired product were collected, concentrated under reduced pressure to afford 2-{[4-(4-amino-2,6-difluorophenoxy)quinolin-7-yl]oxy}ethanol (50 mg, 27%) as a white solid. MS ESI calculated for $C_{17}H_{14}F_2N_2O_3$ [M+H]$^+$, 332.10 found 333.05. $^1$H NMR (400 MHz, DMSO-d$_6$) δ 8.62 (d, J=5.2 Hz, 1H), 8.22 (d, J=9.2 Hz, 1H), 7.45-7.41 (m, 1H), 7.31 (dd, J=9.2, 2.4 Hz, 1H), 6.52 (dd, J=5.2, 1.2 Hz, 1H), 6.45-6.39 (m, 1H), 5.83 (s, 1H), 4.32-4.27 (m, 2H), 3.78-3.73 (m, 2H), 3.35 (s, 2H). $^{19}$F NMR (377 MHz, DMSO-d$_6$) δ −129.34 (2F).

Step 4: N-(3,5-difluoro-4-{[7-(2-hydroxyethoxy)quinolin-4-yl]oxy}phenyl)-4-methoxypyridine-3-carboxamide To a stirred mixture of 4-methoxypyridine-3-carboxylic acid (27 mg, 0.180 mmol) and O-(7-azabenzotriazol-1-yl)-N,N,N',N'-tetramethyluronium hexafluorophosphate (86 mg, 0.225 mmol) in N,N-dimethylformamide (2 mL) were added N,N-diisopropylethylamine (49 mg, 0.375 mmol) and 2-{[4-(4-amino-2,6-difluorophenoxy)quinolin-7-yl]oxy}ethanol (50 mg, 0.150 mmol) at room temperature. The resulting mixture was stirred at 70° C. for 16 h. The crude product was purified by Prep-HPLC with the following conditions (Column: XBridge Shield RP18 OBD Column, 19×250 mm, 10 μm; Mobile Phase A: Water (10 mmol/L ammonium bicarbonate), Mobile Phase B: acetonitrile; Flow rate: 25 mL/min; Gradient: 42% to 45% B in 4.5 min; Detector: UV 254/220 nm. The fractions containing desired product were collected, concentrated, and lyophilized to afford N-(3,5-difluoro-4-{[7-(2-hydroxyethoxy)quinolin-4-yl]oxy}phenyl)-4-methoxypyridine-3-carboxamide (1.3 mg, 2%) as a white solid. MS ESI calculated for $C_{24}H_{19}F_2N_3O_5$ [M+H]$^+$, 468.13 found 468.15. $^1$H NMR (400 MHz, DMSO-d$_6$) δ 10.71 (s, 1H), 8.69-8.59 (m, 3H), 8.27 (d, J=9.1 Hz, 1H), 7.80-7.71 (m, 2H), 7.45 (d, J=2.4 Hz, 1H), 7.35 (dd, J=9.2, 2.4 Hz, 1H), 7.28 (d, J=5.8 Hz, 1H), 6.63 (d, J=5.2 Hz, 1H), 4.98 (t, J=5.4 Hz, 1H), 4.20 (t, J=4.8 Hz, 2H), 3.97 (s, 3H), 3.88-3.82 (m, 2H). $^{19}$F NMR (376 MHz, DMSO-d$_6$) δ −126.76(2F).

Example 42: N-(3,5-difluoro-4-{[7-(2-methoxyethoxy)quinolin-4-yl]oxy}phenyl)-4-methoxypyridine-3-carboxamide

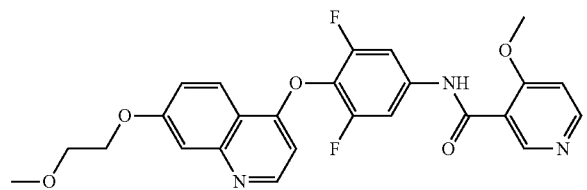 [SMILES: COCCOc1ccc2c(Oc3c(F)cc(NC(=O)c4cnccc4OC)cc3F)ccnc2c1]

Synthesized using the similar method as in example 41. White solid. MS ESI calculated for $C_{25}H_{21}F_2N_3O_5$ [M+H]$^+$, 482.14 found 482.15. $^1$H NMR (400 MHz, DMSO-d$_6$) δ 10.69 (s, 1H), 8.67-8.63 (m, 2H), 8.62 (d, J=6.0 Hz, 1H), 8.27 (d, J=9.2 Hz, 1H), 7.80-7.72 (m, 2H), 7.47 (d, J=2.4 Hz, 1H), 7.36 (dd, J=9.2, 2.4 Hz, 1H), 7.28 (d, J=6.0 Hz, 1H), 6.66-6.60 (m, 1H), 4.36-4.26 (m, 2H), 3.98 (s, 3H), 3.79-3.72 (m, 2H), 3.36 (s, 3H). $^{19}$F NMR (377 MHz, DMSO-d$_6$) δ −126.77 (2F).

Example 43: N-(4-((6,7-bis(2-methoxyethoxy)quinolin-4-yl)oxy)-3,5-difluorophenyl)-4-methoxypyridine-3-carboxamide

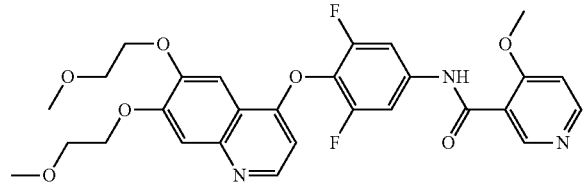 [SMILES: COCCOc1cc2nccc(Oc3c(F)cc(NC(=O)c4cnccc4OC)cc3F)c2cc1OCCOC]

Step 1: 4-chloroquinoline-6,7-diol

To a stirred solution of 4-chloro-6,7-dimethoxyquinoline (5.00 g, 22.35 mmol) in dichloromethane (50 mL) was added boron tribromide (21 mL, 223.55 mmol) dropwise at room temperature. The resulting mixture was stirred at room temperature for 16 h. The reaction was quenched by the addition of methanol (100 mL) at 0° C. The mixture was concentrated under reduced pressure. The residue product was purified by recerse phase chromatography, eluted with 30% acetonitrile in water (plus 10 mmol/L ammonium bicarbonate) and the fractions containing desired product were collected, concentrated under reduced pressure to afford 4-chloroquinoline -6,7-diol (4 g, 91%) as a brown solid. MS ESI calculated for $C_9H_6ClNO_2$ [M+H]$^+$, 196.01, 198.01 found 195.90, 197.90.

Step 2: 4-chloro-6,7-bis(2-methoxyethoxy)quinoline

To a stirred solution of 4-chloroquinoline-6,7-diol (2.00 g, 10.22 mmol) and 2-bromoethyl methyl ether (3.55 g, 25.56 mmol) in 1-methyl-2-pyrrolidinone (20 mL) was added potassium carbonate (4.24 g, 30.67 mmol) at room temperature. The resulting mixture was stirred at 80° C. for 16 h. The mixture was allowed to cool down to room temperature. The reaction was quenched with water at room temperature. The resulting mixture was extracted with ethyl acetate (4×100 mL). The combined organic layers were washed with brine (100 mL), dried over anhydrous sodium sulfate. After filtration, the filtrate was concentrated under reduced pressure. The residue product was purified by reverse phase chromatography, eluted with 50% acetonitrile in water (plus 10 mmol/L ammonium bicarbonate) and the fractions containing desired product were collected and concentrated under reduced pressure to afford 4-chloro-6,7-bis(2-methoxyethoxy)quinoline (800 mg, 25%) as a yellow solid. MS ESI calculated for $C_{15}H_{18}ClNO_4$ [M+H]$^+$, 312.09, 314.09 found 312.30, 314.30. $^1$H NMR (400 MHz, CDCl$_3$) δ 8.58 (d, J=4.8 Hz, 1H), 7.46 (s, 1H), 7.44 (s, 1H), 7.36 (d, J=4.8 Hz, 1H), 4.36-4.34 (m, 4H), 3.94-3.86 (m, 4H), 3.52 (s, 3H), 3.51 (s, 3H).

Step 3: 4-(2,6-difluoro-4-nitrophenoxy)-6,7-bis(2-methoxyethoxy)quinoline

To a stirred solution of 4-chloro-6,7-bis(2-methoxyethoxy)quinoline (0.50 g, 1.60 mmol) and 2,6-difluoro-4-nitrophenol (0.34 g, 1.925 mmol) in 1-methyl-2-pyrrolidinone (0.5 mL) was added N, N-diisopropylethylamine (0.62 g, 4.81 mmol) at room temperature. The resulting mixture was stirred at 140° C. for 16 h. The mixture was allowed to cool down to room temperature. The residue product was purified by reverse phase chromatography, eluted with 45% acetonitrile in water (plus 10 mmol/L ammonium bicarbonate) and the fractions containing desired product were collected, concentrated under reduced pressure to afford 4-(2,6-difluoro-4-nitrophenoxy)-6,7-bis(2-methoxyethoxy)quinoline (490 mg, 68%) as a yellow solid. MS ESI calculated for $C_{21}H_{20}F_2N_2O_7$ [M+H]$^+$, 451.12, found 451.35. $^1$H NMR (400 MHz, CDCl$_3$) δ 8.55 (d, J=5.2 Hz, 1H), 8.12-8.02 (m, 2H), 7.60 (s, 1H), 7.48 (s, 1H), 6.41 (d, J=5.2 Hz, 1H), 4.40-4.32 (m, 4H), 3.95-3.87 (m, 4H), 3.52 (s, 6H).

Step 4: 4-{[6,7-bis(2-methoxyethoxy)quinolin-4-yl]oxy}-3,5-difluoroaniline

To a stirred solution of 4-(2,6-difluoro-4-nitrophenoxy)-6,7-bis(2-methoxyethoxy)quinoline (0.20 g, 0.44 mmol) and iron (0.12 g, 2.22 mmol) in tetrahydrofuran (2 mL) and water (1 mL) was added ammonium chloride (0.11 g, 2.220 mmol) at room temperature. The resulting mixture was stirred at 70° C. for 16 h. The mixture was allowed to cool down to room temperature. The resulting mixture was filtered, the filter cake was washed with methanol (3×100 mL). The filtrate was concentrated under reduced pressure. The residue product was purified by reverse phase chromatography, eluted with 45% acetonitrile in water (plus 0.05% ammonium bicarbonate) and the fractions containing desired product were collected, concentrated under reduced pressure to afford 4-{[6,7-bis(2-methoxyethoxy)quinolin-4-yl]oxy}-3,5-difluoroaniline (180 mg, 96%) as a white solid. MS ESI calculated for $C_{22}H_{22}F_2N_2O_5$ [M+H]$^+$, 421.15 found 421.35. $^1$H NMR (400 MHz, CDCl$_3$) δ 8.51 (d, J=5.2 Hz, 1H), 7.65 (s, 1H), 7.45 (s, 1H), 6.46 (d, J=5.2 Hz, 1H), 6.42-6.31 (m, 2H), 4.39-4.31 (m, 4H), 3.91-3.90 (m, 4H), 3.52 (s, 3H), 3.51 (s, 3H).

Step 5: N-(4-{[6,7-bis(2-methoxyethoxy)quinolin-4-yl]oxy}-3,5-difluorophenyl)-4-methoxypyridine-3-carboxamide To a stirred solution of 4-methoxypyridine-3-carboxylic acid (27 mg, 0.170 mmol) and O-(7-azabenzotriazol-1-yl)-N,N,N',N'-tetramethyluronium hexafluorophosphate (90 mg, 0.231 mmol) in N,N-dimethylformamide (0.5 mL) was added N,N-diisopropylethylamine (46 mg, 0.35 mmol) at room temperature. The resulting mixture was stirred at room temperature for 30 min. To the above mixture was added 4-{[6,7-bis(2-methoxyethoxy)quinolin-4-yl]oxy}-3,5-difluoroaniline (50 mg, 0.112 mmol) at room temperature. The resulting mixture was stirred at 50° C. for 16 h. The mixture was allowed to cool down to room temperature. The reaction was quenched with water at room temperature. The resulting mixture was extracted with ethyl acetate (3×100 mL). The combined organic layers were washed with brine (100 mL), dried over anhydrous sodium sulfate. After filtration, the filtrate was concentrated under reduced pressure. The crude product (40 mg) was purified by Prep-HPLC with the following conditions (Column: XBridge Prep OBD C18 Column, 30×150 mm, 5 μm; Mobile Phase A: water (plus 10 mmol/L Ammonium bicarbonate), Mobile Phase B: acetonitrile; Flow rate: 60 mL/min; Gradient: 31% to 41% B in 8 min; Detector: UV 254/220 nm;). The fractions containing desired product were collected, concentrated, and lyophilized to afford N-(4-{[6,7-bis(2-methoxyethoxy)quinolin-4-yl]oxy}-3,5-difluorophenyl)-4-methoxypyridine-3-carboxamide (14.2 mg, 21%) as a white solid. MS ESI calculated for $C_{28}H_{27}F_2N_3O_7$ [M+H]$^+$, 556.18, found 556.20. $^1$H NMR (400 MHz, DMSO-d$_6$) δ 10.71 (s, 1H), 8.63 (s, 1H), 8.62 (d, J=6.0 Hz, 1H), 8.51 (d, J=5.2 Hz, 1H), 7.81-7.71 (m, 2H), 7.60 (s, 1H), 7.47 (s, 1H), 7.28 (d, J=6.0 Hz, 1H), 6.62 (d, J=5.2 Hz, 1H), 4.35-4.28 (m, 4H), 3.97 (s, 3H), 3.83-3.74 (m, 4H), 3.38 (s, 3H), 3.37 (s, 3H). $^{19}$F-NMR (376 MHz, DMSO-d$_6$) -126.57 (2F).

Example 44: N-(3,5-difluoro-4-((6-methoxy-7-(2-(methylamino)ethoxy)quinolin-4-yl)oxy)phenyl)-6-fluoro-4-methoxypyridine-3-carboxamide

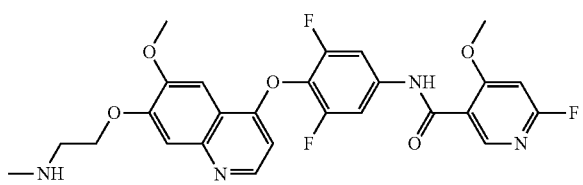

Step 1: methyl 6-fluoro-4-methoxypyridine-3-carboxylate

To a stirred mixture of methyl 6-chloro-4-methoxypyridine-3-carboxylate (1 g, 4.96 mmol) in dimethyl sulfoxide (20 mL) was added colony-stimulating factor (3.77 g, 24.80 mmol) in portions at room temperature. The resulting mixture was stirred at 90° C. for 16 h. The mixture was allowed to cool down to room temperature. The resulting mixture was filtered, the filter cake was washed with dimethyl sulfoxide (10 mL). The residue was purified by reverse phase Flash chromatography with the following conditions: Column: WelFlash™ C18-I, 20-40 μm, 120 g; Eluent A: water (plus 10 mmol/L ammonium bicarbonate); Eluent B:

acetonitrile; Gradient: 30% to 50% B in 25 min; Flow rate: 70 mL/min; Detector: UV 220/254 nm; desired fractions were collected and concentrated under reduced pressure to afford methyl 6-fluoro-4-methoxypyridine -3-carboxylate (380 mg, 41%) as a white solid. MS ESI calculated for $C_8H_8FNO_3$ [M+H]$^+$, 186.05, found 186.20. $^1$H NMR (400 MHz, CDCl$_3$) δ 8.65 (s, 1H), 6.49 (s, 1H), 4.00 (s, 3H), 3.93 (s, 3H).

Step 2: 6-fluoro-4-methoxypyridine-3-carboxylic acid

To a stirred mixture of methyl 6-fluoro-4-methoxypyridine-3-carboxylate (380 mg, 2.052 mmol) in water (2 mL) and tetrahydrofuran (4 mL) was added lithium hydroxide (245 mg, 10.230 mmol) in portions at room temperature. The resulting mixture was stirred at room temperature for 16 h. The residue was acidified to pH 5 with hydrochloric acid. The resulting mixture was concentrated under reduced pressure. The residue was purified by reverse phase Flash chromatography with the following conditions: Column: WelFlash™ C18-I, 20-40 μm, 120 g; Eluent A: water (plus 10 mmol/L formic acid); Eluent B: acetonitrile; Gradient: 15% to 35% B in 25 min; Flow rate: 60 mL/min; Detector: UV 220/254 nm; desired fractions were collected and concentrated under reduced pressure to afford 6-fluoro-4-methoxypyridine-3-carboxylic acid (120 mg, 34%) as a white solid. MS ESI calculated for $C_7H_6FNO_3$ [M+H]$^+$, 172.03 found 172.00. $^1$H NMR (400 MHz, CDCl$_3$) δ 8.89 (s, 1H), 6.57 (s, 1H), 4.12 (s, 3H).

Step 3: tert-butyl N-[2-({4-[2,6-difluoro-4-(6-fluoro-4-methoxypyridine-3-amido)phenoxy]-6-methoxyquinolin-7-yl}oxy)ethyl]-N-methylcarbamate To a stirred mixture of 6-fluoro-4-methoxypyridine-3-carboxylic acid (120 mg, 0.701 mmol) and propylphosphonic acid anhydride (1 N in ethyl acetate, 2 mL) in ethyl acetate (2 mL) was added N,N-diisopropylethylamine (181 mg, 1.400 mmol) and tert-butyl N-(2-{[4-(4-amino-2,6-difluorophenoxy)-6-methoxyquinolin-7-yl]oxy}ethyl)-N-methylcarbamate (266 mg, 0.559 mmol) at room temperature. The resulting mixture was stirred at 70° C. for 16 h. The mixture was allowed to cool down to room temperature. The resulting mixture was concentrated under reduced pressure. The resulting mixture was diluted with water (100 mL). The mixture was basified to pH 8 with saturated sodium bicarbonate. The resulting mixture was extracted with ethyl acetate (3×100 mL) dried over anhydrous sodium sulfate. After filtration, the filtrate was concentrated under reduced pressure. The residue was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 55% to 75% B in 25 min; Flow rate: 60 mL/min; Detector: UV 220/254 nm; desired fractions were collected and concentrated under reduced pressure to afford tert-butyl N-[2-({4-[2,6-difluoro-4-(6-fluoro-4-methoxypyridine-3-amido)phenoxy]-6-methoxyquinolin-7-yl}oxy)ethyl]-N-methylcarbamate (150 mg, 34%) as a yellow solid. MS ESI calculated for $C_{31}H_{31}F_3N_4O_7$ [M+H]$^+$, 629.21, found 629.05. $^1$H NMR (400 MHz, CDCl$_3$) δ 9.35 (s, 1H), 9.05 (s, 1H), 8.54 (d, J=5.2 Hz, 1H), 7.63 (s, 1H), 7.58-7.45 (m, 3H), 6.61 (s, 1H), 6.48 (d, J=5.2 Hz, 1H), 4.42-4.29 (m, 2H), 4.21 (s, 3H), 4.07 (s, 3H), 3.84-3.71 (m, 2H), 3.08 (s, 3H), 1.49 (s, 9H).

Step 4: N-(3,5-difluoro-4-((6-methoxy-7-(2-(methylamino)ethoxy)quinolin-4-yl)oxy)phenyl)-6-fluoro-4-methoxypyridine-3-carboxamide hydrochloride To a stirred mixture of tert-butyl N-[2-({4-[2,6-difluoro-4-(6-fluoro-4-methoxypyridine-3-amido)phenoxy]-6-methoxyquinolin-7-yl}oxy)ethyl]-N-methylcarbamate (150 mg, 0.239 mmol) in dioxane (4 mL) was added hydrochloric acid (gas, 4 N in 1,4-dioxane, 1 mL) dropwise at room temperature. The resulting mixture was stirred at room temperature for 4 h. The resulting mixture was concentrated under reduced pressure. The residue was purified by reverse phase Flash chromatography with the following conditions: Column: WelFlash™ C18-I, 20-40 μm, 120 g; Eluent A: water (plus 10 mmol/L hydrochloric acid); Eluent B: acetonitrile; Gradient: 25% to 45% B in 25 min; Flow rate: 60 mL/min; Detector: UV 220/254 nm; desired fractions were collected and concentrated under reduced pressure to afford N-(3,5-difluoro-4-((6-methoxy-7-(2-(methylamino)ethoxy)quinolin-4-yl)oxy)phenyl)-6-fluoro-4-methoxypyridine-3-carboxamide hydrochloride (33 mg, 26%) as a light yellow solid. MS ESI calculated for $C_{26}H_{23}F_3N_4O_5$ [M+H]$^+$, 529.16, found 529.30. $^1$H NMR (400 MHz, DMSO-d$_6$) 68.92-8.84 (m, 1H), 8.36 (s, 1H), 7.88-7.71 (m, 4H), 7.26-7.16 (m, 1H), 7.08 (s, 1H), 4.62-4.53 (m, 2H), 4.07 (s, 3H), 4.01 (s, 3H), 3.55-3.45 (m, 2H), 2.71 (s, 3H). $^{19}$F NMR (DMSO-d$_6$) δ −62.94 (1F), −126.40 (2F).

Example 45: N-(3,5-difluoro-4-((6-methoxy-7-(2-(methylamino)ethoxy)quinolin-4-yl)oxy)phenyl)-4-methoxy-6-methylpyridine-3-carboxamide

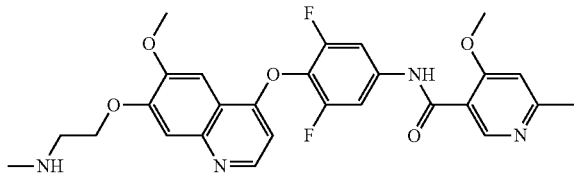

Step 1: methyl 4-methoxy-6-methylpyridine-3-carboxylate

To a stirred mixture of methyl 6-chloro-4-methoxypyridine-3-carboxylate (600 mg, 2.976 mmol) and methylboronic acid (534 mg, 8.928 mmol) in dioxane (5 mL) and water (1 mL) were added cesium carbonate (2909mg, 8.928 mmol) and [1,1'-Bis(diphenylphosphino)ferrocene]-dichloropalladium(II) (218 mg, 0.298 mmol) at room temperature. The resulting mixture was stirred at 100° C. under nitrogen atmosphere for 16 h. The residue was purified by reverse flash chromatography with the following conditions: column, silica gel; mobile phase, acetonitrile in water, 0% to 10% B in 20 min; Detector: UV 254/220 nm. The fractions containing desired product were collected, concentrated under reduced pressure to afford methyl 4-methoxy-6-methylpyridine-3-carboxylate (133 mg, 25%) as a light yellow oil. MS ESI calculated for $C_9H_{11}NO_3$ [M+H]$^+$, 182.07 found 182.30. $^1$H NMR (400 MHz, DMSO-d$_6$) δ 8.66 (s, 1H), 7.17 (d, J=1.8 Hz, 1H), 3.92 (s, 3H), 3.81 (s, 3H), 3.46 (s, 3H).

Step 2: 4-methoxy-6-methylpyridine-3-carboxylic acid

To a stirred mixture of methyl 4-methoxy-6-methylpyridine-3-carboxylate (130 mg, 0.717 mmol) in water (2 mL)

and tetrahydrofuran (4 mL) was added lithium hydroxide (172 mg, 7 mmol) at room temperature. The resulting mixture was stirred at room temperature for 3 h. The residue was purified by reverse flash chromatography with the following conditions: column, silica gel; mobile phase, acetonitrile in water, 40% to 60% B in 4.5 min; Detector: UV 254/220 nm. The fractions containing desired product were collected, concentrated under reduced pressure to afford 4-methoxy-6-methylpyridine-3-carboxylic acid (100 mg, 83%) as a white solid. MS ESI calculated for $C_8H_9NO_3$ [M+H]$^+$, 167.06 found 168.15. $^1$H NMR (400 MHz, DMSO-d$_6$) δ 14.00 (s, 1H), 8.70 (s, 1H), 7.63 (d, J=4.2 Hz, 1H), 4.07 (s, 3H), 2.69 (s, 3H).

Step 3: tert-butyl N-[2-({4-[2,6-difluoro-4-(4-methoxy-6-methylpyridine-3-amido)phenoxy]-6-methoxyquinolin-7-yl}oxy)ethyl]-N-methylcarbamate To a stirred mixture of O-(7-Azabenzotriazol-1-yl)-N,N,N',N'-tetramethyluronium hexafluorophosphate (299 mg, 0.789 mmol) and tert-butyl N-(2-{[4-(4-amino-2,6-difluorophenoxy)-6-methoxyquinolin-7-yl]oxy}ethyl)-N-methylcarbamate (250 mg, 0.526 mmol) in N,N-dimethylformamide (5 mL) were added 4-methoxy-6-methylpyridine-3-carboxylic acid (105 mg, 0.631 mmol) and N,N-diisopropylethylamine (170 mg, 1.315 mmol) at room temperature. The resulting mixture was stirred at 70° C. for 16 h. The mixture was allowed to cool down to room temperature. The residue was purified by reverse flash chromatography with the following conditions: column, silica gel; mobile phase, acetonitrile in water, 40% to 60% B in 4.5 min; Detector: UV 254/220 nm. The fractions containing desired product were collected, concentrated under reduced pressure to afford tert-butyl N-[2-({4-[2,6-difluoro-4-(4-methoxy-6-methylpyridine-3-amido)-phenoxy]-6-methoxyquinolin-7-yl}oxy)ethyl]-N-methylcarbamate (50 mg, 15%) as a white solid. MS ESI calculated for $C_{32}H_{34}F_2N_4O_7$ [M+H]$^+$, 625.24 found 625.20. $^1$H NMR (400 MHz, DMSO-d$_6$) δ 10.54 (s, 1H), 8.54 (d, J=1.8 Hz, 1H), 8.51 (dd,J=5.2, 2.0 Hz, 1H), 7.77 (d, J=11.2 Hz, 2H), 7.57 (d, J=1.8 Hz, 1H), 7.48 (s, 1H), 7.16 (s, 1H), 6.61 (d, J=5.2 Hz, 1H), 4.31 (s, 2H), 3.97 (d, J=1.8 Hz, 6H), 3.65 (s, 2H), 2.94 (d, J=12.0 Hz, 3H), 2.53 (s, 3H), 1.39 (s, 9H). $^{19}$F NMR (377 MHz, DMSO-d$_6$) δ −126.72 (2F).

Step 4: N-[3,5-difluoro-4-({6-methoxy-7-[2-(methylamino)ethoxy]quinolin-4-yl}oxy)phenyl]-4-methoxy-6-methylpyridine-3-carboxamide To a stirred mixture of tert-butyl N-[2-({4-[2,6-difluoro-4-(4-methoxy-6-methylpyridine-3-amido)phenoxy]-6-methoxyquinolin-7-yl}oxy)ethyl]-N-methylcarbamate (50 mg, 0.080 mmol) in dichloromethane (2 mL) was added hydrochloric acid (gas) in 1,4-dioxane (0.5 mL) at room temperature. The resulting mixture was stirred for 2 h at room temperature. The resulting mixture was concentrated under reduced pressure. The crude product was purified by Prep-HPLC with the following conditions (Column: XBridge Shield RP18 OBD Column, 19×250 mm, 10 μm; Mobile Phase A: Water (10 mmol/L ammonium bicarbonate), Mobile Phase B: methyl alcohol —HPLC; Flow rate: 25 mL/min; Gradient: 53% to 63% B in 8 min, 63% B; Wave Length: 254/220 nm;). The fractions containing desired product were collected, concentrated, and lyophilized to afford N-[3,5-difluoro-4-({6-methoxy-7-[2-(methylamino)ethoxy]quinolin-4-yl}oxy)phenyl]-4-methoxy-6-methyl-pyridine-3-carboxamide (16.2 mg, 38%) as a white solid. MS ESI calculated for $C_{27}H_{26}F_2N_4O_5$ [M+H]$^+$, 525.19 found 482.15. $^1$H NMR (400 MHz, DMSO-d$_6$) δ 10.58 (d, J=3.1 Hz, 1H), 8.54-8.50 (m, 2H), 7.78 (d, J=10.6 Hz, 2H), 7.58 (s, 1H), 7.48 (s, 1H), 7.16 (s, 1H), 6.62 (d, J=5.2 Hz, 1H), 4.31 (t, J=5.4 Hz, 2H), 3.98 (d, J=8.2 Hz, 6H), 3.12 (t, J=5.4 Hz, 2H), 2.53 (s, 3H), 2.50 (s, 4H). $^{19}$F NMR (376 MHz, DMSO-d$_6$) δ −126.72 (2F).

Example 46: N-(3,5-difluoro-4-((6-methoxy-7-(2-(methylamino)ethoxy)quinolin-4-yl)oxy)phenyl)-4-methoxy-6-((2-methoxyethyl)amino)pyridine-3-carboxamide

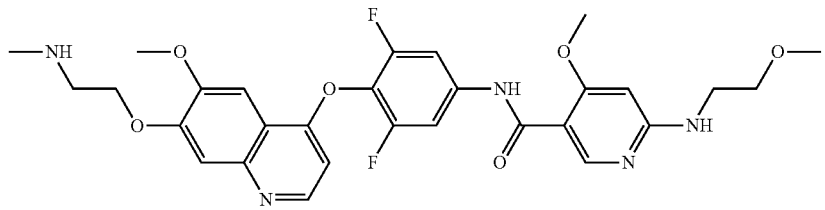

Step 1: tert-butyl N-[2-({4-[4-(6-chloro-4-methoxypyridine-3-amido)-2,6-difluorophenoxy]-6-methoxyquinolin-7-yl}oxy)ethyl]-N-methylcarbamate To a stirred mixture of tert-butyl N-(2-{[4-(4-amino-2,6-difluorophenoxy)-6-methoxyquinolin-7-yl]oxy}ethyl)-N-methylcarbamate (300 mg, 0.631 mmol) and 6-chloro-4-methoxypyridine-3-carboxylic acid (142 mg, 0.757 mmol) in N,N-dimethylformamide (6 mL) were added O-(7-Azabenzotriazol-1-yl)-N,N,N',N'-tetramethyluronium hexafluorophosphate (360 mg, 0.947 mmol) and N,N-diisopropylethylamine (408 mg, 3.155 mmol) at room temperature. The resulting mixture was stirred at 50° C. for 16 h. The mixture was allowed to cool down to room temperature. The residue was purified by silica gel column chromatography, eluted with dichloromethane/methyl alcohol (10/1) concentrated under reduced pressure to afford tert-butyl N-[2-({4-[4-(6-chloro-4-methoxypyridine-3-amido)-2,6-difluorophenoxy]-6-methoxyquinolin-7-yl}oxy)ethyl]-N-methylcarbamate (343 mg, 84%) as a yellow solid. MS ESI calculated for $C_{31}H_{31}ClF_2N_4O_7$ [M+H]$^+$, 645.18, 647.18 found 645.55, 647.55. $^1$H NMR (400 MHz, CDCl$_3$) δ 9.38 (d, J=7.6 Hz, 1H), 9.14 (s, 1H), 8.56-8.53 (m, 1H), 7.63 (s, 1H), 7.58-7.53 (m, 2H), 7.06 (s, 1H), 6.49 (s, 1H), 4.25 (d, J=34.5 Hz, 5H), 4.07 (d, J=1.8 Hz, 3H), 3.77 (s, 2H), 3.08 (s, 3H), 1.49 (s, 9H).

Step 2: tert-butyl N-(2-{[4-(2,6-difluoro-4-{4-methoxy-6-[(2-methoxyethyl)amino]pyridine-3-amido}phenoxy)-6-methoxyquinolin-7-yl]oxy}ethyl)-N-methylcarbamate To a stirred mixture of tert-butyl N-[2-({4-[4-(6-chloro-4-methoxypyridine-3-amido)-2,6-difluorophenoxy]-6-methoxyquinolin-7-yl}oxy)ethyl]-N-methylcarbamate (350 mg, 0.543 mmol) and 2-methoxyethan-1-amine (122 mg, 1.629 mmol) in dioxane (7 mL) was added BrettPhos (CAS:1070663-78-3) (58 mg, 0.109 mmol) and BrettPhos Pd G3 (CAS:1470372-59-8) (49 mg, 0.054 mmol) at room temperature. The resulting mixture was stirred at 90° C. under nitrogen atmosphere for 16 h. The mixture was allowed to cool down to room temperature. The residue was purified by silica gel column chromatography, eluted with dichloromethane/ methyl alcohol (10/1) concentrated under reduced pressure to afford tert-butyl N-(2-{[4-(2,6-difluoro-4-{4-methoxy-6-[(2-methoxyethyl)amino]pyridine-3-amido}phenoxy)-6-methoxyquinolin-7-yl]oxy}ethyl)-N-methylcarbamate (80 mg, 21%) as a yellow solid. MS ESI calculated for $C_{34}H_{39}F_2N_5O_8$ [M+H]$^+$, 684.28 found 684.60. $^1$H NMR (400 MHz, CDCl$_3$) δ 9.42 (s, 1H), 8.92 (s, 1H), 8.53 (d, J=5.4 Hz, 1H), 7.63 (s, 1H), 7.55-7.44 (m, 3H), 6.48 (d, J=5.4 Hz, 1H), 5.93 (s, 1H), 4.34 (s, 2H), 4.19-4.02 (m, 6H), 3.77 (s, 2H), 3.63 (d, J=3.2 Hz, 4H), 3.43 (s, 3H), 3.08 (s, 3H), 1.49 (s, 9H).

Step 3: N-[3,5-difluoro-4-({6-methoxy-7-[2-(methylamino)ethoxy]quinolin-4-yl}oxy)phenyl]-4-methoxy-6-[(2-methoxyethyl)amino]pyridine-3-carboxamide A solution of tert-butyl N-(2-{[4-(2,6-difluoro-4-{4-methoxy-6-[(2-methoxyethyl)amino]-pyridine-3-amido}-phenoxy)-6-methoxyquinolin-7-yl]oxy}ethyl)-N-methylcarbamate (80 mg, 0.117 mmol) in hydrochloric acid (gas) in 1,4-dioxane (1 mL) and dioxane (1 mL) was stirred at room temperature for 2 h. The crude product was purified by Prep-HPLC with the following conditions (Column: XBridge Prep OBD C18 Column, 30*150 mm, 5 μm; Mobile Phase A: Water (plus 10 mmol/L ammonium bicarbonate), Mobile Phase B: acetonitrile; Flow rate: 60 mL/min; Gradient: 25% to 35% B in 8 min, 35% B; Wave Length: 254/220 nm; RT1(min): 7; Number of Runs: 0). The fractions containing desired product were collected, concentrated, and lyophilized to afford N-[3,5-difluoro-4-({6-methoxy-7-[2-(methylamino)ethoxy]quinolin-4-yl}oxy)-phenyl]-4-methoxy-6-[(2-methoxyethyl)amino]pyridine-3-carboxamide (19.7 mg, 29%) as a white solid. MS ESI calculated for $C_{29}H_{31}F_2N_5O_6$ [M+H]$^+$, 584.22 found 584.25. $^1$H NMR (400 MHz, DMSO-d$_6$) δ 10.00 (s, 1H), 8.50 (d, J=5.2 Hz, 1H), 8.38 (s, 1H), 7.82 (d, J=10.6 Hz, 2H), 7.56 (s, 1H), 7.44 (s, 1H), 7.19 (d, J=5.8 Hz, 1H), 6.59 (d, J=5.2 Hz, 1H), 6.18 (s, 1H), 4.28-4.22 (m, 2H), 3.98 (s, 3H), 3.93 (s, 3H), 3.52-3.49 (m, 4H), 3.29 (s, 3H), 2.98-2.94 (m, 2H), 2.39 (s, 3H). $^{19}$F NMR (377 MHz, DMSO-d$_6$) δ −127.19 (2F).

Example 47: N-(3,5-difluoro-4-((6-methoxy-7-(2-(methylamino)ethoxy)quinolin-4-yl)oxy)phenyl)-4-(difluoromethoxy)pyridine-3-carboxamide

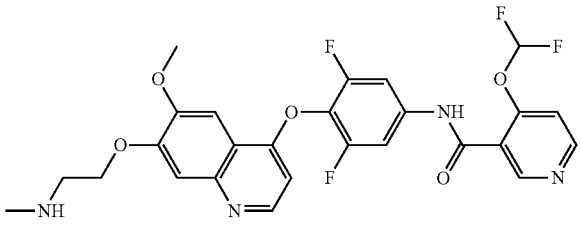 [SMILES: CNCCOc1cc2nccc(Oc3c(F)cc(NC(=O)c4cnccc4OC(F)F)cc3F)c2cc1OC]

Step 1: tert-butyl N-{2-[(4-{4-[4-(difluoromethoxy)pyridine-3-amido]-2,6-difluorophenoxy}-6-methoxyquinolin-7-yl)oxy]ethyl}-N-methylcarbamate To a stirred mixture of tert-butyl N-[2-({4-[2,6-difluoro-4-(4-hydroxypyridine-3-amido)phenoxy]-6-methoxyquinolin-7-yl}oxy)ethyl]-N-methylcarbamate (90 mg, 0.151 mmol) and sodium 2-chloro-2,2-difluoroacetate (46 mg, 0.302 mmol) in water (0.2 mL) and N,N-dimethylformamide (2 mL) was added potassium carbonate (31 mg, 0.226 mmol) at room temperature. The resulting mixture was stirred at 120° C. for 45 min. The mixture was allowed to cool down to room temperature. The mixture was concentrated under reduce pressure. The residue was purified by silica gel column chromatography, eluted with dichloromethane/methyl alcohol (10/1). The fractions containing desired product were collected, concentrated, and lyophilized to afford tert-butyl N-{2-[(4-{4-[4-(difluoromethoxy)pyridine-3-amido]-2,6-difluoro -phenoxy}-6-methoxy quinolin-7-yl)oxy]ethyl}-N-methylcarbamate (45 mg, 46%) as a yellow solid. MS ESI calculated for $C_{31}H_{30}F_4N_4O_7$ [M+H]$^+$, 647.21 found 647.55.

Step 2: N-[3,5-difluoro-4-({6-methoxy-7-[2-(methylamino)ethoxy]quinolin-4-yl}oxy)phenyl]-4-(difluoromethoxy)pyridine-3-carboxamide A solution of tert-butyl N-{2-[4-{4-[4-(difluoromethoxy)pyridine-3-amido]-2,6-difluorophenoxy}-6-methoxyquinolin-7-yl)oxy]ethyl}-N-methylcarbamate (45 mg, 0.070 mmol) in dioxane (1 mL) was added hydrochloric acid (gas, 4 N in 1,4-dioxane, 1 mL). The resulting mixture was stirred at room temperature for 2 h. The mixture was concentrated under reduced pressure. The crude product was purified by Prep-HPLC with the following conditions (Column:) (Bridge Prep Phenyl OBD Column, 19×250 mm, 5 μm; Mobile Phase A: water (plus 10 mmol/L ammonium bicarbonate), Mobile Phase B: MeOH; Flow rate: 25 mL/min; Gradient: 30% to 70% B in 12 min; Detector: UV 254/220 nm). The fractions containing desired product were collected, concentrated, and lyophilized to afford N-[3,5-difluoro-4-({6-methoxy-7-[2-(methylamino)-ethoxy]quinolin-4-yl} oxy)phenyl]-4-(difluoromethoxy)pyridine-3-carboxamide (11.9 mg, 31%) as a white solid. MS ESI calculated for $C_{26}H_{22}F_4N_4O_5$ [M+H]$^+$, 547.15 found 547.20. $^1$H NMR (400 MHz, DMSO-d$_6$) δ 12.51 (s, 1H), 8.99 (d, J=2.4 Hz, 1H), 8.50 (d, J=5.2 Hz, 1H), 8.33 (dd, J=7.8, 2.4 Hz, 1H), 8.06-7.66 (m, 3H), 7.56 (s, 1H), 7.45 (s, 1H), 6.73 (d, J=7.6 Hz, 1H), 6.62 (d, J=5.2 Hz, 1H), 4.23 (t, J=5.6 Hz, 2H), 3.97 (s, 3H), 2.96 (t, J=5.6 Hz, 2H), 2.40 (s, 3H). $^{19}$F NMR (376 MHz, DMSO-d$_6$) δ −126.46 (2F), −94.62 (2F).

Example 48: N-[2,3-difluoro-4-({6-methoxy-7-[2-(methylamino)ethoxy]quinolin-4-yl}oxy)phenyl]-4-(difluoromethoxy)pyridine-3-carboxamide

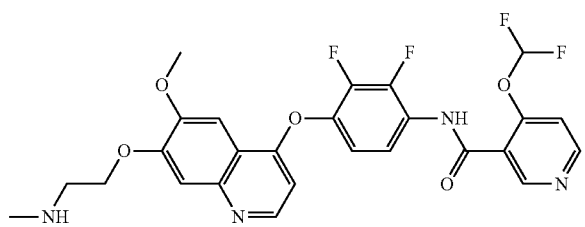 [SMILES: CNCCOc1cc2nccc(Oc3ccc(NC(=O)c4cnccc4OC(F)F)c(F)c3F)c2cc1OC]

Synthesized using the same method as example 47. White solid. MS ESI calculated for C$_{26}$H$_{22}$F$_4$N$_4$O$_5$ [M+H]$^+$, 547.15 found 547.15. $^1$H NMR (400 MHz, CD$_3$OD) δ 9.00 (d, J=2.4 Hz, 1H), 8.48 (dd, J=5.4, 1.2 Hz, 1H), 8.40-8.34 (m, 1H), 8.21 (dd, J=7.8, 2.4 Hz, 1H), 7.75-7.60 (m, 2H), 7.58-7.54(m, 1H), 7.46-7.42 (m, 1H), 6.78 (dd, J=7.8, 1.2 Hz, 1H), 6.63 (dd, J=5.4, 1.2 Hz, 1H), 4.33 (t, J=5.2 Hz, 2H), 4.05 (d, J=1.0 Hz, 3H), 3.12 (d, J=5.2 Hz, 2H), 2.54 (s, 3H). $^{19}$F NMR (377 MHz, CD$_3$OD) δ −96.55 (2F), −150.61 (1F), −154.53 (1F).

Example 49: N-(3,5-difluoro-4-((6-methoxy-7-(2-(methylamino)ethoxy)quinolin-4-yl)oxy)phenyl)-4-ethylpyridine-3-carboxamide

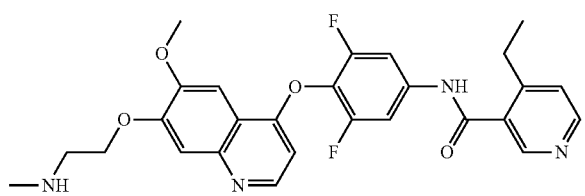 [SMILES: CCc1ccncc1C(=O)Nc1cc(F)c(Oc2ccnc3cc(OCCNC)c(OC)cc23)c(F)c1]

Step 1: methyl 4-vinylnicotinate

To a stirred solution of methyl 4-chloropyridine-3-carboxylate (500 mg, 2.914 mmol), 2-ethenyl-4,4,5,5-tetramethyl-1,3,2-dioxaborolane (898 mg, 5.828 mmol) and potassium phosphate (1.86 g, 8.742 mmol) in dioxane (5 mL) and water (0.5 mL) was added Pd$_2$(dba)$_3$ (CAS: 60748-((7-2, 531 mg, 0.583 mmol) and XantPhos (CAS:161265-03-8, 139 mg, 0.291 mmol) at room temperature under nitrogen atmosphere. The resulting mixture was stirred at 90° C. under nitrogen atmosphere 16 h. The mixture was allowed to cool down to room temperature, the resulting mixture was concentrated under reduced pressure. The residue was purified by silica gel column chromatography, eluted with petroleum ether/ethyl acetate (1/1) concentrated under reduced pressure to afford methyl 4-vinylnicotinate (316 mg, 72%) as a light yellow oil. MS ESI calculated for C$_9$H$_9$NO$_2$ [M+H]$^+$, 164.20 found 164.10. $^1$H NMR (400 MHz, CDCl$_3$) δ 9.10 (s, 1H), 8.68 (d, J=5.2 Hz, 1H), 7.59-7.47 (m, 2H), 5.94-5.84 (m, 1H), 5.61-5.55 (m, 1H), 3.96 (s, 3H).

Step 2: methyl 4-ethylpyridine-3-carboxylate

To a stirred solution of methyl 4-ethenylpyridine-3-carboxylate (316 mg, 1.937 mmol) in methanol (3 mL) was added palladium on carbon (272 mg, 1.937 mmol) in portions at room temperature under nitrogen atmosphere. The resulting mixture was stirred at room temperature under hydrogen atmosphere for 2 h. The resulting mixture was filtered the filter cake was washed with methanol (3×50 mL). The filtrate was concentrated under reduced pressure to afford methyl 4-ethylpyridine-3-carboxylate (285 mg, 89%) as a light yellow oil. MS ESI calculated for C$_9$H$_{11}$NO$_2$ [M+H]$^+$, 166.20 found 166.30. $^1$H NMR (400 MHz, CDCl$_3$) δ 9.05 (s, 1H), 8.61 (d, J=5.2 Hz, 1H), 7.23 (d, J=5.2 Hz, 1H), 3.95 (s, 3H), 3.03 (q, J=7.6 Hz, 2H), 1.27 (t, J=7.6 Hz, 3H).

Step 3: 4-ethylpyridine-3-carboxylic acid

To a stirred solution of methyl 4-ethylpyridine-3-carboxylate (285 mg, 1.725 mmol) in tetrahydrofuran (1.5 mL) and water (1.5 mL) was added lithium hydroxide (165 mg, 6.900 mmol) in portions at room temperature. The resulting mixture was stirred at 70° C. for 4 h. The mixture was allowed to cool down to room temperature and acidified to pH 6 with conc hydrochloric acid. The residue was purified by reverse phase Flash chromatography with the following conditions: Column: WelFlash™ C18-I, 20-40 μm, 80 g; Eluent A: water (plus 10 mmol/L ammonium bicarbonate); Eluent B: acetonitrile; Gradient: 25% to 45% B in 25 min; Flow rate: 60 mL/min; Detector: UV 220/254 nm; desired fractions were collected at 42% B and concentrated under reduced pressure to afford to afford 4-ethylpyridine-3-carboxylic acid (252 mg, 96%) as a light yellow oil. MS ESI calculated for C$_8$H$_9$NO$_2$ [M+H]$^+$, 152.20 found 152.25. $^1$H NMR (400 MHz, CDCl$_3$) δ 9.11 (s, 1H), 8.56 (d, J=5.2 Hz, 1H), 7.23 (d, J=5.2 Hz, 1H), 3.06 (q, J=7.6 Hz, 2H), 1.24 (t, J=7.6 Hz, 3H).

Step 4: tert-butyl N-[2-({4-[4-(4-(4-ethylpyridine-3-amido)-2,6-difluorophenoxy]-6-methoxyquinolin-7-yl}oxy)ethyl]-N-methylcarbamate To a stirred solution of 4-ethylpyridine-3-carboxylic acid (230 mg, 1.522 mmol), tert-butyl N-(2-{[4-(4-amino-2,6-difluorophenoxy)-6-methoxyquinolin-7-yl]oxy}ethyl)-N-methylcarbamate (362 mg, 0.761 mmol) and O-(7-Azabenzotriazol-1-yl)-N,N,N',N'-tetramethyluronium hexafluorophosphate (868 mg, 2.283 mmol) in N,N-dimethylformamide (2.5 mL) was added N, N-diisopropylethylamine (590 mg, 4.566 mmol) at room temperature. The resulting mixture was stirred at room temperature for 16 h. The residue was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 25% to 45% B in 25 min; Flow rate: 60 mL/min; Detector: UV 220/254 nm; desired fractions were collected at 42% B and concentrated under reduced pressure to afford tert-butyl N-[2-({4-[4-(4-ethylpyridine-3-amido)-2,6-difluorophenoxy]-6-methoxyquinolin-7-yl}oxy)ethyl]-N -methylcarbamate (39.8 mg, 4%) as an off-white solid. MS ESI calculated for C$_{32}$H$_{34}$F$_2$N$_4$O$_6$ [M+H]$^+$, 609.70 found 609.50.

Step 5: N-[3,5-difluoro-4-({6-methoxy-7-[2-(methylamino)ethoxy]quinolin-4-yl}oxy)phenyl]-4-ethylpyridine-3-carboxamide To a stirred solution of tert-butyl N-[2-({4-[4-(4-(4-ethylpyridine-3-amido)-2,6-difluorophenoxy]-6-methoxy-quinolin-7-yl}oxy)ethyl]-N-methylcarbamate (39 mg, 0.064 mmol) in dioxane (1 mL) was added hydrochloric acid (gas, 4 N in 1,4-dioxane, 0.6 mL) dropwise at 0° C. The resulting mixture was stirred at room temperature for 2 h. The mixture was concentrated under reduced pressure. The crude product was purified by Prep-HPLC with the following conditions (Column: XBridge Shield RP18 OBD Column, 30×150 mm, 5 μm; Mobile Phase A: water (plus 10 mmol/L ammonium bicarbonate), Mobile Phase B: acetonitrile; Flow rate: 60 mL/min; Gradient: 36% to 46% B in 8 min; Detector: UV 220/254 nm;). The fractions containing desired product were collected, concentrated, and lyophilized to afford N-[3,5-difluoro-4-({6-methoxy-7-[2-(methyl-amino)-ethoxy]quinolin-4-yl}oxy)phenyl]-4-ethylpyridine-3-carboxamide (16 mg, 50%) as an off-white solid. MS ESI calculated for $C_{27}H_{26}F_2N_4O_4$ [M+H]$^+$, 509.50 found 509.30. $^1$H NMR (400 MHz, DMSO-d$_6$) δ 11.06 (s, 1H), 8.70 (s, 1H), 8.64 (d, J=5.2 Hz, 1H), 8.51 (d, J=5.6 Hz, 1H), 7.81-7.71 (m, 2H), 7.56 (s, 1H), 7.48-7.46 (m, 2H), 6.62 (d, J=5.2 Hz, 1H), 4.24 (t, J=5.6 Hz, 2H), 3.98 (s, 3H), 3.03-2.99 (t, J=5.6 Hz, 2H), 2.80 (q, J=7.6 Hz, 2H), 2.42 (s, 3H), 1.22 (t, J=7.6 Hz, 3H). $^{19}$F NMR (376 MHz, DMSO-d$_6$) δ −126.40 (2F).

Example 50: 4-methoxy-N-(2,3,5-trifluoro-4-((6-methoxy-7-(2-(methylamino)ethoxy)quinolin-4-yl)oxy)phenyl)pyridine-3-carboxamide

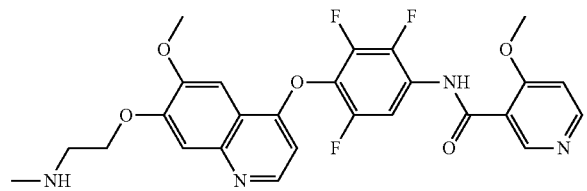

Step 1: tert-butyl N-(2-{[4-(4-amino-2,3,6-trifluorophenoxy)-6-methoxyquinolin-7-yl]oxy}ethyl) -N-methylcarbamate To a stirred solution of tert-butyl N-(2-{[4-(4-amino-2,6-difluorophenoxy)-6-methoxyquinolin-7-yl]oxy}ethyl)-N-methylcarbamate (300 mg, 0.631 mmol) (from example 1) and Selectfluor (224 mg, 0.632 mmol) in acetonitrile (2 mL) and N,N-dimethylformamide (2 mL) at room temperature. The resulting mixture was stirred at room temperature for 16 h. The mixture was quenched with water at room temperature. The resulting mixture was extracted with ethyl acetate (3×10 mL). The combined organic layers were washed with brine (3×10 mL), dried over anhydrous sodium sulfate. After filtration, the filtrate was concentrated under reduced pressure. The residue was purified by silica gel column chromatography, eluted with petroleum ether/ethyl acetate (1/1). The fractions containing desired product were collected, concentrated under reduced pressure to afford tert-butyl N-(2-{[4-(4-amino-2,3,6-trifluorophenoxy)-6-methoxyquinolin-7-yl]oxy}ethyl)-N-methylcarbamate (70 mg, 22%) as a brown yellow solid. MS ESI calculated for $C_{24}H_{26}F_3N_3O_5$ [M+H]$^+$, 494.18 found 494.30. $^1$H NMR (400 MHz, DMSO-d$_6$) δ 8.50 (d, J=5.2 Hz, 1H), 7.53 (s, 1H), 7.46 (s, 1H), 6.70-6.64 (m, 1H), 6.62 (d, J=5.2 Hz, 1H), 5.93 (s, 2H), 4.29 (t, J=5.6 Hz, 2H), 3.95 (s, 3H), 3.64 (t, J=5.6 Hz, 2H), 2.93 (3, 3H), 1.38 (s, 9H).

Step 2: tert-butyl N-[2-({6-methoxy-4-[2,3,6-trifluoro-4-(4-methoxypyridine-3-amido)phenoxy]quinolin-7-yl}oxy)ethyl]-N-methylcarbamate A solution of 4-methoxypyridine-3-carboxylic acid (44 mg, 0.287 mmol) and N,N -diisopropylethylamine (37 mg, 0.286 mmol) in propylphosphonic anhydride (1 N in ethyl acetate, 1 mL) was stirred at room temperature for 20 min, followed by adding tert-butyl N-(2-{[4-(4-amino-2,3,6-trifluorophenoxy)-6-methoxyquinolin-7-yl]oxy}ethyl)-N-methylcarbamate (70 mg, 0.142 mmol) at room temperature. The resulting mixture was stirred at 70° C. for 16 h. The mixture was allowed to cool down to room temperature. The mixture was basified to pH 8 with saturated sodium bicarbonate (aq.). The resulting mixture was extracted with ethyl acetate (3×10 mL). The combined organic layers were washed with brine (3×10 mL), dried over anhydrous sodium sulfate. After filtration, the filtrate was concentrated under reduced pressure. The residue was purified by silica gel column chromatography, eluted with petroleum ether/ethyl acetate (1/1). The fractions containing desired product were collected, concentrated under reduced pressure to afford tert-butyl N-[2-({6-methoxy-4-[2,3,6-trifluoro-4-(4-methoxypyridine-3-amido)phenoxy]quinolin-7-yl}oxy)ethyl]-N-methylcarbamate (30 mg, 33%) as a white solid. MS ESI calculated for $C_{31}H_{31}F_3N_4O_7$ [M+H]$^+$, 629.21 found 629.20.

Step 3: 4-methoxy-N-[2,3,5-trifluoro-4-({6-methoxy-7-[2-(methylamino)ethoxy]quinolin-4-yl}oxy)phenyl]-pyridine-3-carboxamide To a stirred solution of tert-butyl N-[2-({6-methoxy-4-[2,3,6-trifluoro-4-(4-methoxypyridine-3-amido)phenoxy]quinolin-7-yl}oxy)ethyl]-N-methylcarbamate (30 mg, 0.048 mmol) in dichloromethane (4 mL) was added hydrochloric acid (gas, 4 N in 1,4-dioxane, 0.5 mL) at room temperature. The resulting mixture was stirred at room temperature for 2 h. The resulting mixture was concentrated under reduced pressure. The crude product (30 mg) was purified by Prep-HPLC with the following conditions (Column: XBridge Prep OBD C18 Column, 30×150 mm, 5 μm; Mobile Phase A: water (plus 10 mmol/L ammonium bicarbonate), Mobile Phase B: acetonitrile; Flow rate: 60 mL/min; Gradient: 24% to 34% B in 8 min, 34% B; Detector: UV 254/220 nm). The fractions containing desired product were collected, concentrated, and lyophilized to afford 4-methoxy-N-[2,3,5-trifluoro-4-({6-methoxy-7-[2-(methylamino)ethoxy]quinolin-4-yl}oxy)phenyl]pyridine-3-carboxamide (8 mg, 31%) as a white solid. MS ESI calculated for $C_{26}H_{23}F_3N_4O_5$ [M+H]$^+$, 529.16 found 529.20. $^1$H NMR (400 MHz, DMSO-d$_6$) δ 8.78 (s, 1H), 8.64 (d, J=5.6 Hz, 1H), 8.53 (d, J=5.2 Hz, 1H), 8.14 (dd, J=12.0, 4.8 Hz, 1H), 7.56 (s, 1H), 7.46 (s, 1H), 7.31 (d, J=5.6 Hz, 1H), 6.76 (d, J=5.2 Hz, 1H), 4.22 (t, J=5.6 Hz, 2H), 4.03 (s, 3H), 3.98 (s, 3H), 3.64 (s, 1H), 2.95 (t, J=5.6 Hz, 2H), 2.38 (s, 3H). $^{19}$F NMR (376 MHz, DMSO-d$_6$) δ −131.73(1H), −149.78(2H).

Example 51: 4-ethoxy-N-[2,3,5-trifluoro-4-({6-methoxy-7-[2-(methylamino)ethoxy]quinolin-4-yl}oxy)phenyl]pyridine-3-carboxamide

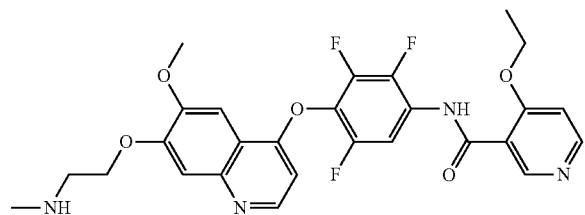

Synthesized using the same method described for example 50. White solid. MS ESI calculated for C$_{27}$H$_{25}$F$_3$N$_4$O$_5$ [M+H]$^+$, 543.18 found 543.25. $^1$H NMR (400 MHz, DMSO-d$_6$) δ 10.41 (s, 1H), 8.89 (s, 1H), 8.64 (d, J=6.0 Hz, 1H), 8.52 (d, J=5.2 Hz, 1H), 8.34-8.25 (m, 1H), 7.56 (s, 1H), 7.46 (s, 1H), 7.31 (d, J=6.0 Hz, 1H), 6.77 (d, J=5.2 Hz, 1H), 4.36 (q, J=6.8 Hz, 2H), 4.24-4.22 (m, 2H), 3.98 (s, 3H), 3.00-2.90 (m, 2H), 2.38 (s, 3H), 1.54-1.49 (t, J=6.8 Hz, 3H). $^{19}$F NMR (376 MHz, DMSO-d$_6$) δ −131.40 (1F), −149.82 (1F), −151.73 (1F).

Example 52: N-(2,5-difluoro-4-((6-methoxy-7-(2-(methylamino)ethoxy)quinolin-4-yl)oxy)phenyl)-4-propoxypyridine-3-carboxamide

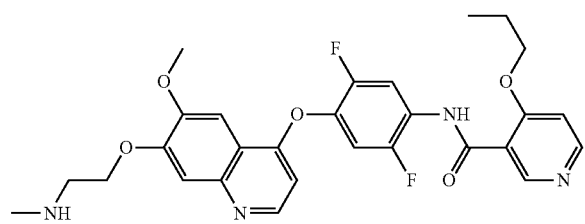 [SMILES: CCCOc1ccncc1C(=O)Nc1cc(F)c(Oc2ccnc3cc(OCCNC)c(OC)cc23)cc1F]

Step 1: tert-butyl N-[2-({4-[4-(4-chloropyridine-3-amido)-2,5-difluorophenoxy]-6-methoxyquinolin-7-yl}oxy)ethyl]-N-methylcarbamate To a stirred solution of tert-butyl N-(2-{[4-(4-amino-2,5-difluorophenoxy)-6-methoxyquinolin yl]oxy}-ethyl)-N-methylcarbamate (500 mg, 1.052 mmol) and 4-chloropyridine-3-carbonyl chloride (370 mg, 2.104 mmol) in dichloromethane (10 mL) were added N,N-diisopropylethylamine (272 mg, 2.104 mmol) at room temperature. The resulting mixture was stirred at room temperature for 16 h. The mixture was quenched with water. The resulting mixture was extracted with ethyl acetate (3×20 mL). The combined organic layers were washed with brine (1×20 mL), dried over anhydrous sodium sulfate. After filtration, the filtrate was concentrated under reduced pressure. The residue was purified by silica gel column chromatography, eluted with petroleum ether/ethyl acetate/ethyl alcohol (4/3/1) and the fractions containing desired product were collected, concentrated under reduced pressure to afford tert-butyl N-[2-({4-[4-(4-chloropyridine-3-amido)-2,5-difluorophenoxy]-6-methoxyquinolin-7-yl}oxy)ethyl]-N-methylcarbamate (520 mg, 80%) as an off-white solid. MS ESI calculated for C$_{30}$H$_{29}$ClF$_2$N$_4$O$_6$ [M+H]$^+$, 615.17, 617.17 found 615.40, 617.40. $^1$H NMR (400 MHz, CDCl$_3$) δ 9.08 (s, 1H), 8.68 (d, J=5.2 Hz, 1H), 8.60 (dd, J=11.6, 7.2 Hz, 1H), 8.56 (d, J=5.2 Hz, 1H), 8.43 (s, 1H), 7.56 (s, 1H), 7.51-7.46 (m, 2H), 7.16 (dd, J=10.4, 6.8 Hz, 1H), 6.52 (d, J=5.6 Hz, 1H), 4.40-4.30 (m, 2H), 4.06 (s, 3H), 3.81-3.74 (m, 2H), 3.08 (s, 3H), 1.49 (s, 9H).

Step 2: tert-butyl (2-((4-(2,5-difluoro-4-(4-propoxynicotinamido)phenoxy)-6-methoxyquinolin-7-yl)oxy)ethyl)(methyl)carbamate To a stirred solution of tert-butyl N-[2-({4-[4-(4-chloropyridine-3-amido)-2,5-difluorophenoxy]-6-methoxy-quinolin-7-yl}oxy)ethyl]-N-methylcarbamate (100 mg, 0.163 mmol) and propanol (98 mg, 1.630 mmol) in dimethyl sulfoxide (2 mL) was added sodium hydroxide (65 mg, 1.630 mmol) at room temperature. The resulting mixture was stirred at 70° C. for 1 h. The mixture was allowed to cool down to room temperature. The residue was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 40% to 80% B in 25 min; Flow rate: 60 mL/min; Detector: UV 220/254 nm. The fractions containing desired product were collected and concentrated under reduced pressure to afford tert-butyl (2-((4-(2,5-difluoro-4-(4-propoxynicotinamido)phenoxy)-6-methoxyquinolin-7-yl)oxy)ethyl)(methyl)-carbamate (24 mg, 27%) as a white solid. MS ESI calculated for C$_{33}$H$_{36}$F$_2$N$_4$O$_7$ [M+H]$^+$, 639.20 found 639.30. $^1$H NMR (400 MHz, DMSO-d$_6$) δ 10.23 (s, 1H), 8.90 (s, 1H), 8.62 (d, J=5.6 Hz, 1H), 8.57-8.49 (m, 1H), 8.43 (dd, J=12.4, 7.2 Hz, 1H), 7.73 (dd, J=10.8, 7.2 Hz, 1H), 7.54 (s, 1H), 7.47 (s, 1H), 7.31 (d, J=5.6 Hz, 1H), 6.61 (d, J=5.2 Hz, 1H), 4.35-4.23 (m, 4H), 3.96 (s, 3H), 3.66 (t, J=5.6 Hz, 2H), 3.00-2.90 (m, 3H), 1.96-1.85 (m, 2H), 1.46-1.32 (m, 9H), 1.03 (t, J=7.4 Hz, 3H).

Step 3: N-[2,5-difluoro-4-({6-methoxy-7-[2-(methylamino)ethoxy]quinolin-4-yl}oxy)phenyl]-4-propoxypyridine-3-carboxamide To a stirred solution of N-[2,5-difluoro-4-({6-methoxy-7-[2-(methylamino)ethoxy]quinolin-4-yl}oxy)-phenyl]-4-propoxypyridine-3-carboxamide (20 mg, 0.037 mmol) in dichloromethane (2 mL) was added hydrochloric acid (gas, 4 N in 1,4-dioxane, 0.5 mL) at room temperature. The resulting mixture was stirred at room temperature for 2 h. The resulting mixture was concentrated under reduced pressure. The crude product (20 mg) was purified by Prep-HPLC with the following conditions (Column: XBridge Shield RP18 OBD Column, 30×150 mm, 5 μm; Mobile Phase A: water (plus 10 mmol/L ammonium bicarbonate), Mobile Phase B: acetonitrile; Flow rate: 60 mL/min; Gradient: 40% to 55% B in 8 min; Detector: UV 254/220 nm). The fractions containing desired product were collected, concentrated and lyophilized to afford N-[2,5-difluoro-4-({6-methoxy-7-[2-(methylamino)ethoxy]quinolin-4-yl}oxy)phenyl]-4-propoxypyridine-3-carboxamide (11 mg, 54%) as a white solid. MS ESI calculated for C$_{28}$H$_{28}$F$_2$N$_4$O$_5$ [M+H]$^+$, 539.20 found 539.25. $^1$H NMR (400 MHz, DMSO-d$_6$) δ 10.24 (s, 1H), 8.90 (s, 1H), 8.63 (d, J=6.0 Hz, 1H), 8.51 (d, J=5.2 Hz, 1H), 8.43 (dd, J=12.4, 7.2 Hz, 1H), 7.74 (dd, J=10.8, 7.2 Hz, 1H), 7.53 (s, 1H), 7.43 (s, 1H), 7.32 (d, J=6.0

Hz, 1H), 6.60 (d, J=5.2 Hz, 1H), 4.34-4.17 (m, 4H), 3.96 (s, 3H), 2.97-2.93 (m, 2H), 2.38 (s, 3H), 1.90-1.89 (m, 2H), 1.03 (t, J=7.4 Hz, 3H). $^{19}$F NMR (376 MHz, DMSO-d$_6$) δ −128.60 (1F), −132.50 (1F).

Example 53: 4-cyclopropoxy-N-[3,5-difluoro-4-({6-methoxy-7-[3-(morpholin-4-yl)propoxy]quinolin-4-yl}oxy)phenyl]pyridine-3-carboxamide

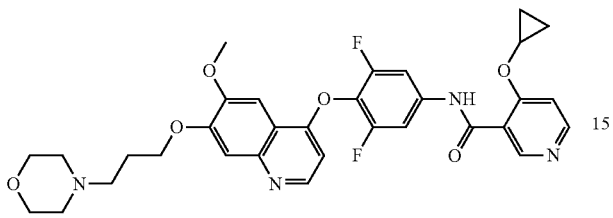

Synthesized using the similar method as in example 52. White solid. MS ESI calculated for C$_{32}$H$_{32}$F$_2$N$_4$O$_6$ [M+H]$^+$, 607.23 found 607.20; $^1$H NMR (400 MHz, DMSO-d$_6$) δ 10.65 (s, 1H), 8.64 (d, J=6.0 Hz, 1H), 8.62 (s, 1H), 8.50 (d, J=5.2 Hz, 1H), 7.76-7.66 (m, 2H), 7.55 (s, 1H), 7.51 (d, J=6.0 Hz, 1H), 7.43 (s, 1H), 6.61 (d, J=5.2 Hz, 1H), 4.22 (t, J=6.4 Hz, 2H), 4.14-4.06 (m, 1H), 3.97 (s, 3H), 3.60 (t, J=4.6 Hz, 4H), 2.47 (t, J=6.4 Hz, 2H), 2.40 (t, J=4.6 Hz, 4H), 2.04-1.94 (m, 2H), 0.94-0.75 (m, 4H). $^{19}$F NMR (376 MHz, DMSO-d$_6$) δ −126.25 (2F).

Example 54: 4-cyclopropoxy-N-[3,5-difluoro-4-({6-methoxy-7-[2-(methylamino)ethoxy]quinolin-4-yl}oxy)phenyl]pyridine-3-carboxamide

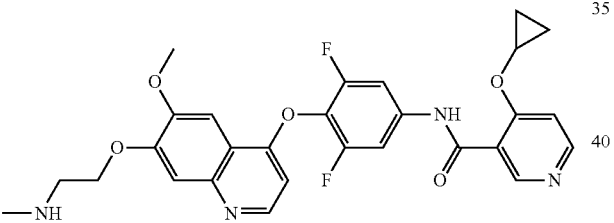

Synthesized using the similar method as in example 52. White solid. MS ESI calculated for C$_{28}$H$_{26}$F$_2$N$_4$O$_5$ [M+H]$^+$, 537.19 found 537.20; $^1$H NMR (400 MHz, DMSO-d$_6$) δ 10.64 (s, 1H), 8.69-8.60 (m, 2H), 8.50 (d, J=5.2 Hz, 1H), 7.79-7.67 (m, 2H), 7.61-7.41 (m, 3H), 6.62 (d, J=5.2 Hz, 1H), 4.25-4.22 (m, 2H), 4.11-4.07 (m, 1H), 3.98 (s, 3H), 2.97 (t, J=5.6 Hz, 2H), 2.38 (s, 3H), 0.93-0.78 (m, 4H). $^{19}$F NMR (377 MHz, DMSO-d$_6$) δ −126.49 (2F).

Example 55: 4-cyclobutoxy-N-(3,5-difluoro-4-((6-methoxy-7-(2-(methylamino)ethoxy)quinolin-4-yl)oxy)phenyl)pyridine-3-carboxamide

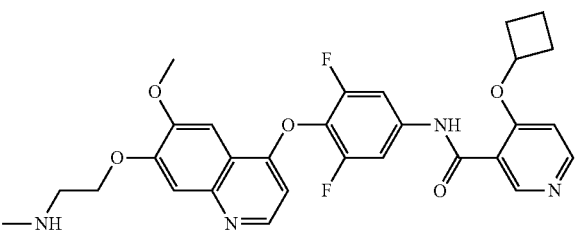 [SMILES: CNCCOc1cc2nccc(Oc3c(F)cc(NC(=O)c4cnccc4OC4CCC4)cc3F)c2cc1OC]

Synthesized using the similar method as in example 52. White solid. MS ESI calculated for C$_{29}$H$_{28}$F$_2$N$_4$O$_5$ [M−H]$^−$, 549.20, found 549.25. $^1$H NMR (400 MHz, DMSO-d$_6$) δ 10.68 (s, 1H), 8.63 (s, 1H), 8.55 (d, J=6.0 Hz, 1H), 8.51 (d, J=5.2 Hz, 1H), 7.76-7.74 (m, 2H), 7.56 (s, 1H), 7.45 (s, 1H), 7.08 (d, J=6.0 Hz, 1H), 6.63 (d, J=5.2 Hz, 1H), 4.93 (p, J=7.2 Hz, 1H), 4.22 (t, J=5.6 Hz, 2H), 3.98 (s, 3H), 2.94 (t, J=5.6 Hz, 2H), 2.56-2.54 (m, 1H), 2.50-2.46 (m, 1H), 2.38 (s, 3H), 2.21-2.15 (m, 2H), 1.89-1.81 (m, 1H), 1.79-1.71 (m, 1H). $^{19}$F NMR (376 MHz, DMSO -d$_6$) δ −126.49 (2F).

Example 56: N-[3,5-difluoro-4-({6-methoxy-7-[2-(methylamino)ethoxy]quinolin-4-yl}oxy)phenyl]-4-propoxypyridine-3-carboxamide

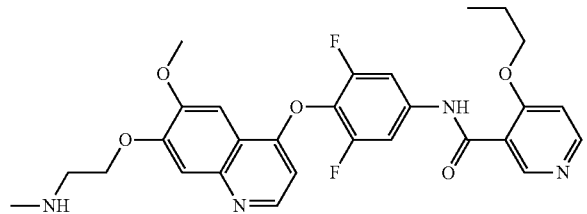 [SMILES: CCCOc1ccncc1C(=O)Nc1cc(F)c(Oc2ccnc3cc(OCCNC)c(OC)cc23)c(F)c1]

Synthesized using the similar method as in example 52. White solid. MS ESI calculated for C$_{28}$H$_{28}$F$_2$N$_4$O$_5$ [M+H]$^+$, 539.20 found 539.25; $^1$H NMR (400 MHz, DMSO-d$_6$) δ 10.67 (s, 1H), 8.63 (s, 1H), 8.58 (d, J=5.6 Hz, 1H), 8.51 (d, J=5.2 Hz, 1H), 7.76-7.69 (m, 2H), 7.56 (s, 1H), 7.45 (s, 1H), 7.26 (d, J=5.6 Hz, 1H), 6.62 (d, J=5.2 Hz, 1H), 4.21-4.19 (m, 4H), 3.98 (s, 3H), 2.94 (t, J=5.6 Hz, 2H), 2.39 (s, 3H), 1.85-1.76 (m, 2H), 0.99 (t, J=7.2 Hz, 3H). $^{19}$F NMR (377 MHz, DMSO-d$_6$) δ −126.48 (2F).

Example 57: N-[3,5-difluoro-4-({6-methoxy-7-[2-(methylamino)ethoxy]quinolin-4-yl}oxy)phenyl]-4-(3,3-difluorocyclobutoxy)pyridine-3-carboxamide

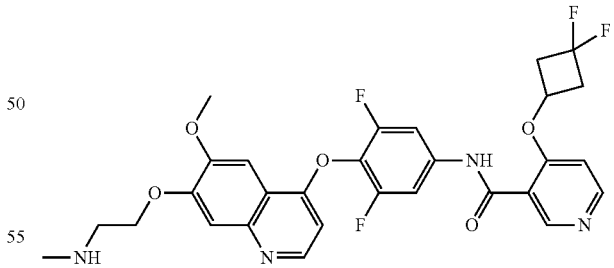

Synthesized using the similar method as in example 52. White solid. MS ESI calculated for C$_{29}$H$_{26}$F$_4$N$_4$O$_5$ [M+H]$^+$ 587.18 found 587.20. $^1$H NMR (400 MHz, CD$_3$OD) δ 8.77 (s, 1H), 8.58 (d, J=6.0 Hz, 1H), 8.49 (d, J=5.2 Hz, 1H), 7.55-7.76 (m, 3H), 7.44 (s, 1H), 7.15 (d, J=6.0 Hz, 1H), 6.63 (d, J=5.2 Hz, 1H), 5.12-5.04 (m, 1H), 4.34 (t, J=5.2 Hz, 2H), 4.07 (s, 3H), 3.32-3.24 (m, 2H), 3.15 (t, J=5.2 Hz, 2H), 2.93-2.91 (m, 2H), 2.56 (s, 3H). $^{19}$F NMR (400 MHz, CD$_3$OD -d$_4$) δ −86.90 (1F), −97.00 (1F), 127.95 (2F).

Example 58: N-[3,5-difluoro-4-({6-methoxy-7-[2-(methylamino)ethoxy]quinolin-4-yl}oxy)phenyl]-4-(3-fluoropropoxy)pyridine-3-carboxamide

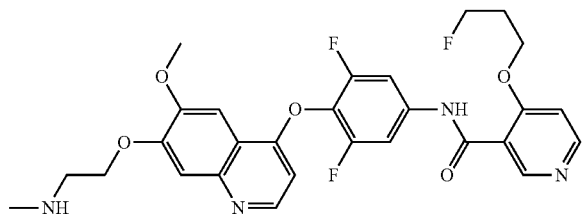

Synthesized using the similar method as in example 52. White solid. MS ESI calculated for $C_{28}H_{27}F_3N_4O_5$ [M+H]$^+$, 557.19 found 557.25. $^1$H NMR (400 MHz, DMSO-d$_6$) δ 10.70 (s, 1H), 8.65 (s, 1H), 8.60 (d, J=6.0 Hz, 1H), 8.51 (d, J=5.2 Hz, 1H), 7.78-7.68 (m, 2H), 7.56 (s, 1H), 7.45 (s, 1H), 7.30 (d, J=6.0 Hz, 1H), 6.62 (d, J=5.2 Hz, 1H), 4.69 (t, J=6.0 Hz, 1H), 4.57 (t, J=6.0 Hz, 1H), 4.31 (t, J=6.0 Hz, 2H), 4.23 (t, J=5.2 Hz, 2H), 3.98 (s, 3H), 2.96 (t, J=5.2 Hz, 2H), 2.41 (s, 3H), 2.25-2.12 (m, 2H). $^{19}$F NMR (376 MHz, DMSO-d$_6$) δ −126.47 (2F), −126.15 (1F).

Example 59: N-[3,5-difluoro-4-({6-methoxy-7-[2-(methylamino)ethoxy]quinolin-4-yl}oxy)phenyl]-4-isopropoxypyridine-3-carboxamide

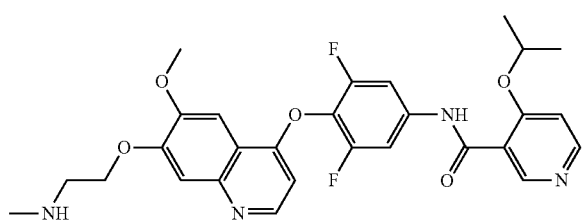 [SMILES: CNCCOc1cc2nccc(Oc3c(F)cc(NC(=O)c4cnccc4OC(C)C)cc3F)c2cc1OC]

Synthesized using the similar method as in example 52. White solid. MS ESI calculated for $C_{28}H_{28}F_2N_4O_5$ [M+H]$^+$, 539.20 found 539.25. $^1$H NMR (400 MHz, DMSO-d$_6$) δ 10.62 (s, 1H), 8.62 (s, 1H), 8.56 (d, J=5.8 Hz, 1H), 8.51 (d, J=5.2 Hz, 1H), 7.73 (d, J=10.2 Hz, 2H), 7.56 (s, 1H), 7.45 (s, 1H), 7.28 (d, J=6.0 Hz, 1H), 6.62 (d, J=5.2 Hz, 1H), 4.95-4.84 (m, 1H), 4.22 (t, J=5.6 Hz, 2H), 3.98 (s, 3H), 2.95 (t, J=5.4 Hz, 2H), 2.39 (s, 3H), 1.37 (d, J=6.0 Hz, 6H). $^{19}$F NMR (376 MHz, DMSO-d$_6$) δ −126.48 (2F).

Example 60: N-[3,5-difluoro-4-({6-methoxy-7-[2-(methylamino)ethoxy]quinolin-4-yl}oxy)phenyl]-4-(2,2-difluoroethoxy)pyridine-3-carboxamide

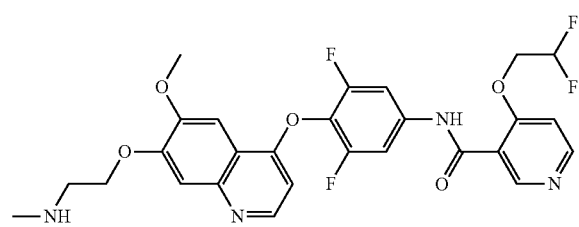

Synthesized using the similar method as in example 52. White solid. MS ESI calculated for $C_{27}H_{24}F_4N_4O_5$ [M+H]$^+$, 561.17 found 561.15. $^1$H NMR (400 MHz, DMSO-d$_6$) δ 10.72 (s, 1H), 8.68 (s, 1H), 8.65 (d, J=6.0 Hz, 1H), 8.51 (d, J=5.2 Hz, 1H), 7.77-7.68 (m, 2H), 7.56 (s, 1H), 7.45 (s, 1H), 7.36 (d, J=6.0 Hz, 1H), 6.63-6.32 (m, 2H), 4.60-4.59 (m, 2H), 4.22 (t, J=5.6 Hz, 2H), 3.98 (s, 3H), 2.94 (t, J=5.6 Hz, 2H), 2.39 (s, 3H). $^{19}$F NMR (376 MHz, DMSO-d$_6$) δ −125.89 (2F), −126.45 (2F).

Example 61: N-[3,5-difluoro-4-({6-methoxy-7-[2-(methylamino)ethoxy]quinolin-4-yl}oxy)phenyl]-4-[(2R)-2-fluoropropoxy]pyridine-3-carboxamide

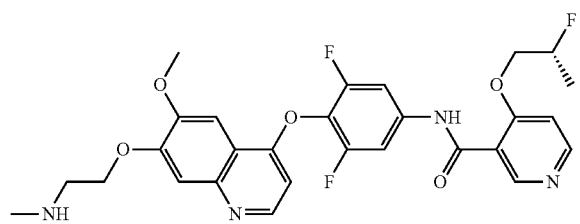 [SMILES: CNCCOc1cc2nccc(Oc3c(F)cc(NC(=O)c4cnccc4OC[C@@H](C)F)cc3F)c2cc1OC]

Synthesized using the similar method as in example 52 with chiral purification. Obtained a White solid. MS ESI calculated for $C_{28}H_{27}F_3N_4O_5$ [M+H]$^+$, 557.19 found 557.15; $^1$H NMR (400 MHz, DMSO-d$_6$) δ 10.71 (s, 1H), 8.67 (s, 1H), 8.62 (d, J=5.6 Hz, 1H), 8.51 (d, J=5.2 Hz, 1H), 7.78-7.67 (m, 2H), 7.56 (s, 1H), 7.45 (s, 1H), 7.31 (d, J=5.6 Hz, 1H), 6.63 (d, J=5.2 Hz, 1H), 5.25-5.00 (m, 1H), 4.49-4.26 (m, 2H), 4.22 (t, J=5.6 Hz, 2H), 3.98 (s, 3H), 2.94 (t, J=5.6 Hz, 2H), 2.39 (s, 3H), 1.40 (dd, J=6.8, 6.4 Hz, 3H). $^{19}$F NMR (376 MHz, DMSO-d$_6$) δ −126.48 (1F), −178.30 (2F).

Example 62: N-[3,5-difluoro-4-({6-methoxy-7-[2-(methylamino)ethoxy]quinolin-4-yl}oxy)phenyl]-4-[(2S)-2-fluoropropoxy]pyridine-3-carboxamide

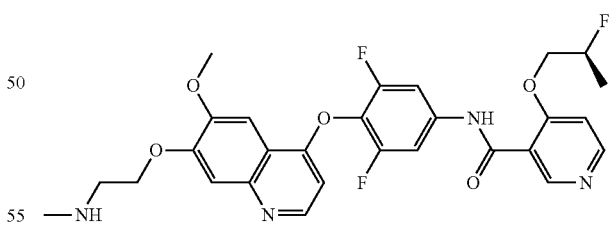

Synthesized using the similar method as in example 52 with chiral purification. White solid. MS ESI calculated for $C_{28}H_{27}F_3N_4O_5$ [M+H]$^+$, 557.19 found 557.15; $^1$H NMR (400 MHz, DMSO -d$_6$) δ 10.71 (s, 1H), 8.67 (s, 1H), 8.62 (d, J=5.6 Hz, 1H), 8.51 (d, J=5.2 Hz, 1H), 7.78-7.67 (m, 2H), 7.56 (s, 1H), 7.45 (s, 1H), 7.31 (d, J=5.6 Hz, 1H), 6.63 (d, J=5.2 Hz, 1H), 5.25-5.00 (m, 2H), 4.49-4.26 (m, 2H), 4.22 (t, J=5.6 Hz, 2H), 3.98 (s, 3H), 2.94 (t, J=5.6 Hz, 2H), 2.39 (s, 3H), 1.40 (dd, J=6.8, 6.4 Hz, 3H). $^{19}$F NMR (376 MHz, DMSO-d$_6$) δ −126.48 (1F), −178.30 (2F).

Example 63: N-[3,5-difluoro-4-({6-methoxy-7-[2-(methylamino)ethoxy]quinolin-4-yl}oxy)phenyl]-4-(2-hydroxyethoxy)pyridine-3-carboxamide

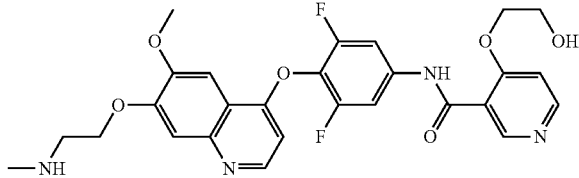 [SMILES: CNCCOc1cc2nccc(Oc3c(F)cc(NC(=O)c4cnccc4OCCO)cc3F)c2cc1OC]

Synthesized using the similar method as in example 52. Yellow solid. MS ESI calculated for $C_{27}H_{26}F_2N_4O_6$ [M+H]$^+$ 541.18 found 541.25. $^1$H NMR (400 MHz, DMSO-d$_6$) δ 10.62 (s, 1H), 8.79 (s, 1H), 8.62 (d, J=6.0 Hz, 1H), 8.51 (d, J=5.2 Hz, 1H), 7.71-7.84 (m, 2H), 7.56 (s, 1H), 7.45 (s, 1H), 7.32 (d, J=6.0 Hz, 1H), 6.62 (d, J=5.2 Hz, 1H), 5.24 (s, 1H), 4.33 (t, J=4.8 Hz, 2H), 4.22 (t, J=5.6 Hz, 2H), 3.98 (s, 3H), 3.85 (t, J=4.8 Hz, 2H), 2.94 (t, J=5.6 Hz, 2H), 2.38 (s, 3H). $^{19}$F NMR (376 MHz, DMSO-d$_6$) δ −126.48 (2F).

Example 64: (S)-N-(3,5-difluoro-4-((6-methoxy-7-(2-(methylamino)ethoxy)quinolin-4-yl)oxy)phenyl)-4-(2-hydroxypropoxy)pyridine-3-carboxamide

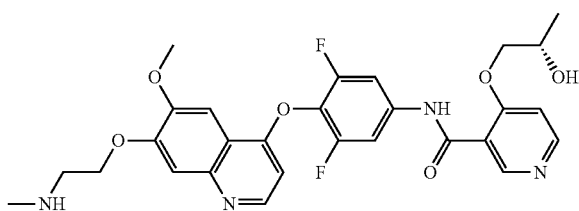 [SMILES: CNCCOc1cc2nccc(Oc3c(F)cc(NC(=O)c4cnccc4OC[C@H](C)O)cc3F)c2cc1OC]

Synthesized using the similar method as in example 52 with chiral purification. White solid. MS ESI calculated for $C_{28}H_{28}F_2N_4O_6$ [M+H]$^+$, 555.20 found 555.15. $^1$H NMR (400 MHz, DMSO -d$_6$) δ 10.67 (s, 1H), 8.79 (s, 1H), 8.61 (d, J=6.0 Hz, 1H), 8.52 (d, J=5.2 Hz, 1H), 7.83-7.75 (m, 2H), 7.58 (s, 1H), 7.49 (s, 1H), 7.31 (d, J=6.0 Hz, 1H), 6.63 (d, J=5.2 Hz, 1H), 5.27 (d, J=5.6 Hz, 1H), 4.34 (t, J=5.6 Hz, 2H), 4.25-4.16 (m, 1H), 4.15-4.05 (m, 2H), 3.99 (s, 3H), 3.17 (t, J=5.6 Hz, 2H), 2.53 (s, 3H), 1.21 (d, J=5.6 Hz, 3H). $^{19}$F NMR (377 MHz, DMSO-d$_6$) δ −126.48 (2F).

Example 65: (R)-N-(3,5-difluoro-4-((6-methoxy-7-(2-(methylamino)ethoxy)quinolin-4-yl)oxy)phenyl)-4-(2-hydroxypropoxy)pyridine-3-carboxamide

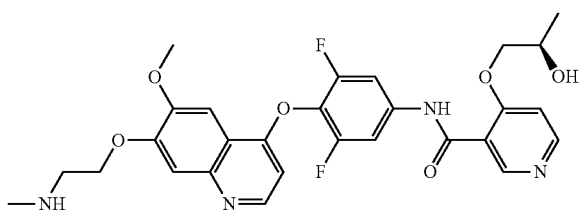 [SMILES: CNCCOc1cc2nccc(Oc3c(F)cc(NC(=O)c4cnccc4OC[C@@H](C)O)cc3F)c2cc1OC]

Synthesized using the similar method as in example 52 with chiral purification. White solid. MS ESI calculated for $C_{28}H_{28}F_2N_4O_6$ [M+H]$^+$, 555.20 found 555.15; $^1$H NMR (400 MHz, DMSO -d$_6$) δ 10.64 (s, 1H), 8.79 (s, 1H), 8.62 (d, J=6.0 Hz, 1H), 8.52 (d, J=5.2 Hz, 1H), 7.80-7.77 (m, 2H), 7.58 (s, 1H), 7.48 (s, 1H), 7.32 (d, J=6.0 Hz, 1H), 6.63 (d, J=5.2 Hz, 1H), 5.25 (d, J=5.6 Hz, 1H), 4.29 (t, J=5.6 Hz, 2H), 4.25-4.18 (m, 1H), 4.14-4.07 (m, 2H), 3.99 (s, 3H), 3.10 (t, J=5.6 Hz, 2H), 2.48 (s, 3H), 1.21 (d, J=5.6 Hz, 3H); $^{19}$F NMR (377 MHz, DMSO-d$_6$) δ −126.47 (2F).

Example 66: N-(3,5-difluoro-4-((6-methoxy-7-(2-(methylamino)ethoxy)quinolin-4-yl)oxy)phenyl)-4-(2-hydroxy-2-methylpropoxy)pyridine-3-carboxamide

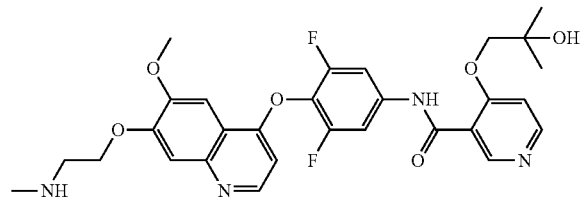 [SMILES: CNCCOc1cc2nccc(Oc3c(F)cc(NC(=O)c4cnccc4OCC(C)(C)O)cc3F)c2cc1OC]

Synthesized using the similar method as in example 52. White solid. MS ESI calculated for $C_{29}H_{30}F_2N_4O_6$ [M+H]$^+$, 569.21 found 569.25. $^1$H NMR (400 MHz, DMSO-d$_6$) δ 10.73 (s, 1H), 8.61 (d, J=5.6 Hz, 1H), 8.51 (d, J=5.2 Hz, 1H), 8.30 (s, 1H), 7.85-7.76 (m, 2H), 7.57 (s, 1H), 7.46 (s, 1H), 7.30 (d, J=5.6 Hz, 1H), 6.62 (d, J=5.2 Hz, 1H), 4.25 (d, J=5.6 Hz, 2H), 3.98 (s, 2H), 3.94 (s, 3H), 3.03 (d, J=5.6 Hz, 2H), 2.44 (s, 3H), 1.21 (s, 6H). $^{19}$F NMR (377 MHz, DMSO-d$_6$) δ −126.46 (2F).

Example 67: N-[3,5-difluoro-4-({6-methoxy-7-[2-(methylamino)ethoxy]quinolin-4-yl}oxy)phenyl]-4-(2-methoxyethoxy)pyridine-3-carboxamide

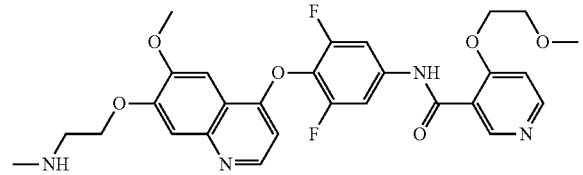

Synthesized using the similar method as in example 52. White solid. MS ESI calculated for $C_{28}H_{28}F_2N_4O_6$ [M+H]$^+$, 555.20 found 555.35. $^1$H NMR (400 MHz, DMSO-d$_6$) δ 10.62 (s, 1H), 8.72 (s, 1H), 8.61 (d, J=6.0 Hz, 1H), 8.51 (d, J=5.2 Hz, 1H), 7.68-7.75 (m, 2H), 7.56 (s, 1H), 7.45 (s, 1H), 7.31 (d, J=6.0 Hz, 1H), 6.62 (d, J=5.2 Hz, 1H), 4.25-4.53 (m, 2H), 4.23 (t, J=5.6 Hz, 2H), 3.98 (s, 3H), 3.64-3.88 (m, 2H), 3.33 (s, 3H), 2.96 (t, J=5.6 Hz, 2H), 2.40 (s, 3H). $^{19}$F NMR (376 MHz, DMSO-d$_6$) δ −126.48 (2F).

Example 68: N-[3,5-difluoro-4-({6-methoxy-7-[2-(methylamino)ethoxy]quinolin-4-yl}oxy)phenyl]-4-(oxetan-3-yloxy)pyridine-3-carboxamide

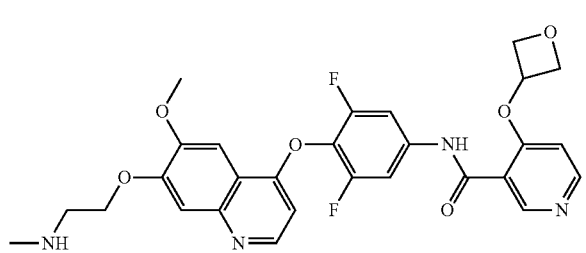 [SMILES: CNCCOc1cc2nccc(Oc3c(F)cc(NC(=O)c4cnccc4OC4COC4)cc3F)c2cc1OC]

Synthesized using the similar method as in example 52. White solid. MS ESI calculated for $C_{28}H_{26}F_2N_4O_6$ [M+H]$^+$ 553.18 found 553.20. $^1$H NMR (400 MHz, DMSO-d$_6$) δ 10.75 (s, 1H), 8.69 (s, 1H), 8.58 (d, J=6.0 Hz, 1H), 8.51 (d, J=5.2 Hz, 1H), 7.81-7.71 (m, 2H), 7.57 (s, 1H), 7.45 (s, 1H), 6.90 (d, J=6.0 Hz, 1H), 6.63 (d, J=5.2 Hz, 1H), 5.56-5.47 (m, 1H), 5.02-4.97 (m, 2H), 4.65-4.62 (m, 2H), 4.23 (t, J=5.6 Hz, 2H), 3.98 (s, 3H), 2.95 (t, J=5.6 Hz, 2H), 2.39 (s, 3H). $^{19}$F NMR (376 MHz, DMSO-d$_6$) δ −126.49 (2F).

Example 69: 4-butoxy-N-[3,5-difluoro-4-({6-methoxy-7-[2-(methylamino)ethoxy]quinolin-4-yl}oxy)phenyl]pyridine-3-carboxamide

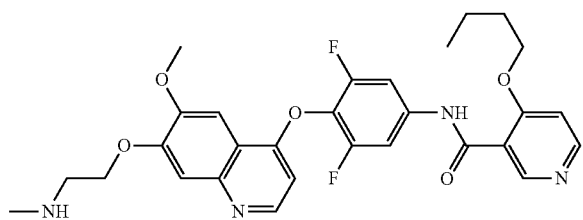 [SMILES: CCCCOc1ccncc1C(=O)Nc1cc(F)c(Oc2ccnc3cc(OCCNC)c(OC)cc23)c(F)c1]

Synthesized using the similar method as in example 52. White solid. MS ESI calculated for $C_{29}H_{30}F_2N_4O_5$ [M+H]$^+$, 553.22 found 553.25. $^1$H NMR (400 MHz, DMSO-d$_6$) δ 10.69 (s, 1H), 8.62 (s, 1H), 8.59 (d, J=5.8 Hz, 1H), 8.51 (d, J=5.2 Hz, 1H), 7.69-7.76 (m, 2H), 7.56 (s, 1H), 7.45 (s, 1H), 7.27 (d, J=5.8 Hz, 1H), 6.61 (d, J=5.2 Hz, 1H), 4.21 (m, J=6.8, 6.2 Hz, 4H), 3.98 (s, 3H), 2.94 (t, J=5.6 Hz, 2H), 2.39 (s, 3H), 1.84-1.77 (m, 2H), 1.41-1.48 (m, 2H), 0.92 (t, J=7.4 Hz, 3H). $^{19}$F NMR (376 MHz, DMSO-d$_6$) δ −126.50 (2F).

Example 70: N-[3,5-difluoro-4-({6-methoxy-7-[2-(methylamino)ethoxy]quinolin-4-yl}oxy)phenyl]-4-[(3R)-oxolan-3-yloxy]pyridine-3-carboxamide

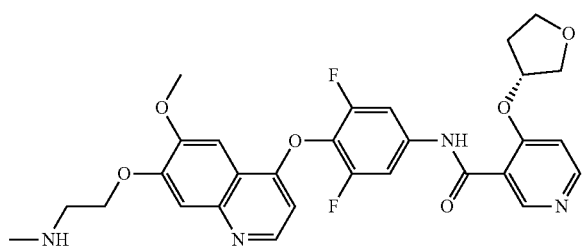 [SMILES: CNCCOc1cc2nccc(Oc3c(F)cc(NC(=O)c4cnccc4O[C@@H]4CCOC4)cc3F)c2cc1OC]

Synthesized using the similar method as in example 52. White solid. MS ESI calculated for $C_{29}H_{28}F_2N_4O_6$ [M+H]$^+$, 567.20 found 567.20. $^1$H NMR (400 MHz, DMSO-d$_6$) δ 10.64 (s, 1H), 8.65 (s, 1H), 8.60 (d, J=6.0 Hz, 1H), 8.51 (d, J=5.2 Hz, 1H), 7.77-7.67 (m, 2H), 7.55 (s, 1H), 7.44 (s, 1H), 7.27 (d, J=6.0 Hz, 1H), 6.63 (d, J=5.2 Hz, 1H), 5.32-5.26 (m, 1H), 4.22 (t, J=5.6 Hz, 2H), 3.98 (s, 3H), 3.96-3.74 (m, 4H), 2.93 (t, J=5.6 Hz, 2H), 2.38 (s, 3H), 2.34-2.27 (m, 1H), 2.07-2.05 (m, 1H). $^{19}$F-NMR (376 MHz, DMSO-d$_6$) δ −126.41 (2F).

Example 71: N-[3,5-difluoro-4-({6-methoxy-7-[2-(methylamino)ethoxy]quinolin-4-yl}oxy)phenyl]-4-[(3S)-oxolan-3-yloxy]pyridine-3-carboxamide

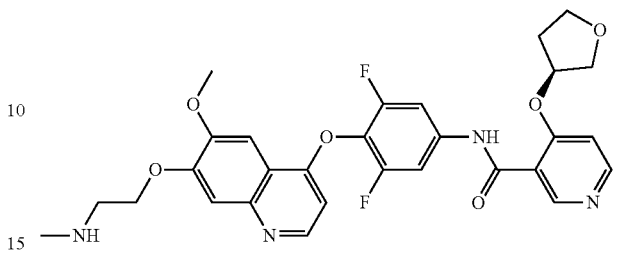

Synthesized using the similar method as in example 52. White solid. MS ESI calculated for $C_{29}H_{28}F_2N_4O_6$ [M+H]$^+$, 567.20 found 567.20. $^1$H NMR (400 MHz, DMSO-d$_6$) δ 10.64 (s, 1H), 8.65 (s, 1H), 8.59 (d, J=6.0 Hz, 1H), 8.51 (d, J=5.2 Hz, 1H), 7.77-7.67 (m, 2H), 7.56 (s, 1H), 7.44 (s, 1H), 7.27 (d, J=6.0 Hz, 1H), 6.63 (d, J=5.2 Hz, 1H), 5.29-5.29 (m, 1H), 4.22 (t, J=5.6 Hz, 2H), 3.98 (s, 3H), 3.92-3.74 (m, 4H), 2.94 (t, J=5.6 Hz, 2H), 2.38 (s, 3H), 2.36-2.28 (m, 1H), 2.06-2.02 (m, 1H). $^{19}$F NMR (376 MHz, DMSO-d$_6$) δ −126.41 (2F).

Example 72: 4-(cyclopropylmethoxy)-N-[3,5-difluoro-4-({6-methoxy-7-[2-(methylamino)ethoxy]quinolin-4-yl}oxy)phenyl]pyridine-3-carboxamide

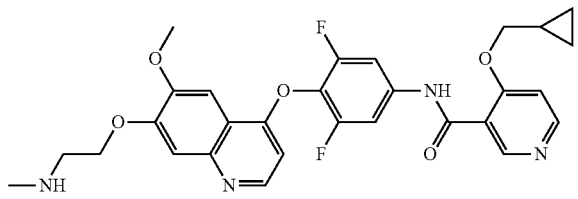 [SMILES: CNCCOc1cc2nccc(Oc3c(F)cc(NC(=O)c4cnccc4OCC4CC4)cc3F)c2cc1OC]

Synthesized using the similar method as in example 52. White solid. MS ESI calculated for $C_{29}H_{28}F_2N_4O_5$ [M+H]$^+$, 551.20 found 551.30. $^1$H NMR (400 MHz, DMSO-d$_6$) δ 10.67 (s, 1H), 8.66 (s, 1H), 8.58 (d, J=5.6 Hz, 1H), 8.51 (d, J=5.2 Hz, 1H), 7.80-7.68 (m, 2H), 7.56 (s, 1H), 7.45 (s, 1H), 7.24 (d, J=5.6 Hz, 1H), 6.63 (d, J=5.2 Hz, 1H), 4.22 (t, J=5.6 Hz, 2H), 4.09 (d, J=7.2 Hz, 2H), 3.98 (s, 3H), 2.94 (t, J=5.6 Hz, 2H), 2.39 (s, 3H), 1.39-1.27 (m, 1H), 0.64-0.56 (m, 2H), 0.48-0.40 (m, 2H). $^{19}$F NMR (376 MHz, DMSO-d$_6$) δ −126.20 (2F).

Example 73: N-[3,5-difluoro-4-({6-methoxy-7-[2-(methylamino)ethoxy]quinolin-4-yl}oxy)phenyl]-4-(prop-2-yn-1-yloxy)pyridine-3-carboxamide

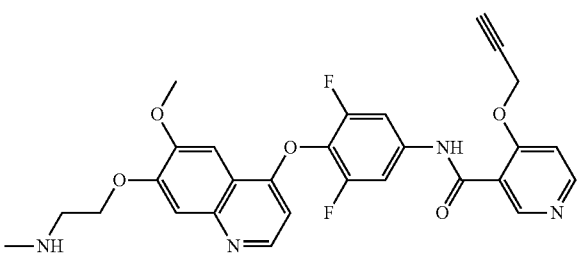 [SMILES: C#CCOc1ccncc1C(=O)Nc1cc(F)c(Oc2ccnc3cc(OCCNC)c(OC)cc23)c(F)c1]

Synthesized using the similar method as in example 52. White solid. MS ESI calculated for $C_{28}H_{24}F_2N_4O_5$ [M+H]$^+$, 535.17 found 535.25. $^1$H NMR (400 MHz, DMSO-d$_6$) δ 10.80 (s, 1H), 8.66-8.63 (m, 2H), 8.50 (d, J=5.2 Hz, 1H), 7.78-7.70 (m, 2H), 7.56 (s, 1H), 7.45 (s, 1H), 7.32 (d, J=6.0 Hz, 1H), 6.62 (d, J=5.2 Hz, 1H), 5.07 (d, J=2.4 Hz, 2H), 4.22 (t, J=5.6 Hz, 2H), 3.98 (s, 3H), 3.77 (t, J=2.4 Hz, 1H), 2.94 (t, J=5.6 Hz, 2H), 2.39 (s, 3H). $^{19}$F NMR (376 MHz, DMSO-d$_6$) δ -126.49 (2F).

Example 74: N-(4-{[7-(azetidin-3-yloxy)-6-methoxyquinolin-4-yl]oxy}-3,5-difluorophenyl)-4-cyclopropoxypyridine-3-carboxamide

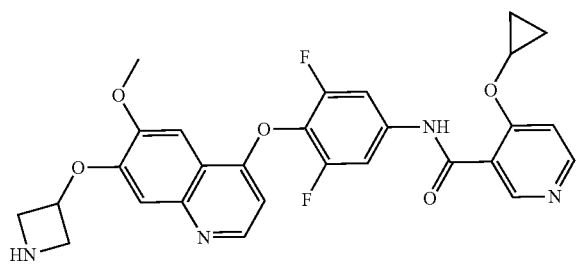 [SMILES: COc1cc2c(Oc3c(F)cc(NC(=O)c4cnccc4OC4CC4)cc3F)ccnc2cc1OC1CNC1]

Synthesized using the similar method as in example 52. White solid. MS ESI calculated for $C_{28}H_{24}F_2N_4O_5$ [M+H]$^+$, 534.17 found 534.25. $^1$H NMR (400 MHz, DMSO-d$_6$) δ 10.65 (s, 1H), 8.63 (d, J=6.0 Hz, 1H), 8.61 (s, 1H), 8.50 (d, J=5.2 Hz, 1H), 7.75-7.68 (m, 2H), 7.58 (s, 1H), 7.51 (d, J=6.0 Hz, 1H), 7.10 (s, 1H), 6.63 (d, J=5.2 Hz, 1H), 5.21-5.19 (m, 1H), 4.12-4.09 (m, 1H), 3.99 (s, 3H), 3.89 (t, J=7.6 Hz, 2H), 3.61 (t, J=7.6 Hz, 2H), 0.94-0.84 (m, 2H), 0.82-0.81 (m, 2H). $^{19}$F NMR (377 MHz, DMSO-d$_6$) δ -126.52 (2F).

Example 75: 4-cyclopropoxy-N-[4-({7-[2-(ethyl-amino)ethoxy]-6-methoxyquinolin-4-yl}oxy)-3,5-difluorophenyl]pyridine-3-carboxamide

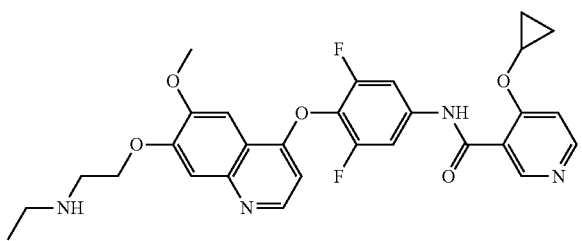 [SMILES: CCNCCOc1cc2nccc(Oc3c(F)cc(NC(=O)c4cnccc4OC4CC4)cc3F)c2cc1OC]

Synthesized using the similar method as in example 52. White solid. MS ESI calculated for $C_{29}H_{28}F_2N_4O_5$ [M+H]$^+$, 551.20 found 551.35; $^1$H NMR (400 MHz, DMSO-d$_6$) δ 10.64 (s, 1H), 8.64 (d, J=5.6 Hz, 1H), 8.62 (s, 1H), 8.50 (d, J=5.2 Hz, 1H), 7.74-7.68 (m, 2H), 7.56 (s, 1H), 7.51 (d, J=5.6 Hz, 1H), 7.44 (s, 1H), 6.62 (d, J=5.2 Hz, 1H), 4.21 (t, J=5.6 Hz, 2H), 4.11-4.07 (m, 1H), 3.98 (s, 3H), 2.98 (t, J=5.6 Hz, 2H), 2.65 (q, J=7.2 Hz, 2H), 1.95-1.67 (m, 1H), 1.05 (t, J=7.2 Hz, 3H), 0.92-0.77 (m, 4H). $^{19}$F NMR (377 MHz, DMSO-d$_6$) δ -126.49 (2F).

Example 76: 4-cyclopropoxy-N-[3,5-difluoro-4-({6-methoxy-7-[2-(methylamino)ethoxy]quinolin-4-yl}oxy)phenyl]pyrimidine-5-carboxamide

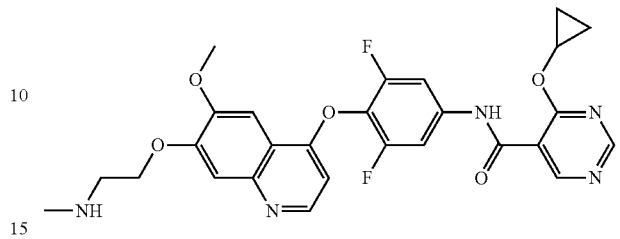

Synthesized using the similar method as in example 52. Colorless solid. MS ESI calculated for $C_{27}H_{25}F_2N_5O_5$ [M+H]$^+$, 538.18 found 538.25. $^1$H NMR (400 MHz, DMSO-d$_6$) δ 10.77 (s, 1H), 9.00 (s, 1H), 8.83 (s, 1H), 8.50 (d, J=5.2 Hz, 1H), 7.69-7.78 (m, 2H), 7.67 (s, 1H), 7.45 (s, 1H), 6.61 (d, J=5.2 Hz, 1H), 4.48-4.45 (m, 1H), 4.21 (t, J=5.6 Hz, 2H), 3.97 (s, 3H), 2.93 (t, J=5.6 Hz, 2H), 2.37 (s, 3H), 0.86-0.83 (m, 4H). $^{19}$F NMR (377 MHz, DMSO-d$_6$) δ -126.30 (2F).

Example 77: 3-cyclopropoxy-N-[3,5-difluoro-4-({6-methoxy-7-[2-(methylamino)ethoxy]quinolin-4-yl}oxy)phenyl]pyridine-2-carboxamide

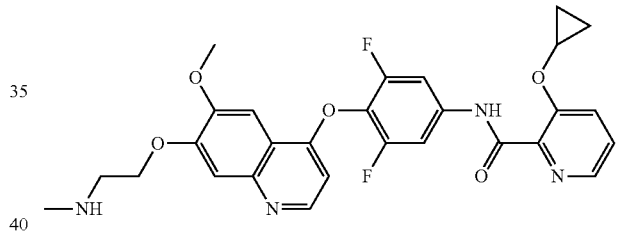

Synthesized using the similar method as in example 52. White solid. MS ESI calculated for $C_{28}H_{26}F_2N_4O_5$ [M+H]$^+$ 537.19 found 537.20. $^1$H NMR (400 MHz, DMSO-d$_6$) δ 10.87 (s, 1H), 8.51 (d, J=5.2 Hz, 1H), 8.30 (dd, J=4.8, 1.2 Hz, 1H), 7.96 (dd, J=8.4, 1.2 Hz, 1H), 7.85-7.77 (m, 2H), 7.64 (dd, J=8.4, 4.8 Hz, 1H), 7.57 (s, 1H), 7.45 (s, 1H), 6.62 (d, J=5.2 Hz, 1H), 4.22 (t, J=5.6 Hz, 2H), 4.06-4.01 (m, 1H), 3.98 (s, 3H), 2.94 (t, J=5.6 Hz, 2H), 2.39 (s, 3H), 0.89-0.81 (m, 2H), 0.76-0.68 (m, 2H). $^{19}$F NMR (376 MHz, DMSO-d$_6$) δ -126.68 (2F).

Example 78: 2-cyclopropoxy-N-[3,5-difluoro-4-({6-methoxy-7-[2-(methylamino)ethoxy]quinolin-4-yl}oxy)phenyl]pyridine-3-carboxamide

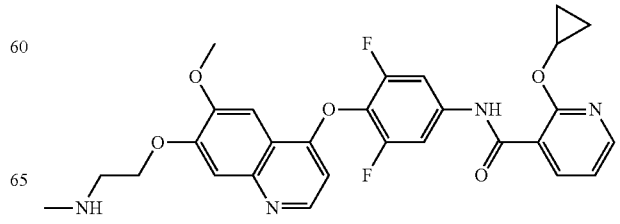

Synthesized using the similar method as in example 52. White solid. MS ESI calculated for $C_{28}H_{26}F_2N_4O_5$ [M+H]+, 537.19 found 537.10; 1H NMR (400 MHz, DMSO-$d_6$) δ 10.56 (s, 1H), 8.51 (d, J=5.2 Hz, 1H), 8.41 (dd, J=4.8, 2.0 Hz, 1H), 8.04 (dd, J=7.2, 2.0 Hz, 1H), 7.77-7.68 (m, 2H), 7.56 (s, 1H), 7.45 (s, 1H), 7.21 (dd, J=7.2, 4.8 Hz, 1H), 6.61 (d, J=5.2 Hz, 1H), 4.42-4.37 (m, 1H), 4.22 (t, J=5.6 Hz, 2H), 3.98 (s, 3H), 2.94 (t, J=5.6 Hz, 2H), 2.39 (s, 3H), 0.85-0.74 (m, 4H). 19F NMR (377 MHz, DMSO-$d_6$) δ −126.52 (2F).

Example 79: 2-cyclopropoxy-N-[3,5-difluoro-4-({7-[2-(methylamino)ethoxy]quinolin-4-yl}oxy)phenyl]pyridine-3-carboxamide

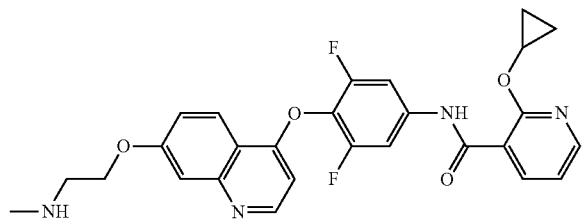 [SMILES: CNCCOc1ccc2c(Oc3c(F)cc(NC(=O)c4cccnc4OC4CC4)cc3F)ccnc2c1]

Synthesized using the similar method as in example 52. White solid. MS ESI calculated for $C_{27}H_{24}F_2N_4O_4$ [M+H]+, 507.18 found 507.20; 1H NMR (400 MHz, DMSO-$d_6$) δ 10.57 (s, 1H), 8.64 (d, J=5.2 Hz, 1H), 8.41 (dd, J=4.8, 2.0 Hz, 1H), 8.26 (d, J=9.2 Hz, 1H), 8.03 (dd, J=7.2, 2.0 Hz, 1H), 7.74-7.69 (m, 2H), 7.45 (d, J=2.4 Hz, 1H), 7.35 (dd, J=9.2, 2.4 Hz, 1H), 7.21 (dd, J=7.4, 4.8 Hz, 1H), 6.63 (d, J=5.2 Hz, 1H), 4.41-4.36 (m, 1H), 4.22 (t, J=5.6 Hz, 2H), 2.92 (t, J=5.6 Hz, 2H), 2.38 (s, 3H), 0.82-0.77 (m, 4H). 19F NMR (377 MHz, DMSO-$d_6$) δ −126.71 (2F).

Example 80: 3-cyclopropoxy-N-[3,5-difluoro-4-({7-[2-(methylamino)ethoxy]quinolin-4-yl}oxy)phenyl]pyridine-2-carboxamide

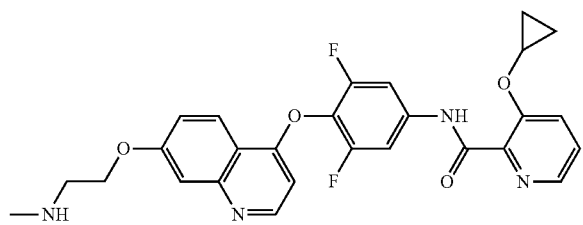

Synthesized using the similar method as in example 52. White solid. MS ESI calculated for $C_{27}H_{24}F_2N_4O_4$ [M+H]+ 507.18 found 507.30. 1H NMR (400 MHz, DMSO-$d_6$) δ 10.89 (s, 1H), 8.64 (d, J=5.2 Hz, 1H), 8.30 (d, J=4.4 Hz, 1H), 8.27 (d, J=9.2 Hz, 1H), 7.96 (d, J=8.8 Hz, 1H), 7.85-7.76 (m, 2H), 7.64 (dd, J=8.8, 4.4 Hz, 1H), 7.46 (d, J=2.4 Hz, 1H), 7.35 (dd, J=9.2, 2.4 Hz, 1H), 6.64 (d, J=5.2 Hz, 1H), 4.24 (t, J=5.6 Hz, 2H), 4.05-4.03 (m, 1H), 2.97 (t, J=5.6 Hz, 2H), 2.41 (s, 3H), 0.93-0.79 (m, 2H), 0.77-0.74 (m, 2H). 19F NMR (376 MHz, DMSO-$d_6$) δ −126.88 (2F).

Example 81: 3-cyclopropoxy-N-(3,5-difluoro-4-((7-(2-(methylamino)ethoxy)quinolin-4-yl)oxy)phenyl)isonicotinamide

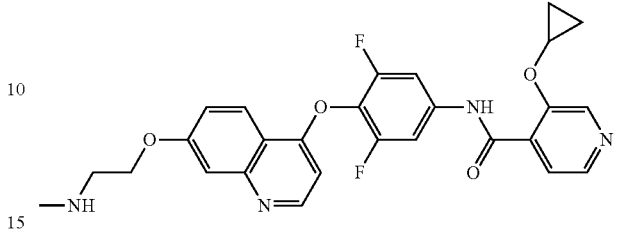

Synthesized using the similar method as in example 52. White solid. MS ESI calculated for $C_{27}H_{24}F_2N_4O_4$ [M+H]+, 507.18, found 507.25. 1H NMR (400 MHz, DMSO-$d_6$) δ 10.77 (s, 1H), 8.85 (s, 1H), 8.65 (d, J=5.2 Hz, 1H), 8.40 (d, J=4.8 Hz, 1H), 8.28 (d, J=9.2 Hz, 1H), 7.73-7.65 (m, 2H), 7.53 (d, J=4.8 Hz, 1H), 7.47 (d, J=2.4 Hz, 1H), 7.36 (dd, J=9.2, 2.4 Hz, 1H), 6.65 (d, J=5.2 Hz, 1H), 4.29 (t, J=5.6 Hz, 2H), 4.14-4.12 (m, 1H), 3.05 (t, J=5.6 Hz, 2H), 2.48 (s, 1H), 2.46 (s, 3H), 0.97-0.76 (m, 4H). 19F NMR (376 MHz, DMSO-$d_6$) δ −126.55 (2F)

Example 82: N-[2,3-difluoro-4-({6-methoxy-7-[2-(methylamino)ethoxy]quinolin-4-yl}oxy)phenyl]-4-propoxypyridine-3-carboxamide

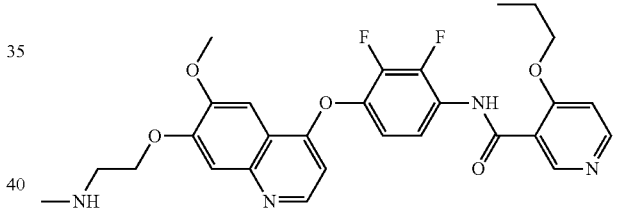

Synthesized using the similar method as in example 52. White solid. MS ESI calculated for $C_{28}H_{28}F_2N_4O_5$ [M−H]−, 537.20 found 537.20. 1H NMR (400 MHz, DMSO-$d_6$) δ 10.24 (s, 1H), 8.84 (s, 1H), 8.61 (d, J=6.0 Hz, 1H), 8.52 (d, J=5.2 Hz, 1H), 8.12-8.07 (m, 1H), 7.54 (s, 1H), 7.44 (s, 1H), 7.40-7.27 (m, 2H), 6.63 (d, J=5.2 Hz, 1H), 4.23-4.19 (m, 4H), 3.97 (s, 3H), 2.93 (t, J=5.6 Hz, 2H), 2.38 (s, 3H), 1.87-1.83 (m, 2H), 1.03 (t, J=7.2 Hz, 3H). 19F NMR (376 MHz, DMSO) δ −146.00 (1F), −152.67 (1F).

Example 83: 4-cyclopropoxy-N-[2,3-difluoro-4-({6-methoxy-7-[2-(methylamino)ethoxy]quinolin-4-yl}oxy)phenyl]pyridine-3-carboxamide

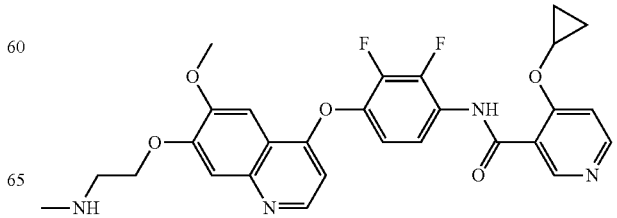

Synthesized using the similar method as in example 52. White solid. MS ESI calculated for $C_{28}H_{26}F_2N_4O_5$ [M+H]$^+$, 537.19 found 537.25. $^1$H NMR (400 MHz, DMSO-d$_6$) δ 10.10 (s, 1H), 8.82 (s, 1H), 8.66 (d, J=5.8 Hz, 1H), 8.52 (d, J=5.2 Hz, 1H), 8.03 (t, J=8.6 Hz, 1H), 7.54 (d, J=3.8 Hz, 2H), 7.45 (s, 1H), 7.39-7.32 (m, 1H), 6.62 (d, J=5.2 Hz, 1H), 4.21 (q, J=5.4 Hz, 3H), 3.97 (s, 3H), 2.94 (t, J=5.6 Hz, 2H), 2.39 (s, 3H), 0.98-0.87 (m, 4H). $^{19}$F NMR (376 MHz, DMSO-d$_6$) δ −145.73 (1F), −152.73 (1F).

Example 84: 4-cyclopropoxy-N-(3,5-difluoro-4-((6-methoxy-7-(3-(methylamino)propoxy)quinolin-4-yl)oxy)phenyl)pyridine-3-carboxamide

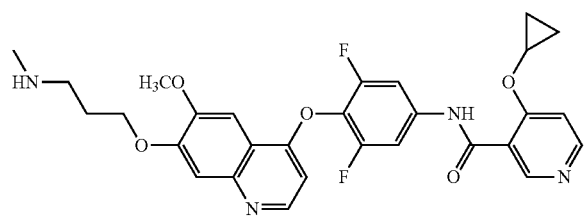 [SMILES: CNCCCOc1cc2nccc(Oc3c(F)cc(NC(=O)c4cnccc4OC4CC4)cc3F)c2cc1OC]

Synthesized using the similar method as in example 52. Light brown semi solid in the form of TFA salt. $^1$H NMR (400 MHz, DMSO-d$_6$): δ 10.71 (s, 1H), 8.66-8.63 (m, 3H), 8.42 (bs, 2H), 7.72 (d, J=10.4Hz, 2H), 7.64 (s, 1H), 7.57 (d, J=5.6Hz, 1H), 7.52 (s, 1H), 6.83 (bs, 1H), 4.29 (t, J=5.6Hz, 2H), 4.12 (bs, 1H), 4.01 (s, 3H), 3.35 (t, J=6.8Hz, 2H), 3.12-3.11 (m, 2H), 2.64 (t, J=5.6 Hz, 3H), 2.17 (t, J=6.4Hz, 2H), 1.66-1.55 (m, 6H), 1.12 (s, 1H), 0.91 (bs, 2H), 0.81 (bs, 2H), ppm; LCMS: RT 4.00; m/z: 551.43 [M+H]$^+$.

Example 85: 4-cyclobutoxy-N-(3,5-difluoro-4-((6-methoxy-7-(3-(methylamino)propoxy)quinolin-4-yl)oxy)phenyl)pyridine-3-carboxamide

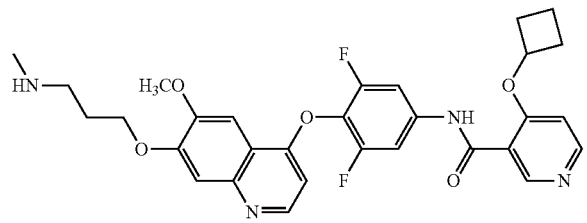 [SMILES: CNCCCOc1cc2nccc(Oc3c(F)cc(NC(=O)c4cnccc4OC4CCC4)cc3F)c2cc1OC]

Synthesized using the similar method as in example 52. Light brown semi-solid in the form of TFA salt. $^1$H NMR (400 MHz, DMSO-d$_6$) δ 10.78 (s 1H), 8.71-8.61 (m, 3H), 8.40 (brs, 1H), 7.77 (d, J=10 Hz, 2H), 7.66 (s, 1H), 7.52 (s, 1H), 7.19 (d, J=5.6Hz, 1H), 6.88 (brs, 1H), 5.01-4.94 (m, 1H), 4.30 (t, J=5.2. Hz, 2H), 3.96 (s, 3H), 3.16-3.11 (m 2H), 2.65-2.63, (m, 3H), 2.17-2.07 (m, 4H), 1.85-1.65 (m, 4H), 1.67-1.65 (m, 2H). ppm; LCMS: RT 4.20.34; m/z: 565.59 [M+H]$^+$.

Example 86: N-(3,5-difluoro-4-((6-methoxy-7-(3-(methylamino)propoxy)quinolin-4-yl)oxy)phenyl)-4-(oxetan-3-yloxy)pyridine-3-carboxamide

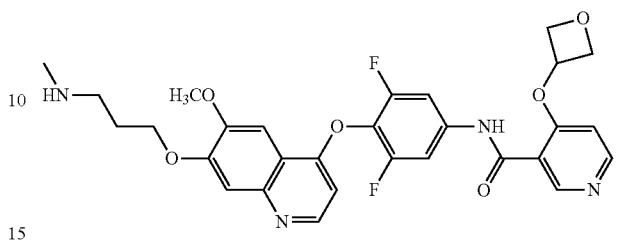

Synthesized using the similar method as in example 52. Colorless semi solid in the form of TFA salt. $^1$H NMR (400 MHz DMSO-d$_6$) δ 10.77 (s, 1H), 8.68 (s, 1H), 8.58 (t, J=5.6 Hz, 2H), 8.38 (brs, 1H), 7.77 (d, J=10 Hz, 2H), 7.61 (s, 1H), 7.48 (s, 1H), 6.92 (d, J=6.0 Hz, 1H), 6.73-6.71 (brs, 1H), 5.51 (t, J=5.6 Hz, 1H), 5.00 (t, J=7.2 Hz, 2H), 4.63 (dd, J=7.2Hz, 5.2 Hz, 2H), 4.30 (t, J=5.6 Hz, 2H), 3.99 (s, 3H), 3.20-3.10 (m, 2H), 2.68-2.62 (m, 3H), 2.19-2.15 (m, 2H) ppm. LCMS: RT 1.34; m/z: 557[M+H]$^+$.

Example 87: 4-cyclopropoxy-N-[3,5-difluoro-4-({7-[2-(methylamino)ethoxy]quinolin-4-yl}oxy)phenyl]pyridine-3-carboxamide

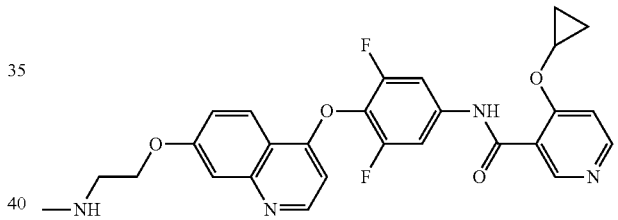

Synthesized using the similar method as in example 52. White solid. MS ESI calculated for $C_{27}H_{24}F_2N_4O_4$ [M+H]$^+$, 507.18 found 507.25 $^1$H NMR (400 MHz, DMSO-d$_6$) δ 10.63 (s, 1H), 8.67-8.59 (m, 3H), 8.26 (d, J=9.2 Hz, 1H), 7.75-7.65 (m, 2H), 7.51 (d, J=6.0 Hz, 1H), 7.45 (d, J=2.4 Hz, 1H), 7.35 (dd, J=9.2, 2.4 Hz, 1H), 6.64 (d, J=5.2 Hz, 1H), 4.23 (t, J=5.6 Hz, 2H), 4.12-4.09 (m, 1H), 2.93 (t, J=5.6 Hz, 2H), 2.38 (s, 3H), 0.91-0.89 (m, 2H), 0.85-0.81 (m, 2H). $^{19}$F NMR (377 MHz, DMSO-d$_6$) δ −126.69 (2F).

Example 88: N-[4-({7-[(2R)-2-aminopropoxy]quinolin-4-yl}oxy)-3,5-difluorophenyl]-4-cyclopropoxypyridine-3-carboxamide

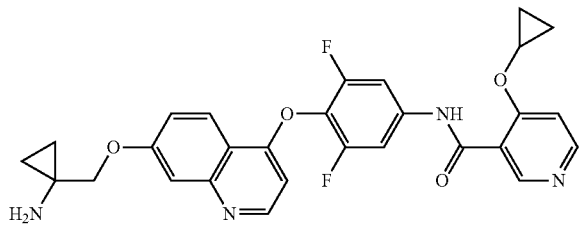 [SMILES: NC1(COc2ccc3c(Oc4c(F)cc(NC(=O)c5cnccc5OC5CC5)cc4F)ccnc3c2)CC1]

Synthesized using the similar method as in example 52. White solid. MS ESI calculated for $C_{28}H_{24}F_2N_4O_4$ [M+H]$^+$, 519.18 found 519.15. $^1$H NMR (400 MHz, DMSO-d$_6$) δ 10.62 (s, 1H), 8.67-8.60 (m, 3H), 8.27 (d, J=9.2 Hz, 1H), 7.74-7.68 (m, 2H), 7.51 (d, J=5.6 Hz, 1H), 7.44-7.36 (m, 2H), 6.63 (d, J=5.2 Hz, 1H), 4.12-4.08 (m, 1H), 4.06 (s, 2H), 0.93-0.86 (m, 2H), 0.85-0.78 (m, 2H), 0.69-0.56 (m, 4H); $^{19}$F NMR (376 MHz, DMSO-d$_6$) δ −126.68 (2F).

Example 89: N-(4-{[7-(azetidin-3-yloxy)quinolin-4-yl]oxy}-3,5-difluorophenyl)-4-cyclopropoxypyridine-3-carboxamide

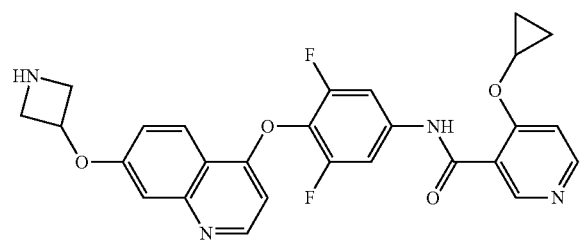 [SMILES: O=C(Nc1cc(F)c(Oc2ccnc3cc(OC4CNC4)ccc23)c(F)c1)c1cnccc1OC1CC1]

Synthesized using the similar method as in example 52. Off-white solid. MS ESI calculated for $C_{27}H_{22}F_2N_4O_4$ [M+H]$^+$, 505.16 found 505.15. $^1$H NMR (400 MHz, DMSO-d$_6$) δ 10.63 (s, 1H), 8.82-8.63 (m, 3H), 8.28 (d, J=9.2 Hz, 1H), 7.75-7.66 (m, 2H), 7.51 (d, J=6.0 Hz, 1H), 7.33 (dd, J=9.2, 2.4 Hz, 1H), 7.18 (d, J=2.4 Hz, 1H), 6.65 (d, J=5.2 Hz, 1H), 5.25-5.18 (m, 1H), 4.30-4.05 (m, 2H), 3.92-3.85 (m, 2H), 3.64-3.57 (m, 2H), 0.93-0.77 (m, 4H). $^{19}$F NMR (376 MHz, DMSO-d$_6$) δ −126.72 (2F).

Example 90: 4-cyclopropoxy-N-{3,5-difluoro-4-[(7-methoxyquinolin-4-yl)oxy]phenyl}pyridine-3-carboxamide

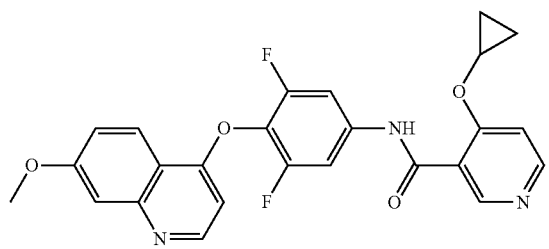 [SMILES: COc1ccc2c(Oc3c(F)cc(NC(=O)c4cnccc4OC4CC4)cc3F)ccnc2c1]

Synthesized using the similar method as in example 52. White solid. MS ESI calculated for $C_{25}H_{19}F_2N_3O_4$ [M+H]$^+$, 464.13 found 464.15. $^1$H NMR (400 MHz, DMSO-d$_6$) δ 10.62 (s, 1H), 8.67-8.59 (m, 3H), 8.27 (d, J=9.2 Hz, 1H), 7.75-7.66 (m, 2H), 7.51 (d, J=6.0 Hz, 1H), 7.46 (d, J=2.4 Hz, 1H), 7.35 (dd, J=9.2, 2.4 Hz, 1H), 6.64 (d, J=5.2 Hz, 1H), 4.12-4.06 (m, 1H), 3.96 (s, 3H), 0.98-0.78 (m, 4H). $^{19}$F NMR (377 MHz, DMSO-d$_6$) δ −126.70 (2F).

Example 91: 4-cyclopropoxy-N-{4-[(6,7-dimethoxyquinolin-4-yl)oxy]-3,5-difluorophenyl}pyridine-3-carboxamide

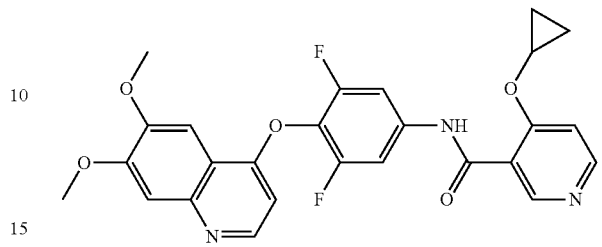

Synthesized using the similar method as in example 52. White solid. MS ESI calculated for $C_{26}H_{21}F_2N_3O_5$ [M+H]$^+$, 494.14 found 494.15. $^1$H NMR (400 MHz, DMSO-d$_6$) δ 10.64 (s, 1H), 8.64 (d, J=6.0 Hz, 1H), 8.62 (s, 1H), 8.51 (d, J=5.2 Hz, 1H), 7.74-7.68 (m, 2H), 7.55 (s, 1H), 7.51 (d, J=6.0 Hz, 1H), 7.44 (s, 1H), 6.62 (d, J=5.2 Hz, 1H), 4.12-4.06 (m, 1H), 4.00-3.93 (m, 6H), 0.79-0.92 (m, 4H). $^{19}$F NMR (376 MHz, DMSO-d$_6$) δ −126.49 (2F).

Example 92: 4-cyclopropoxy-N-{4-[(6,7-dimethoxyquinolin-4-yl)oxy]-2,3,5-trifluorophenyl}pyridine-3-carboxamide

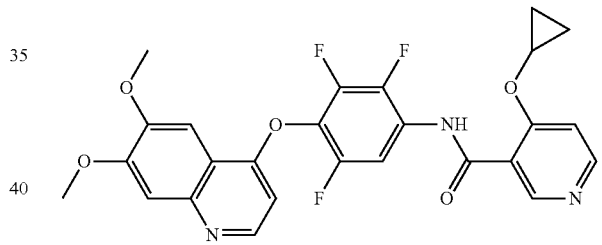

Synthesized using the similar methods as in examples 52 and 50. White solid. MS ESI calculated for $C_{26}H_{20}F_3N_3O_5$ [M+H]$^+$ 512.14 found 512.15. $^1$H NMR (400 MHz, DMSO-d$_6$) δ 10.29 (s, 1H), 8.83 (s, 1H), 8.68 (d, J=6.0 Hz, 1H), 8.54 (d, J=5.2 Hz, 1H), 8.22 (s, 1H), 7.58-7.53 (m, 2H), 7.46 (s, 1H), 6.77 (d, J=5.2 Hz, 1H), 4.27-7.18 (m, 1H), 3.98 (s, 6H), 0.99-0.83 (m, 4H).

Example 93: 4-cyclopropoxy-N-[2,3,5-trifluoro-4-({6-methoxy-7-[2-(methylamino)ethoxy]quinolin-4-yl}oxy)phenyl]pyridine-3-carboxamide

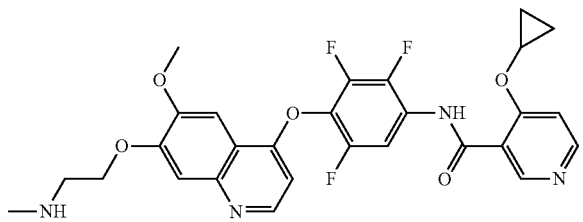 [SMILES: CNCCOc1cc2nccc(Oc3c(F)cc(NC(=O)c4cnccc4OC4CC4)c(F)c3F)c2cc1OC]

Synthesized using the similar methods as in examples 52 and 50. White solid. MS ESI calculated for $C_{28}H_{25}F_3N_4O_5$ [M+H]$^+$, 555.18 found 555.20. $^1$H NMR (400 MHz, DMSO-d$_6$) δ 10.28 (s, 1H), 8.82 (s, 1H), 8.68 (d, J=6.0 Hz, 1H), 8.52 (d, J=5.2 Hz, 1H), 8.26-8.16 (m, 1H), 7.57-7.53 (m, 2H), 7.46 (s, 1H), 6.76 (d, J=5.2 Hz, 1H), 4.26-4.18 (m, 3H), 3.98 (s, 3H), 2.98-2.95 (m, 2H), 2.39 (s, 3H), 0.99-0.86 (m, 4H). $^{19}$F NMR (376 MHz, DMSO-d$_6$) δ −131.50(1F), −149.75 (1F), −151.23 (1F).

Example 94: 4-cyclopropoxy-N-[2,3,5-trifluoro-4-({7-[2-(methylamino)ethoxy]quinolin-4-yl}oxy)phenyl]pyridine-3-carboxamide

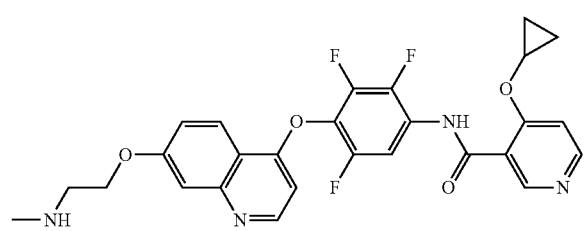

Synthesized using the similar methods as in examples 52 and 50. White solid. MS ESI calculated for $C_{27}H_{23}F_3N_4O_4$ [M+H]$^+$, 525.17 found 525.10; $^1$H NMR (400 MHz, DMSO-d$_6$) δ 10.28 (s, 1H), 8.82 (s, 1H), 8.69-8.64 (m, 2H), 8.26 (d, J=9.2 Hz, 1H), 8.24-2.17 (m, 1H), 7.55 (d, J=6.0 Hz, 1H), 7.46 (d, J=2.4 Hz, 1H), 7.36 (dd, J=9.2, 2.4 Hz, 1H), 6.77 (d, J=5.2 Hz, 1H), 4.25-4.19 (m, 3H), 2.92 (d, J=5.6 Hz, 2H), 2.37 (s, 3H), 0.98-0.85 (m, 4H). $^{19}$F NMR (376 MHz, DMSO-d$_6$) δ −132.26 (1F), −149.91 (1F), −151.11 (1F).

Example 95: N-{4-[(6,7-dimethoxyquinolin-4-yl)oxy]-3,5-difluorophenyl}-4-(2-hydroxyethoxy)pyridine-3-carboxamide

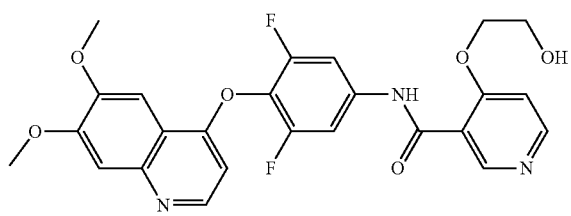 [SMILES: COc1cc2nccc(Oc3c(F)cc(NC(=O)c4cnccc4OCCO)cc3F)c2cc1OC]

Synthesized using the similar method as in in example 52. White solid. MS ESI calculated for $C_{25}H_{21}F_2N_3O_6$ [M+H]$^+$, 498.14 found 498.15. $^1$H NMR (400 MHz, DMSO-d$_6$) δ 10.60 (s, 1H), 8.79 (s, 1H), 8.62 (d, J=4.8 Hz, 1H), 8.51 (d, J=5.2 Hz, 1H), 7.86-7.71 (m, 2H), 7.55 (s, 1H), 7.44 (s, 1H), 7.31 (d, J=5.2 Hz, 1H), 6.62 (d, J=4.8 Hz, 1H), 5.21 (b s, 1H), 4.32 (t, J=4.4 Hz, 2H), 3.96 (s, 6H), 3.84 (t, J=4.4 Hz, 2H); $^{19}$F NMR (376 MHz, CDCl$_3$) δ −126.50 (2F).

Example 96: 4-cyclopropoxy-N-{3,5-difluoro-4-[(7-methoxy-1,6-naphthyridin-4-yl)oxy]phenyl}pyridine-3-carboxamide

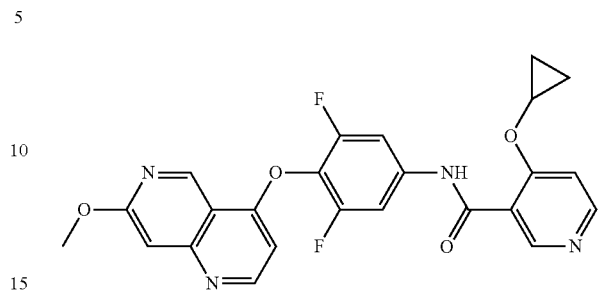

Synthesized using the similar method as in in example 52. Off-white solid. MS ESI calculated for $C_{24}H_{18}F_2N_4O_4$ [M+H]$^+$, 465.40 found 465.15. $^1$H NMR (400 MHz, DMSO-d$_6$) δ 10.64 (s, 1H), 9.51 (s, 1H), 8.82 (d, J=5.2 Hz, 1H), 8.64 (d, J=5.6 Hz, 1H), 8.62 (s, 1H), 7.78-7.67 (m, 2H), 7.51 (d, J=5.6 Hz, 1H), 7.28 (s, 1H), 6.73 (d, J=5.2 Hz, 1H), 4.12-4.09 (m, 1H), 4.04 (s, 3H), 0.93-0.78 (m, 4H). $^{19}$F NMR (377 MHz, DMSO-d$_6$) δ −126.55 (2F).

Example 97: 4-cyclopropoxy-N-(3,5-difluoro-4-((7-(2-hydroxyethoxy)-6-methoxyquinolin-4-yl)oxy)phenyl)pyridine-3-carboxamide

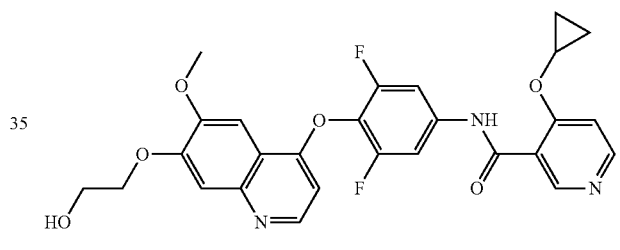

Step 1: 7-{2-[(tert-butyldimethylsilyl)oxy]ethoxy}-4-chloro-6-methoxyquinoline

To a stirred mixture of 4-chloro-6-methoxyquinolin-7-ol (1 g, 4.77 mmol) and triphenyl phosphine (2 g, 7.63 mmol) in tetrahydrofuran (10 mL) was added diisopropyl azodicarboxylate (2 g, 9.89 mmol) and 2-[(tert-butyldimethylsilyl)oxy]ethanol (1 g, 5.67 mmol) under nitrogen atmosphere. The resulting mixture was stirred at room temperature under nitrogen atmosphere for 16 h. The resulting mixture was concentrated under reduced pressure. The residue was purified by silica gel column chromatography, eluted with petroleum ether/ethyl acetate (1/1) concentrated under reduced pressure to afford 7-{2-[(tert-butyldimethyl-silyl)oxy]ethoxy}-4-chloro-6-methoxyquinoline (1.5 g, 85%) as a white solid. MS ESI calculated for $C_{18}H_{26}ClNO_3Si$ [M+H]$^+$, 368.14, 370.14 found 368.20, 370.20. $^1$H NMR (400 MHz, CDCl$_3$) δ 8.58 (d, J=5.6 Hz, 1H), 7.46 (s, 1H), 7.41 (s, 1H), 7.36 (d, J=5.6 Hz, 1H), 4.28 (t, J=4.4 Hz, 2H), 4.12 (t, J=4.4 Hz, 2H), 4.04 (s, 3H), 0.92 (s, 9H), 0.13 (s, 6H).

Step 2: 7-{2-[(tert-butyldimethylsilyl)oxy]ethoxy}-4-(2,6-difluoro-4-nitrophenoxy)-6-methoxyquinoline To a stirred mixture of 7-{2-[(tert-butyldimethylsilyl)oxy]ethoxy}-4-chloro-6-methoxyquinoline (1.5 g, 4.08 mmol)

and 2,6-difluoro-4-nitrophenol (0.86 g, 4.91 mmol) in 1-methyl-2-pyrrolidinone (15 mL) was added N,N-diisopropylethylamine (0.79 g, 6.11 mmol) at room temperature. The resulting mixture was stirred at 140° C. for 16 h. The mixture was allowed to cool down to room temperature. The residue was purified by reverse phase Flash chromatography with the following conditions: Column: WelFlash™ C18-I, 20-40 µm, 120 g; Eluent A: water (plus 10 mmol/L ammonium bicarbonate); Eluent B: acetonitrile; Gradient: 35% to 55% B in 25 min; Flow rate: 60 mL/min; Detector: UV 220/254 nm; desired fractions were concentrated under reduced pressure to afford 7-{2-[(tert-butyldimethylsilyl)oxy]ethoxy}-4-(2,6-difluoro-4-nitrophenoxy)-6-methoxyquinoline (1 g, 48%) as a white solid. MS ESI calculated for $C_{24}H_{28}F_2N_2O_6Si$ [M+H]$^+$, 507.17 found 507.20. $^1$H NMR (400 MHz, DMSO-d$_6$) δ 8.53 (d, J=5.2 Hz, 1H), 8.45-8.40 (m, 2H), 7.56 (s, 1H), 7.47 (s, 1H), 6.76 (d, J=5.2 Hz, 1H), 4.24 (t, J=4.4 Hz, 2H), 4.04 (t, J=4.4 Hz, 2H), 3.97 (s, 3H), 0.89 (s, 9H), 0.11 (s, 6H). $^{19}$F NMR (376 MHz, DMSO-d$_6$) δ −122.69 (2F).

Step 3: 4-[(7-{2-[(tert-butyldimethylsilyl)oxy]ethoxy}-6-methoxyquinolin-4-yl)oxy]-3,5-difluoroaniline To a stirred mixture of 7-{2-[(tert-butyldimethylsilyl)oxy]ethoxy}-4-(2,6-difluoro-4-nitrophenoxy)-6-methoxyquinoline (900 mg, 1.777 mmol) in water (4 mL) and tetrahydrofuran (8 mL) was added iron powder (496 mg, 8.881 mmol) and ammonium chloride (475 mg, 8.880 mmol) at room temperature. The resulting mixture was stirred at 70° C. for 16 h. The mixture was allowed to cool down to room temperature. The residue was purified by reverse phase Flash chromatography with the following conditions: Column: WelFlash™ C18-I, 20-40 µm, 120 g; Eluent A: water (plus 10 mmol/L ammonium bicarbonate); Eluent B: acetonitrile; Gradient: 85% to 100% B in 25 min; Flow rate: 60 mL/min; Detector: UV 220/254 nm; desired fractions were concentrated under reduced pressure to afford 4-[(7-{2-[(tert-butyldimethylsilyl)oxy]ethoxy}-6-methoxy-quinolin-4-yl)oxy]-3,5-difluoroaniline (500 mg, 59%) as a white solid. MS ESI calculated for $C_{24}H_{30}F_2N_2O_4Si$ [M+H]$^+$, 477.19 found 477.20 . $^1$H NMR (400 MHz, DMSO-d$_6$) δ 8.48 (d, J=5.2 Hz, 1H), 7.51 (s, 1H), 7.41 (s, 1H), 6.50 (d, J=5.2 Hz, 1H), 6.44-6.42 (m, 2H), 5.82 (s, 2H), 4.21 (t, J=4.4 Hz, 2H), 4.03 (t, J=4.4 Hz, 2H), 3.95 (s, 3H), 0.88 (s, 9H), 0.10 (s, 6H). $^{19}$F NMR (376 MHz, DMSO-d$_6$) δ −129.15 (2F).

Step 4: N-{4-[(7-{2-[(tert-butyldimethylsilyl)oxy]ethoxy}-6-methoxyquinolin-4-yl)oxy]-3,5-difluorophenyl}-4-chloropyridine-3-carboxamide To a stirred mixture of 4-chloropyridine-3-carboxylic acid (149 mg, 0.946 mmol) in thionyl chloride (2 mL) at room temperature. The resulting mixture was stirred at 80° C. for 3 h. The mixture was allowed to cool down to room temperature. The mixture was concentrated under reduced pressure. The above resulted mixture was added to 4-[(7-{2-[(tert-butyldimethylsilypoxy]ethoxy}-6-methoxyquinolin-4-yl)oxy]-3,5-difluoroaniline (300 mg, 0.629 mmol) in tetrahydrofuran (8 mL) in portion, followed by adding N,N-diisopropylethylamine (163 mg, 1.261 mmol) over 5 min at room temperature. The resulting mixture was stirred at room temperature for additional 12 h. The residue was purified by reverse phase Flash chromatography with the following conditions: Column: WelFlash™ C18-I, 20-40 µm, 120 g; Eluent A: water (plus 10 mmol/L ammonium bicarbonate); Eluent B: acetonitrile; Gradient: 55% to 65% B in 20 min; Flow rate: 60 mL/min; Detector: UV 220/254 nm; the fractions containing desired product were collected and concentrated under reduced pressure to afford N-{4-[(7-{2-[(tert -butyldimethylsilyl)oxy]ethoxy}-6-methoxyquinolin-4-yl)oxy]-3,5-difluorophenyl}-4-chloropyridine-3-carboxamide (150 mg, 39%) as a white solid. MS ESI calculated for $C_{30}H_{32}ClF_2N_3O_5Si$ [M+H]$^+$, 616.18, 618.18 found 616.20, 618.20.

Step 5: 4-cyclopropoxy-N-(3,5-difluoro-4-{[7-(2-hydroxyethoxy)-6-methoxyquinolin-4-yl]oxy}phenyl)pyridine-3-carboxamide To a stirred mixture of N-{4-[(7-{2-[(tert-butyldimethylsilyl)oxy]ethoxy}-6-methoxyquinolin-4-yl)oxy]-3,5-difluorophenyl}-4-chloropyridine-3-carboxamide (150 mg, 0.299 mmol) and cyclopropanol (35 mg, 0.603 mmol) in dimethyl sulfoxide (3 mL) was added 1,8-diazabicyclo[5.4.0]undec-7-ene (91mg, 0.598 mmol) at room temperature. The resulting mixture was stirred at 70° C. for 12 h. The mixture was allowed to cool down to room temperature. The residue was purified by reverse phase Flash chromatography with the following conditions: Column: WelFlash™ C18-I, 20-40 µm, 120 g; Eluent A: water (plus 10 mmol/L ammonium bicarbonate); Eluent B: acetonitrile; Gradient: 25% to 45% B in 25 min; Flow rate: 60 mL/min; Detector: UV 220/254 nm; the fractions containing desired product were collected, concentrated and lyophilized under reduced pressure to afford 4-cyclopropoxy-N-(3,5-difluoro-4-{[7-(2-hydroxyethoxy)-6-methoxyquinolin-4-yl]oxy}-phenyl)pyridine-3-carboxamide (74 mg, 57%) as a white solid. MS ESI calculated for $C_{27}H_{23}F_2N_3O_6$ [M+H]$^+$, 524.16 found 524.10. $^1$H NMR (400 MHz, DMSO-d$_6$) δ 10.64 (s, 1H), 8.64 (d, J=5.6 Hz, 1H), 8.62 (s, 1H), 8.50 (d, J=5.2 Hz, 1H), 7.74-7.67 (m, 2H), 7.56 (s, 1H), 7.51 (d, J=5.6 Hz, 1H), 7.44 (s, 1H), 6.62 (d, J=5.2 Hz, 1H), 4.97 (t, J=5.2 Hz, 1H), 4.19 (t, J=4.8 Hz, 2H), 4.12-4.09 (m, 1H), 3.98 (s, 3H), 3.88-3.81 (m, 2H), 0.92-0.78 (m, 4H). $^{19}$F NMR (376 MHz, DMSO-d$_6$) δ −126.47 (2F).

Example 98: 4-cyclopropoxy-N-[3,5-difluoro-4-({7-[(2S)-2-hydroxypropoxy]-6-methoxyquinolin-4-yl}oxy)phenyl]pyridine-3-carboxamide

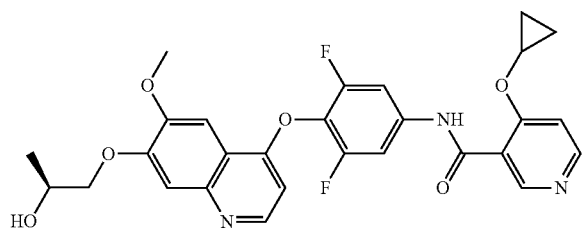 [SMILES: COc1cc2c(Oc3c(F)cc(NC(=O)c4cnccc4OC4CC4)cc3F)ccnc2cc1OC[C@H](C)O]

Synthesized using the similar method as in example 97. White solid. MS ESI calculated for $C_{28}H_{25}F_2N_3O_6$ [M+H]$^+$, 538.17 found 538.15. $^1$H NMR (400 MHz, DMSO-d$_6$) δ 10.64 (s, 1H), 8.64 (d, J=6.0 Hz, 1H), 8.62 (s, 1H), 8.50 (d, J=5.2 Hz, 1H), 7.75-7.67 (m, 2H), 7.56 (s, 1H), 7.51 (d, J=6.0 Hz, 1H), 7.43 (s, 1H), 6.62 (d, J=5.2 Hz, 1H), 4.96 (d, J=4.4 Hz, 1H), 4.13-4.02 (m, 3H), 4.01-3.95 (m, 4H), 1.22 (d, J=6.4 Hz, 3H), 0.93-0.66 (m, 4H). $^{19}$F NMR (376 MHz, DMSO-d$_6$) δ −126.49 (2F).

Example 99: 4-cyclopropoxy-N-[3,5-difluoro-4-({7-[(2R)-2-hydroxypropoxy]-6-methoxyquinolin-4-yl}oxy)phenyl]pyridine-3-carboxamide

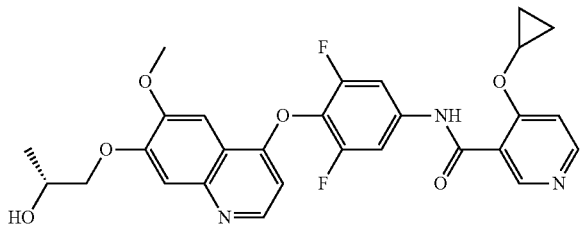 [SMILES: COc1cc2c(Oc3c(F)cc(NC(=O)c4cnccc4OC4CC4)cc3F)ccnc2cc1OC[C@@H](C)O]

Synthesized using the similar method as in example 97. White solid. MS ESI calculated for $C_{28}H_{25}F_2N_3O_6[M+H]^+$, 538.17 found 538.20. $^1H$ NMR (400 MHz, DMSO-$d_6$) δ 10.64 (s, 1H), 8.64 (d, J=6.0 Hz, 1H), 8.62 (s, 1H), 8.51 (d, J=5.2 Hz, 1H), 7.75-7.67 (m, 2H), 7.56 (s, 1H), 7.51 (d, J=6.0 Hz, 1H), 7.43 (s, 1H), 6.63 (d, J=5.2 Hz, 1H), 4.99-4.93 (m, 1H), 4.12-4.02 (m, 3H), 3.99-3.9 (m, 1H), 3.97 (s, 3H), 1.22 (d, J=6.0 Hz, 3H), 0.91-0.88 (m, 2H), 0.83-0.79 (m, 2H). $^{19}F$ NMR (376 MHz, DMSO-$d_6$) δ −126.48 (2F).

Example 100: 4-cyclopropoxy-N-(3,5-difluoro-4-{[7-(2-hydroxyethoxy)quinolin-4-yl]oxy}phenyl)pyridine-3-carboxamide

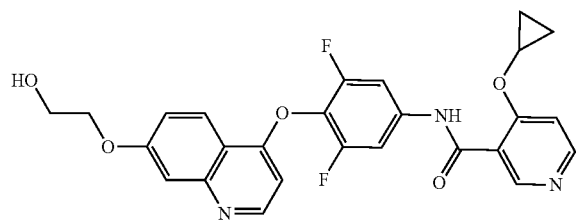 [SMILES: O=C(Nc1cc(F)c(Oc2ccnc3cc(OCCO)ccc23)c(F)c1)c1cnccc1OC1CC1]

Synthesized using the similar method as in example 97. White solid. MS ESI calculated for $C_{26}H_{21}F_2N_3O_5$ [M+H]$^+$, 494.14 found 494.15. $^1H$ NMR (400 MHz, DMSO-$d_6$) δ 10.62 (s, 1H), 8.67-8.60 (m, 3H), 8.27 (d, J=9.2 Hz, 1H), 7.77-7.65 (m, 2H), 7.51 (d, J=5.6 Hz, 1H), 7.45 (d, J=2.4 Hz, 1H), 7.36 (d, J=9.2, 2.4 Hz, 1H), 6.64 (d, J=5.2 Hz, 1H), 4.95 (t, J=5.6 Hz, 1H), 4.20 (t, J=4.8 Hz, 2H), 4.14-4.06 (m, 1H), 3.87-3.78 (m, 2H), 0.98-0.78 (m, 4H). $^{19}F$ NMR (377 MHz, DMSO-$d_6$) δ −126.69 (2F).

Example 101: 4-cyclopropoxy-N-[3,5-difluoro-4-({7-[(2R)-2-hydroxypropoxy]quinolin-4-yl}oxy)phenyl]pyridine-3-carboxamide

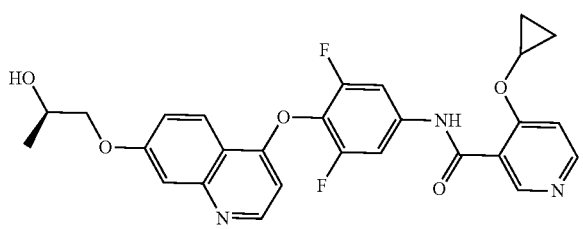 [SMILES: C[C@@H](O)COc1ccc2c(Oc3c(F)cc(NC(=O)c4cnccc4OC4CC4)cc3F)ccnc2c1]

Synthesized using the similar method as in example 97. White solid. MS ESI calculated for $C_{27}H_{23}F_2N_3O_5$ [M+H]$^+$, 508.20 found 508.15. $^1H$ NMR (400 MHz, DMSO-$d_6$) δ 10.63 (s, 1H), 8.67-8.59 (m, 3H), 8.27 (d, J=9.2 Hz, 1H), 7.75-7.68 (m, 2H), 7.51 (d, J=5.6 Hz, 1H), 7.43 (d, J=2.4 Hz, 1H), 7.36 (dd, J=9.2, 2.4 Hz, 1H), 6.64 (d, J=5.2 Hz, 1H), 4.96 (d, J=4.4 Hz, 1H), 4.13-3.99 (m, 4H), 1.22 (d, J=5.6 Hz, 3H), 0.95-0.77 (m, 4H). $^{19}F$ NMR (376 MHz, DMSO-$d_6$) δ −126.69 (2F).

Example 102: 4-cyclopropoxy-N-[3,5-difluoro-4-({7-[(2S)-2-hydroxypropoxy]quinolin-4-yl}oxy)phenyl]pyridine-3-carboxamide

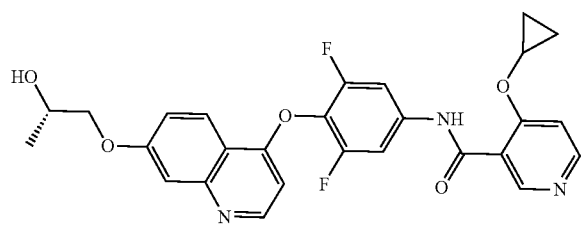 [SMILES: C[C@H](O)COc1ccc2c(Oc3c(F)cc(NC(=O)c4cnccc4OC4CC4)cc3F)ccnc2c1]

Synthesized using the similar method as in example 97. White solid. MS ESI calculated for $C_{27}H_{23}F_2N_3O_5$ [M+H]$^+$, 508.20 found 508.15. $^1H$ NMR (400 MHz, DMSO-$d_6$) δ 10.63 (s, 1H), 8.67-8.60 (m, 3H), 8.27 (d, J=9.2 Hz, 1H), 7.75-7.68 (m, 2H), 7.51 (d, J=5.6 Hz, 1H), 7.43 (d, J=2.4 Hz, 1H), 7.36 (dd, J=9.2, 2.4 Hz, 1H), 6.64 (d, J=5.2 Hz, 1H), 4.96 (d, J=4.4 Hz, 1H), 4.15-3.93 (m, 4H), 1.22 (d, J=5.6 Hz, 3H), 0.93-0.78 (m, 4H). $^{19}F$ NMR (376 MHz, DMSO-$d_6$) δ −126.69 (2F).

Example 103: (R)-4-cyclopropoxy-N-(3,5-difluoro-4-((7-(3-hydroxybutoxy)quinolin-4-yl)oxy)phenyl)pyridine-3-carboxamide

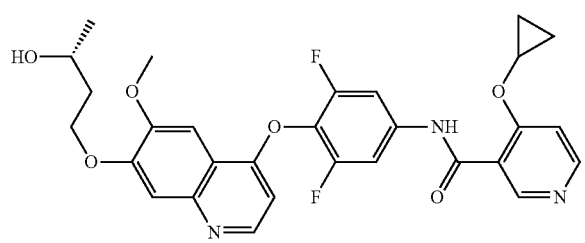

Synthesized using the similar method as in example 97. Light brown solid. $^1H$ NMR (400 MHz, DMSO-$d_6$) δ 10.65 (brs, 1H), 8.63 (d, J=5.2 Hz, 1H), 8.59-8.57 (brs, 2H), 8.26 (d, J=9.2 Hz, 1H), 7.67 (d, J=10.8 Hz, 2H), 7.47 (d, J=6.0 Hz, 1H), 7.43(d, J=2 Hz, 1H), 7.33-7.30 (m, 1H), 6.61 (d, J=4.8 Hz, 1H), 4.62 (brs, 1H), 4.27-4.24 (m, 2H), 4.06 (brs, 1H), 3.89-3.86 (m, 1H), 1.90-1.78 (m, 2H), 1.16 (d, J=4.8 Hz, 3H), 0.98-0.83 (m, 4H) ppm; LCMS m/z: 522.44 [M+H]$^+$.

Example 104: 4-cyclopropoxy-N-(3,5-difluoro-4-{[7-(2-hydroxy-2-methylpropoxy)quinolin-4-yl]oxy}phenyl)pyridine-3-carboxamide

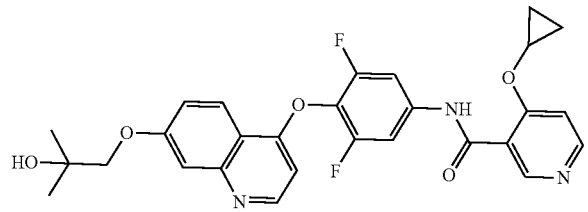 [SMILES: CC(C)(O)COc1ccc2c(Oc3c(F)cc(NC(=O)c4cnccc4OC4CC4)cc3F)ccnc2c1]

Synthesized using the similar methods as in example 97 and 40. White solid. MS ESI calculated for $C_{28}H_{25}F_2N_3O_5$ [M+H]$^+$, 522.20 found 522.20. $^1$H NMR (400 MHz, DMSO-d$_6$) δ 10.64 (s, 1H), 8.65 (d, J=5.2 Hz, 1H), 8.63 (d, J=6.0 Hz, 1H), 8.62 (s, 1H), 8.27 (d, J=9.2 Hz, 1H), 7.75-7.67 (m, 2H), 7.51 (d, J=6.0 Hz, 1H), 7.42 (d, J=2.4 Hz, 1H), 7.37 (dd, J=9.2, 2.4 Hz, 1H), 6.64 (d, J=5.2 Hz, 1H), 4.73 (s, 1H), 4.09-4.04 (m, 1H), 3.93 (s, 2H), 1.27 (s, 6H), 0.94-0.76 (m, 4H). $^{19}$F NMR (376 MHz, DMSO-d$_6$) δ −126.68 (2F).

Example 105: 4-cyclopropoxy-N-(3,5-difluoro-4-{[7-(2-methoxyethoxy)quinolin-4-yl]oxy}phenyl)pyridine-3-carboxamide

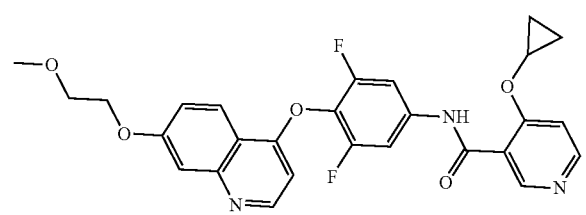 [SMILES: COCCOc1ccc2c(Oc3c(F)cc(NC(=O)c4cnccc4OC4CC4)cc3F)ccnc2c1]

Synthesized using the similar methods as in examples 97 and 41. Light yellow solid. MS ESI calculated for $C_{27}H_{23}F_2N_3O_5$ [M+H]$^+$, 508.10 found 508.15. $^1$H NMR (400 MHz, DMSO-d$_6$) δ 10.64 (s, 1H), 8.66-8.59 (m, 3H), 8.26 (d, J=9.2 Hz, 1H), 7.73-7.67 (m, 2H), 7.51 (d, J=6.0 Hz, 1H), 7.47 (d, J=2.4 Hz, 1H), 7.36 (dd, J=9.2, 2.4 Hz, 1H), 6.64 (d, J=5.2 Hz, 1H), 4.33-4.28 (m, 2H), 4.12-4.09 (m, 1H), 3.79-3.73 (m, 2H), 3.36 (s, 3H), 0.92-0.86 (m, 2H), 0.86-0.80 (m, 2H). $^{19}$F NMR (376 MHz, DMSO-d$_6$) δ −126.68 (2F).

Example 106: 4-cyclopropoxy-N-(3,5-difluoro-4-{[6-methoxy-7-(2-methoxyethoxy)quinolin-4-yl]oxy}phenyl)pyridine-3-carboxamide

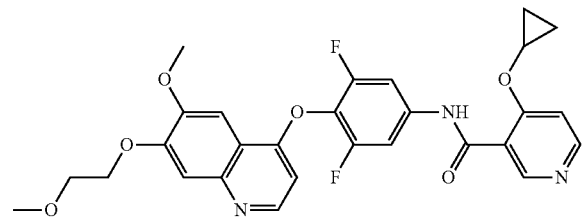 [SMILES: COCCOc1cc2nccc(Oc3c(F)cc(NC(=O)c4cnccc4OC4CC4)cc3F)c2cc1OC]

Synthesized using the similar methods as in examples 97 and 41. White solid. MS ESI calculated for $C_{28}H_{25}F_2N_3O_6$ [M+H]$^+$, 538.17 found 538.10. $^1$H NMR (400 MHz, DMSO-d$_6$) δ 10.64 (s, 1H), 8.64 (d, J=6.0 Hz, 1H), 8.62 (s, 1H), 8.50 (d, J=5.2 Hz, 1H), 7.76-7.64 (m, 2H), 7.56 (s, 1H), 7.51 (d, J=6.0 Hz, 1H), 7.46 (s, 1H), 6.62 (d, J=5.2 Hz, 1H), 4.35-4.22 (m, 2H), 4.11-4.07 (m, 1H), 3.98 (s, 3H), 3.80-3.69 (m, 2H), 3.36 (s, 3H), 0.93-0.86 (m, 2H), 0.84-0.80 (m, 2H). $^{19}$F NMR (376 MHz, DMSO-d$_6$) δ −126.48 (2F).

Example 107: 4-cyclopropoxy-N-(3,5-difluoro-4-((6-(2-hydroxyethoxy)-7-methoxyquinolin-4-yl)oxy)phenyl)pyridine-3-carboxamide

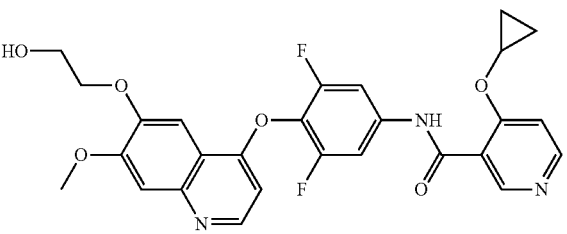 [SMILES: COc1cc2nccc(Oc3c(F)cc(NC(=O)c4cnccc4OC4CC4)cc3F)c2cc1OCCO]

Step 1: 4-chloro-7-methoxyquinolin-6-ol

A mixture of 4-chloro-6,7-dimethoxyquinoline (1.50 g, 6.71 mmol) and (2S)-2-amino-4-(methylsulfanyl)butanoic acid (2.02 g, 13.55 mmol) in methanesulfonic acid (10 mL) was stirred at 120° C. for 16 h. The mixture was allowed to cool down to room temperature. The mixture was neutralized to pH 8 with ammonium hydroxide (aq). The resulting mixture was concentrated under reduced pressure. The residue was purified by reverse phase Flash chromatography with the following conditions: Column: WelFlash™ C18-I, 20-40 μm, 120 g; Eluent A: Water (plus 10 mmol/L ammonium bicarbonate); Eluent B: acetonitrile; Gradient: 42% to 62% B in 25 min; Flow rate: 60 mL/min; Detector: 220/254 nm; desired fractions were concentrated under reduced pressure to afford 4-chloro-7-methoxyquinolin-6-ol (800 mg, 57%) as a yellow solid. MS ESI calculated for $C_{10}H_8ClNO_2$ [M+H]$^+$, 210.02, 212.02 found 210.00, 212.00. $^1$H NMR (400 MHz, DMSO-d$_6$) δ 10.27 (s, 1H), 8.54 (d, J=4.8 Hz, 1H), 7.49 (d, J=4.8 Hz, 1H), 7.43 (s, 1H), 7.40 (s, 1H), 3.97 (s, 3H).

Step 2: 6-{2-[(tert-butyldimethylsilyl)oxy]ethoxy}-4-chloro-7-methoxyquinoline To a stirred mixture of 4-chloro-7-methoxyquinolin-6-ol (400 mg, 1.908 mmol) and 2-[(tert-butyldimethyl-silyl)oxy]ethanol (404 mg, 2.290 mmol) in tetrahydrofuran (8 mL) was added triphenylphosphine (751 mg, 2.862 mmol) and diisopropyl azodicarboxylate (771 mg, 3.816 mmol) at 0° C. The resulting mixture was stirred at room temperature under nitrogen atmosphere for 16 h. The resulting mixture was concentrated under reduced pressure. The residue was purified by silica gel column chromatography, eluted with petroleum ether/ethyl acetate (1/1) and the desired fractions were concentrated under reduced pressure to afford 6-{2-[(tert -butyldimethylsilyl)oxy]ethoxy}-4-chloro-7-methoxyquinoline (622 mg, 88%) as a brown solid. MS ESI calculated for $C_{18}H_{26}ClNO_3Si$ [M+H]$^+$, 368.14, 370.14 found 368.16, 370.16. $^1$H NMR (400 MHz, CDCl$_3$) δ 8.59 (d, J=4.8 Hz, 1H), 7.47 (d, J=6.4 Hz, 2H), 7.37 (d, J=4.8 Hz, 1H), 4.30 (t, J=5.2 Hz, 2H), 4.13 (t, J=5.2 Hz, 2H), 4.04 (s, 3H), 1.30-1.27 (m, 9H), 0.19-0.10 (m, 6H).

Step 3: 6-{2-[(tert-butyldimethylsilyl)oxy]ethoxy}-4-(2,6-difluoro-4-nitrophenoxy)-7-methoxyquinoline To a stirred mixture of 6-{2-[(tert-butyldimethylsilyl)oxy]ethoxy}-4-chloro-7-methoxyquinoline (622 mg, 1.690 mmol) and 2,6-difluoro-4-nitrophenol (355 mg, 2.028 mmol) in 1-methyl-2-pyrrolidinone (15 mL) was added N,N-diisopropylethylamine (437 mg, 3.380 mmol) at room temperature. The resulting mixture was stirred at 140° C. for 16 h. The mixture was allowed to cool down to room temperature. The residue was purified by reverse phase Flash chromatography with the following conditions: Eluent A: Water (plus 10 mmol/L ammonium bicarbonate); Eluent B: acetonitrile; Gradient: 15% to 35% B in 25 min; Flow rate: 60 mL/min; Detector: 220/254 nm; desired fractions were concentrated under reduced pressure to afford 6-{2-[(tert -butyldimethylsilyl)oxy]ethoxy}-4-(2,6-difluoro-4-nitrophenoxy)-7-methoxyquinoline (178 mg, 21%) as a brown solid. MS ESI calculated for $C_{24}H_{28}F_2N_2O_6Si$ [M+H]$^+$, 507.17 found 507.15. $^1$H NMR (400 MHz, CDCl$_3$) δ 8.56 (d, J=5.2 Hz, 1H), 8.16-8.02 (m, 2H), 7.64 (s, 1H), 7.54 (s, 1H), 7.28 (s, 1H), 4.33 (t, J=5.6 Hz, 2H), 4.14 (t, J=5.6 Hz, 2H), 4.07 (s, 3H), 0.92 (s, 9H), 0.14 (s, 6H).

Step 4: 4-[(6-{2-[(tert-butyldimethylsilyl)oxy]ethoxy}-7-methoxyquinolin-4-yl)oxy]-3,5-difluoroaniline To a stirred mixture of 6-{2-[(tert-butyldimethylsilyl)oxy]ethoxy}-4-(2,6-difluoro-4-nitrophenoxy)-7-methoxyquinoline (178 mg, 0.351 mmol) and iron powder (98 mg, 1.755 mmol) in tetrahydrofuran (3 mL) and water (1 mL) was added ammonium chloride (37 mg, 0.702 mmol) at room temperature. The resulting mixture was stirred at 70° C. for 6 h. The mixture was allowed to cool down to room temperature. The resulting mixture was filtered; the filter cake was washed with methanol (3×10 mL). The filtrate was concentrated under reduced pressure. The residue was purified by silica gel column chromatography, eluted with petroleum ether/ethyl acetate (1/1) and concentrated under reduced pressure to afford 4-[(6-{2-[(tert-butyl -dimethylsilyl)oxy]ethoxy}-7-methoxyquinolin-4-yl)oxy]-3,5-difluoroaniline (145 mg, 86%) as a yellow solid. MS ESI calculated for $C_{24}H_{30}F_2N_2O_4Si$ [M+H]$^+$, 477.19 found 477.20. $^1$H NMR (400 MHz, CDCl$_3$) δ 8.51 (d, J=5.2 Hz, 1H), 7.69 (s, 1H), 7.61 (s, 1H), 7.31-7.28 (m, 2H), 6.54 (d, J=5.2 Hz, 1H), 6.39 (d, J=5.2 Hz, 1H), 4.32 (t, J=5.6 Hz, 2H), 4.13 (t, J=5.6 Hz, 2H), 4.06 (s, 3H), 0.93 (s, 9H), 0.14 (s, 6H).

Step 5: 4-chloro-N-(3,5-difluoro-4-{[6-(2-hydroxyethoxy)-7-methoxyquinolin-4-yl]oxy}phenyl)pyridine-3-carboxamide To a stirred mixture of 4-[(6-{2-[(tert-butyldimethylsilyl)oxy]ethoxy}-7-methoxyquinolin-4-yl)oxy]-3,5-difluoroaniline (100 mg, 0.210 mmol) and 4-chloropyridine-3-carbonyl chloride (111 mg, 0.630 mmol) in tetrahydrofuran (2 mL) was added N,N-diisopropylethylamine (81 mg, 0.630 mmol) at room temperature. The resulting mixture was stirred at room temperature for 5 h. The resulting mixture was concentrated under reduced pressure. The residue was purified by reverse phase Flash chromatography with the following conditions: Column: WelFlash™ C18-I, 20-40 μm, 120 g; Eluent A: Water (plus 10 mmol/L ammonium bicarbonate); Eluent B: acetonitrile; Gradient: 25% to 45% B in 25 min; Flow rate: 60 mL/min; Detector: 220/254 nm; desired fractions were concentrated under reduced pressure to afford 4-chloro-N-(3,5-difluoro-4-{[6-(2-hydroxyethoxy)-7-methoxyquinolin-4-yl]oxy}phenyl)pyridine-3-carboxamide (71 mg, 67%) as a yellow solid. MS ESI calculated for $C_{24}K_8ClF_2N_3O_5$ [M+H]$^+$, 502.09, 504.09 found 502.10, 504.10.

Step 6: 4-cyclopropoxy-N-(3,5-difluoro-4-{[6-(2-hydroxyethoxy)-7-methoxyquinolin-4-yl]oxy}phenyl)pyridine-3-carboxamide To a stirred mixture of 4-chloro-N-(3,5-difluoro-4-{[6-(2-hydroxyethoxy)-7-methoxyquinolin-4-yl]oxy}phenyl)pyridine-3-carboxamide (61 mg, 0.122 mmol) and cyclopropanol (63 mg, 1.098 mmol) in dimethyl sulfoxide (2 mL) was added 1,8-diazabicyclo[5.4.0]undec-7-ene (37 mg, 0.244 mmol) at room temperature. The resulting mixture was stirred at 70° C. for 16 h. The mixture was allowed to cool down to room temperature. The crude product was purified by Prep -HPLC with the following conditions (Column: Xselect CSH C18 OBD Column 30*150mm 5 μm; Mobile Phase A: Water (plus 10 mmol/L ammonium bicarbonate), Mobile Phase B: acetonitrile; Flow rate: 60 mL/min; Gradient: 32% to 37% B in 8 min; Detector: 254/220 nm). The fractions containing desired product were collected, concentrated and lyophilized to afford 4-cyclopropoxy-N-(3,5-difluoro-4-{[6-(2-hydroxyethoxy)-7-methoxyquinolin-4-yl]oxy}phenyl)pyridine-3-carboxamide (11.4 mg, 18%) as a brown solid. MS ESI calculated for $C_{27}H_{23}F_2N_3O_6$ [M+H]$^+$, 524.16 found 524.15. $^1$H NMR (400 MHz, DMSO-d$_6$) δ 10.61 (s, 1H), 8.63 (d, J=5.6 Hz, 1H), 8.62 (s, 1H), 8.51 (d, J=5.2 Hz, 1H), 7.72 (s, 1H), 7.69 (s, 1H), 7.58 (s, 1H), 7.51 (d, J=5.6 Hz, 1H), 7.45 (s, 1H), 6.62 (d, J=5.2 Hz, 1H), 4.92 (t, J=5.2 Hz, 1H), 4.20 (t, J=5.2 Hz, 2H), 4.11-4.09 (m, 1H), 3.82 (q, J=5.2 Hz, 2H), 0.96-0.90 (m, 2H), 0.87-0.82 (m, 2H), $^{19}$F NMR (376 MHz, DMSO-d$_6$) δ −126.53 (2F).

Example 108: 4-cyclopropoxy-N-(3,5-difluoro-4-((7-((1-hydroxy-2-methylpropan-2-yl)oxy)quinolin-4-yl)oxy)phenyl)pyridine-3-carboxamide

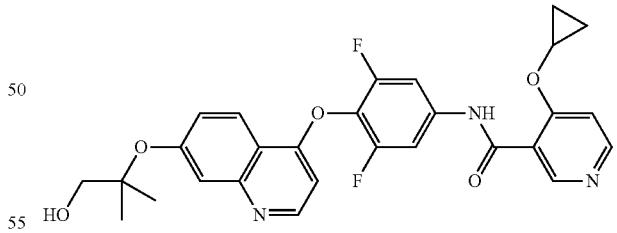

Step 1: ethyl 2-[(4-chloroquinolin-7-yl)oxy]-2-methylpropanoate

To a stirred solution of 4-chloroquinolin-7-ol (2 g, 11.13 mmol) and ethyl α-bromoisobutyrate (4.34 g, 22.25 mmol) in N,N-dimethylformamide (20 mL) was added potassium carbonate (3.08 g, 22.28 mmol) at room temperature. The resulting mixture was stirred at 70° C. for 16 h. The mixture was allowed to cool down to room temperature. The reaction was quenched by the addition of water (100 mL) at room temperature. The resulting mixture was extracted with ethyl acetate (3×100 mL). The combined organic layers were washed with brine (100 mL), dried over anhydrous sodium sulfate. After filtration, the filtrate was concentrated under reduced pressure. The residue was purified by silica gel column chromatography, eluted with petroleum ether/ethyl acetate (1/1) and concentrated under reduced pressure to afford ethyl 2-[(4-chloroquinolin-7-yl)oxy]-2-methylpropanoate (1.9 g, 57%) as a white solid. MS ESI calculated for $C_{15}H_{16}ClNO_3$ [M+H]$^+$, 294.08, 296.08 found 294.00, 296.00. $^1$H NMR (400 MHz, CDCl$_3$) δ 8.69 (d, J=4.8 Hz, 1H), 8.13 (d, J=9.2 Hz, 1H), 7.36 (d, J=4.8 Hz, 1H), 7.33-7.28 (m, 2H), 4.28 (q, J=7.2 Hz, 2H), 1.74 (s, 6H), 1.24 (t, J=7.2 Hz, 3H)

Step 2: 2-[(4-chloroquinolin-7-yl)oxy]-2-methylpropan-1-ol

To a stirred solution of ethyl 2-[(4-chloroquinolin-7-yl)oxy]-2-methylpropanoate (2 g, 6.80 mmol) in methanol (20 mL) was added sodium borohydride (0.52 g, 13.61 mmol) at 0° C. The resulting mixture was stirred at room temperature for 16 h. The reaction was quenched by the addition of saturated ammonium chloride (aq.) (100 mL) at room temperature. The resulting mixture was extracted with ethyl acetate (3×100 mL). The combined organic layers were washed with brine (200 mL), dried over anhydrous sodium sulfate. After filtration, the filtrate was concentrated under reduced pressure. The residue was purified by silica gel column chromatography, eluted with petroleum ether/ethyl acetate (5/1) and concentrated under reduced pressure to afford 2-[(4-chloroquinolin-7-yl)oxy]-2-methylpropan-1-ol (0.9 g, 50%) as a light yellow oil. MS ESI calculated for $C_{13}H_{14}ClNO_2$ [M+H]$^+$, 252.07, 254.07 found 252.20, 254.20; $^1$H NMR (400 MHz, CDCl$_3$) δ 8.74 (d, J=4.8 Hz, 1H), 8.15 (d, J=9.2 Hz, 1H), 7.73 (d, J=2.4 Hz, 1H), 7.42 (d, J=4.8 Hz, 1H), 7.33 (dd, J=9.2, 2.4 Hz, 1H), 3.72 (s, 2H), 1.48 (s, 6H).

Step 3: 2-{[4-(2,6-difluoro-4-nitrophenoxy)quinolin-7-yl]oxy}-2-methylpropan-1-ol To a stirred solution of 2-[(4-chloroquinolin-7-yl)oxy]-2-methylpropan-1-ol (900 mg, 3.576 mmol) and 2,6-difluoro-4-nitrophenol (751 mg, 4.291 mmol) in 1-methyl-2-pyrrolidinone (10 mL) was added N,N-diisopropylethylamine (924 mg, 7.152 mmol) at room temperature. The resulting mixture was stirred at 140° C. for 16 h. The mixture was allowed to cool down to room temperature. The reaction was quenched by the addition of water (100 mL) at room temperature. The resulting mixture was extracted with ethyl acetate (3×100 mL). The combined organic layers were washed with brine (100 mL), dried over anhydrous sodium sulfate. After filtration, the filtrate was concentrated under reduced pressure. The residue was purified by silica gel column chromatography, eluted with petroleum ether/ethyl acetate (1/1) and concentrated under reduced pressure to afford to afford 2-{[4-(2,6-difluoro-4-nitrophenoxy)quinolin-7-yl]oxy}-2-methylpropan-1-ol (650 mg, 46%) as a light yellow solid. MS ESI calculated for $C_{19}K_6F_2N_2O_5$ [M+H]$^+$, 391.10 found 391.10; $^1$H NMR (400 MHz, CDCl$_3$) 68.64 (d, J=5.2 Hz, 1H), 8.34 (d, J=9.2 Hz, 1H), 8.14-8.00 (m, 2H), 7.75 (d, J=2.4 Hz, 1H), 7.291 (dd, J=9.2, 2.4 Hz, 1H), 6.43 (d, J=5.2 Hz, 1H), 3.73 (s, 2H), 1.53 (s, 6H).

Step 4: 2-{[4-(4-amino-2,6-difluorophenoxy)quinolin-7-yl]oxy}-2-methylpropan-1-ol To a stirred mixture of 2-{[4-(2,6-difluoro-4-nitrophenoxy)quinolin-7-yl]oxy}-2-methylpropan-1-ol (650 mg, 1.665 mmol), iron powder (465 mg, 8.327 mmol) in tetrahydrofuran (8 mL) and water (4 mL) was added ammonium chloride (356 mg, 6.655 mmol) at room temperature. The resulting mixture was stirred at 70° C. for 16 h. The mixture was allowed to cool down to room temperature. The resulting mixture was filtered, the filter cake was washed with ethyl acetate (3×20 mL). The filtrate was concentrated under reduced pressure. The residue was purified by silica gel column chromatography, eluted with dichloromethane/methanol (10/1) and concentrated under reduced pressure to afford 2-{[4-(4-amino-2,6-difluorophenoxy)quinolin-7-yl]oxy}-2-methylpropan-1-ol (520 mg, 86%) as a light yellow solid. MS ESI calculated for $C_{19}K_8F_2N_2O_3$ [M+H]$^+$, 361.13 found 361.15. $^1$H NMR (400 MHz, CDCl$_3$) δ 8.66 (d, J=5.2 Hz, 1H), 8.34 (d, J=9.2 Hz, 1H), 7.72 (d, J=2.4 Hz, 1H), 7.29 (dd, J=9.2, 2.4 Hz, 1H), 6.51 (d, J=5.2 Hz, 1H), 6.41-6.34 (m, 2H), 3.96 (s, 2H), 3.72 (s, 2H), 1.47 (s, 6H).

Step 5: 4-chloro-N-[3,5-difluoro-4-({7-[(1-hydroxy-2-methylpropan-2-yl)oxy]quinolin-4-yl}oxy)phenyl]pyridine-3-carboxamide To a stirred solution of 2-{[4-(4-amino-2,6-difluorophenoxy)quinolin-7-yl]oxy}-2-methylpropan-1-ol (300 mg, 0.832 mmol) and 4-chloropyridine-3-carbonyl chloride (176 mg, 1.000 mmol) in dichloromethane (5 mL) was added N,N-diisopropylethylamine (215 mg, 1.663 mmol) at room temperature. The resulting mixture was stirred at room temperature for 2 h. The resulting mixture was concentrated under reduced pressure. The residue was purified by silica gel column chromatography, eluted with petroleum ether/ethyl acetate/ethanol (4/3/1) and concentrated under reduced pressure to afford 4-chloro-N-[3,5-difluoro-4-({7-[(1-hydroxy-2-methylpropan-2-yl)oxy]quinolin-4-yl}oxy)phenyl]pyridine-3-carboxamide (240 mg, 57%) as an off-white solid. MS ESI calculated for $C_{25}H_{20}ClF_2N_3O_4$ [M+H]$^+$, 500.11, 502.11 found 500.00, 501.65. $^1$H NMR (400 MHz, CDCl$_3$) δ 8.97 (s, 1H), 8.65 (d, J=5.2 Hz, 1H), 8.64 (d, J=5.2 Hz, 1H), 8.51 (s, 1H), 8.34 (d, J=9.2 Hz, 1H), 7.69 (d, J=2.4 Hz, 1H), 7.61-7.53 (m, 2H), 7.45 (d, J=5.2 Hz, 1H), 7.32 (dd, J=9.2, 2.4 Hz, 1H), 6.48 (d, J=5.2 Hz, 1H), 3.73 (s, 2H), 1.48 (s, 6H).

Step 6: 4-cyclopropoxy-N-[3,5-difluoro-4-({7-[(1-hydroxy-2-methylpropan-2-yl)oxy]quinolin-4-yl}oxy)phenyl]pyridine-3-carboxamide To a stirred solution of 4-chloro-N-[3,5-difluoro-4-({7-[(1-hydroxy-2-methylpropan-2-yl)oxy]quinolin-4-yl}oxy)phenyl]pyridine-3-carboxamide (240 mg, 0.480 mmol) and cyclopropanol (279 mg, 4.800 mmol) in dimethyl sulfoxide (5 mL) was added 1,8-diazabicyclo[5.4.0]undec-7-ene (731 mg, 4.800 mmol) at room temperature. The resulting mixture was stirred at 70° C. for 16 h. The mixture was allowed to cool down to room temperature. The reaction was quenched by the addition of water (50 mL) at room temperature. The resulting mixture was extracted with ethyl acetate (3×40 mL). The combined organic layers were washed with brine (50 mL), dried over anhydrous sodium sulfate. After filtration, the filtrate was concentrated under reduced pressure. The residue was purified by silica gel column chromatography, eluted with petroleum ether/ethyl acetate/ethanol (4/3/1) and concentrated under reduced pressure to afford the crude product (150 mg). The crude product was purified by Prep -HPLC with the following conditions (Column: XBridge Prep Phenyl OBD Column, 19×250 mm, 5 μm; Mobile Phase A: water (plus 10 mmol/L ammonium bicarbonate), Mobile Phase B: acetonitrile; Flow rate: 25 mL/min; Gradient: 45% to 50% B in 10 min; Detector: UV 220/254 nm). The fractions containing desired product were collected, concentrated and lyophilized to afford 4-cyclopropoxy-N-[3,5-difluoro-4-({7-[(1-hydroxy-2-methylpropan-2-yl)oxy]quinolin-4-yl}oxy)phenyl]pyridine-3-carboxamide (81 mg, 32%) as a white solid. MS ESI calculated for $C_{28}H_{25}F_2N_3O_5$ [M+H]$^+$, 522.18 found 522.20. $^1$H NMR (400 MHz, DMSO-d$_6$) δ 10.63 (s, 1H), 8.66 (d, J=5.2 Hz, 1H), 8.64 (d, J=6.0 Hz, 1H), 8.62 (s, 1H), 8.27 (d, J=9.2 Hz, 1H), 7.77-7.66 (m, 2H), 7.62 (d, J=2.4 Hz, 1H), 7.51 (d, J=6.0 Hz, 1H), 7.40 (dd, J=9.2, 2.4 Hz, 1H), 6.68 (d, J=5.2 Hz, 1H), 5.04 (t, J=5.6 Hz, 1H), 4.12-4.09 (m, 1H), 3.51 (d, J=5.6 Hz, 2H), 1.35 (s, 6H), 0.94-0.84 (m, 2H), 0.82-0.81 (m, 2H). $^{19}$F NMR (376 MHz, DMSO-d$_6$) δ −126.69 (2F).

Example 109: 4-cyclopropoxy-N-(3,5-difluoro-4-((7-(2-(methylamino)ethoxy)quinolin-4-yl)oxy)phenyl)-6-fluoropyridine-3-carboxamide

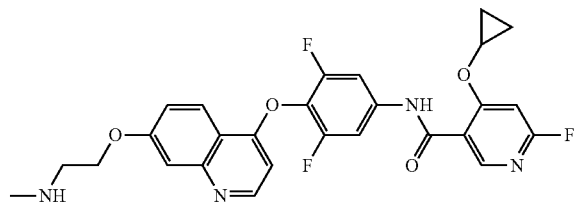 [SMILES: CNCCOc1ccc2c(Oc3c(F)cc(NC(=O)c4cnc(F)cc4OC4CC4)cc3F)ccnc2c1]

Step 1: ethyl 6-chloro-4-cyclopropoxypyridine-3-carboxylate

To a stirred mixture of ethyl 4,6-dichloropyridine-3-carboxylate (10 g, 45.44 mmol) and 1,8-diazabicyclo[5.4.0]undec-7-ene (34.6 g, 227.22 mmol) in dimethyl sulfoxide (100 mL) was added cyclopropanol (13.2 g, 227.22 mmol) at room temperature. The resulting mixture was stirred at 70° C. for 16 h. The mixture was allowed to cool down to room temperature. The reaction was quenched with water (500 mL) at room temperature. The resulting mixture was extracted with ethyl acetate (5×300 mL). dried over anhydrous sodium sulfate. After filtration, the filtrate was concentrated under reduced pressure. The residue was purified by silica gel column chromatography, eluted with petroleum ether/ethyl acetate (5/1) and concentrated under reduced pressure to afford ethyl 6-chloro-4-cyclopropoxypyridine-3-carboxylate (3.8 g, 33%) as a white solid. MS ESI calculated for $C_{11}H_{12}ClNO_3$ [M+H]$^+$, 242.05, 244.05 found 242.00, 244.00. $^1$H NMR (400 MHz, CDCl$_3$) δ 8.70 (s, 1H), 7.31 (s, 1H), 4.36 (q, J=7.2 Hz, 2H), 3.93-3.84 (m, 1H), 1.38 (t, J=7.2 Hz, 3H), 1.02-0.89 (m, 4H).

Step 2: ethyl 4-cyclopropoxy-6-fluoropyridine-3-carboxylate

To a stirred mixture of ethyl 6-chloro-4-cyclopropoxypyridine-3-carboxylate (500 mg, 2.069 mmol) and cesium fluoride (3,14 g, 20.69 mmol) in dimethyl sulfoxide (10 mL) at room temperature. The resulting mixture was stirred at 90° C. for 16 h. The mixture was allowed to cool down to room temperature. The reaction was quenched with water (100 mL) at room temperature. The resulting mixture was extracted with ethyl acetate (3×100 mL), dried over anhydrous sodium sulfate. After filtration, the filtrate was concentrated under reduced pressure. The residue was purified by silica gel column chromatography, eluted with petroleum ether/ethyl acetate (1/1) and concentrated under reduced pressure to afford ethyl 4-cyclopropoxy-6-fluoropyridine-3-carboxylate (428 mg, 80%) as a white solid. MS ESI calculated for $C_{11}H_{12}FNO_3$ [M+H]$^+$, 226.08 found 226.05. $^1$H NMR (400 MHz, CDCl$_3$) δ 8.62 (s, 1H), 6.86 (s, 1H), 4.37 (q, J=7.2 Hz, 2H), 3.94-3.85 (m, 1H), 1.39 (t, J=7.2 Hz, 3H), 0.95-0.82 (m, 4H).

Step 3: 4-cyclopropoxy-6-fluoropyridine-3-carboxylic acid

To a stirred mixture of ethyl 4-cyclopropoxy-6-fluoropyridine-3-carboxylate (420 mg, 1.865 mmol) in tetrahydrofuran (4 mL) and water (4 mL) was added lithium hydroxide (223 mg, 9.325 mmol) at room temperature. The resulting mixture was stirred at room temperature for 16 h. The resulting mixture was concentrated under reduced pressure. The mixture was acidified to pH 6 with hydrochloric acid (aq.). The precipitated solids were collected by filtration and washed with water (3×5 mL) to afford 4-cyclopropoxy-6-fluoropyridine-3-carboxylic acid (198 mg, 48%) as a white solid. MS ESI calculated for $C_9H_8FNO_3$ [M+H]$^+$, 198.05 found 198.05. $^1$H NMR (400 MHz, CDCl$_3$) δ 8.85 (s, 1H), 6.93 (s, 1H), 4.11-4.00 (m, 1H), 1.05-0.99 (m, 4H).

Step 4: tert-butyl N-[2-({4-[4-(4-cyclopropoxy-6-fluoropyridine-3-amido)-2,6-difluorophenoxy]quinolin-7-yl}oxy)ethyl]-N-methylcarbamate To a stirred mixture of 4-cyclopropoxy-6-fluoropyridine-3-carboxylic acid (80 mg, 0.406 mmol) and O-(7-azabenzotriazol-1-yl)-N,N,N',N'-tetramethyluronium hexafluorophosphate (231 mg, 0.609 mmol) in N,N-dimethylformamide (2 mL) was added N,N-diisopropylethylamine (209 mg, 1.624 mmol) and tert-butyl N-(2-{[4-(4-amino-2,6-difluorophenoxy)quinolin-7-yl]oxy}ethyl)-N-methylcarbamate (180 mg, 0.406 mmol) at room temperature. The resulting mixture was stirred at room temperature for 16 h. The mixture was purified by reverse phase Flash chromatography with the following conditions: Column: WelFlash™ C18-I, 20-40 μm, 40 g; Eluent A: water (plus 10 mmol/L ammonium bicarbonate); Eluent B: acetonitrile; Gradient: 25% to 65% B; Flow rate: 30 mL/min; Detector: UV 220/254 nm; desired fractions were collected and concentrated under reduced pressure to afford tert-butyl N-[2-({4-[4-(4-cyclopropoxy-6-fluoropyridine-3-amido)-2,6-difluorophenoxy]quinolin-7-yl}oxy)ethyl]-N-methylcarbamate (101 mg, 39%) as a white solid. MS ESI calculated for $C_{32}H_{31}F_3N_4O_6$ [M+H]$^+$, 625.22 found 625.20. $^1$H NMR (400 MHz, CDCl$_3$) δ 9.33 (s, 1H), 9.04 (s, 1H), 8.65 (d, J=5.2 Hz, 1H), 8.34 (d, J=9.2 Hz, 1H), 7.53-7.43 (m, 3H), 6.98 (s, 1H), 6.47 (d, J=5.2 Hz, 1H), 4.30 (t, J=5.2 Hz, 2H), 4.18-4.13 (m, 1H), 3.73 (t, J=5.2 Hz, 2H), 3.05 (s, 3H), 1.50 (s, 9H), 1.20-1.10 (m, 2H), 1.13-1.02 (m, 2H).

Step 5: 4-cyclopropoxy-N-[3,5-difluoro-4-({7-[2-(methylamino)ethoxy]quinolin-4-yl}oxy)phenyl]-6-fluoropyridine-3-carboxamide A mixture of tert-butyl N-[2-({4-[4-(4-cyclopropoxy-6-fluoropyridine-3-amido)-2,6-difluorophenoxy]-quinolin-7-yl}oxy)ethyl]-N-methylcarbamate (101 mg, 0.162 mmol) and hydrochloric acid (gas, 4 N in 1,4-dioxane, 1 mL) in 1,4-dioxane (1 mL) was stirred at room temperature for 2 h.

The precipitated solids were collected by filtration and washed with diethyl ether (3×5 mL). The crude product (101 mg) was purified by Prep-HPLC with the following conditions (Column: XBridge Prep OBD C18 Column, 30×150 mm, 5 μm; Mobile Phase A: water (plus 10 mmol/L ammonium bicarbonate), Mobile Phase B: acetonitrile; Flow rate: 60 mL/min; Gradient: 34% to 44% B; Detector: UV 220/254 nm;), The fractions containing desired product were collected, concentrated and lyophilized to afford 4-cyclopropoxy-N-[3,5-difluoro-4-({7-[2-(methyl-amino)ethoxy]quinolin-4-yl}oxy)phenyl]-6-fluoropyridine-3-carboxamide (35.8 mg, 42%) as a white solid. MS ESI calculated for $C_{27}H_{23}F_3N_4O_4$ [M+H]$^+$, 525.17 found 525.25. $^1$H NMR (400 MHz, CD$_3$OD) δ 8.61 (d, J=5.2 Hz, 1H), 8.48 (s, 1H), 8.36 (d, J=9.2 Hz, 1H), 7.69-7.58 (m, 2H), 7.44 (d, J=2.4 Hz, 1H), 7.41 (dd, J=9.2, 2.4 Hz, 1H), 7.20 (s, 1H), 6.66 (d, J=5.2 Hz, 1H), 4.33 (t, J=5.2 Hz, 2H), 4.21-4.16 (m, 1H), 3.12 (t, J=5.2 Hz, 2H), 2.55 (s, 3H), 1.06-0.91 (m, 4H). $^{19}$F NMR (377 MHz, CD$_3$OD) δ −64.57 (1F), −128.09 (2F).

Example 110: 4-cyclopropoxy-N-[3,5-difluoro-4-({6-methoxy-7-[2-(methylamino)ethoxy]quinolin-4-yl}oxy)phenyl]-6-fluoropyridine-3-carboxamide

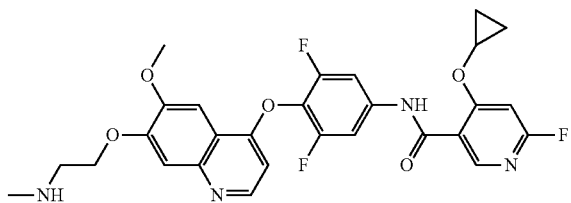 [SMILES: CNCCOc1cc2nccc(Oc3c(F)cc(NC(=O)c4cnc(F)cc4OC4CC4)cc3F)c2cc1OC]

Synthesized using the similar method as in example 109. White solid. MS ESI calculated for $C_{28}H_{25}F_3N_4O_5$ [M+H]$^+$, 555.18 found 555.15. $^1$H NMR (400 MHz, CD$_3$OD) δ 8.49 (d, J=5.2 Hz, 1H), 8.48 (s, 1H), 7.71 (s, 1H), 7.68-7.61 (m, 2H), 7.44 (s, 1H), 7.20 (s, 1H), 6.62 (d, J=5.2 Hz, 1H), 4.36 (t, J=5.2 Hz, 2H), 4.21-4.16 (m, 1H), 4.07 (s, 3H), 3.18 (t, J=5.2 Hz, 2H), 2.58 (s, 3H), 1.06-0.94 (m, 4H). $^{19}$F NMR (377 MHz, DMSO-d$_6$) δ −63.19 (1F), −126.45 (2F).

Example 111: 4-cyclopropoxy-N-(3,5-difluoro-4-((7-(2-hydroxyethoxy)-6-methoxyquinolin-4-yl)oxy)phenyl)-6-methoxypyridine-3-carboxamide

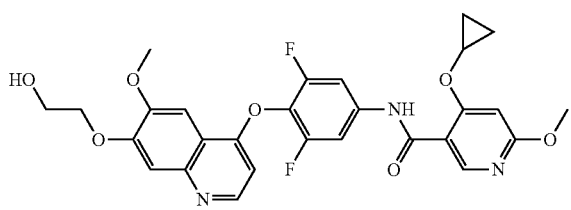 [SMILES: COc1cc(OC2CC2)c(C(=O)Nc2cc(F)c(Oc3ccnc4cc(OCCO)c(OC)cc34)c(F)c2)cn1]

Synthesized using the similar method as in example 109. White solid. MS ESI calculated for $C_{28}H_{25}F_2N_3O_7$ [M+H]$^+$, 554.17; found. 554.20. $^1$H NMR (400 MHz, DMSO-d$_6$) δ 10.36 (s, 1H), 8.53 (d, J=5.2 Hz, 1H), 8.35 (s, 1H), 7.76-7.68 (m, 2H), 7.57 (s, 1H), 7.45 (s, 1H), 6.81 (s, 1H), 6.66 (d, J=5.2 Hz, 1H), 4.96 (t, J=4.8 Hz, 1H), 4.20 (t, J=4.8 Hz, 2H), 4.11-4.04 (m, 1H), 3.99 (s, 3H), 3.94 (s, 3H), 3.84 (t, J=4.8 Hz, 2H), 0.94-0.78 (m, 4H). $^{19}$F NMR (376 MHz, CDCl$_3$) δ −126.63 (2F).

Example 112: 6-chloro-4-cyclopropoxy-N-[3,5-difluoro-4-({6-methoxy-7-[2-(methylamino)ethoxy]quinolin-4-yl}oxy)phenyl]pyridine-3-carboxamide

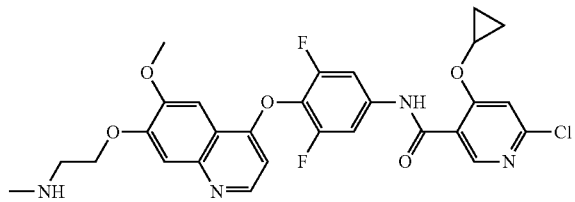

Synthesized using the similar method as in example 109. White solid. MS ESI calculated for $C_{28}H_{25}ClF_2N_4O_5$ [M+H]$^+$, 570.15, 572.15 found 570.20, 572.20. $^1$H NMR (400 MHz, DMSO-d$_6$) δ 11.08 (s, 1H), 8.56-8.45 (m, 2H), 7.78-7.67 (m, 2H), 7.56 (s, 1H), 7.45 (s, 1H), 7.23 (s, 1H), 6.62 (d, J=5.2 Hz, 1H), 4.31 (tt, J=6.3, 3.0 Hz, 1H), 4.22 (t, J=5.6 Hz, 2H), 3.98 (s, 3H), 2.95 (q, J=6.2, 5.6 Hz, 2H), 2.39 (s, 3H), 0.89-0.81 (m, 2H), 0.81-0.69 (m, 2H). $^{19}$F NMR (377 MHz, DMSO-d$_6$) δ −126.28 (2F).

Example 113: 6-chloro-4-cyclopropoxy-N-[3,5-difluoro-4-({7-[2-(methylamino)ethoxy]quinolin-4-yl}oxy)phenyl]pyridine-3-carboxamide

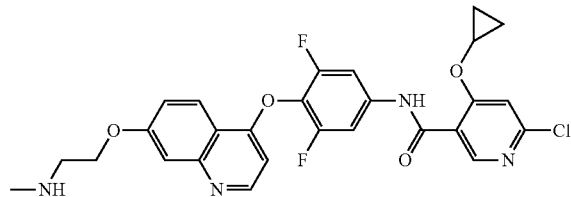 [SMILES: CNCCOc1ccc2c(Oc3c(F)cc(NC(=O)c4cnc(Cl)cc4OC4CC4)cc3F)ccnc2c1]

Synthesized using the similar method as in example 109. White solid. MS ESI calculated for $C_{27}H_{23}ClF_2N_4O_4$ [M+H]$^+$, 541.14, 543.14, found 541.25, 543.25; $^1$H NMR (400 MHz, DMSO -d$_6$) δ 8.64 (d, J=5.2 Hz, 1H), 8.48 (s, 1H), 8.26 (d, J=9.2 Hz, 1H), 7.72-7.64 (m, 2H), 7.59 (s, 1H), 7.45 (d, J=2.4 Hz, 1H), 7.35 (dd, J=9.2, 2.4 Hz, 1H), 6.63 (d, J=5.2 Hz, 1H), 4.22 (t, J=5.6 Hz, 2H), 4.20-4.15 (m, 1H), 2.92 (t, J=5.6 Hz, 2H), 2.38 (s, 3H), 0.95-0.80 (m, 4H). $^{19}$F NMR (377 MHz, DMSO-d$_6$) δ −126.57 (2F).

Example 114: 4-cyclopropoxy-N-[3,5-difluoro-4-({6-methoxy-7-[2-(methylamino)ethoxy]quinolin-4-yl}oxy)phenyl]-2-methylpyrimidine-5-carboxamide

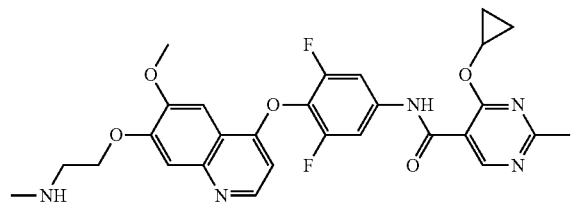

Synthesized using the similar method as in example 109. Off-white solid. MS ESI calculated for $C_{28}H_{27}F_2N_5O_5$

[M+H]⁺, 552.60 found 552.30. ¹H NMR (400 MHz, DMSO-d₆) δ 10.59 (s, 1H), 8.73 (s, 1H), 8.50 (d, J=5.2 Hz, 1H), 7.74-7.64 (m, 2H), 7.56 (s, 1H), 7.45 (s, 1H), 6.61 (d, J=5.2 Hz, 1H), 4.55-4.46 (m, 1H), 4.22 (t, J=5.6 Hz, 2H), 3.98 (s, 3H), 2.95 (d, J=5.6 Hz, 2H), 2.64 (s, 3H), 2.39 (s, 3H), 0.88-0.81 (m, 4H). ¹⁹F NMR (376 MHz, DMSO-d₆) δ −126.42 (2F).

Example 115: 4-cyclopropoxy-N-(3,5-difluoro-4-((7-(2-(methylamino)ethoxy)quinolin-4-yl)oxy)phenyl)-6-methylpyridine-3-carboxamide

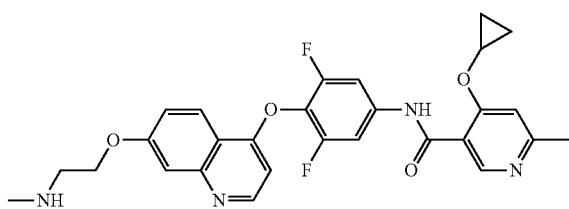

Step 1: methyl 6-bromo-4-cyclopropoxypyridine-3-carboxylate

To a stirred mixture of methyl 6-bromo-4-chloropyridine-3-carboxylate (1 g, 3.99 mmol) and cyclopropanol (1.16 g, 19.96 mmol) in dimethyl sulfoxide (10.00 mL) was added 1,8-diazabicyclo[5.4.0]undec-7-ene (1.19 mL, 7.984 mmol) at room temperature. The resulting mixture was stirred at 70° C. for 16 h. The mixture was allowed to cool down to room temperature. The mixture was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 2% to 5% B; Flow rate: 40 mL/min; Detector: UV 220/254 nm; desired fractions were collected and concentrated under reduced pressure to afford methyl 6-bromo-4-cyclopropoxypyridine-3-carboxylate (190 mg, 19%) as a yellow solid. MS ESI calculated for C₁₀H₁₀BrNO₃ [M+H]⁺, 271.98, 273.98 found 272.05, 274.05.

Step 2: methyl 4-cyclopropoxy-6-methylpyridine-3-carboxylate

To a stirred mixture of methyl 6-bromo-4-cyclopropoxypyridine-3-carboxylate (190 mg, 0.698 mmol) and trimethyl-1,3,5,2,4,6-trioxatriborinane (175 mg, 1.396 mmol) and potassium carbonate (337 mg, 2.443 mmol) in dioxane (2 mL) was added Pd(dppf)Cl₂ (51 mg, 0.070 mmol, CAS: 72287-26-4) at room temperature under nitrogen atmosphere. The resulted mixture was stirred at 100° C. under nitrogen atmosphere for 16 h. The mixture was allowed to cool down to room temperature. The reaction was quenched with water (50 mL) at room temperature. The resulting mixture was extracted with ethyl acetate (3×50 mL). The combined organic layers were washed with water (50 mL), dried over anhydrous sodium sulfate. After filtration, the filtrate was concentrated under reduced pressure. The residue was purified by silica gel column chromatography, eluted with petroleum ether/ethyl acetate/ethanol (4/3/1) and concentrated under reduced pressure to afford methyl 4-cyclopropoxy-6-methylpyridine-3-carboxylate (110 mg, 76%) as a white solid. MS ESI calculated for C₁₁H₁₃NO₃ [M+H]⁺, 208.10 found 208.10. ¹H NMR (400 MHz, CDCl₃) δ 8.84 (s, 1H), 7.16 (s, 1H), 3.89 (s, 3H), 3.89-3.85 (m, 1H), 2.63 (s, 3H), 0.95-0.89 (m, 4H).

Step 3: 4-cyclopropoxy-6-methylpyridine-3-carboxylic acid

A mixture of methyl 4-cyclopropoxy-6-methylpyridine-3-carboxylate (110 mg, 0.531 mmol) and lithium hydroxide (63 mg, 2.655 mmol) in tetrahydrofuran (1 mL) and water (1 mL) was stirred at room temperature for 2 h. The mixture was acidified to pH 6 with hydrochloric acid (4 N in water). The mixture was concentrated under reduced pressure. The residue was purified by reverse phase Flash chromatography with the following conditions: Column: WelFlash™ C18-I, 20-40 μm, 40 g; Eluent A: water (plus 10 mmol/L hydrochloric acid); Eluent B: acetonitrile; Gradient: 2% to 5% B in 10 min; Flow rate: 40 mL/min; Detector: UV 220/254 nm; desired fractions were concentrated under reduced pressure to afford 4-cyclopropoxy-6-methylpyridine -3-carboxylic acid (270 mg, crude) as a white solid. MS ESI calculated for C₁₀H₁₁NO₃ [M+H]⁺, 194.10 found 194.05. ¹H NMR (400 MHz, DMSO-d₆) δ 8.73 (s, 1H), 7.80 (s, 1H), 7.38 (s, 1H), 4.23-4.18 (m, 1H), 2.71 (s, 3H), 0.96-0.92 (m, 2H), 0.82-0.78 (m, 2H).

Step 4: tert-butyl N-[2-({4-[4-(4-cyclopropoxy-6-methylpyridine-3-amido)-2,6-difluorophenoxy]quinolin-7-yl}oxy)ethyl]-N-methylcarbamate A mixture of 4-cyclopropoxy-6-methylpyridine-3-carboxylic acid (160 mg, 0.828 mmol) and N,N-diisopropylethylamine (58 mg, 0.448 mmol) in propylphosphonic acid anhydride (2 mL, 1 N in ethyl acetate) was stirred at room temperature for 5 min. To the above mixture was added tert-butyl N-(2-{[4-(4-amino-2,6-difluorophenoxy)quinolin-7-yl]oxy}ethyl)-N-methylcarbamate (100 mg, 0.224 mmol) at room temperature. The resulting mixture was stirred at 70° C. for 2 h. The mixture was allowed to cool down to room temperature. The mixture was basified to pH 8 with saturated sodium bicarbonate. The resulting mixture was extracted with ethyl acetate (3×50 mL), dried over anhydrous sodium sulfate. The mixture was concentrated under reduced pressure. The mixture was purified by silica gel column chromatography, eluted with petroleum ether/ethyl acetate/ethanol (4/3/1) and concentrated under reduced pressure to afford tert-butyl N-[2-({4-[4-(4-cyclopropoxy-6-methylpyridine-3-amido)-2,6-difluorophenoxy]quinolin-7-yl}oxy)ethyl]-N -methyl-carbamate (85 mg, 61%) as a white oil. MS ESI calculated for C₃₃H₃₄F₂N₄O₆ [M+H]⁺, 621.20 found 621.20.

Step 5: 4-cyclopropoxy-N-[3,5-difluoro-4-({7-[2-(methylamino)ethoxy]quinolin-4-yl}oxy)phenyl]-6-methylpyridine-3-carboxamide To a stirred mixture of tert-butyl N-[2-({4-[4-(4-cyclopropoxy-6-methylpyridine-3-amido)-2,6-difluorophenoxy]quinolin-7-yl}oxy)ethyl]-N-methylcarbamate (85 mg, 0.137 mmol) in dichloromethane (4 mL) was added hydrochloric acid (4 mL, 4 N in dioxane) at 0° C. The resulting mixture was stirred at room temperature for 2 h. The mixture was basified to pH 8 with ammonia (gas, 7 N in methanol). The resulting mixture was concentrated under reduced pressure. The crude product was purified by Prep-HPLC with the following conditions (Column: XBridge Prep OBD C18 Column, 30×150 mm, 5 μm; Mobile Phase A: water (plus 10 mmol/L ammonium bicarbonate), Mobile Phase B: acetonitrile; Flow rate: 60 mL/min; Gradient: 29% to 39% B; Detector: UV 220/254 nm). The fractions containing desired product were collected, concentrated under reduced pressure to afford 4-cyclopropoxy-N-[3,5-difluoro-4-({7-[2-(methylamino)ethoxy]quinolin-4-yl}oxy)phenyl]-6-methylpyridine-3-carboxamide (32.4 mg, 45%) as a white solid. MS ESI calculated for $C_{28}H_{26}F_2N_4O_4$ [M+H]$^+$, 521.20 found 521.20. $^1$H NMR (400 MHz, DMSO-d$_6$) δ 10.47 (s, 1H), 8.64 (d, J=5.2 Hz, 1H), 8.51 (s, 1H), 8.26 (d, J=9.2 Hz, 1H), 7.76-7.66 (m, 2H), 7.45 (d, J=2.4 Hz, 1H), 7.37 (s, 1H), 7.35 (dd, J=9.2, 2.4 Hz, 1H), 6.63 (d, J=5.2 Hz, 1H), 4.22 (t, J=5.6 Hz, 2H), 4.06-4.02 (m, 1H), 2.92 (t, J=5.6 Hz, 2H), 2.55 (s, 3H), 2.38 (s, 3H), 0.93-0.80 (m, 4H). $^{19}$F NMR (376 MHz, DMSO-d$_6$) δ −126.79 (2F).

Example 116: 4-cyclopropoxy-N-(3,5-difluoro-4-{[7-(2-hydroxyethoxy)-6-methoxyquinolin-4-yl]oxy}phenyl)-6-methylpyridine-3-carboxamide

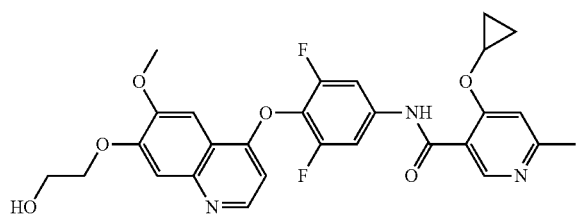 [SMILES: COc1cc2c(Oc3c(F)cc(NC(=O)c4cnc(C)cc4OC4CC4)cc3F)ccnc2cc1OCCO]

Synthesized using the similar methods as in examples 97 and 115. White solid. MS ESI calculated for $C_{28}H_{25}F_2N_3O_6$ [M+H]$^+$, 538.20 found 538.10. $^1$H NMR (400 MHz, DMSO-d$_6$) δ 10.46 (s, 1H), 8.52 (s, 1H), 8.50 (d, J=5.2 Hz, 1H), 7.75-7.67 (m, 2H), 7.56 (s, 1H), 7.44 (s, 1H), 7.37 (s, 1H), 6.61 (d, J=5.2 Hz, 1H), 4.95 (t, J=5.2 Hz, 1H), 4.19 (t, J=5.2 Hz, 2H), 4.10-4.03 (m, 1H), 3.98 (s, 3H), 3.84-3.80 (m, 2H), 2.55 (s, 3H), 0.95-0.78 (m, 4H). $^{19}$F NMR (376 MHz, DMSO-d$_6$) δ −126.59 (2F).

Example 117: 4-cyclopropoxy-N-[3,5-difluoro-4-({6-methoxy-7-[2-(methylamino)ethoxy]quinolin-4-yl}oxy)phenyl]-6-methylpyridine-3-carboxamide

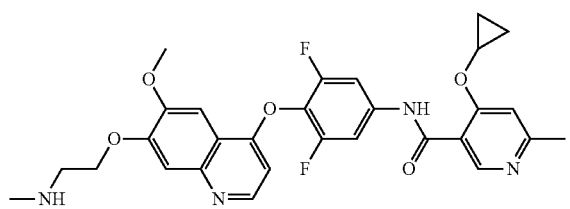

Synthesized using the similar methods as in examples 52 and 115. White solid. MS ESI calculated for $C_{29}H_{28}F_2N_4O_5$ [M+H]$^+$, 551.20; found 551.30. $^1$H NMR (400 MHz, DMSO-d$_6$) δ 10.47 (s, 1H), 8.54-8.48 (m, 2H), 7.75-7.67 (m, 2H), 7.56 (s, 1H), 7.45 (s, 1H), 7.38 (s, 1H), 6.61 (d, J=5.2 Hz, 1H), 4.22 (t, J=5.6 Hz, 2H), 4.10-4.04 (m, 1H), 3.98 (s, 3H), 2.94 (d, J=5.6 Hz, 2H), 2.55 (s, 3H), 2.39 (s, 3H), 0.94-0.77 (m, 4H). $^{19}$F NMR (377 MHz, DMSO-d$_6$) δ −126.60 (2F).

Example 118: 4-cyclopropoxy-N-(3,5-difluoro-4-4(7-(2-hydroxyethoxy)-6-methoxyquinolin-4-yl)oxy) phenyl)-2-fluoropyridine-3-carboxamide

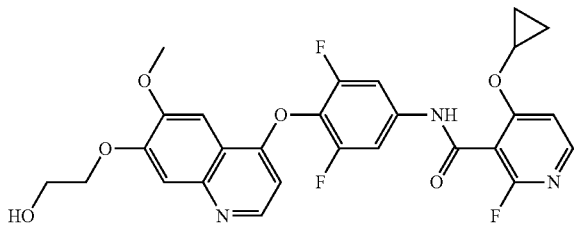 [SMILES: COc1cc2c(Oc3c(F)cc(NC(=O)c4c(OC5CC5)ccnc4F)cc3F)ccnc2cc1OCCO]

Step 1: ethyl 2-chloro-4-cyclopropoxypyridine-3-carboxylate

To a stirred solution of ethyl 2,4-dichloropyridine-3-carboxylate (2 g, 9.09 mmol) and cyclopropanol (2.1 g, 36.35 mmol) in dimethyl sulfoxide (20 mL) was added 1,8-diazabicyclo[5.4.0]undec-7-ene (2.7 g, 18.17 mmol) at room temperature. The resulting mixture was stirred at 70° C. for 16 h. The mixture was allowed to cool down to room temperature. The reaction was quenched by the addition of water (100 mL) at room temperature. The resulting mixture was extracted with ethyl acetate (3×100 mL). The combined organic layers were washed with brine (200 mL), dried over anhydrous sodium sulfate. After filtration, the filtrate was concentrated under reduced pressure. The residue was purified by silica gel column chromatography, eluted with petroleum ether/ethyl acetate (1/1) and concentrated under reduced pressure to afford ethyl 2-chloro-4-cyclopropoxypyridine-3-carboxylate (800 mg, 36%) as a yellow oil. MS ESI calculated for $C_{11}H_{12}ClNO_3$ [M+H]$^+$, 242.05, 244.05 found 242.00, 244.00. $^1$H NMR (400 MHz, CDCl$_3$) δ 8.29 (d, J=6.0 Hz, 1H), 7.18 (d, J=6.0 Hz, 1H), 4.40 (q, J=7.2 Hz, 2H), 3.88-3.86 (m, 1H), 1.37 (t, J=7.2 Hz, 3H), 0.92-0.78 (m, 4H).

Step 2: ethyl 4-cyclopropoxy-2-fluoropyridine-3-carboxylate

To a stirred solution of ethyl 2-chloro-4-cyclopropoxypyridine-3-carboxylate (800 mg, 3.310 mmol) in dimethyl sulfoxide (10 mL) was added cesium fluoride (2.51 g, 16.55 mmol) at room temperature. The resulting mixture was stirred at 90° C. for 96 h. The mixture was allowed to cool down to room temperature. The reaction was quenched by the addition of water (50 mL) at room temperature. The resulting mixture was extracted with ethyl acetate (3×100 mL). The combined organic layers were washed with brine (150 mL), dried over anhydrous sodium sulfate. After filtration, the filtrate was concentrated under reduced pressure. The crude product was purified by Prep-HPLC with the following conditions (Column: XBridge Prep Phenyl OBD Column, 19×250 mm, 5 μm; Mobile Phase A: water (plus 10 mmol/L ammonium bicarbonate), Mobile Phase B: acetonitrile; Flow rate: 25 mL/min; Gradient: 40% to 42% B in 12 min, Detector: UV 220/254 nm) and concentrated under reduced pressure to afford ethyl 4-cyclopropoxy-2-fluoropyridine carboxylate (150 mg, 20%) as a white solid. MS ESI calculated for $C_{11}th2FNO_3$ [M+H]$^+$, 226.08 found 226.05; $^1$H NMR (400 MHz, CDCl$_3$) δ 8.17 (d, J=6.0 Hz, 1H), 7.17 (d, J=6.0 Hz, 1H), 4.40 (q, J=7.2 Hz, 2H), 3.95-3.86 (m, 1H), 1.38 (t, J=7.2 Hz, 3H), 0.90-0.89 (m, 4H).

Step 3: 4-cyclopropoxy-2-fluoropyridine-3-carboxylic acid

To a stirred solution of ethyl 4-cyclopropoxy-2-fluoropyridine-3-carboxylate (150 mg, 0.666 mmol) in tetrahydrofuran (2 mL) was added lithium hydroxide (80 mg, 3.340 mmol) and water (1 mL) at room temperature. The resulting mixture was stirred at room temperature for 16 h. The mixture was acidified to pH 5 with hydrochloric acid (aq.). The resulting mixture was concentrated under reduced pressure. The residue was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 30% to 60% B in 25 min; Flow rate: 60 mL/min; Detector: UV 220/254 nm. The fractions containing desired product were collected and concentrated under reduced pressure to afford 4-cyclopropoxy-2-fluoropyridine-3-carboxylic acid (69 mg, 52%) as a white solid. MS ESI calculated for $C_9H_8FNO_3$ [M+H]$^+$, 198.05 found 198.00; $^1$H NMR (400 MHz, CDCl$_3$) δ 8.24 (d, J=6.0 Hz, 1H), 7.23 (d, J=6.0 Hz, 1H), 3.97-3.91 (m, 1H), 0.95-0.91 (m, 4H).

Step 4: N-{4-[(7-{2-[(tert-butyldimethylsilyl)oxy]ethoxy}-6-methoxyquinolin-4-yl)oxy]-3,5-difluorophenyl}-4-cyclopropoxy-2-fluoropyridine-3-carboxamide A solution of 4-cyclopropoxy-2-fluoropyridine-3-carboxylic acid (69 mg, 0.350 mmol) in oxalyl chloride (1 mL) was stirred at room temperature for 16 h. The resulting mixture was concentrated under reduced pressure. Dichloromethane (2 mL) was added to the above mixture, followed by adding 4-[(7-{2-[(tert-butyldimethylsilyl)oxy]ethoxy}-6-methoxyquinolin-4-yl)oxy]-3,5-difluoroaniline (100 mg, 0.210 mmol) in portion. Then N,N-diisopropylethylamine (90 mg, 0.700 mmol) was added to the above mixture under stirring. The resulting mixture was stirred at room temperature for 2 h. The reaction was quenched by the addition of water (10 mL) at room temperature. The resulting mixture was extracted with ethyl acetate (3×20 mL). The combined organic layers were washed with brine (20 mL), dried over anhydrous sodium sulfate. After filtration, the filtrate was concentrated under reduced pressure. The residue was purified by silica gel column chromatography, eluted with petroleum ether/ethyl acetate (1/1) and concentrated under reduced pressure to afford N-{4-[(7-{2-[tert-butyldimethylsilyl)oxy]ethoxy}-6-methoxyquinolin-4-yl)oxy]-3,5-difluorophenyl}-4-cyclopropoxy -2-fluoropyridine-3-carboxamide (25 mg, 10%) as a white solid. MS ESI calculated for $C_{33}H_{36}F_3N_3O_6Si$ [M+H]$^+$, 656.23 found 656.20.

Step 5: 4-cyclopropoxy-N-(3,5-difluoro-4-{[7-(2-hydroxyethoxy)-6-methoxyquinolin-4-yl]oxy}phenyl)-2-fluoropyridine-3-carboxamide To a stirred solution of N-{4-[(7-{2-[(tert-butyldimethylsilyl)oxy]ethoxy}-6-methoxyquinolin-4-yl)oxy]-3,5-difluorophenyl}-4-cyclopropoxy-2-fluoropyridine-3-carboxamide (20 mg, 0.030 mmol) in dichloromethane (2 mL) was added trifluoroacetic acid (1 mL) at room temperature. The resulting mixture was stirred at room temperature for 16 h. The mixture was basified to pH 8 with ammonia (7 N in methanol). The resulting mixture was concentrated under reduced pressure. The crude product (30 mg) was purified by Prep-HPLC with the following conditions (Column: XBridge Prep OBD C18 Column, 30×150 mm, 5 μm; Mobile Phase A: water (plus 10 mmol/L ammonium bicarbonate), Mobile Phase B: acetonitrile; Flow rate: 60 mL/min; Gradient: 30% to 40% B in 8 min; Detector: UV 220/254 nm). The fractions containing desired product were collected, concentrated and lyophilized to afford 4-cyclopropoxy-N-(3,5-difluoro-4-{[7-(2-hydroxyethoxy)-6-methoxy-quinolin-4-yl]oxy}phenyl)-2-fluoropyridine-3-carboxamide (1.9 mg, 11%) as a white solid. MS ESI calculated for $C_{27}H_{22}F_3N_3O_6$ [M+H]$^+$, 542.15 found 542.10. $^1$H NMR (400 MHz, CD$_3$OD) δ 8.49 (d, J=5.2 Hz, 1H), 8.25 (d, J=6.0 Hz, 1H), 7.70 (s, 1H), 7.66-7.57 (m, 2H), 7.48 (d, J=6.0 Hz, 1H), 7.43 (s, 1H), 6.62 (d, J=5.2 Hz, 1H), 4.28 (t, J=4.4 Hz, 2H), 4.14-4.10 (m, 1H), 4.07 (s, 3H), 4.03 (t, J=4.4 Hz, 2H), 1.05-0.95 (m, 2H), 0.88-0.86 (m, 2H). $^{19}$F NMR (377 MHz, CD$_3$OD) δ −73.95 (1F), −127.76 (2F).

Example 119: N-(3,5-difluoro-4-((6-methoxy-7-(3-(methylamino)propoxy)quinolin-4-yl)oxy)phenyl)-4-ethoxypyridine-3-carboxamide

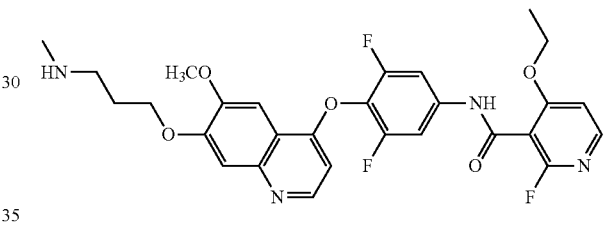

Synthesized using the similar method as in example 118. Light brown solid. $^1$H NMR (400 MHz DMSO-d$_6$) δ 11.18 (s, 1H), 8.77 (brs, 1H), 8.76 (brs, 2H), 8.26 (d, J=5.2 Hz, 1H), 7.73 (s, 2H), 7.71 (s, 1H), 7.61 (s, 1H), 7.26 (d, J=6.0 Hz, 1H), 7.12 (brs, 1H), 4.35-4.25 (m, 4H), 4.04 (s, 3H), 3.20-3.10 (m, 2H), 2.62 (t, J=5.6 Hz, 3H), 2.23-2.18 (m, 2H), 1.34 (t, J=6.8 Hz, 3H), 1.24 (brs, 1H) ppm. LCMS m/z: 557 [M+H]$^+$.

Example 120: 4-cyclopropoxy-N-(3,5-difluoro-4-((7-(2-methoxyethoxy)quinolin-4-yl)oxy)phenyl)pyridazine-3-carboxamide

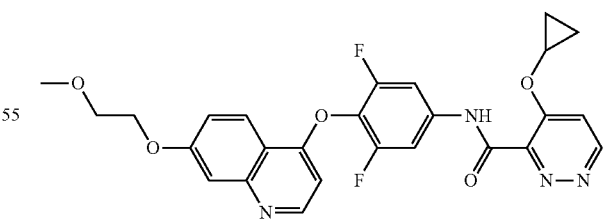

Step 1: ethyl 6-chloro-4-cyclopropoxypyridazine-3-carboxylate

To a stirred mixture of ethyl 4,6-dichloropyridazine-3-carboxylate (1 g, 4.52 mmol) and cyclopropanol (0.39 g, 6.78 mmol) in dimethyl sulfoxide (10 mL) was added 1,8-diazabicyclo[5.4.0]undec-7-ene (1.38 g, 9.05 mmol) at room temperature. The resulting mixture was stirred at 50° C. for 16 h. The mixture was allowed to cool down to room temperature. The residue was purified by reverse phase Flash chromatography with the following conditions: Column: WelFlash™ C18-I, 20-40 μm, 330 g; Eluent A: water (plus 10 mmol/L ammonium bicarbonate); Eluent B: acetonitrile; Gradient: 30% to 60% B in 25 min; Flow rate: 80 mL/min; Detector: UV 220/254 nm; desired fractions were concentrated under reduced pressure to afford ethyl 6-chloro-4-cyclopropoxypyridazine-3-carboxylate (500 mg, 46%) as a yellow oil. MS ESI calculated for $C_{10}H_{11}ClN_2O_3$ [M+H]$^+$, 243.05 found 243.20. $^1$H NMR (400 MHz, DMSO-$d_6$) δ 7.33 (s, 1H), 4.41-4.36 (m, 1H), 3.47 (q, J=7.2 Hz, 2H), 1.60 (t, J=7.2 Hz, 3H), 0.84-0.79 (m, 2H), 0.75-0.69 (m, 2H).

Step 2: ethyl 4-cyclopropoxypyridazine-3-carboxylate

A solution of ethyl 6-chloro-4-cyclopropoxypyridazine-3-carboxylate (500 mg, 2.060 mmol) and Pd/C (387 mg, 1.030 mmol) in methanol (10 mL) was stirred at room temperature under hydrogen atmosphere for 2 h. The resulting mixture was filtered, the filter cake was washed with methanol (3×10 mL). The filtrate was concentrated under reduced pressure to afford ethyl 4-cyclopropoxypyridazine-3-carboxylate (374 mg, 87%) as a yellow solid. MS ESI calculated for $C_{10}H_{12}N_2O_3$ [M+H]$^+$, 209.08 found 209.05. $^1$H NMR (400 MHz, DMSO-$d_6$) δ 9.19 (d, J=6.4 Hz, 1H), 7.72 (d, J=6.4 Hz, 1H), 4.38 (q, J=7.2 Hz, 2H), 4.21-4.15 (m, 1H), 1.31 (t, J=7.2 Hz, 3H), 0.99-0.86 (m, 2H), 0.82-0.75 (m, 2H).

Step 3: 4-cyclopropoxypyridazine-3-carboxylic acid

A mixture of ethyl 4-cyclopropoxypyridazine-3-carboxylate (374 mg, 1.796 mmol) and lithium hydroxide (215 mg, 8.980 mmol) in tetrahydrofuran (4 mL) and water (2 mL) was stirred at room temperature for 5 h. The resulting mixture was concentrated under reduced pressure. The mixture was acidified to pH 6 with hydrochloric acid (aq.). The precipitated solids were collected by filtration and washed with water (2×10 mL) to afford 4-cyclopropoxypyridazine-3-carboxylic acid (258 mg, 79%) as a white solid. MS ESI calculated for $C_8H_8N_2O_3$ [M+H]$^+$, 181.05 found 181.20.

Step 4: 4-cyclopropoxy-N-(3,5-difluoro-4-{[7-(2-methoxyethoxy)quinolin-4-yl]oxy}phenyl) pyridazine-3-carboxamide A mixture of 4-cyclopropoxypyridazine-3-carboxylic acid (31 mg, 0.173 mmol) in oxalyl chloride (2 mL) was stirred at 75° C. for 16 h. The mixture was allowed to cool down to room temperature. The resulting mixture was concentrated under reduced pressure. To the above reaction was added 3,5-difluoro-4-{[7-(2-methoxyethoxy)quinolin-4-yl]oxy}aniline (60 mg, 0.173 mmol) and tetrahydrofuran (2 mL) was stirred at room temperature for 5 min. To the final reaction was added N,N-diisopropylethylamine (45 mg, 0.346 mmol) and stirred at room temperature for 5 h. The resulting mixture was concentrated under reduced pressure. The crude product was purified by Prep-HPLC with the following conditions: (Column: XBridge Prep OBD C18 Column, 30×150 mm, 5 μm; Mobile Phase A: water (plus 10 mmol/L ammonium bicarbonate), Mobile Phase B: acetonitrile; Flow rate: 60 mL/min; Gradient: 36% to 46% B in 8 min; Detector: UV 220/254 nm;). The fractions containing desired product were collected, concentrated and lyophilized to afford 4-cyclopropoxy-N-(3,5-difluoro-4-{[7-(2-methoxyethoxy)quinolin-4-yl]oxy}phenyl)pyridazine-3-carboxamide (0.9 mg, 1%) as a yellow solid. MS ESI calculated for $C_{26}H_{22}F_2N_4O_5$ [M+H]$^+$, 509.16 found 509.15. $^1$H NMR (400 MHz, DMSO-$d_6$) δ 11.24 (s, 1H), 9.25 (d, J=6.4 Hz, 1H), 8.65 (d, J=5.2 Hz, 1H), 8.27 (d, J=9.2 Hz, 1H), 7.82-7.78 (m, 2H), 7.77 (d, J=6.4 Hz, 1H), 7.46 (d, J=2.4 Hz, 1H), 7.36 (dd, J=9.2, 2.4 Hz, 1H), 6.66 (d, J=5.2 Hz, 1H), 4.34 (t, J=5.6 Hz, 2H), 4.19-4.16 (m, 1H), 3.76 (t, J=5.6 Hz, 2H), 3.39 (s, 3H), 0.95-0.88 (m, 2H), 0.81-0.79 (m, 2H). $^{19}$F NMR (376 MHz, DMSO-$d_6$) δ −126.51 (2F).

Example 121: N-(3,5-difluoro-4-((7-(2-hydroxy-ethoxy)-6-methoxyquinolin-4-yl)oxy)phenyl)-4-methoxypyridine-3-carboxamide

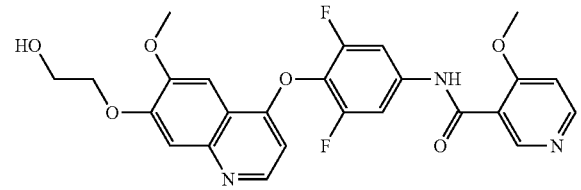

Step 1: N-{4-[(7-{2-[(tert-butyldimethylsilyl)oxy] ethoxy}-6-methoxyquinolin-4-yl)oxy]-3,5-difluoro-phenyl}-4-methoxypyridine-3-carboxamide To a stirred mixture of 4-methoxypyridine-3-carboxylic acid (128 mg, 0.840 mmol) and propylphosphonic anhydride (1.5 mL, 50% in ethyl acetate) in pyridine (3 mL) was added 4-[(7-{2-[(tert-butyldimethylsilyl)oxy]ethoxy}-6-methoxyquinolin-4-yl)oxy]-3,5-difluoroaniline (200 mg, 0.420 mmol, synthesized in step 3 of example 97) at room temperature. The resulting mixture was stirred at room temperature for 1 h. The mixture was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 55% to 75% B in 25 min; Flow rate: 60 mL/min; Detector: UV 220/254 nm; desired fractions were collected and concentrated under reduced pressure to afford N-{4-[(7-{2-[(tert -butyldimethylsilyl)oxy]ethoxy}-6-methoxyquinolin-4-yl)oxy]-3,5-difluorophenyl}-4-methoxypyridine-3-carboxamide (143 mg, 56%) as a white solid. MS ESI calculated for $C_{31}H_{35}F_2N_3O_6Si$ [M+H]$^+$, 612.23 found 612.15. $^1$H NMR (400 MHz, CDCl$_3$) δ 9.54 (s, 1H), 9.37 (s, 1H), 8.73 (d, J=6.0 Hz, 1H), 8.54 (d, J=5.2 Hz, 1H), 7.64 (s, 1H), 7.60-7.53 (m, 2H), 7.28 (s, 1H), 7.03 (d, J=6.0 Hz, 1H), 6.56 (d, J=5.2 Hz, 1H), 4.33 (t, J=5.2 Hz, 2H), 4.20 (s, 3H), 4.14 (t, J=5.2 Hz, 2H), 4.08 (s, 3H), 0.94 (s, 9H), 0.15 (s, 6H).

Step 2: N-(3,5-difluoro-4-{[7-(2-hydroxyethoxy)-6-methoxyquinolin-4-yl]oxy}phenyl)-4-methoxypyridine-3-carboxamide To a stirred solution of N-{4-[(7-{2-[(tert-butyldimethylsilyl)oxy]ethoxy}-6-methoxyquinolin-4-yl)oxy]-3,5-difluorophenyl}-4-methoxypyridine-3-carboxamide (143 mg, 0.234 mmol) in dichloromethane (1.5 mL) was added trifluoroacetic acid (1.5 mL) at room temperature. The resulting mixture was stirred at room temperature for 1 h. The mixture was basified to pH 8 with saturated sodium bicarbonate (aq.). The resulting mixture was concentrated under reduced pressure. The residue was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 30% to 50% B in 25 min; Flow rate: 60 mL/min; Detector: UV 220/254 nm; desired fractions were concentrated under reduced pressure to afford N-(3,5-difluoro-4-{[7-(2-hydroxyethoxy)-6-methoxyquinolin-4-yl]oxy}phenyl)-4-methoxypyridine-3-carboxamide (48 mg, 41%) as a white solid. MS ESI calculated for $C_{25}H_{21}F_2N_3O_6$ [M+H]$^+$, 498.14 found 498.30. $^1$H NMR (400 MHz, DMSO-d$_6$) δ 10.70 (s, 1H), 8.64 (s, 1H), 8.62 (d, J=6.0 Hz, 1H), 8.50 (d, J=5.2 Hz, 1H), 7.81-7.71 (m, 2H), 7.56 (s, 1H), 7.45 (s, 1H), 7.28 (d, J=6.0 Hz, 1H), 6.61 (d, J=5.2 Hz, 1H), 4.96 (t, J=5.2 Hz, 1H), 4.20 (t, J=4.8 Hz, 2H), 3.98 (s, 3H), 3.97 (s, 3H), 3.88-3.84 (m, 2H). $^{19}$F NMR (376 MHz, DMSO-d$_6$) δ −126.56 (2F).

Example 122: N-(3,5-difluoro-4-{[6-(2-hydroxyethoxy)-7-methoxyquinolin-4-yl]oxy}phenyl)-4-methoxypyridine-3-carboxamide

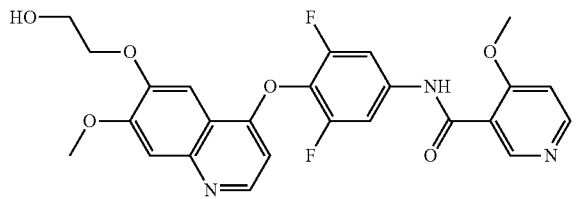 [SMILES: COc1cc2nccc(Oc3c(F)cc(NC(=O)c4cnccc4OC)cc3F)c2cc1OCCO]

Step 1: 1-(benzyloxy)-2-methoxy-4-nitrobenzene

To a stirred mixture of 2-methoxy-4-nitrophenol (100.00 g, 591.24 mmol) and potassium carbonate (245.14 g, 1773.72 mmol) in N,N-dimethylformamide (1 L) was added benzyl bromide (121.35 g, 709.49 mmol) at room temperature. The resulting mixture was stirred at 90° C. for 1.5 hours. The mixture was allowed to cool down to room temperature and quenched with water (1×3 L). The resulting mixture was extracted with ethyl acetate (3×3 L). The combined organic layers were washed with water (5×2 L), dried over anhydrous sodium sulfate. After filtration, the filtrate was concentrated under reduced pressure to afford 1-(benzyloxy)-2-methoxy-4-nitrobenzene (143.40 g, 94%) as a yellow solid. $^1$H NMR (400 MHz, CDCl$_3$) δ 7.86 (dd, J=8.8, 2.4 Hz, 1H), 7.78 (d, J=2.4 Hz, 1H), 7.49-7.26 (m, 5H), 6.95 (d, J=8.8 Hz, 1H), 5.27 (s, 2H), 3.98 (s, 3H).

Step 2: 4-(benzyloxy)-3-methoxyaniline

To a stirred mixture of 1-(benzyloxy)-2-methoxy-4-nitrobenzene (73.40 g, 283.11 mmol) and iron powder (79.05 g, 1415.56 mmol) in tetrahydrofuran (700 mL) was added ammonium chloride (30.29 g, 566.22 mmol) and water (700 mL) at room temperature. The resulting mixture was stirred at 70° C. for 4 hours. The mixture was allowed to cool down to room temperature. The resulting mixture was filtered, the filter cake was washed with methanol (5×200 mL). The filtrate was concentrated under reduced pressure. The precipitated solids were collected by filtration and washed with water (10×200 mL). The solid was collected and dried under reduced pressure to give 4-(benzyloxy)-3-methoxyaniline (64 g, crude) as a yellow solid. MS ESI calculated for $C_{14}H_{15}NO_2$[M+H]$^+$, 230.11 found 229.85.

Step 3: 5-({[4-(benzyloxy)-3-methoxyphenyl]amino}methylidene)-2,2-dimethyl-1,3-dioxane-4,6-dione A mixture of 4-(benzyloxy)-3-methoxyaniline (64.00 g, 279.13 mmol), 5-(methoxymethylidene) -2,2-dimethyl-1,3-dioxane-4,6-dione (62.36 g, 334.96 mmol) in isopropyl alcohol (600 mL) was stirred at 110° C. for 4 hours. After the reaction, the mixture was allowed to cool down to room temperature. The precipitated solids were collected by filtration and washed with isopropyl alcohol (5×200 mL). The solid was collected and dried under reduced to give 5-({[4-(benzyloxy)-3-methoxyphenyl]amino}methylidene)-2,2-dimethyl-1,3-dioxane-4,6-dione (92 g, crude) as a yellow solid. MS ESI calculated for $C_{21}H_{21}NO_6$[M+H]$^+$, 384.14 found 383.95.

Step 4: 6-(benzyloxy)-7-methoxyquinolin-4-ol

A mixture of 5-({[4-(benzyloxy)-3-methoxyphenyl]amino}methylidene)-2,2-dimethyl-1,3-dioxane-4,6-dione (92.00 g, 239.96 mmol) in diphenyl ether (1 L) was stirred at 220° C. for 1 hour. The mixture was allowed to cool down to room temperature. The residue was dissolved in petroleum ether (5 L). The precipitated solids were collected by filtration and washed with petroleum ether (5×500 mL). The solid was collected and dried under reduced to give 6-(benzyloxy)-7-methoxyquinolin-4-ol (66.30 g, crude) as a yellow solid. MS ESI calculated for $C_{17}H_{15}NO_3$[M+H]$^+$, 282.11 found 281.95.

Step 5: 6-(benzyloxy)-4-chloro-7-methoxyquinoline

To a stirred mixture of 6-(benzyloxy)-7-methoxyquinolin-4-ol (66.30 g, 235.68 mmol) and phosphorus oxychloride (54.20 g, 353.52 mmol) in 1,2-dichloroethane (600 mL) was added N,N -diisopropylethylamine (60.92 g, 471.36 mmol) at room temperature. The resulting mixture was stirred at 80° C. for 4 hours. After the reaction was completed, the mixture was allowed to cool down to room temperature. The resulting mixture was quenched with water (1 L) and extracted with dichloromethane (5×2 L). The combined organic layers were washed with water (3×1 L), dried over anhydrous sodium sulfate. After filtration, the filtrate was concentrated under reduced pressure to afford 6-(benzyloxy)-4-chloro-7-methoxyquinoline (76 g, crude) as a yellow solid. MS ESI calculated for $C_{17}H_{14}ClNO_2$ [M+H]$^+$, 300.07, 302.07 found 299.85, 301.85.

Step 6: 6-(benzyloxy)-4-(2,6-difluoro-4-nitrophenoxy)-7-methoxyquinoline

To a stirred mixture of 6-(benzyloxy)-4-chloro-7-methoxyquinoline (17.00 g, 56.71 mmol) and 2,6-difluoro-4-nitrophenol (11.92 g, 68.06 mmol) in 1-methyl-2-pyrrolidinone (170 mL) was added N,N-diisopropylethylamine (14.66 g, 113.43 mmol) at room temperature. The resulting mixture was stirred at 140° C. for 16 hours. After the reaction was completed, the mixture was allowed to cool down to room temperature. The resulting mixture was quenched with water (1 L) and extracted with ethyl acetate (4×2 L). The combined organic layers were washed with water (5×2 L), dried over anhydrous sodium sulfate. After filtration, the filtrate was concentrated under reduced pressure. This resulted in 6-(benzyloxy)-4-(2,6-difluoro-4-nitrophenoxy)-7-methoxyquinoline (17 g, crude) as a yellow solid. MS ESI calculated for $C_{23}H_{16}F_2N_2O_5$ [M+H]$^+$, 439.10 found 439.00.

Step 7: 4-(4-amino-2,6-difluorophenoxy)-7-methoxyquinolin-6-ol

A mixture of 6-(benzyloxy)-4-(2,6-difluoro-4-nitrophenoxy)-7-methoxyquinoline (17 g, 38.78 mmol) and palladium on carbon (16.51 g, 155.11 mmol) in methanol (170 mL) was stirred at room temperature under hydrogen atmosphere for 16 h. After the reaction was completed, the reaction mixture was filtered, the filter cake was washed with methanol (5×100 mL). The filtrate was concentrated under reduced pressure to afford the crude product 4-(4-amino-2,6-difluorophenoxy)-7-methoxyquinolin-6-ol (5.9 g) as a yellow solid. MS ESI calculated for $C_{16}H_{12}F_2N_2O_3$ [M+H]$^+$, 319.08, found 318.90.

Step 8: 4-[(6-{2-[(tert-butyldimethylsilyl)oxy]ethoxy}-7-methoxyquinolin-4-yl)oxy]-3,5-difluoroaniline To a stirred mixture of 4-(4-amino-2,6-difluorophenoxy)-7-methoxyquinolin-6-ol (5.9 g, crude) and 2-[(tert-butyldimethylsilyl)oxy]ethanol (3.60 g, 20.39 mmol) in tetrahydrofuran (60 mL) was added triphenylphosphine (9.72 g, 37.07 mmol) and diisopropyl azodicarboxylate (7.50 g, 37.07 mmol) at room temperature under nitrogen atmosphere. The resulting mixture was stirred at room temperature for another 16 h. After the reaction was completed, the reaction mixture was concentrated under reduced pressure. The residue was purified by silica gel column chromatography, eluted with petroleum ether/ethyl acetate/ethanol (4/3/1) to afford 4-[(6-{2-[(tert-butyldimethylsilyl)oxy]ethoxy}-7-methoxyquinolin-4-yl)oxy]-3,5-difluoroaniline (1.6 g) as a yellow solid. MS ESI calculated for $C_{24}H_{30}F_2N_2O_4Si$ [M+H]$^+$, 477.19 found 477.35.

Step 9: N-{4-[(6-{2-[(tert-butyldimethylsilyl)oxy]ethoxy}-7-methoxyquinolin-4-yl)oxy]-3,5-difluorophenyl}-4-methoxypyridine-3-carboxamide To a mixture of 4-[(6-{2-[(tert-butyldimethylsilyl)oxy]ethoxy}-7-methoxyquinolin-4-yl)oxy]-3,5-difluoroaniline (1.6 g, 3.36 mmol) and 4-methoxypyridine-3-carboxylic acid (0.62 g, 4.05 mmol) in pyridine (16 mL) was added propylphosphonic anhydride (8 mL, 50% in ethyl acetate) at room temperature. The resulting mixture was stirred at room temperature for another 2 h. After the reaction was completed, the reaction mixture was purified by reverse phase Flash chromatography with the following conditions: Column: WelFlash™ C18-I, 20-40 μm, 330 g; Eluent A: water (plus 10 mmol/L ammonium bicarbonate); Eluent B: acetonitrile; Gradient: 25% to 45% B in 25 min; Flow rate: 100 mL/min; Detector: 220/254 nm; desired fractions were collected at 42% B and concentrated under reduced pressure to afford N-{4-[(6-{2-[(tert -butyldimethylsilyl)oxy]ethoxy}-7-methoxyquinolin-4-yl)oxy]-3,5-difluorophenyl}-4-methoxypyridine-3-carboxamide (1.3 g, 63%) as a white solid. MS ESI calculated for $C_{31}H_{35}F_2N_3O_6Si$ [M+H]$^+$, 612.23 found 612.35.

Step 10: N-(3,5-difluoro-4-{[6-(2-hydroxyethoxy)-7-methoxyquinolin-4-yl]oxy}phenyl)-4-methoxypyridine-3-carboxamide To a stirred mixture of N-{4-[(6-{2-[(tert-butyldimethylsilyl)oxy]ethoxy}-7-methoxyquinolin-4-yl)oxy]-3,5-difluorophenyl}-4-methoxypyridine-3-carboxamide (100 mg, 0.163 mmol) in dichloromethane (5 mL) was added trifluoroacetic acid (1 mL). The resulting mixture was stirred at room temperature for 2 h. The mixture was neutralized to pH 8 with saturated ammonium chloride (aq.). The crude product was purified by reverse phase Flash chromatography with the following conditions: Column: WelFlash™ C18-I, 20-40 μm, 330 g; Eluent A: water (plus 10 mmol/L ammonium bicarbonate); Eluent B: acetonitrile; Gradient: 25% to 75% B in 25 min; Flow rate: 80 mL/min; Detector: 220/254 nm; desired fractions were collected at 45% B. The fractions containing desired product were collected, concentrated and lyophilized to afford N -(3,5-difluoro-4-{[6-(2-hydroxyethoxy)-7-methoxyquinolin-4-yl]oxy}phenyl)-4-methoxypyridine -3-carboxamide (49.7 mg, 61%) as a white solid. MS ESI calculated for $C_{25}H_{21}F_2N_3O_6$ [M+H]$^+$, 498.14 found 498.05. $^1$H NMR (400 MHz, DMSO-d$_6$) δ 10.70 (s, 1H), 8.64 (s, 1H), 8.62 (d, J=6.0 Hz, 1H), 8.51 (d, J=5.2 Hz, 1H), 7.79-7.72 (m, 2H), 7.58 (s, 1H), 7.45 (s, 1H), 7.28 (d, J=6.0 Hz, 1H), 6.61 (d, J=5.2 Hz, 1H), 4.92 (t, J=5.2 Hz, 1H), 4.20 (t, J=5.2 Hz, 2H), 3.98 (s, 6H), 3.87-3.82 (m, 2H). $^{19}$F NMR (376 MHz, DMSO-d$_6$) δ -126.59 (2F).

Example 123: (S)-N-(3,5-difluoro-4-{[6-(2-hydroxypropoxy)-7-methoxyquinolin-4-yl]oxy}phenyl)-4-methoxypyridine-3-carboxamide

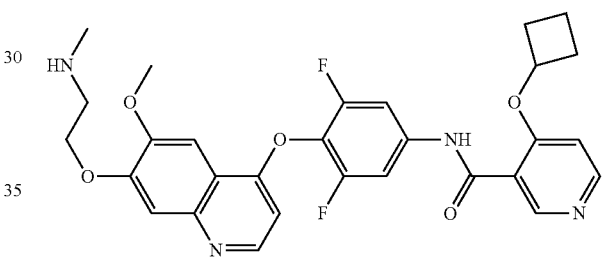

Synthesized using the similar method as in example 122. Off-white solid. MS ESI calculated for $C_{26}H_{23}F_2N_3O_6$ [M+H]$^+$, 512.16 found 512.20. $^1$H NMR (400 MHz, DMSO-d$_6$) δ 10.70 (s, 1H), 8.63 (s, 1H), 8.61 (d, J=6.0 Hz, 1H), 8.50 (d, J=5.2 Hz, 1H), 7.80-7.70 (m, 2H), 7.56 (s, 1H), 7.44 (s, 1H), 7.28 (d, J=6.0 Hz, 1H), 6.61 (d, J=5.2 Hz, 1H), 4.91 (d, J=4.8 Hz, 1H), 4.12-3.89 (m, 9H), 1.21 (d, J=6.0 Hz, 3H). $^{19}$F NMR (377 MHz, DMSO-d$_6$) δ -126.61 (2F).

Example 124: (R)-N-(3,5-difluoro-4-{[6-(2-hydroxypropoxy)-7-methoxyquinolin-4-yl]oxy}phenyl)-4-methoxypyridine-3-carboxamide

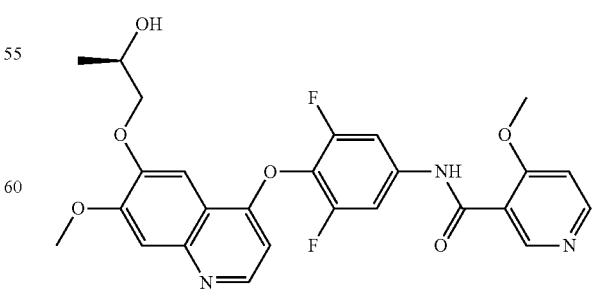

Synthesized using the similar method as in example 122. Off-white solid. MS ESI calculated for $C_{26}H_{23}F_2N_3O_6$

[M+H]+, 512.16 found 512.20. 1H NMR (400 MHz, DMSO-d6) δ 10.70 (s, 1H), 8.64 (s, 1H), 8.62 (d, J=6.0 Hz, 1H), 8.51 (d, J=5.2 Hz, 1H), 7.81-7.71 (m, 2H), 7.57 (s, 1H), 7.45 (s, 1H), 7.28 (d, J=6.0 Hz, 1H), 6.61 (d, J=5.2 Hz, 1H), 4.91 (d, J=4.4 Hz, 1H), 4.13-3.93 (m, 9H), 1.22 (d, J=6.0 Hz, 3H). 19F NMR (377 MHz, DMSO-d6) δ −126.62 (2F).

Example 125: N-(3,5-difluoro-4-{[6-(2-hydroxy-2-methylpropoxy)-7-methoxyquinolin-4-yl]oxy}phenyl)-4-methoxypyridine-3-carboxamide

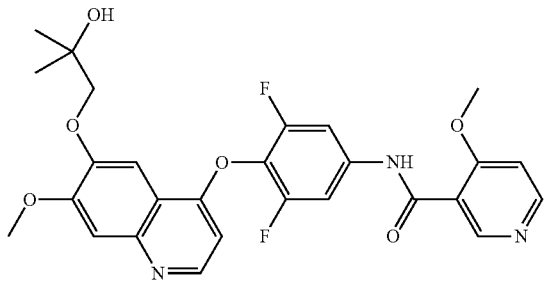 [SMILES: COc1cc2nccc(Oc3c(F)cc(NC(=O)c4cnccc4OC)cc3F)c2cc1OCC(C)(C)O]

Synthesized using the similar method as in example 122. White solid. MS ESI calculated for $C_{27}H_{25}F_2N_3O_6$ [M+H]+, 526.17 found 526.20. 1H NMR (400 MHz, DMSO-d6) δ 10.65 s, 1H), 8.64 (s, 1H), 8.61 (d, J=6.0 Hz, 1H), 7.82 (d, J=7.6 Hz, 1H), 7.71 (d, J=10.4 Hz, 2H), 7.46 (s, 1H), 7.29-7.23 (m, 2H), 5.96 (d, J=7.6 Hz, 1H), 4.83 (s, 1H), 4.24 (s, 2H), 4.03 (s, 3H), 3.97 (s, 3H), 1.18 (s, 6H). 19F NMR (376 MHz, DMSO-d6) δ −126.64 (2F).

Example 126: (S)-N-(3,5-difluoro-4-{[6-((1-hydroxypropan-2-yl)oxy)-7-methoxyquinolin-4-yl]oxy}phenyl)-4-methoxypyridine-3-carboxamide

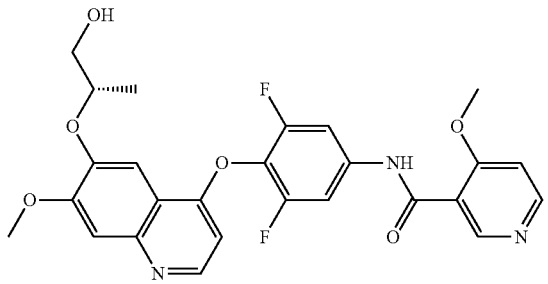

Step 1: 4-(2,6-difluoro-4-nitrophenoxy)-7-methoxyquinolin-6-ol

A mixture of 6-(benzyloxy)-4-(2,6-difluoro-4-nitrophenoxy)-7-methoxyquinoline as a yellow solid (225 g, 0.5 mol) and 33% HBr in acetic acid (450 mL) was heated at 33-35° C. for 3 hours. The mixture was cooled down to 25-30° C. and added to methyl t-butyl ether (1575 mL) and stirred for additional 3 hours. The precipitation was collected by filtration, washed with 7% NaHCO3 aqueous solution, water, methanol and dried in blast oven to yield 4-(2,6-difluoro-4-nitrophenoxy)-7-methoxyquinolin-6-ol (162 g, 90%). LC/MS [M+H]+348.8. 1H NMR (400 MHz, d6-DMSO) δ 10.2 (s, 1H), 8.5-8.4 (m, 3H), 7.5-7.3 (m, 2H), 6.7 (s, 1H), 4.0 (s, 3H).

Step 2: (S)-6-41-(benzyloxy)propan-2-yl)oxy)-4-(2,6-difluoro-4-nitrophenoxy)-7-methoxyquinoline To a solution of 4-(2,6-difluoro-4-nitrophenoxy)-7-methoxyquinolin-6-ol (1 g, 2.87 mmol) and PPh3 (2.25 g, 8.61 mmol) in tetrahydrofuran (20 mL) were added (R)-1-(benzyloxy)propan-2-ol (0.72 g, 4.30 mmol) and di-ethyl azodicarboxylate (1.25 g, 7.17 mmol) at 0° C. under nitrogen atmosphere and stirred for 10 min. The resulting reaction mixture was stirred at room temperature under nitrogen atmosphere for 4 h. After completion of the reaction (monitored by TLC), the resulting reaction mixture was diluted with ice cold water (50 mL) and extracted with ethyl acetate (3×45 mL). The combined organic layers were washed with brine (3×60 mL), dried over anhydrous sodium sulphate. After filtration, the filtrate was concentrated under reduced pressure. The residue was purified by silica gel column chromatography, eluted with petroleum ether/ethyl acetate (1/2) to afford (S)-6-((1-(benzyloxy)propan-2-yl)oxy)-4-(2,6-difluoro-4-nitrophenoxy)-7-methoxyquinoline 3 (0.5 g, 35%) as a light yellow solid. LC-MS: m/z 497.42 [M+H]+.

Step 3: (S)-2-((4-(4-amino-2,6-difluorophenoxy)-7-methoxyquinolin-6-yl)oxy)propan-1-ol To a stirred solution of (S)-6-((1-(benzyloxy)propan-2-yl)oxy)-4-(2,6-difluoro-4-nitrophenoxy)-7-methoxyquinoline (0.5 g, 1.00 mmol) in MeOH (10 mL) was added Pd/C (100 mg, 10%) and the reaction mixture was stirred under hydrogen atmosphere for 16 h. The progress of the reaction monitored by LCMS. After completion of the reaction, the reaction mass was filtered through a small pad of Celite and washed with MeOH (15 mL). The filtrate was concentrated under reduced pressure to afford crude (S)-2-((4-(4-amino-2,6-difluorophenoxy)-7-methoxyquinolin-6-yl)oxy) propan-1-ol 4 (0.2 g, crude) as a yellow solid, which was used in the next step without further purification. LC-MS: m/z 377.27 [M+H]+.

Step 4: (S)-N-(3,5-difluoro-4-{[6-((1-hydroxypropan-2-yl)oxy)-7-methoxyquinolin-4-yl]oxy}phenyl)-4-methoxypyridine-3-carboxamide To a stirred solution of 4-methoxynicotinic acid (48.8 mg, 0.32 mmol) in dry DMF (1.5 mL) were added DIPEA (103 mg, 0.79 mmol) and HATU (202.2 mg, 0.53 mmol) at room temperature. After stirring for 30 minutes at room temperature, (S)-2-((4-(4-amino-2,6-difluorophenoxy)-7-methoxyquinolin-6-yl)oxy)propan-1-ol (100 mg, 0.26 mmol) was added into the reaction mixture and heated at 80° C. for additional 3 h under microwave irradiation. The reaction mixture was poured into ice water (30 mL) and extracted with EtOAc (3×20 mL). The combined organic layer was washed with brine (50 mL), dried over anhydrous Na2SO4 and concentrated under reduced pressure to give crude product, which was purified by prep-HPLC to get (S)-N-(3,5-difluoro-4-((6-((1-hydroxypropan-2-yl)oxy)-7-methoxyquinolin-4-yl)oxy)phenyl)-4-methoxypyridine-3-carboxamide (15 mg, 11%) as an off-white solid. 1H NMR (400 MHz, DMSO-d6) δ: 10.69 (s, 1H), 8.62-8.59 (m, 2H), 8.49 (d, J=5.2 Hz, 1H), 7.74 (d, J=10.0 Hz, 2H), 7.63 (s, 1H), 7.43 (s, 1H), 7.27 (d, J=6.0 Hz, 1H), 6.59 (d, J=5.2 Hz, 1H), 4.90 (m, 1H), 4.67 (q, J=5.6 Hz, 1H), 3.96 (s, 3H), 3.95 (s, 3H), 3.65 (m, 1H), 3.56 (m, 1H), 1.30 (d, J=6 Hz, 3H); LC-MS: m/z 512.33 [M+H]+;

Example 127: (S)-N-(3,5-difluoro-4-((6-((1-hydroxypropan-2-yl)oxy)-7-methoxyquinolin-4-yl)oxy)phenyl)-3-methoxyisonicotinamide

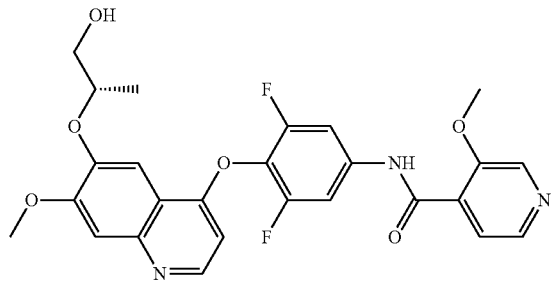 [SMILES: COc1cc2nccc(Oc3c(F)cc(NC(=O)c4ccncc4OC)cc3F)c2cc1O[C@@H](C)CO]

Synthesized using the similar method as in example 126. White solid. MS ESI calculated for $C_{26}H_{23}F_2N_3O_6$ [M+H]$^+$, 512.16 found 512.25. $^1$H NMR (400 MHz, DMSO-d$_6$) δ 10.82 (s, 1H), 8.63 (s, 1H), 8.50 (d, J=5.2 Hz, 1H), 8.39 (d, J=4.8 Hz, 1H), 7.80-7.68 (m, 2H), 7.64 (s, 1H), 7.55 (d, J=4.8 Hz, 1H), 7.44 (s, 1H), 6.61 (d, J=5.2 Hz, 1H), 4.92 (t, J=5.6 Hz, 1H), 4.72-4.68 (m, 1H), 4.02 (s, 3H), 3.96 (s, 3H), 3.69-3.59 (m, 2H), 1.31 (d, J=6.4 Hz, 3H). $^{19}$F NMR (376 MHz, DMSO-d$_6$) δ −126.48 (2F).

Example 129: (S)-4-cyclopropoxy-N-(3,5-difluoro-4-((6-((1-hydroxypropan-2-yl)oxy)-7-methoxyquinolin-4-yl)oxy)phenyl)nicotinamide

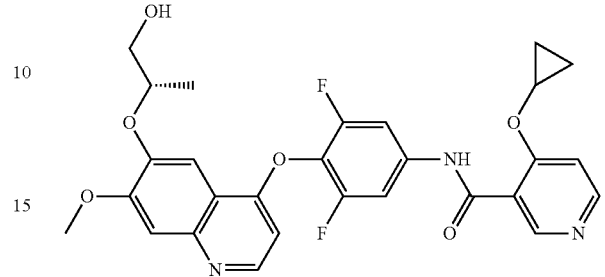

Synthesized using the similar method as in example 126. White solid. MS ESI calculated for $C_{28}H_{25}F_2N_3O_6$ [M+H]$^+$, 538.17 found 538.05. $^1$H NMR (400 MHz, DMSO-d$_6$) δ 10.62 (s, 1H), 8.64 (d, J=5.6 Hz, 1H), 8.62 (s, 1H), 8.50 (d, J=5.2 Hz, 1H), 7.72-7.69 (m, 2H), 7.64 (s, 1H), 7.51 (d, J=5.6 Hz, 1H), 7.44 (s, 1H), 6.61 (d, J=5.2 Hz, 1H), 4.92 (t, J=5.6 Hz, 1H), 4.71-4.67 (m, 1H), 4.12-4.09 (m, 1H), 3.96 (s, 3H), 3.69-3.67 (m, 1H), 3.59-3.56 (m, 1H), 1.31 (d, J=6.0 Hz, 3H), 0.97-0.86 (m, 2H), 0.86-0.76 (m, 2H). $^{19}$F NMR (376 MHz, DMSO-d$_6$) δ −126.58 (2F).

Example 128: (S)-N-(3,5-difluoro-4-((7-methoxy-6-((1-methoxypropan-2-yl)oxy)quinolin-4-yl)oxy)phenyl)-4-methoxynicotinamide

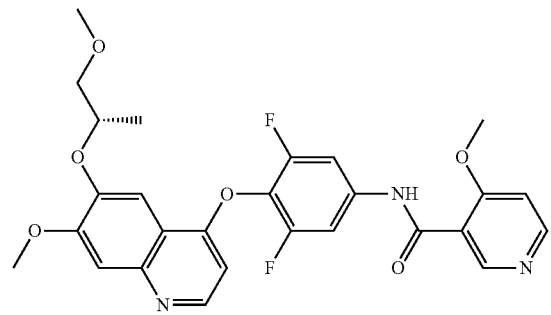 [SMILES: COC[C@H](C)Oc1cc2c(Oc3c(F)cc(NC(=O)c4cnccc4OC)cc3F)ccnc2cc1OC]

Synthesized using the similar method as in example 126. White solid. MS ESI calculated for $C_{27}H_{25}F_2N_3O_6$ [M+H]$^+$, 526.17 found 526.15. $^1$H NMR (400 MHz, DMSO-d$_6$) δ 10.69 (s, 1H), 8.64 (s, 1H), 8.62 (d, J=6.0 Hz, 1H), 8.51 (d, J=5.2 Hz, 1H), 7.77-7.74 (m, 2H), 7.65 (s, 1H), 7.44 (s, 1H), 7.28 (d, J=6.0 Hz, 1H), 6.61 (d, J=5.2 Hz, 1H), 4.93-4.87 (m, 1H), 3.98 (s, 3H), 3.96 (s, 3H), 3.67-3.47 (m, 2H), 1.32 (d, J=6.0 Hz, 3H). $^{19}$F NMR (400 MHz, DMSO-d$_6$) δ −126.67 (2F).

Example 130: (S)-N-(3,5-difluoro-4-((6-((1-hydroxypropan-2-yl)oxy)quinolin-4-yl)oxy)phenyl)-4-methoxynicotinamide

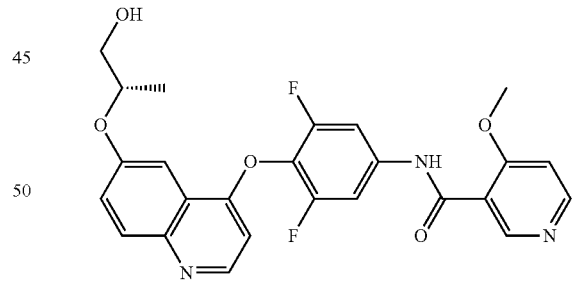

Synthesized using the similar method as in example 126. White solid. MS ESI calculated for $C_{25}H_{21}F_2N_3O_5$ [M+H]$^+$, 482.14 found 482.10. $^1$H NMR (400 MHz, DMSO-d$_6$) δ 10.70 (s, 1H), 8.64 (s, 1H), 8.62 (d, J=6.0 Hz, 1H), 8.56 (d, J=5.2 Hz, 1H), 7.98 (d, J=9.2 Hz, 1H), 7.78-7.76 (m, 2H), 7.66 (d, J=2.8 Hz, 1H), 7.50 (dd, J=9.2, 2.8 Hz, 1H), 7.28 (d, J=6.0 Hz, 1H), 6.74 (d, J=5.2 Hz, 1H), 4.93 (t, J=6.0 Hz, 1H), 4.73-4.70 (m, 1H), 3.98 (s, 3H), 3.66-3.61 (m, 2H), 1.32 (d, J=6.0 Hz, 3H). $^{19}$F NMR (400 MHz, DMSO-d$_6$) δ −126.68 (2F).

Example 131: (R)-N-(3,5-difluoro -4-{[6-((1-hydroxypropan-2-yl)oxy)-7-methoxyquinolin-4-yl]oxy}phenyl)-4-methoxypyridine-3-carboxamide

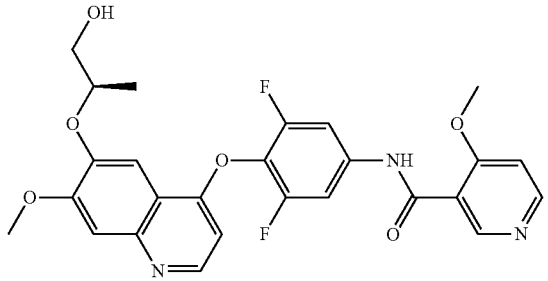

Synthesized using the similar method as in example 126. Off-white solid. $^1$H NMR (400 MHz, DMSO-d$_6$) δ: 10.70 (s, 1H), 8.62 (s, 1H), 8.60 (d, J=6.0 Hz, 1H), 8.49 (d, J=5.2 Hz, 1H), 7.75 (d, J=10.0 Hz, 2H), 7.63 (s, 1H), 7.43 (s, 1H), 7.27 (d, J=6.0 Hz, 1H), 6.59 (d, J=5.2 Hz, 1H), 4.92 (m, 1H), 4.67 (q, J=5.6 Hz, 1H), 3.96 (s, 3H), 3.95 (s, 3H), 3.64 (m, 1H), 3.56 (m, 1H), 1.30 (d, J=6 Hz, 3H); LC-MS: m/z 512.33 [M+H]$^+$.

Example 132: N-(3,5-difluoro-4-((6-(1-(hydroxymethyl)cyclopropoxy)-7-methoxyquinolin-4-yl)oxy)phenyl)-4-methoxynicotinamide

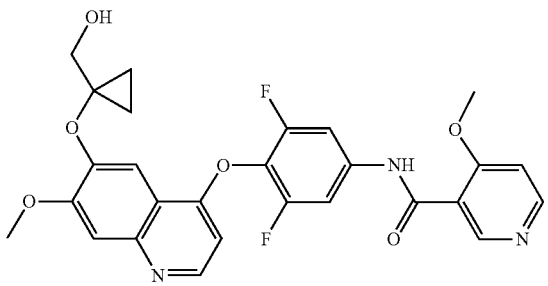 [SMILES: COc1cc2nccc(Oc3c(F)cc(NC(=O)c4cnccc4OC)cc3F)c2cc1OC1(CO)CC1]

Step 1: tert-Butyl-4-bromo-2-((4-(2,6-difluoro-4-nitrophenoxy)-7-methoxyquinolin-6-yl)oxy)butanoate To a stirred solution of 4-(2,6-difluoro-4-nitrophenoxy)-7-methoxyquinolin-6-ol (2 g, 5.74 mmol) in DMF (20 mL) was added K$_2$CO$_3$ (1.18 g, 8.35 mmol). Then tert-butyl 2,4-dibromobutanoate (1.73 g, 5.74 mmol) was added at 0° C. under nitrogen atmosphere. The resulting mixture was stirred at 70° C. under nitrogen atmosphere for 2h. After completion of the reaction, the reaction mixture was quenched with ice cold water (20 mL) and extracted with ethyl acetate (3×30 mL). The combined organic layers were washed with brine (2×60 mL), dried over anhydrous sodium sulphate, filtered and the filtrate was concentrated under reduced pressure to get the crude compound. The crude compound was purified by silica gel column chromatography, eluted with petroleum ether/ethyl acetate (1:2) to afford tert-butyl-4-bromo-2((4-(2,6-difluoro-4-nitrophenoxy)-7-methoxyquinolin-6-yl)oxy)butanoate (1.48 g, 35%) as a light yellow solid. LC -MS: m/z 569.25 [M+H]$^+$; $^1$H NMR (400 MHz, CDCl$_3$) δ: 8.55 (d, J=5.2 Hz, 1H), 8.06-8.03 (m, 2H), 7.54 (s, 1H), 7.48 (d, J=2.8 Hz, 1H), 6.37 (d, J=5.2 Hz, 1H), 4.93-4.91 (m, 1H), 4.04 (s, 3H), 3.76-3.65 (m, 2H), 2.66-2.63 (m, 1H), 2.55-2.47 (m, 1H), 1.43 (s, 9H).

Step 2: tert-Butyl-1-((4-(2,6-difluoro-4-nitrophenoxy)-7-methoxyquinolin-6-yl)oxy)cyclopropane-1-carboxylate A stirred solution of tert-butyl 4-bromo-2-((4-(2,6-difluoro-4-nitrophenoxy)-7-methoxyquinolin -6-yl)oxy)butanoate (1.48 g, 2.60 mmol) in THF (20 mL) was treated with potassium tert-butoxide (0.43 g, 3.9 mmol) at 0° C. under nitrogen atmosphere. The resulting mixture was stirred at room temperature for 2h. The reaction mixture was quenched with ice cold water (50 mL) and extracted with ethyl acetate (3×45 mL). The combined organic layers were washed with brine (2×60 mL) and dried over anhydrous sodium sulphate. After filtration, the filtrate was concentrated under reduced pressure to get the residue. The residue was purified by silica gel column chromatography, eluted with 30% ethyl acetate in petroleum ether to afford tert-butyl-1-((4-(2,6-difluoro-4-nitrophenoxy)-7-methoxyquinolin-6-yl)oxy)cyclopropane-1-carboxylate (1 g, 83.3%) as a light yellow solid. $^1$H NMR (400 MHz, CDCl$_3$) δ: 8.55 (d, J=5.2 Hz, 1H), 8.05 (dd, J=4.0, 10.4 Hz, 2H), 7.66 (s, 1H), 7.48 (s, 1H), 6.38 (d, J=5.2 Hz 1H), 4.04 (s, 3H), 1.79-1.64 (m, 2H), 1.49-1.45 (m, 2H), 1.39 (s, 9H); LCMS: m/z 489.60 [M+H]$^+$.

Step 3: tert-Butyl-1-((4-(4-amino-2,6-difluorophenoxy)-7-methoxyquinolin-6-yl)oxy)cyclopropane-1-carboxylate To a stirred solution of tert-butyl 1-((4-(2,6-difluoro-4-nitrophenoxy)-7-methoxyquinolin-6-yl)oxy)cyclopropane-1-carboxylate (0.5 g, 1.02 mmol) in EtOAc (10 mL) was added Pd/C 10% (100 mg) and the reaction mixture was stirred under hydrogen atmosphere for 16 h. After completion of starting material, the reaction mass was filtered through a small pad of Celite and washed with MeOH (15 mL). The filtrate was concentrated to get crude compound. The crude compound was purified by Prep-HPLC to get the tert-butyl-1-((4-(4-amino-2,6-difluorophenoxy) -7-methoxyquinolin-6-yl)oxy)cyclopropane-1-carboxylate (0.2 g, 43%) as an off-white solid. LC -MS: m/z 459.28 [M+H]$^+$; $^1$H NMR (400 MHz, DMSO-d$_6$) δ: 8.51 (d, J=5.2 Hz, 1H), 7.53 (s, 1H), 7.43 (s, 1H), 6.51 (d, J=5.2 Hz, 1H), 6.40 (d, J=10.8 Hz, 2H), 5.82 (s, 2H), 3.94 (s, 3H), 1.58-1.55 (m, 2H), 1.39-1.36 (m, 2H), 1.29 (s, 9H);

Step 4: tert-Butyl 1-((4-(2,6-difluoro-4-(4-methoxynicotinamido)phenoxy)-7-methoxyquinolin-6-yl)oxy)cyclopropane-1-carboxylate To a stirred solution of 4-methoxynicotinic acid (31 mg, 0.208 mmol) in dry DMF (1.5 mL) were added DIPEA (0.067 mg, 0.522 mmol) and HATU (99 mg, 0.261 mmol) at room temperature and stirred for 30 minutes. Then tert-butyl 1-((4-(4-amino-2,6-difluorophenoxy)-7-methoxyquinolin -6-yl)oxy)cyclopropane-1-carboxylate (80 mg, 0.174 mmol) was added and heated at 80° C. for 3 h. The progress of the reaction monitored by TLC. After complete consumption of starting material, the reaction mixture was poured in ice water (30 mL), extracted with EtOAc (3×20 mL). The organic layer was washed with brine solution (50 mL), dried over anhydrous Na$_2$SO$_4$ and concentrated under reduced pressure to give crude product, which was purified by reverse phase prep-HPLC to afford tert-butyl 1-((4-(2,6-difluoro-4-(4-methoxynicotinamido)phenoxy)-7-methoxyquinolin-6-yl)oxy)cyclopropane-1-carboxylate (15 mg, 14.5%) as an off-white solid. ¹H NMR (400 MHz, DMSO-d₆) δ: 10.69 (s, 1H), 8.62 (s, 1H), 8.61 (d, J=6.0 Hz, 1H), 8.53 (d, J=5.6 Hz, 1H), 7.74 (d, J=10.0 Hz, 2H), 7.56 (s, 1H), 7.47 (s, 1H), 7.27 (d, J=6.0 Hz, 1H), 6.62 (d, J=5.6 Hz, 1H), 3.97 (s, 3H), 3.96 (s, 3H), 3.64 (m, 1H), 1.59-1.56 (m, 2H), 1.41-1.37 (m, 2H), 1.31 (s, 9H); LCMS: m/z 594.32 [M+H]⁺.

Step 5: N-(3,5-difluoro-4-((6-(1-(hydroxymethyl)cyclopropoxy)-7-methoxyquinolin-4-yl)oxy)phenyl)-4-methoxynicotinamide To a stirred solution of tert-butyl 1-((4-(2,6-difluoro-4-(4-methoxynicotinamido)phenoxy)-7-methoxyquinolin-6-yl)oxy)cyclopropane-1-carboxylate (0.170 g, 0.286 mmol) in THF (2.5 mL) was added LiAlH₄ (0.286 mL, 0.286 mmol, 1M in THF) at 0° C. After 1 hour, the reaction mixture was poured in saturated sodium sulphate solution (20 mL) and extracted with EtOAc (20 mL×3). The organic layer was washed with brine solution (50 mL), dried over anhydrous Na₂SO₄ and concentrated under reduced pressure to give crude product. The crude compound was purified by reverse phase prep-HPLC to afford N-(3,5-difluoro-4-((6-(1-(hydroxymethyl)-5 cyclopropoxy)-7-methoxyquinolin-4-yl)oxy)phenyl)-4-ethoxynicotinamide (16 mg, 10%) as an off-white solid. ¹H NMR (400 MHz, DMSO-d₆) δ: 10.69 (s, 1H), 8.63 (s, 1H), 8.61 (d, J=5.6 Hz, 1H), 8.50 (d, J=5.2 Hz, 1H), 7.84 (s, 1H), 7.75 (d, J=10.0 Hz, 2H), 7.42 (s, 1H), 7.27 (d, J=6.0 Hz, 1H), 6.60 (d, J=5.2 Hz, 1H), 5.03 (m, 1H), 3.97 (s, 3H), 3.93 (s, 3H), 3.79 (d, J=5.6 Hz, 2H), 1.02-0.96 (m, 4H); LC-MS: m/z 524.55 [M+H]⁺.

Example 133: (S)-4-methoxy-N-(2,3,5-trifluoro-4-((6-((1-hydroxypropan-2-yl)oxy)-7-methoxyquinolin-4-yl)oxy)phenyl)nicotinamide

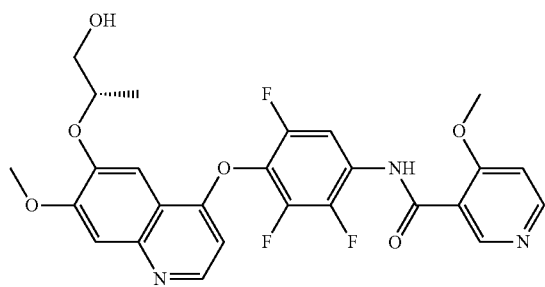 [SMILES: COc1cc2nccc(Oc3c(F)cc(NC(=O)c4cnccc4OC)c(F)c3F)c2cc1O[C@@H](C)CO]

Synthesized using the similar method as in example 50 and example 126. White solid. MS ESI calculated for C₂₆H₂₂F₃N₃O₆ [M+H]⁺, 530.15 found 530.15. ¹H NMR (400 MHz, DMSO-d₆) δ 10.44 (s, 1H), 8.78 (s, 1H), 8.64 (d, J=5.6 Hz, 1H), 8.52 (d, J=5.2 Hz, 1H), 8.15-8.12 (m, 1H), 7.65 (s, 1H), 7.45 (s, 1H), 7.31 (d, J=5.6 Hz, 1H), 6.74 (d, J=5.2 Hz, 1H), 4.93 (t, J=5.6 Hz, 1H), 4.71-4.68 (m, 1H), 4.03 (s, 3H), 3.96 (s, 3H), 3.69-3.67 (m, 1H), 3.57-3.55 (m, 1H), 1.31 (d, J=6.0 Hz, 3H). ¹⁹F NMR (400 MHz, CDCl₃) δ −128.98 (1F), −149.01 (1F), −156.76 (1F).

Example 134: N-(3,5-difluoro-4-((7-(2-hydroxyethoxy)-6-methoxyquinolin-4-yl)oxy)phenyl)-2-fluorobenzamide

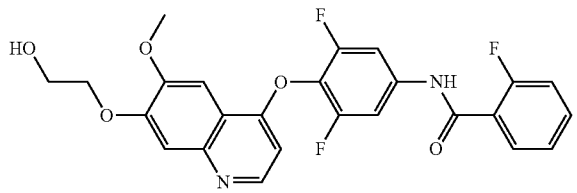 [SMILES: COc1cc2c(Oc3c(F)cc(NC(=O)c4ccccc4F)cc3F)ccnc2cc1OCCO]

Synthesized using the similar method as in example 121. White solid. MS ESI calculated for C₂₅H₁₉F₃N₂O₅ [M+H]⁺, 485.12 found 485.10. ¹H NMR (400 MHz, DMSO-d₆) δ 10.93 (s, 1H), 8.50 (d, J=5.2 Hz, 1H), 7.79-7.69 (m, 3H), 7.65-7.63 (m, 1H), 7.56 (s, 1H), 7.44 (s, 1H), 7.41-7.36 (m, 2H), 6.62 (d, J=5.2 Hz, 1H), 4.96 (t, J=5.2 Hz, 1H), 4.19 (t, J=5.2 Hz, 2H), 3.98 (s, 3H), 3.88-3.83 (m, 2H). ¹⁹F NMR (376 MHz, DMSO-d₆) δ −114.56 (2F), −126.46 (1F).

Example 135: N-(3,5-difluoro-4-((7-(2-hydroxyethoxy)-6-methoxyquinolin-4-yl)oxy)phenyl)-4-(2,2-difluoroethoxy)pyridine-3-carboxamide

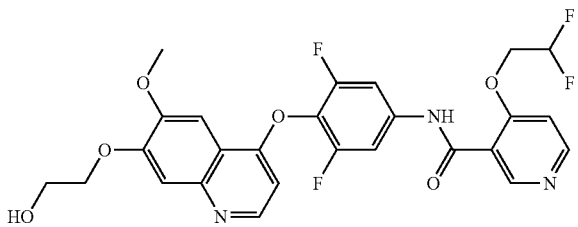 [SMILES: COc1cc2c(Oc3c(F)cc(NC(=O)c4cnccc4OCC(F)F)cc3F)ccnc2cc1OCCO]

Synthesized using the similar method as in example 97. White solid. MS ESI calculated for C₂₆H₂₁F₄N₃O₆ [M+H]⁺, 548.14 found 548.30. ¹H NMR (400 MHz, DMSO-d₆) δ 10.71 (s, 1H), 8.68 (s, 1H), 8.65 (d, J=6.0 Hz, 1H), 8.51 (d, J=5.2 Hz, 1H), 7.76-7.67 (m, 2H), 7.56 (s, 1H), 7.45 (s, 1H), 7.36 (d, J=6.0 Hz, 1H), 6.62 (d, J=4.8 Hz, 1H), 6.48-6.34 (m, 1H), 4.95 (t, J=5.2 Hz, 1H), 4.62-4.59 (m, 2H), 4.20 (t, J=4.8 Hz, 2H), 3.98 (s, 3H), 3.88-3.84 (m, 2H). ¹⁹F NMR (376 MHz, DMSO-d₆) δ −125.87 (2F), −126.45 (2F).

Example 136: 4-cyclopropoxy-N-(3,5-difluoro-4-((6-methoxy-7-(2-methoxyethoxy)-1,5-naphthyridin-4-yl)oxy)phenyl)pyridine-3-carboxamide

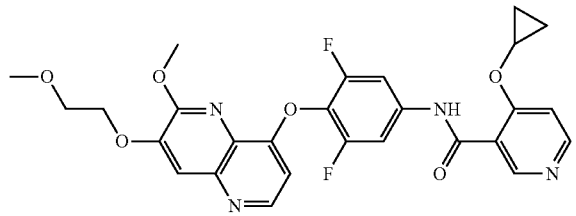 [SMILES: COCCOc1cc2nccc(Oc3c(F)cc(NC(=O)c4cnccc4OC4CC4)cc3F)c2nc1OC]

Step 1: 8-(2,6-difluoro-4-nitrophenoxy)-2-methoxy-3-(2-methoxyethoxy)-1,5-naphthyridine To a stirred mixture of 8-(2,6-difluoro-4-nitrophenoxy)-2-methoxy-1,5-naphthyridin-3-ol (400 mg, 1.145 mmol), 2-methoxyethanol (130 mg, 1.718 mmol) and triphenylphosphine (450 mg, 1.718 mmol, synthesized in step 6 of example 138) in tetrahydrofuran (5 mL) was added diisopropyl azodicarboxylate (694 mg, 3.435 mmol) at 0° C. The resulting mixture was stirred at room temperature under nitrogen atmosphere for 16 h. The reaction was quenched with water (50 mL) at room temperature. The resulting mixture was extracted with ethyl acetate (3×50 mL). The combined organic layers were washed with brine (80 mL), dried over anhydrous sodium sulfate. After filtration, the filtrate was concentrated under reduced pressure. The residue was purified by silica gel column chromatography, eluted with petroleum ether/ethyl acetate (1/1). The fractions containing desired product were concentrated under reduced pressure to afford 8(2,6-difluoro-4-nitrophenoxy)-2-methoxy-3-(2-methoxyethoxy)-1,5-naphthyridine (300 mg, 64%) as a light yellow solid. MS ESI calculated for $C_{18}H_{15}F_2N_3O_6[M+H]^+$, 408.09 found 408.10. $^1H$ NMR (400 MHz, $CDCl_3$) δ 8.67 (d, J=5.2 Hz, 1H), 8.01-7.90 (m, 2H), 7.66 (s, 1H), 7.17 (d, J=5.2 Hz, 1H), 4.37-4.29 (m, 2H), 3.92-3.82 (m, 2H), 3.72 (s, 3H), 3.48 (s, 3H).

Step: 2: 3,5-difluoro-4-{[6-methoxy-7-(2-methoxyethoxy)-1,5-naphthyridin-4-yl]oxy}aniline To a stirred mixture of 8-(2,6-difluoro-4-nitrophenoxy)-2-methoxy-3-(2-methoxyethoxy)-1,5-naphthyridine (300 mg, 0.737 mmol) in tetrahydrofuran (3 mL) and water (1.5 mL) was added iron powder (205 mg, 3.685 mmol) and ammonium chloride (197 mg, 3.685 mmol) at room temperature. The resulting mixture was stirred at 70° C. for 16 h. The mixture was allowed to cool down to room temperature. The resulting mixture was filtered; the filter cake was washed with methanol (3×30 mL). The filtrate was concentrated under reduced pressure. The residue was purified by silica gel column chromatography, eluted with dichloromethane/methyl alcohol (10/1). The fractions containing desired product were concentrated under reduced pressure to afford 3,5-difluoro-4-{[6-methoxy-7-(2-methoxyethoxy)-1,5-naphthyridin-4-yl]oxy}aniline (130 mg, 47%) as a light yellow solid. MS ESI calculated for $C_{18}H_{17}F_2N_3O_4$ $[M+H]^+$, 378.12 found 378.10. $^1H$ NMR (400 MHz, $CDCl_3$) δ 8.52 (d, J=5.2 Hz, 1H), 7.61 (s, 1H), 6.74 (d, J=5.2 Hz, 1H), 6.46-6.21 (m, 2H), 4.37-4.31 (m, 2H), 4.17 (s, 3H), 3.93-3.88 (m, 2H), 3.50 (s, 3H).

Step 3: 4-chloro-N-(3,5-difluoro-4-{[6-methoxy-7-(2-methoxyethoxy)-1,5-naphthyridin-4-yl]oxy}phenyl)pyridine-3-carboxamide To a stirred mixture of 4-chloropyridine-3-carboxylic acid (100 mg, 0.636 mmol) and propylphosphonic anhydride (1 mL, 50% in ethyl acetate) in pyridine (2 mL) was added 3,5-difluoro-4-{[6-methoxy-7-(2-methoxyethoxy)-1,5-naphthyridin-4-yl]oxy}aniline (120 mg, 0.318 mmol) at room temperature. The resulting mixture was stirred at room temperature for 1 h. The resulting mixture was concentrated under reduced pressure. The residue was purified by reverse phase Flash chromatography with the following conditions: Column: WelFlash™ C18-I, 20-40 µm, 40 g; Eluent A: water (plus 10 mmol/L ammonium bicarbonate); Eluent B: acetonitrile; Gradient: 55% to 75% B in 25 min; Flow rate: 45 mL/min; Detector: UV 220/254 nm; desired fractions were collected and concentrated under reduced pressure to afford 4-chloro-N-(3,5-difluoro-4-{[6-methoxy-7-(2-methoxyethoxy)-1,5-naphthyridin-4-yl]oxy}phenyl)pyridine-3-carboxamide (110 mg, 67%) as a light yellow solid. MS ESI calculated for $C_{24}H_{19}ClF_2N_4O_5$ $[M+H]^+$, 517.10, 519.10 found 517.25, 519.25.

Step 4: 4-cyclopropoxy-N-(3,5-difluoro-4-{[6-methoxy-7-(2-methoxyethoxy)-1,5-naphthyridin-4-yl]oxy}phenyl)pyridine-3-carboxamide To a stirred mixture of 4-chloro-N-(3,5-difluoro-4-{[7-(2-hydroxyethoxy)-6-methoxy-1,5-naphthyridin-4-yl]oxy}phenyl)pyridine-3-carboxamide (100 mg, 0.199 mmol) and cyclopropanol (173 mg, 2.985 mmol) in dimethyl sulfoxide was added 1,8-diazabicyclo[5.4.0]undec-7-ene (121 mg, 0.796 mmol) at room temperature. The resulting mixture was stirred at 70° C. for 16 h. The mixture was allowed to cool down to room temperature. The reaction was quenched with water (50 mL) at room temperature. The resulting mixture was extracted with ethyl acetate (3×50 mL). The combined organic layers were washed with brine (80 mL), dried over anhydrous sodium sulfate. After filtration, the filtrate was concentrated under reduced pressure. The residue was purified by reverse phase Flash chromatography with the following conditions: Column: WelFlash™ C18-I, 20-40 µm, 40 g; Eluent A: water (plus 10 mmol/L ammonium bicarbonate); Eluent B: acetonitrile; Gradient: 45% to 65% B in 25 min; Flow rate: 45 mL/min; Detector: UV 220/254 nm; desired fractions were collected and concentrated under reduced pressure to afford 4-cyclopropoxy-N-(3,5-difluoro-4-{[6-methoxy-7-(2-methoxyethoxy)-1,5-naphthyridin-4-yl]oxy}phenyl)pyridine-3-carboxamide (61 mg, 57%) as a white solid. MS ESI calculated for $C_{27}H_{24}F_2N_4O_6$ $[M+H]^+$, 539.17 found 539.30. $^1H$ NMR (400 MHz, DMSO-$d_6$) δ 10.57 (s, 1H), 8.63 (d, J=6.0 Hz, 1H), 8.61 (s, 1H), 8.56 (d, J=5.2 Hz, 1H), 7.70 (s, 1H), 7.69-7.64 (m, 2H), 7.51 (d, J=6.0 Hz, 1H), 6.94 (d, J=5.2 Hz, 1H), 4.38-4.27 (m, 2H), 4.13-4.09 (m, 1H), 3.98 (s, 3H), 3.82-3.70 (m, 2H), 3.35 (s, 3H), 1.02-0.70 (m, 4H). $^{19}F$ NMR (376 MHz, DMSO-$d_6$) δ -126.59 (2F).

Example 137: N-(3,5-difluoro-4-((6-methoxy-7-(2-methoxyethoxy)-1,5-naphthyridin-4-yl)oxy)phenyl)-4-methoxypyridine-3-carboxamide

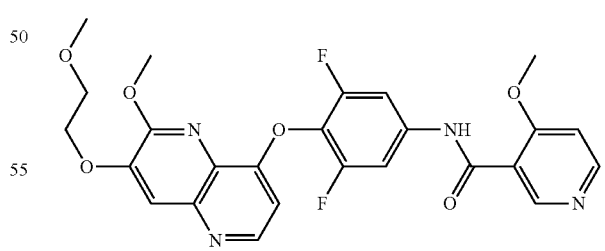

Synthesized using the similar method as in in example 136. White solid. MS ESI calculated for $C_{25}H_{22}F_2N_4O_6$ $[M+H]^+$, 513.15 found 513.10. $^1H$ NMR (400 MHz, DMSO-$d_6$) δ 10.64 (s, 1H), 8.64 (s, 1H), 8.61 (d, J=6.0 Hz, 1H), 8.56 (d, J=5.2 Hz, 1H), 7.77-7.67 (m, 3H), 7.27 (d, J=6.0 Hz, 1H), 6.93 (d, J=5.2 Hz, 1H), 4.47-4.26 (m, 2H), 3.98 (d, J=3.2 Hz, 6H), 3.84-3.70 (m, 2H), 3.35 (s, 3H). $^{19}F$ NMR (377 MHz, DMSO-$d_6$) δ -126.67 (2F).

Example 138: N-(3,5-difluoro-4-((7-(2-hydroxyethoxy)-6-methoxy-1,5-naphthyridin-4-yl)oxy)phenyl)-4-methoxypyridine-3-carboxamide

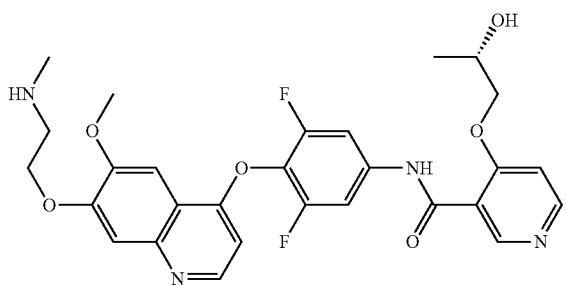 [SMILES: CNCCOc1cc2nccc(Oc3c(F)cc(NC(=O)c4cnccc4OC[C@H](C)O)cc3F)c2cc1OC]

Synthesized using the similar method as in in example 136. White solid. MS ESI calculated for C$_{24}$H$_{20}$F$_2$N$_4$O$_6$ [M+H]$^+$, 499.10 found 499.20. $^1$H NMR (400 MHz, DMSO-d$_6$) δ 10.64 (s, 1H), 8.64 (s, 1H), 8.61 (d, J=6.0 Hz, 1H), 8.56 (d, J=5.2 Hz, 1H), 7.72 (d, J=10.4 Hz, 2H), 7.69 (s, 1H), 7.27 (d, J=6.0 Hz, 1H), 6.92 (d, J=5.2 Hz, 1H), 4.97 (t, J=5.2 Hz, 1H), 4.23 (t, J=4.8 Hz, 2H), 3.98 (d, J=3.2 Hz, 6H), 3.82-3.78 (m, 2H). $^{19}$F NMR (377 MHz, DMSO-d$_6$) δ −126.67 (2F).

Example 139: N-(3,5-difluoro-4-((7-(2-methoxyethoxy)-1,5-naphthyridin-4-yl)oxy)phenyl)-4-methoxypyridine-3-carboxamide

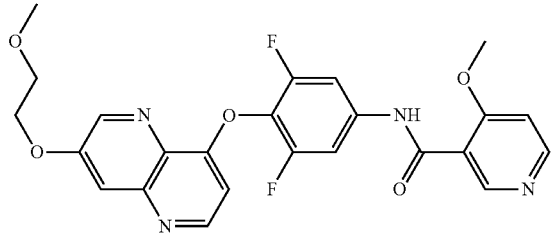

Step 1: 3-bromo-5-(2-methoxyethoxy)pyridine

To a stirred solution of 5-bromopyridin-3-ol (5g, 28.74 mmol) in DMF (50 mL) under argon atmosphere was charged Cs$_2$CO$_3$ (18.7 g, 57.47 mmol) and 1-bromo-2-methoxyethane (5.99 g, 43.10 mmol) at room temperature. The resulting reaction mixture was heated to 90° C. for 2 h. Progress of the reaction was monitored by TLC. (TLC: Mobile phase: 30% EtOAc-hexane, Rf: 0.6, UV visible). After completion of the reaction, the reaction mixture was poured into ice cold water and compound was extracted using EtOAc (3×50 mL). The combined organic layers were washed with water (200 mL), brine solution (2×100 mL), dried over anhydrous Na$_2$SO$_4$ and concentrated under reduced pressure to get 3-bromo-5-(2-methoxyethoxy)pyridine (6 g, 90%) as a light yellow syrup. The compound was used for the next step without further purification. LC-MS: m/z [M+H]$^+$=232.08; $^1$H NMR (400 MHz, DMSO-d$_6$) δ: 8.31-8.28 (m, 2H), 7.73 (t, J=2.4 Hz, 1H), 4.21 (t, J=4.4 Hz, 2H), 3.67-3.65 (m, 2H), 3.32 (s, 3H).

Step 2: 5-(2-methoxyethoxy)pyridin-3-amine

To a stirred solution of 3-bromo-5-(2-methoxyethoxy)pyridine (10 g, 43.08 mmol) in toluene (150 mL) were added diphenylmethanimine (11.7 g, 64.63 mmol), Pd(OAc)2 (0.96 g, 4.31 mmol), BINAP (5.3 g, 8.61 mmol), NaOtBu (8.28 g, 86.17 mmol) at room temperature under N$_2$ purging.

The resulting reaction mixture was stirred for 16 h at 90° C. The progress of the reaction monitored by LCMS, after completion of starting material, the reaction mixture was filtered through a small pad of Celite and washed with EtOAc (100 mL) and concentrated under reduced pressure. The crude compound was dissolved in THF (100 mL) and was added 4M HCl in dioxane (20 mL) at room temperature and stirred for 4 h. After completion of the reaction, the reaction mixture was concentrated under reduced pressure to get the crude reaction mass. The crude mass was dissolved in 10% TEA in DCM (250 mL) for basification and concentrated to give crude product (2.5 g). This crude compound was used for the next step without further purification. LC-MS: m/z 168 [M+H]$^+$.

Step 3: 7-(2-methoxyethoxy)-1,5-naphthyridin-4-ol

To a stirred solution of 5-(2-methoxyethoxy)pyridin-3-amine (1.2 g, 7.13 mmol) in EtOH (10 mL), was added 2-(ethoxymethylene)-5,5-dimethyl-1,3-dioxane-4,6-dione (2.14 g, 10.7 mmol) at room temperature. The resulting reaction mixture was heated at 90° C. for 1 h. The progress of the reaction was monitored by TLC. After complete consumption of starting material, the reaction mixture was diluted with EtOH (30 mL) and filtered to obtain solid mass which was dried to get off white solid. Obtained solid was heated to 225° C. in diphenyl ether for 30 min. After completion of the reaction (monitored by TLC), the reaction mixture was allowed to room temperature and diluted with pet ether (70 mL). The pet ether was decanted and again stirred in ethyl acetate (30 mL), filtered and dried to give 7-(2-methoxyethoxy)-1,5-naphthyridin-4-ol 7 (300 mg, 19%) as an off-white solid. The structure was confirmed by 2D NMR analysis. $^1$H NMR (400 MHz, DMSO-d$_6$) δ: 11.63 (s, 1H), 8.34 (d, J=2.4 Hz, 1H), 7.84 (m, 1H), 7.32 (d, J=2.4 Hz, 1H), 6.10 (d, J=7.2 Hz, 1H), 4.25 (t, J=4.4 Hz, 2H), 3.73 (t, J=4.4 Hz, 2H), 3.36 (s, 3H); LC-MS: m/z 220.0 [M+H]$^+$.

Step 4: 8-(2,6-difluoro-4-nitrophenoxy)-3-(2-methoxyethoxy)-1,5-naphthyridine To a stirred solution of 7-(2-methoxyethoxy)-1,5-naphthyridin-4-ol (1 g, 4.54 mmol) in DMF (25 mL) was added 1,2,3-trifluoro-5-nitrobenzene (0.96 g, 5.4 mmol) and Cs$_2$CO$_3$ (2.21 g, 6.811 mmol) at room temperature. Then the resulting reaction mixture was stirred for 1 h. The progress of the reaction monitored by TLC. After complete consumption of starting material, the reaction mixture was diluted with EtOAc (100 mL) and washed with ice cold water (100 mL) and followed by brine solution (60 mL). The organic layer was dried over Na$_2$SO$_4$, filtered and concentrated under reduced pressure. The crude product was stirred in methanol (30 mL), filtered and dried to get 8-(2,6-difluoro-4-nitrophenoxy)-3-(2-methoxyethoxy)-1,5-naphthyridine (510 mg 31%) as an off-white solid and used for the nest step without further purification. $^1$H NMR (400 MHz, CDCl$_3$) δ: 8.79 (d, J=2.8 Hz, 1H), 8.75 (d, J=2.8 Hz, 1H), 8.03 (d, J=4.0 Hz, 1H), 8.00 (d, J=4.4 Hz, 1H), 7.69 (d, J=2.8 Hz, 1H), 6.75 (d, J=5.2 Hz, 1H), 4.33-4.31 (m, 2H), 3.88-3.86 (m, 2H), 3.50 (s, 3H); LC-MS: m/z 378 [M+H]$^+$.

Step 5: 3,5-difluoro-4-((7-(2-methoxyethoxy)-1,5-naphthyridin-4-yl)oxy)aniline

To a stirred solution of 8-(2,6-difluoro-4-nitrophenoxy)-3-(2-methoxyethoxy)-1,5-naphthyridine (0.3 g, 0.79 mmol) in EtOH (15 mL), was added Iron (0.24 g, 4.37 mmol) and con. HCl(0.02 mL, 0.76 mmol) at room temperature. Then the resulting reaction mixture was stirred for 1 h. The progress of the reaction monitored by TLC. After complete consumption of starting material, the reaction mixture was diluted with MeOH (20 mL) and filtered through Celite pad. The filtrate was concentrated under reduced pressure to get 3,5-difluoro-4-((7-(2-methoxyethoxy)-1,5-naphthyridin-4-yl)oxy)aniline (310 mg, crude) as a brown solid which was used for the next step without further purification. LC-MS: m/z 348 [M+H]$^+$.

Step 6: N-(3,5-difluoro-4-((7-(2-methoxyethoxy)-1,5-naphthyridin-4-yl)oxy)phenyl)-4-methoxypyridine-3-carboxamide To a stirred solution of 3,5-difluoro-4-((7-(2-methoxyethoxy)-1,5-naphthyridin-4-yl)oxy)aniline (0.12 g, 0.79 mmol) in DMF (5 mL), was added 4-methoxynicotinic acid (0.24 g, 4.37 mmol), HATU (328 mg, 1.58 mmol) and DIPEA (0.15 mL, 1.97 mmol) at room temperature. The resulting reaction mixture was irradiated under micro wave condition at 90° C. for 3 h. The progress of the reaction was monitored by LCMS. After complete consumption of starting material, the reaction mixture was diluted with EtOAc (20 mL) and washed with water (30 mL). The organic layer was dried over anhydrous Na$_2$SO$_4$ and concentrated under reduced pressure. The crude product was purified by MS-prep HPLC to obtained N-(3,5-difluoro-4-((7-(2-methoxyethoxy)-1,5-naphthyridin-4-yl)oxy)phenyl)-4 methoxypyridine-3-carboxamide (25 mg, 15%) as a pale brown solid. $^1$H NMR (400 MHz, DMSO-d$_6$) δ: 10.70 (s, 1H), 8.78 (d, J=2.8 Hz, 1H), 8.72 (d, J=5.2 Hz, 1H), 8.62 (S, 1H), 8.61 (d, J=6.0 Hz, 1H), 7.85 (d, J=2.8 Hz, 1H), 7.76-7.73 (m, 2H), 7.27 (d, J=6.0 Hz, 1H), 6.89 (d, J=5.2 Hz, 1H), 4.39-4.37 (m, 2H), 3.96 (s, 3H), 3.78-3.76 (m, 2H), 3.35 (s, 3H); LC-MS: m/z 483.12 [M+H]$^+$.

Example 140: N-(3,5-difluoro-4-((7-(2-methoxyethoxy)-1,5-naphthyridin-4-yl)oxy)phenyl)-2-fluorobenzamide

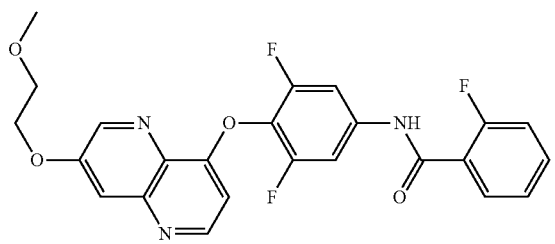 [SMILES: COCCOc1cnc2c(Oc3c(F)cc(NC(=O)c4ccccc4F)cc3F)ccnc2c1]

Synthesized using the similar method as in in example 139. Off white solid. $^1$H NMR (400 MHz, DMSO-d$_6$) δ: 10.95 (s, 1H), 8.78 (d, J=2.8 Hz, 1H), 8.72 (d, J=5.2 Hz, 1H), 7.85 (d, J=2.8 Hz, 1H), 7.77-7.61 (m, 4H), 7.43-7.36 (m, 2H), 6.90 (d, J=5.2 Hz, 1H), 4.39-4.37 (m, 2H), 3.79-3.76 (m, 2H), 3.35 (s, 3H); LC-MS: m/z 470.14 [M+H]$^+$.

Example 141: N-(3,5-difluoro-4-((7-(2-hydroxyethoxy)-6-methoxyquinolin-4-yl)oxy)phenyl)-4-(2,2-difluoroethoxy)-2-fluoropyridine-3-carboxamide

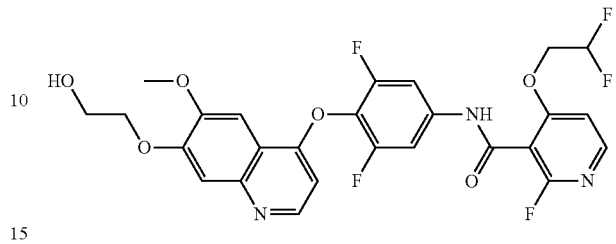

Synthesized using the similar method as in example 118. White solid. MS ESI calculated for C$_{26}$H$_{20}$F$_5$N$_3$O$_6$ [M+H]$^+$, 566.13 found 566.05.$^1$HNMR (400 MHz, DMSO-d$_6$) δ 11.14 (s, 1H), 8.50 (d, J=5.2 Hz, 1H), 8.33 (d, J=6.0 Hz, 1H), 7.70-7.60 (m, 2H), 7.56 (s, 1H), 7.45 (s, 1H), 7.37 (d, J=6.0 Hz, 1H), 6.65 (d, J=5.2 Hz, 1H), 6.42-6.38 (m, 1H), 4.95 (t, J=5.2 Hz, 1H), 4.67-4.60 (m, 2H), 4.20 (t, J=5.2 Hz, 2H), 3.98 (s, 3H), 3.90-3.81 (m, 2H). $^{19}$F NMR (376 MHz, DMSO-d$_6$) δ −71.64 (1F), −126.15 (4F).

Example 142: N-(3,5-difluoro-4-((6-(2-hydroxyethoxy)-7-methoxyquinolin-4-yl)oxy)phenyl)-4-(2,2-difluoroethoxy)-2-fluoropyridine-3-carboxamide

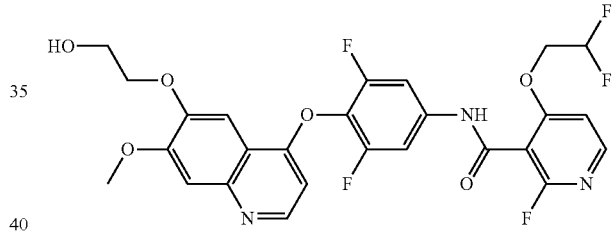

Synthesized using the similar method as in example 107 and example 118. White solid. MS ESI calculated for C$_{26}$H$_{20}$F$_5$N$_3$O$_6$ [M+H]$^+$, 566.13 found 566.05. $^1$H NMR (400 MHz, DMSO-d$_6$) δ 11.13 (s, 1H), 8.51 (d, J=5.2 Hz, 1H), 8.33 (d, J=6.0 Hz, 1H), 7.69-7.61 (m, 2H), 7.57 (s, 1H), 7.45 (s, 1H), 7.37 (d, J=6.0 Hz, 1H), 6.65 (d, J=5.2 Hz, 1H), 6.43-6.41 (m, 1H), 4.92 (t, J=4.8 Hz, 1H), 4.70-4.58 (m, 2H), 4.20 (t, J=4.8 Hz, 2H), 3.98 (s, 3H), 3.85-3.82 (m, 2H). $^{19}$F NMR (376 MHz, DMSO-d$_6$) δ −71.64 (1F), −126.15 (4F).

Example 143: N-(3,5-difluoro-4-((6-(2-hydroxyethoxy)-7-methoxyquinolin-4-yl)oxy)phenyl)-4-(2,2-difluoroethoxy)pyridine-3-carboxamide

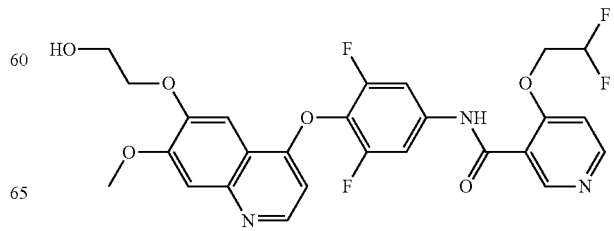

Synthesized using the similar method as example 107. Off-white solid. MS ESI calculated for $C_{26}H_{21}F_4N_3O_6$ [M+H]$^+$, 548.14 found 548.15. $^1$H NMR (400 MHz, DMSO-d$_6$) δ 10.72 (s, 1H), 8.68 (s, 1H), 8.64 (d, J=6.0 Hz, 1H), 8.51 (d, J=5.2 Hz, 1H), 7.76-7.66 (m, 2H), 7.57 (s, 1H), 7.45 (s, 1H), 7.36 (d, J=6.0 Hz, 1H), 6.62 (d, J=5.2 Hz, 1H), 6.44-6.41 (m, 1H), 4.93 (t, J=5.2 Hz, 1H), 4.62-4.59 (m, 2H), 4.19 (t, J=5.2 Hz, 2H), 3.97 (s, 3H), 3.85-3.82 (m, 2H). $^{19}$F NMR (376 MHz, DMSO-d$_6$) δ −125.88 (2F), −126.48 (2F).

Example 144: 4-cyclopropoxy-N-(4-((6,7-dimethoxy-1,5-naphthyridin-4-yl)oxy)-3,5-difluorophenyl)-2-fluoropyridine-3-carboxamide

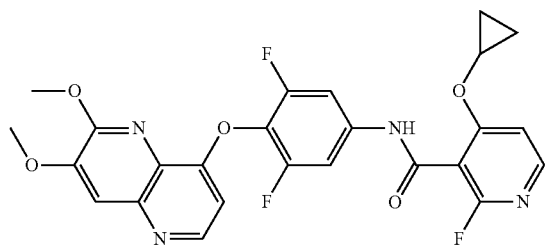 [SMILES: COc1cc2nccc(Oc3c(F)cc(NC(=O)c4c(OC5CC5)ccnc4F)cc3F)c2nc1OC]

Step 1: 5-{[(5-bromo-6-methoxypyridin-3-yl)amino]methylidene}-2,2-dimethyl-1,3-dioxane-4,6-dione To a stirred mixture of 5-bromo-6-methoxypyridin-3-amine (63 g, 310.28 mmol) and 5-(methoxymethylidene)-2,2-dimethyl-1,3-dioxane-4,6-dione (69.32 g, 372.34 mmol) in propan-2-ol (1 L) at room temperature. The resulting mixture was stirred at 110° C. for 2 h. The mixture was allowed to cool down to room temperature. The precipitated solids were collected by filtration and washed with propan-2-ol (3×1 L). The resulting mixture was concentrated under reduced pressure to afford 5-{[(5-bromo-6-methoxypyridin-3-yl)amino]methylidene}-2,2-dimethyl-1,3-dioxane-4,6-dione (101 g, 91%) as a white solid. MS ESI calculated for $C_{13}H_{13}BrN_2O_5$ [M+H]$^+$, 357.00, 359.00 found 356.95, 358.95. $^1$H NMR (400 MHz, CDCl$_3$) δ 11.16 (d, J=14.0 Hz, 1H), 8.48 (d, J=14.0 Hz, 1H), 8.09 (d, J=2.4 Hz, 1H), 7.85 (d, J=2.4 Hz, 1H), 4.04 (s, 3H), 1.77 (s, 6H).

Step 2: 7-bromo-6-methoxy-1,5-naphthyridin-4-ol

To a stirred solution of 5-{[(5-bromo-6-methoxypyridin-3-yl)amino]methylidene}-2,2-dimethyl-1,3-dioxane-4,6-dione (30 g, 83.99 mmol) in phenyl ether (250 mL) at room temperature. The resulting mixture was stirred at 220° C. for 1 h. The mixture was allowed to cool down to room temperature. The product was precipitated by the addition of petroleum ether. The precipitated solids were collected by filtration and washed with petroleum (5×2 L). The resulting mixture was concentrated under reduced pressure to afford 7-bromo-6-methoxy-1,5-naphthyridin-4-ol (17 g, 79%) as a brown yellow solid. MS ESI calculated for $C_9H_7BrN_2O_2$ [M+H]$^+$, 254.97, 256.97 found 255.00, 257.00. $^1$H NMR (400 MHz, DMSO-d$_6$) δ 8.37-8.25 (m, 1H), 8.12-7.85 (m, 1H), 7.28-6.86 (m, 1H), 3.97 (s, 3H).

Step 3: 3-bromo-8-chloro-2-methoxy-1,5-naphthyridine

To a stirred mixture of 7-bromo-6-methoxy-1,5-naphthyridin-4-ol (26 g, 101.93 mmol) and N,N-diisopropylethylamine (41.22 g, 203.86 mmol) in 1,2-dichloroethane (500 mL) were added phosphoryl trichloride (18.75 g, 122.32 mmol) at room temperature. The resulting mixture was stirred at 80° C. for 1 h. The mixture was allowed to cool down to room temperature. The reaction was quenched with ice at 0° C. The resulting mixture was diluted with water (500 mL). The resulting mixture was extracted with dichloromethane (5×800 mL), dried over anhydrous sodium sulfate. After filtration, the filtrate was concentrated under reduced pressure. The residue was purified by silica gel column chromatography, eluted with petroleum ether/ethyl acetate (4/1). The resulting mixture was concentrated under reduced pressure to afford 3-bromo-8-chloro -2-methoxy-1,5-naphthyridine (12 g, 43%) as a brown yellow solid. MS ESI calculated for $C_9H_6BrClN_2O$ [M+H]$^+$, 273.94, 275.94 found 273.00, 275.00. $^1$H NMR (400 MHz, CDCl$_3$) δ 8.61 (dd, J=4.8, 0.8 Hz, 1H), 8.48 (d, J=0.8 Hz, 1H), 7.62 (dd, J=4.8, 0.8 Hz, 1H), 3.97 (s, 3H).

Step 4: 3-bromo-8-chloro-2-methoxy-1,5-naphthyridine

To a stirred mixture of 3-bromo-8-chloro-2-methoxy-1,5-naphthyridine (12 g, 43.87 mmol) and 2,6-difluoro-4-nitrophenol (9.22 g, 52.65 mmol) in 1-methyl-2-pyrrolidinone (150 mL) was added N,N-diisopropylethylamine (17.01 g, 131.62 mmol) at room temperature. The resulting mixture was stirred at 140° C. for 8 h. The mixture was allowed to cool down to room temperature. The resulting mixture was diluted with water (700 mL). The resulting mixture was extracted with ethyl acetate (3×1 L). The combined organic layers were washed with brine (3×800 mL), dried over anhydrous sodium sulfate. After filtration, the filtrate was concentrated under reduced pressure. The residue was purified by silica gel column chromatography, eluted with petroleum ether/ethyl acetate (3/1). The resulting mixture was concentrated under reduced pressure to afford 3-bromo-8-(2,6-difluoro-4-nitrophenoxy)-2-methoxy-1,5-naphthyridine (4 g, 22%) as a yellow solid. MS ESI calculated for $Ci_5H_8BrF_2N_3O_4$ [M+H]$^+$, 411.97, 413.97 found 411.95, 413.95. $^1$H NMR (400 MHz, CDCl$_3$) δ 8.75 (d, J=5.2 Hz, 1H), 8.59 (s, 1H), 8.00-7.95 (m, 2H), 7.26 (d, J=5.2 Hz, 1H), 3.76 (s, 3H).

Step 5: 8-(2,6-difluoro-4-nitrophenoxy)-2-methoxy-3-(4,4,5,5-tetramethyl-1,3,2-dioxaborolan-2-yl)-1,5-naphthyridine To a stirred mixture of 3-bromo-8-(2,6-difluoro-4-nitrophenoxy)-2-methoxy-1,5-naphthyridine (4 g, 9.71 mmol) and bis(pinacolato)diboron (2.96 g, 11.65 mmol) in N,N-dimethylformamide (50 mL) was added potassium acetate (1.90 g, 19.41 mmol) and Pd(PPh3)$_2$Cl$_2$ (CAS: 13965-03-2) (681 mg, 0.970 mmol) at room temperature under nitrogen atmosphere. The resulting mixture was stirred at 100° C. under nitrogen atmosphere for 16 h. The mixture was allowed to cool down to room temperature. The resulting mixture was concentrated under reduced pressure. The crude product mixture was used in the next step directly without further purification.

Step 6: 8-(2,6-difluoro-4-nitrophenoxy)-2-methoxy-1,5-naphthyridin-3-ol

To a stirred mixture of 8-(2,6-difluoro-4-nitrophenoxy)-2-methoxy-3-(4,4,5,5-tetramethyl-1,3,2-dioxaborolan-2-yl)-1,5-naphthyridine (4 g, 8.71 mmol) in hydrogen peroxide (20 mL) and tetrahydrofuran (20 mL) was added acetic acid (2.62 g, 43.55 mmol) at room temperature. The resulting mixture was stirred at room temperature for 2 h. The mixture was basified to pH 8 with saturated sodium bicarbonate (aq.). The resulting mixture was extracted with ethyl acetate (3×500 mL), dried over anhydrous sodium sulfate. After filtration, the filtrate was concentrated under reduced pressure. The residue was purified by silica gel column chromatography, eluted with dichloromethane/methanol (10/1). The fractions containing desired product were collected and concentrated under reduced pressure to afford 8-(2,6-difluoro-4-nitrophenoxy)-2-methoxy-1,5-naphthyridin-3-ol (1.5 g, 49%) as a yellow solid. MS ESI calculated for $C_{15}H_9F_2N_3O_5$ [M+H]$^+$, 350.05 found 350.10. $^1$H NMR (400 MHz, DMSO-d$_6$) δ 10.86 (s, 1H), 8.61 (d, J=5.2 Hz, 1H), 8.36-8.28 (m, 2H), 7.49 (s, 1H), 7.28 (d, J=5.2 Hz, 1H), 3.65 (s, 3H).

Step 7: 8-(2,6-difluoro-4-nitrophenoxy)-2,3-dimethoxy-1,5-naphthyridine

To a stirred mixture of 8-(2,6-difluoro-4-nitrophenoxy)-2-methoxy-1,5-naphthyridin-3-ol (300 mg, 0.859 mmol) and potassium carbonate (238 mg, 1.722 mmol) in N,N-dimethylformamide (5 mL) was added methyl iodide (146 mg, 1.029 mmol) dropwise at room temperature. The resulting mixture was stirred at room temperature for 2 h. The resulting mixture was diluted with water (100 mL). The resulting mixture was extracted with ethyl acetate (3×100 mL). The combined organic layers were washed with brine (200 mL), dried over anhydrous sodium sulfate. After filtration, the filtrate was concentrated under reduced pressure. The residue was purified by silica gel column chromatography, eluted with petroleum ether/ethyl acetate/ethanol (1/1/1). The fractions containing desired product were collected, concentrated and lyophilized to afford 8-(2,6-difluoro-4-nitrophenoxy)-2,3-dimethoxy-1,5-naphthyridine (150 mg, 48%) as a yellow solid. MS ESI calculated for $C_{16}H_{11}F_2N_3O_5$[M+H]$^+$, 364.07 found 364.15. $^1$H NMR (400 MHz, CDCl$_3$) δ 8.68 (d, J=5.2 Hz, 1H), 8.02-7.91 (m, 2H), 7.60 (s, 1H), 7.16 (d, J=5.2 Hz, 1H), 4.04 (s, 3H), 3.75 (s, 3H).

Step 8: 4-[(6,7-dimethoxy-1,5-naphthyridin-4-yl)oxy]-3,5-difluoroaniline

To a stirred mixture of 8-(2,6-difluoro-4-nitrophenoxy)-2,3-dimethoxy-1,5-naphthyridine (150 mg, 0.413 mmol), ammonium chloride (110 mg, 2.065 mmol) and iron powder (115 mg, 2.065 mmol) in tetrahydrofuran (2 mL) and water (1 mL) at room temperature. The resulting mixture was stirred at 70° C. for 2 h. The mixture was allowed to cool down to room temperature. The resulting mixture was filtered; the filter cake was washed with methanol (3×10 mL). The filtrate was concentrated under reduced pressure. The residue was purified by silica gel column chromatography, eluted with dichloromethane/methanol (15/1). The fractions containing desired product were collected, concentrated and lyophilized to afford 4-[(6,7-dimethoxy-1,5-naphthyridin-4-yl)oxy]-3,5-difluoroaniline (100 mg, 72%) as a white solid. MS ESI calculated for $C_{16}H_{13}F_2N_3O_3$ [M+H]$^+$, 334.09 found 334.10. $^1$H NMR (400 MHz, CDCl$_3$) δ 8.53 (d, J=5.2 Hz, 1H), 7.57 (s, 1H), 6.74 (d, J=5.2 Hz, 1H), 6.40-6.30 (m, 2H), 4.20 (s, 3H), 4.05 (s, 3H).

Step 9: 4-cyclopropoxy-N-{4-[(6,7-dimethoxy-1,5-naphthyridin-4-yl)oxy]-3,5-difluorophenyl}-2-fluoropyridine-3-carboxamide To a stirred mixture of 4-cyclopropoxy-2-fluoropyridine-3-carboxylic acid (71 mg, 0.360 mmol) and 2,4,6-tripropyl-1,3,5,2,4,6-trioxatriphosphinane 2,4,6-trioxide (1 mL) in pyridine (1 mL) was added 4-[(6,7-dimethoxy-1,5-naphthyridin-4-yl)oxy]-3,5-difluoroaniline (100 mg, 0.300 mmol) at room temperature. The resulting mixture was stirred at room temperature for 2 h. The mixture was purified by reverse phase Flash chromatography with the following conditions: Column: WelFlash™ C18-I, 20-40 μm, 120 g; Eluent A: water (plus 10 mmol/L ammonium bicarbonate); Eluent B: acetonitrile; Gradient: 25% to 45% B in 25 min; Flow rate: 60 mL/min; Detector: UV 220/254 nm; desired fractions were collected and concentrated under reduced pressure to afford 4-cyclopropoxy-N-{4-[(6,7-dimethoxy-1,5-naphthyridin-4-yl)oxy]-3,5-difluorophenyl}-2-fluoropyridine-3-carboxamide (80 mg, 52%) as a white solid. MS ESI calculated for $C_{25}K_9F_3N_4O_5$ [M+H]$^+$, 513.13 found 513.20. $^1$H NMR (400 MHz, DMSO-d$_6$) δ 11.10 (s, 1H), 8.63 (d, J=5.2 Hz, 1H), 8.12 (d, J=5.6 Hz, 1H), 7.78-7.54 (m, 3H), 7.49 (d, J=5.6 Hz, 1H), 6.93 (d, J=5.2 Hz, 1H), 4.22-4.10 (m, 1H), 4.03-3.95 (m, 6H), 0.99-0.69 (m, 4H). $^{19}$F NMR (377 MHz, DMSO-d$_6$) δ −72.07 (1F), −126.22 (2F).

Example 145: (S)-N-(3,5-difluoro-4-((6-((1-hydroxypropan-2-yl)oxy)-7-methoxy-1,5-naphthyridin-4-yl)oxy)phenyl)-4-methoxynicotinamide

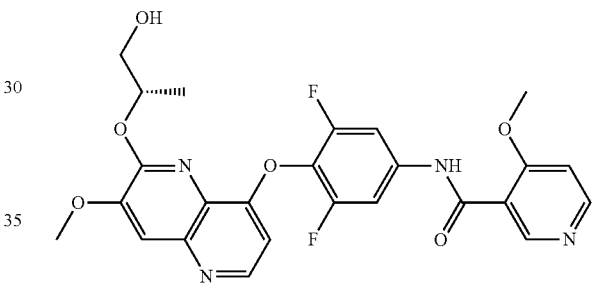

Synthesized using the similar method as in example 136 and example 144. White solid. MS ESI calculated for $C_{25}H_{22}F_2N_4O_6$ [M+H]$^+$, 513.15 found 513.26. $^1$H NMR (400 MHz, DMSO-d$_6$) δ 10.61 (s, 1H), 8.63 (s, 1H), 8.61 (d, J=6.0 Hz, 1H), 8.56 (d, J=5.2 Hz, 1H), 7.75-7.66 (m, 2H), 7.65 (s, 1H), 7.27 (d, J=6.0 Hz, 1H), 6.96 (d, J=5.2 Hz, 1H), 5.33-5.24 (m, 1H), 4.83 (t, J=5.6 Hz, 1H), 3.97 (s, 3H), 3.96 (s, 3H), 3.67-3.46 (m, 2H), 1.24 (d, J=6.0 Hz, 3H). $^{19}$F NMR (400 MHz, DMSO-d$_6$) δ −127.05 (2F).

Example 146: (S)-N-(3,5-difluoro-4-((7-methoxy-6-((1-methoxypropan-2-yl)oxy)-1,5-naphthyridin-4-yl)oxy)phenyl)-4-methoxynicotinamide

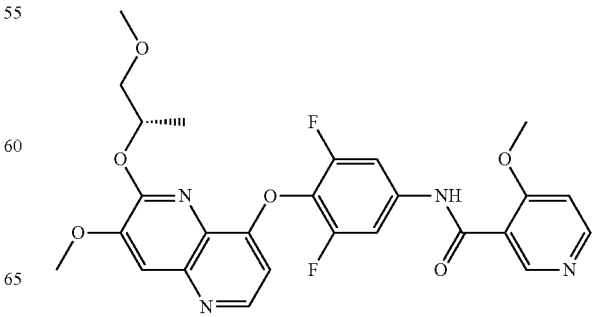

Synthesized using the similar method as in example 136 and example 144. Off white solid. $^1$H NMR (400 MHz, DMSO-$d_6$) δ: 10.63 (br s, 1H), 8.60-8.54 (m, 3H), 7.71-7.65 (m, 3H), 7.26 (d, J=6.0 Hz, 1H), 7.01 (d, J=5.2 Hz, 1H), 5.39-5.31 (m, 1H), 3.96 (s, 3H), 3.95 (s, 3H), 3.57-3.53 (m, 1H), 3.46-3.42 (m, 1H), 3.26 (s, 3H), 1.23 (d, J=6.4 Hz, 3H); LC-MS: 99.59%, m/z 527.28 [M+H]$^+$.

Example 147: N-(3,5-difluoro-4-((6-(1-(hydroxymethyl)cyclopropoxy)-7-methoxy-1,5-naphthyridin-4-yl)oxy)phenyl)-4-methoxynicotinamide

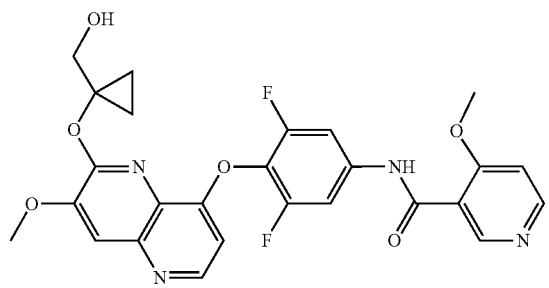 [SMILES: COc1ccncc1C(=O)Nc1cc(F)c(Oc2ccnc3cc(OC)c(OC4(CO)CC4)nc23)c(F)c1]

Step 1: methyl 1-((3-methoxy-5-nitropyridin-2-yl)oxy)cyclopropane-1-carboxylate

To a stirred solution of methyl 1-hydroxycyclopropane-1-carboxylate (0.92 g, 7.96 mmol) in DMF (10 mL) was added sodium hydride (0.191 g, 7.96 mmol) at 0° C. The reaction mixture was stirred for 15 mins and then 2-chloro-3-methoxy-5-nitropyridine (1.0 g, 5.30 mmol) was added. The resulting reaction mixture was allowed to stir at room temperature for 3 h. The progress of the reaction was monitored by TLC. (TLC: Mobile phase: 20% EtOAc-hexane, Rf: 0.25, UV visible). After completion of the reaction, the reaction mixture was poured into ice cold water and extracted using EtOAc (3×150 mL). The combined organic layers were washed with water (50 mL), brine solution (2×50 mL), dried over anhydrous Na2SO$_4$ and concentrated under reduced pressure to get methyl 1-((3-methoxy-5-nitropyridin-2-yl)oxy)cyclopropane-1-carboxylate (1 g, 70%) as a white solid. The compound was used for the next step without further purification. LC -MS: 94.33%, m/z [M+H]$^+$=269.06.

Step 2: methyl 1-((5-amino-3-methoxypyridin-2-yl)oxy)cyclopropane-1-carboxylate

To stirred solution of methyl 1-((3-methoxy-5-nitropyridin-2-yl)oxy)cyclopropane-1-carboxylate 3 (1.0 g, 3.73 mmol) in ethanol (10 mL) and water (2 mL) was added Iron powder (1.04 g, 18.64 mmol) and ammonium chloride (1.99 g, 37.28 mmol). The resulting reaction mixture was allowed to stir at 70° C. for 3 h. The progress of the reaction monitored by LCMS, after completion of starting material, the reaction mixture was filtered through a small pad of Celite and washed with EtOAc (100 mL) and concentrated under reduced pressure. The crude compound was dissolved in ethyl acetate (50 mL) and the organic layer washed with water (50 mL), brine (50 mL) and dried over sodium sulphate. The organic layer was concentrated under reduced pressure to get methyl 1-((5-amino-3-methoxypyridin-2-yl)oxy)cyclopropane-1-carboxylate (0.6 g, 67%). The crude compound was used for the next step without further purification. LC-MS: 75%, m/z [M+H]$^+$=239.13.

Step 3: methyl 1-((8-hydroxy-3-methoxy-1,5-naphthyridin-2-yl)oxy)cyclopropane-1-carboxylate To a stirred solution of methyl 1-((5-amino-3-methoxypyridin-2-yl)oxy)cyclopropane-1-carboxylate 4 (2 g, 8.39 mmol) in EtOH (20 mL), was added 2-(ethoxymethylene)-5,5-dimethyl -1,3-dioxane-4,6-dione (2.34 g, 12.59 mmol) at room temperature. The resulting reaction mixture was heated at 90° C. for 1 h. The progress of the reaction was monitored by TLC. After complete consumption of starting material, the reaction mixture was diluted with EtOH (30 mL) and filtered to obtain solid mass which was dried to get off white solid. Obtained solid was heated to 225° C. in diphenyl ether for 30 min. After completion of the reaction (monitored by TLC), the reaction mixture was allowed to cool to room temperature and diluted with pet ether (100 mL). The pet ether was decanted and again stirred in ethyl acetate (50 mL), filtered and dried to obtain methyl 1-((8-hydroxy-3-methoxy-1,5-naphthyridin-2-yl)oxy)cyclopropane-1-carboxylate (600 mg, 40%) as a brown solid. The structure was confirmed by nOe analysis. $^1$H NMR (400 MHz, DMSO-$d_6$) δ: 11.55 (br s, 1H), 7.78 (br s, 1H), 7.28 (s, 1H), 6.07 (br s, 1H), 3.89 (s, 3H), 3.57 (s, 3H), 1.55-1.52 (m, 2H), 1.30-1.27 (m, 2H); LC-MS: 93.27%, m/z 291.13 [M+H]$^+$.

Step 4: methyl 1-48-(2,6-difluoro-4-nitrophenoxy)-3-methoxy-1,5-naphthyridin-2-yl) oxy)cyclopropane-1-carboxylate To a stirred solution of 1-((8-hydroxy-3-methoxy-1,5-naphthyridin-2-yl)oxy)cyclopropane-1-carboxylate (1.6 g, 5.51 mmol) in ACN (25 mL) was added 1,2,3-trifluoro-5-nitrobenzene (0.75 mL, 6.61 mmol) and Cs2CO$_3$ (3.59 g, 11.02 mmol) at room temperature. Then the resulting reaction mixture was stirred for 16 h. The progress of the reaction monitored by TLC. After complete consumption of starting material, the reaction mixture was filtered through a small pad of Celite and washed with EtOAc (100 mL) and concentrated under reduced pressure. The crude compound was dissolved in ethyl acetate (100 mL) and the organic layer washed with water (50 mL) and brine (50 mL), dried over sodium sulphate and concentrated to get crude compound which was purified by column chromatography using pet-ether and ethyl acetate as an eluent to get methyl 1-((8-(2,6-difluoro-4-nitrophenoxy)-3-methoxy-1,5-naphthyridin-2-yl) oxy)cyclo propane-1-carboxylate (1.0 g, 40%) as a yellow solid. $^1$H NMR (400 MHz, CDCl$_3$) δ: 8.69 (d, J=5.2 Hz, 1H), 7.94-7.89 (m, 2H), 7.59 (s, 1H), 7.10 (d, J=5.2 Hz, 1H), 4.01 (s, 3H), 3.59 (s, 3H), 1.33-1.30 (m, 2H), 1.24-1.19 (m, 2H); LC-MS: 96.98%, m/z 448.2 [M+H]$^+$.

Step 5: methyl 1-((8-(4-amino-2,6-difluorophenoxy)-3-methoxy-1,5-naphthyridin-2-yl)oxy)cyclopropane-1-carboxylate To stirred solution of methyl 1-((3-methoxy-5-nitropyridin-2-yl)oxy)cyclopropane-1-carboxylate (0.9 g, 2.012 mmol) in ethanol (20 mL) and water (4 mL) was added Iron powder (0.56 g, 10.05 mmol) and ammonium chloride (1.07 g, 20.11 mmol). The resulting reaction mixture was allowed to stir at 70° C. for 3 h. The progress of the reaction monitored by LCMS. After completion of starting material, the reaction mixture was filtered through a small pad of Celite and washed with EtOAc (100 mL) and concentrated under reduced pressure. The crude compound was dissolved in ethyl acetate (300 mL) and the organic layer washed with water (50 mL) and brine (50 mL), dried over anhydrous sodium sulphate. The organic layer was concentrated to get methyl 1-((5-amino-3-methoxypyridin-2-yl)oxy)cyclopropane-1-carboxylate (0.65 g, 77%) as off white solid. The crude compound was used for the next step without further purification. $^1$H NMR (400 MHz, DMSO-$d_6$) δ: 8.54 (d, J=5.2 Hz, 1H), 7.69 (s, 1H), 6.71 (d, J=5.6 Hz, 1H), 6.40 (d, J=10.8 Hz, 2H), 5.78 (s, 2H), 3.98 (s, 3H), 3.56 (s, 3H), 1.56-1.52 (m, 2H), 1.37-1.34 (m, 2H); LC-MS: 98.76%, m/z [M+H]$^+$=418.19.

Step 6: methyl 1-((8-(2,6-difluoro-4-(4-methoxynicotinamido)phenoxy)-3-methoxy-1,5-naphthyridin-2-yl)oxy)cyclopropane-1-carboxylate To a stirred solution of methyl 1-((5-amino-3-methoxypyridin-2-yl)oxy)cyclopropane-1-carboxylate (0.6 g, 1.43 mmol) in DCM (15 mL) were added DIPEA (0.59 mL, 3.59 mmol) and 4-methoxynicotinoyl chloride (0.247 g, 1.43 mmol) at 0° C. The resulting reaction mixture was stirred at room temperature for 30 minutes. The progress of the reaction monitored by LCMS. After completion of starting material, the reaction mixture was diluted with DCM (50 mL) and the organic layer washed with water (50 mL) and brine (50 mL) and dried over anhydrous sodium sulphate. The organic layer was concentrated under reduced pressure to get methyl 1-((8-(2,6-difluoro-4-(4-methoxynicotinamido)phenoxy)-3-methoxy-1,5-naphthyridin-2-yl)oxy)cyclopropane-1-carboxylate (0.35 g, 44%) as off-white solid. The crude compound was used for the next step without further purification. $^1$H NMR (400 MHz, DMSO-$d_6$) δ: 10.65 (br s, 1H), 8.62-8.58 (m, 3H), 7.73-7.68 (m, 3H), 7.26 (d, J=6.0 Hz, 1H), 6.91 (d, J=5.2 Hz, 1H), 3.99 (s, 3H), 3.96 (s, 3H), 3.57 (s, 3H), 1.50-1.49 (m, 2H), 1.35-1.33 (m, 2H); LC-MS: 96.36%, m/z [M+H]$^+$=553.26.

Step 7: N-(3,5-difluoro-4-((6-(1-(hydroxymethyl)cyclopropoxy)-7-methoxy-1,5-naphthyridin-4-yl)oxy)phenyl)-4-methoxynicotinamide To a stirred solution of methyl 1-((8-(2,6-difluoro-4-(4-methoxynicotinamido)phenoxy)-3-methoxy-1,5-naphthyridin-2-yl)oxy)cyclopropane-1-carboxylate (0.35 g, 0.63 mmol) in THF (5 mL) was added LAH (0.63 mL, 1.267 mmol) (2M solution in THF) at -78° C. The resulting reaction mixture was stirred at RT for 30 minutes. The progress of the reaction was monitored by LCMS. After completion of starting material, the reaction mixture was quenched with ice water (0.5 mL) and followed by 1N sodium hydroxide (1 mL) at 0° C. Ice water (10 mL) was added again, and the reaction mixture was filtered through a small pad of Celite and washed with EtOAc (100 mL). The organic layer was concentrated under reduced pressure to get crude compound which was purified by prep HPLC to afford N-(3,5-difluoro-4-((6-(1-(hydroxymethyl)cyclopropoxy)-7-methoxy-1,5-naphthyridin-4-yl)oxy)phenyl)-4-methoxy nicotinamide (53 mg, 15%) as an off white solid. $^1$H NMR (400 MHz, DMSO-$d_6$) δ: 10.59 (br s, 1H), 8.62-8.56 (m, 3H), 7.72-7.67 (m, 3H), 7.26 (d, J=6.0 Hz, 1H), 6.93 (d, J=5.2 Hz, 1H), 5.09 (t, J=6.0 Hz, 1H), 3.96 (s, 3H), 3.95 (s, 3H), 3.81 (d, J=5.6 Hz, 2H), 0.91-0.89 (m, 4H); LC-MS: 98.55%, m/z 525.27 [M+H]$^+$.

Example 148: 4-cyclopropoxy-N-(3,5-difluoro-4-((7-(2-hydroxyethoxy)-6-methoxyquinolin-4-yl)oxy)phenyl)pyridazine-3-carboxamide

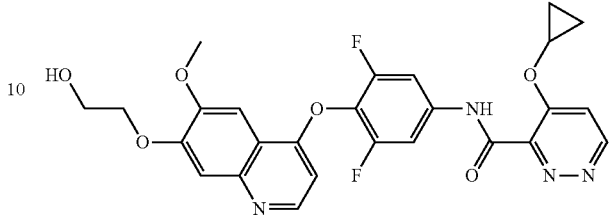

Synthesized using the similar method as in example 120. White solid. MS ESI calculated for $C_{26}H_{22}F_2N_4O_6$ [M+H]$^+$, 525.15 found 525.20. $^1$H NMR (400 MHz, DMSO-$d_6$) δ 11.25 (s, 1H), 9.26 (d, J=6.0 Hz, 1H), 8.51 (d, J=5.2 Hz, 1H), 7.81 (s, 1H), 7.83-7.79 (m, 2H), 7.57 (s, 1H), 7.45 (s, 1H), 6.64 (d, J=5.2 Hz, 1H), 4.97 (t, J=5.2 Hz, 1H), 4.24-4.13 (m, 3H), 3.98 (s, 3H), 3.88-3.84 (m, 2H), 0.96-0.88 (m, 2H), 0.82-0.75 (m, 2H). $^{19}$F NMR (376 MHz, DMSO-$d_6$) δ -126.31(2F).

Example 149: 4-cyclopropoxy-N-(4-((6,7-dimethoxyquinolin-4-yl)oxy)-3,5-difluorophenyl)pyridazine-3-carboxamide

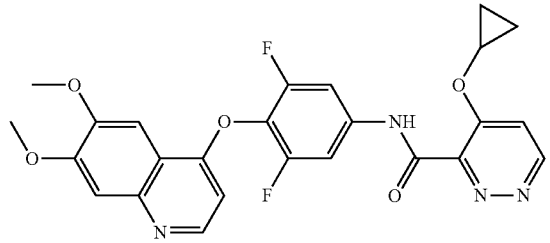

Synthesized using the similar method as in example 120. White solid. MS ESI calculated for $C_{25}H_{20}F_2N_4O_5$ [M+H]$^+$, 495.14 found 495.25. $^1$H NMR (400 MHz, DMSO-$d_6$) δ 11.25 (s, 1H), 9.26 (d, J=6.4 Hz, 1H), 8.51 (d, J=5.2 Hz, 1H), 7.85-7.78 (m, 2H), 7.78 (d, J=6.4 Hz, 1H), 7.56 (s, 1H), 7.44 (s, 1H), 6.64 (d, J=5.2 Hz, 1H), 4.21-4.17 (m, 1H), 3.97 (s, 6H), 0.96-0.88 (m, 2H), 0.81-0.79 (m, 2H). $^{19}$F NMR (376 MHz, DMSO-$d_6$) δ -126.32 (2F).

II. Biological Evaluation

Example 1a: MET Mobility Shift Assay

Small molecule inhibition of MET kinase activity was evaluated using a fluorescence-based microfluidic mobility shift assay. MET catalyzes the production of ADP from ATP during phosphoryl transfer to the substrate peptide, FLPeptide30 (5-FAM-KKKKEEIYFFF-CONH$_2$) (Perkin Elmer, 760430). MET enzme (Carna Biosciences, 08-151) at 0.625 nM was prepared with 10 mM MgCl$_2$ and 1.5 μM substrate peptide in a buffer containing 50 mM HEPES, 1 mM EGTA, 0.01% Brij-35, 0.05% BSA, and 2 mM DTT and pre-incubated at room temperature for 30 min prior to the start of the reaction. 100 μM ATP was added to start the reaction.

The mobility shift assay electrophoretically separates the fluorescently labeled peptides (substrate and phosphorylated product) following the 60 minute kinase reaction. The reaction was terminated by addition of 0.5 M EDTA. Both substrate and product were measured and the ratio of these values used to generate % conversion of substrate to product by the LabChip EZ reader (Perkin Elmer). IC50 values were calculated using the inhibition of conversion ratio using Dotmatics Knowledge Solutions Studies curve fitting environment (Dotmatics, Bishops Stortford, UK, CM23) and are presented in Table 2.

Example 1b: MET D1228N Mobility Shift Assay

Small molecule inhibition of MET D1228N kinase activity was evaluated using a fluorescence -based microfluidic mobility shift assay. MET D1228N catalyzes the production of ADP from ATP during phosphoryl transfer to the substrate peptide, FLPeptide30 (5-FAM-KKKKEEIYFFF -CONH$_2$) (Perkin Elmer, 760430). MET D1228N enzyme (Signalchem, M52-12IG) at 0.313 nM was prepared with 10 mM MgCl$_2$ and 1.5 µM substrate peptide in a buffer containing 50 mM HEPES, 1 mM EGTA, 0.01% Brij-35, 0.05% BSA, and 2 mM DTT and pre-incubated at room temperature for 30 min prior to the start of the reaction. 100 µM ATP was added to start the reaction. The mobility shift assay electrophoretically separates the fluorescently labeled peptides (substrate and phosphorylated product) following the 60 minute kinase reaction. The reaction was terminated by addition of 0.5 M EDTA. Both substrate and product were measured and the ratio of these values used to generate % conversion of substrate to product by the LabChip EZ reader (Perkin Elmer). IC50 values were calculated using the inhibition of conversion ratio using Dotmatics Knowledge Solutions Studies curve fitting environment (Dotmatics, Bishops Stortford, UK, CM23) and are presented in Table 2.

Example 1c: CellTiter-Glo Cell Viability Assay

Ba/F$_3$-TPR-MET and Ba/F$_3$-TPR-MET-D1228N cells were seeded at 3000 cells per well in a 96 well plate in 90 µL growth media and allowed to incubate overnight at 37° C. with 5% CO$_2$. The following day, compounds were serially diluted from a 10 mM top dose for a 9-point 3-fold dilution curve in DMSO. Following a 100-fold dilution in growth media, a further 10-fold dilution was made into the cell plate for a final volume of 100 µL and 0.1% DMSO. Compounds and cells were incubated together for 72 hours at 37° C. with 5% CO$_2$. The CellTiter-Glo® 2.0 Assay determines the number of viable cells in culture by quantifying ATP, which indicates the presence of metabolically active cells. Luminescence readout is directly proportional to the number of viable cells in culture. CellTiter-Glo reagent (Promega, G9243) and cell plates were allowed to equilibrate to room temperature for at least 15 min, then 100 µL of CellTiter-Glo was added to each well for a 1:1 ratio of reagent to media. Samples were placed on a shaker for 2 min prior to a 30 min incubation at room temperature protected from light. Luminescence was read on a Perkin Elmer Envision plate reader 2105 and used to calculate IC50 values within the Dotmatics Knowledge Solutions Studies curve fitting environment (Dotmatics, Bishops Stortford, UK, CM23) and are presented in Table 2.

Representative data for exemplary compounds is presented in Table 2.

TABLE 2

| # | MET | MET-D1228N | Ba/F3-TPR-MET | Ba/F3-TPR-MET-D1228N |
|---|-----|------------|---------------|----------------------|
| 1 | A | A | A | A |
| 2 | A | A | C | B |
| 3 | A | A | A | B |
| 4 | A | A | B | B |
| 5 | A | A | A | A |
| 6 | A | A | B | B |
| 7 | A | A | C | B |
| 8 | A | A | B | B |
| 9 | A | A | B | A |
| 10 | A | A | A | A |
| 11 | A | A | NT | NT |
| 12 | A | A | A | A |
| 13 | A | A | B | A |
| 14 | A | A | B | B |
| 15 | A | A | B | B |
| 16 | A | A | B | B |
| 17 | A | A | A | A |
| 18 | A | A | B | A |
| 19 | A | A | D | D |
| 20 | A | A | A | A |
| 21 | A | A | B | B |
| 22 | A | A | B | B |
| 23 | A | A | B | A |
| 24 | A | A | B | A |
| 25 | A | A | B | B |
| 26 | A | A | NT | NT |
| 27 | A | A | B | B |
| 28 | A | A | A | A |
| 29 | A | A | A | A |
| 30 | A | A | A | A |
| 31 | A | A | B | B |
| 32 | A | A | B | B |
| 33 | A | A | NT | NT |
| 34 | A | A | B | A |
| 35 | A | A | B | B |
| 36 | A | A | B | B |
| 37 | A | A | B | B |
| 38 | A | A | D | D |
| 39 | A | A | B | A |
| 40 | A | A | B | B |
| 41 | A | A | B | A |
| 42 | A | A | B | A |
| 43 | A | A | A | A |
| 44 | A | A | B | B |
| 45 | A | A | B | B |
| 46 | A | A | A | A |
| 47 | A | A | B | B |
| 48 | A | A | NT | NT |
| 49 | A | A | B | B |
| 50 | A | A | A | A |
| 51 | A | A | B | A |
| 52 | A | A | B | B |
| 53 | A | A | A | A |
| 54 | A | A | A | A |
| 55 | A | A | B | A |
| 56 | A | A | A | A |
| 57 | A | A | B | B |
| 58 | A | A | A | A |
| 59 | A | A | A | A |
| 60 | A | A | A | A |
| 61 | A | A | A | A |
| 62 | A | A | A | A |
| 63 | A | A | B | B |
| 64 | A | A | B | B |
| 65 | A | A | B | A |
| 66 | A | A | B | B |
| 67 | A | A | B | B |
| 68 | A | A | B | A |
| 69 | A | A | A | A |
| 70 | A | A | B | B |
| 71 | A | A | B | B |
| 72 | A | A | B | A |
| 73 | A | A | A | A |
| 74 | A | A | B | B |
| 75 | A | A | A | A |
| 76 | A | A | B | B |
| 77 | A | A | A | A |

TABLE 2-continued

| # | MET | MET-D1228N | Ba/F3-TPR-MET | Ba/F3-TPR-MET-D1228N |
|---|---|---|---|---|
| 78 | A | A | B | B |
| 79 | A | A | B | B |
| 80 | A | A | B | A |
| 81 | A | A | A | A |
| 82 | A | A | B | B |
| 83 | A | A | NT | NT |
| 84 | A | A | B | A |
| 85 | A | A | B | B |
| 86 | A | A | B | B |
| 87 | A | A | A | A |
| 88 | A | A | B | A |
| 89 | A | A | B | B |
| 90 | A | A | B | A |
| 91 | A | A | A | A |
| 92 | A | A | B | B |
| 93 | A | A | A | A |
| 94 | A | A | A | A |
| 95 | A | A | B | B |
| 96 | A | A | B | B |
| 97 | A | A | A | A |
| 98 | A | A | A | A |
| 99 | A | A | A | A |
| 100 | A | A | B | A |
| 101 | A | A | B | B |
| 102 | A | A | B | B |
| 103 | A | A | C | B |
| 104 | A | A | C | B |
| 105 | A | A | B | A |
| 106 | A | A | A | A |
| 107 | A | A | A | A |
| 108 | A | A | C | C |
| 109 | A | A | A | A |
| 110 | A | A | A | A |
| 111 | A | A | A | A |
| 112 | A | A | B | B |
| 113 | A | A | A | A |
| 114 | A | A | B | B |
| 115 | A | A | A | A |
| 116 | A | A | A | A |
| 117 | A | A | A | A |
| 118 | A | A | A | A |
| 119 | A | A | B | B |
| 120 | A | A | B | B |
| 121 | A | A | A | A |
| 122 | A | A | A | A |
| 123 | A | A | A | A |
| 124 | A | A | A | A |
| 125 | A | A | A | A |
| 126 | A | A | A | A |
| 127 | A | A | A | A |
| 128 | A | A | A | A |
| 129 | A | A | A | A |
| 130 | A | A | B | A |
| 131 | A | A | A | A |
| 132 | A | A | NT | NT |
| 133 | A | A | A | A |
| 134 | A | A | A | A |
| 135 | A | A | A | A |
| 136 | A | A | A | A |
| 137 | A | A | A | A |
| 138 | A | A | A | A |
| 139 | A | A | A | A |
| 140 | A | A | A | A |
| 141 | A | A | A | A |
| 142 | A | A | A | A |
| 143 | A | A | A | A |
| 144 | A | A | A | A |
| 145 | A | A | A | A |
| 146 | A | A | A | A |
| 147 | A | A | A | A |
| 148 | A | A | A | A |
| 149 | A | A | B | A |

Note:
Biochemical Assay IC$_{50}$ data and cell assay EC$_{50}$ data are designated within the following ranges:
A: ≤0.10 μM
B: >0.10 μM to ≤1.0 μM
C: >1.0 μM to ≤10 μM
D: >10 μM
NT: not tested

III. Preparation of Pharmaceutical Dosage Forms

Example 1: Oral Capsule

The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or a pharmaceutically acceptable salt or solvate thereof, having the structure of Formula (II):

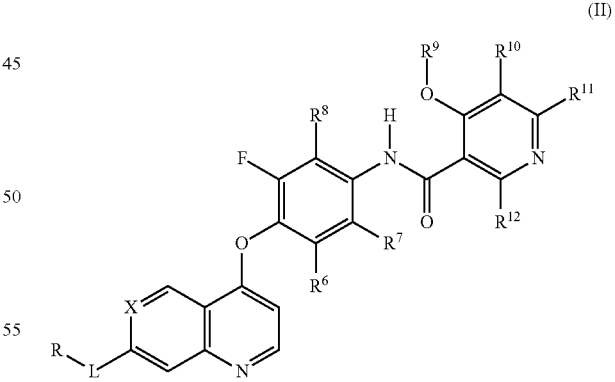

wherein,
X is C—L$^1$—R$^1$, and L$^1$ is —O—;
L is —O—;
R is selected from the group consisting of H, halogen, —CN, optionally substituted C1-C6 alkyl, optionally substituted C1-C6 alkenyl, optionally substituted C1-C6 alkynyl, optionally substituted C3-C6 cycloalkyl, optionally substituted cycloalkylalkyl, optionally substituted heterocyclyl, optionally substituted heterocyclylalkyl, optionally substituted heteroaryl, and optionally substituted heteroarylalkyl;

$R^1$ is selected from the group consisting of H, halogen, —CN, optionally substituted C1-C6 alkyl, optionally substituted C1-C6 alkenyl, optionally substituted C1-C6 alkynyl, optionally substituted C3-C6 cycloalkyl, optionally substituted cycloalkylalkyl, optionally substituted heterocyclyl, optionally substituted heterocyclylalkyl, optionally substituted heteroaryl, and optionally substituted heteroarylalkyl;

$R^6$, $R^7$ and $R^8$ are each independently selected from H or halogen; provided that at least one of $R^6$, $R^7$ or $R^8$ is not H;

$R^9$ is selected from the group consisting of optionally substituted C1-C6 alkyl, optionally substituted C3-C6 cycloalkyl, and optionally substituted cycloalkylalkyl;

$R^{10}$ is H;

$R^{11}$ is H, halogen, —NH$_2$, —CN, optionally substituted C1-C6 alkyl, optionally substituted C1-C6 alkoxy, —NH(optionally substituted C1-C6 alkyl), or —N(optionally substituted C1-C6 alkyl)$_2$; and $R^{12}$ is H, halogen, —NH$_2$, —CN, optionally substituted C1-C6 alkyl or optionally substituted C1-C6 alkoxy.

2. The compound of claim 1, or a pharmaceutically acceptable salt or solvate thereof, wherein $R^1$ is optionally substituted C1-C6 alkyl, or optionally substituted C3-C6 cycloalkyl; and R is optionally substituted C1-C6 alkyl, or optionally substituted C3-C6 cycloalkyl.

3. The compound of claim 2, or a pharmaceutically acceptable salt or solvate thereof, wherein $R^1$ is optionally substituted C3-C6 cycloalkyl.

4. The compound of claim 2, or a pharmaceutically acceptable salt or solvate thereof, wherein $R^1$ is optionally substituted C1-C6 alkyl.

5. The compound of claim 2, or a pharmaceutically acceptable salt or solvate thereof, wherein $R^1$ is optionally substituted C1-C2 alkyl.

6. The compound of claim 2, or a pharmaceutically acceptable salt or solvate thereof, wherein $R^1$ is optionally substituted C1 alkyl.

7. The compound of claim 2, or a pharmaceutically acceptable salt or solvate thereof, wherein R is optionally substituted C1-C6 alkyl.

8. The compound of claim 2, or a pharmaceutically acceptable salt or solvate thereof, wherein R is optionally substituted C1-C4 alkyl.

9. The compound of claim 2, or a pharmaceutically acceptable salt or solvate thereof, wherein R is optionally substituted C1-C2 alkyl.

10. The compound of claim 1, or a pharmaceutically acceptable salt or solvate thereof, wherein $R^9$ is optionally substituted C1-C6 alkyl, or optionally substituted C3-C6 cycloalkyl.

11. The compound of claim 10, or a pharmaceutically acceptable salt or solvate thereof, wherein $R^9$ is optionally substituted C1-C4 alkyl.

12. The compound of claim 10, or a pharmaceutically acceptable salt or solvate thereof, wherein $R^9$ is optionally substituted C1 alkyl.

13. The compound of claim 10, or a pharmaceutically acceptable salt or solvate thereof, wherein $R^9$ is $CH_3$.

14. The compound of claim 10, or a pharmaceutically acceptable salt or solvate thereof, wherein $R^9$ is optionally substituted C3-C6 cycloalkyl.

15. The compound of claim 10, or a pharmaceutically acceptable salt or solvate thereof, wherein $R^9$ is optionally substituted cyclopropyl.

16. The compound of claim 10, or a pharmaceutically acceptable salt or solvate thereof, wherein $R^9$ is cyclopropyl.

17. The compound of claim 1, or a pharmaceutically acceptable salt or solvate thereof, wherein $R^{11}$ is hydrogen.

18. The compound of claim 1, or a pharmaceutically acceptable salt or solvate thereof, wherein $R^8$ is fluoro.

19. The compound of claim 1, or a pharmaceutically acceptable salt or solvate thereof, wherein $R^8$ is hydrogen.

20. The compound of claim 1, or a pharmaceutically acceptable salt or solvate thereof, wherein $R^6$ is hydrogen.

21. The compound of claim 1, or a pharmaceutically acceptable salt or solvate thereof, wherein $R^6$ is fluoro.

22. The compound of claim 2, or a pharmaceutically acceptable salt or solvate thereof, wherein $R^9$ is optionally substituted C1-C6 alkyl, or optionally substituted C3-C6 cycloalkyl.

23. The compound of claim 22, or a pharmaceutically acceptable salt or solvate thereof, wherein $R^6$ is fluoro.

24. The compound of claim 10, or a pharmaceutically acceptable salt or solvate thereof, wherein $R^6$ is fluoro.

25. The compound of claim 2, or a pharmaceutically acceptable salt or solvate thereof, wherein $R^{11}$ is hydrogen.

26. The compound of claim 10, or a pharmaceutically acceptable salt or solvate thereof, wherein $R^{11}$ is hydrogen.

27. The compound of claim 21, or a pharmaceutically acceptable salt or solvate thereof, wherein $R^{11}$ is hydrogen.

28. The compound of claim 22, or a pharmaceutically acceptable salt or solvate thereof, wherein $R^{11}$ is hydrogen.

29. The compound of claim 23, or a pharmaceutically acceptable salt or solvate thereof, wherein $R^{11}$ is hydrogen.

30. A pharmaceutical composition comprising a compound, or pharmaceutically acceptable salt or solvate thereof, as described in claim 1, and a pharmaceutically acceptable excipient.

* * * * *